US007960428B2

(12) United States Patent
Storer et al.

(10) Patent No.: US 7,960,428 B2
(45) Date of Patent: Jun. 14, 2011

(54) ENANTIOMERICALLY PURE PHOSPHOINDOLES AS HIV INHIBITORS

(75) Inventors: Richard Storer, Folkestone (GB);
Francois-Rene Alexandre, Montpellier (FR); Cyril Dousson, Canet (FR); Adel M. Moussa, Burlington, MA (US);
Edward Bridges, Lewisburg, WV (US);
Alistair Stewart, Somerville, MA (US);
Jing Yang Wang, Acton, MA (US);
Benjamin Alexander Mayes, Boston, MA (US)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 287 days.

(21) Appl. No.: 11/906,095

(22) Filed: Sep. 28, 2007

(65) Prior Publication Data

US 2008/0213217 A1 Sep. 4, 2008

Related U.S. Application Data

(60) Provisional application No. 60/848,584, filed on Sep. 29, 2006, provisional application No. 60/857,980, filed on Nov. 9, 2006, provisional application No. 60/903,115, filed on Feb. 23, 2007.

(51) Int. Cl.
*A61K 31/40* (2006.01)
*C07D 209/42* (2006.01)
(52) U.S. Cl. .................. 514/419; 514/415; 548/492
(58) Field of Classification Search .................. 514/419, 514/415; 548/492
See application file for complete search history.

(56) References Cited

U.S. PATENT DOCUMENTS

| 4,866,084 | A | 9/1989 | Gunasekera et al. |
| 5,124,327 | A | 6/1992 | Greenlee et al. |
| 5,424,329 | A | 6/1995 | Boschelli et al. |
| 5,489,685 | A | 2/1996 | Houpis et al. |
| 5,527,819 | A | 6/1996 | Williams et al. |
| 5,565,446 | A | 10/1996 | Boschelli et al. |
| 5,703,069 | A | 12/1997 | Connor et al. |
| 5,830,894 | A | 11/1998 | Pevear et al. |
| 5,852,011 | A | 12/1998 | Matsunaga et al. |
| 5,929,114 | A | 7/1999 | Domagala et al. |
| 5,935,982 | A | 8/1999 | Dykstra et al. |
| 5,945,440 | A | 8/1999 | Kleinschroth et al. |
| 5,981,525 | A | 11/1999 | Farina et al. |
| 6,017,903 | A | 1/2000 | Slusher et al. |
| 6,025,345 | A | 2/2000 | Jackson et al. |
| 6,025,390 | A | 2/2000 | Farina et al. |
| 6,297,270 | B1 | 10/2001 | Beller et al. |
| 6,506,787 | B2 | 1/2003 | Fujishita et al. |
| 6,710,068 | B2 | 3/2004 | La Colla et al. |
| 6,716,605 | B2 | 4/2004 | Fujishita et al. |
| 6,825,201 | B2 | 11/2004 | Wang et al. |
| 6,900,206 | B2 | 5/2005 | Kadow et al. |
| 7,534,809 | B2 * | 5/2009 | Storer et al. ............ 514/419 |
| 2002/0019434 | A1 | 2/2002 | Fujishita et al. |
| 2003/0096825 | A1 | 5/2003 | Wang et al. |
| 2003/0236277 | A1 | 12/2003 | Kadow et al. |
| 2004/0006090 | A1 | 1/2004 | Kadow et al. |
| 2004/0063746 | A1 | 4/2004 | Regueiro-Ren et al. |
| 2006/0074054 | A1 * | 4/2006 | Storer et al. ............ 514/80 |
| 2009/0163444 | A1 | 6/2009 | Storer et al. |

FOREIGN PATENT DOCUMENTS

| EP | 1799696 B1 | 11/2008 |
| WO | WO 94/19321 | 9/1994 |
| WO | WO 96/29077 | 9/1996 |
| WO | WO 97/48399 | 12/1997 |
| WO | WO 97/48400 | 12/1997 |
| WO | WO 97/48409 | 12/1997 |
| WO | WO 98/13046 | 4/1998 |
| WO | WO 98/38332 | 9/1998 |
| WO | WO 98/53812 | 12/1998 |
| WO | WO 99/52915 | 10/1999 |
| WO | WO 01/02388 | 1/2001 |
| WO | WO 03/068221 | 8/2003 |
| WO | WO 03/090690 | 11/2003 |
| WO | WO 03/090691 | 11/2003 |
| WO | WO 03/091264 | 11/2003 |
| WO | WO 2004/014364 | 2/2004 |
| WO | WO 2006/054182 A2 | 5/2006 |
| WO | WO 2008/042240 A2 | 4/2008 |

OTHER PUBLICATIONS

Alexandre et al., "Synthesis and Antiviral Activity of Phospho-Indoles as Novel NNRTI with Potent Anti-HIV Activity and Enhanced Barrier to Resistance," Poster presented at ASMC07, St. Petersburg, Russia (Aug. 28-31, 2007).
Alexandre et al., "IDX 12899; A Novel and Highly Potent anti-HIV Non-Nucleosidic-Reverse-Transcriptase-Inhibitor with Enhanced Barrier to Resistance Profile," Poster 21 presented at 14$^{th}$ SCI-RSC Medicinal Chemistry Symposium, Cambridge, UK (Sep. 23-26, 2007).
Aoyagi et al., "Studies on Chromogenic and Fluorogenic Substrates for Detection of Enzymatic Activities," J. Fac. Eng. Chiba Univ., 26(49):185-191 (1974).
Artico et al., "2-Sulfonyl-4-Chloroanilino Moiety: A Potent Pharmacophore for the Anti-Human Immunodeficiency Virus Type 1 Activity of Pyrrolyl Aryl Sulfones," J. Med. Che., 39:522-530 (1996).
Artico et al., "1-Arylsulfonyl-3-(α-hydroxybenzyl)-1H-Pyrroles, a Novel Class of Anti-HIV-1 Reverse Transcriptase Inhibitors," Bioorganic & Med. Chem. Letters 7:1931-1936 (1997).
Artico et al., "Strucure-Based Design, Synthesis, and Biological Evaluation of Novel Pyrrolyl Aryl Sulfones: HIV-1 Non-Nucleoside Reverse Transcriptase Inhibitors Active at Nanomolar Concentrations," J. Med. Chem., 43:1886-1891 (2000).
Baba et al., "Highly Potent and Selective Inhibition of HIV-1 Replication by 6-Phenylthiouracil Derivatives," Antiviral Res., 17:245-264 (1992).

(Continued)

Primary Examiner — Rei-tsang Shiao
(74) Attorney, Agent, or Firm — Jones Day

(57) ABSTRACT 3-phosphoindole compounds substantially in the form of a single enantiomer useful for the treatment of Flaviviridae virus infections, and particularly for HIV infections are provided. Also provided are pharmaceutical compositions comprising the 3-phosphoindole compounds alone or in combination with one or more other anti-viral agents, processes for their preparation, and methods of manufacturing a medicament incorporating these compounds.

42 Claims, 4 Drawing Sheets

OTHER PUBLICATIONS

Balzarini et al., "2'5'-Bis-O-(tert-Butyldimethylsilyl)-3'-Spiro5"-(4"-Amino-1",2"-Oxathiole-2",2"-Dioxide) Pyrimidine (TSAO) Nucleoside Analogues: Highly Selective Inhibitors of Human Immunodeficiency Virus Type 1 that are Targeted at the Viral Reverse Transcriptase," PNAS, 89:4392-4396 (1992).

Beilstein Registry No. 284968, Chemical Name "di-indol-3-yl-phosphinic acid," Beilstein Entry Date: Jun. 27, 1988.

Bell et al., "Phenethylthiazolethiourea (PETT) Compounds, a New Class of HIV-1 Reverse Transcriptase Inhibitors. 1. Synthesis and Basic Structure-Activity Relationship Studies of PETT Analogs," J. Med. Chem., 38:4929-4936 (1995).

Cantrell et al., "Phenethylthiazolylthiourea (PETT) Compounds as a New Class of HIV-1 Reverse Transcriptase Inhibitors. 2. Synthesis and Further Structure-Activity Relationship Studies of PETT Analogs," J. Med. Chem., 39:4261-4274 (1996).

Chen et al., "Synthesis of Indoles via a Palladium-Catalyzed Annulation between Iodoanilines and Ketones," J. Org. Chem., 62(9):2676-2677 (1997).

Danel et al., "Synthesis of Potent Anti-HIV-1 Activity of Novel 6-Benzyluracil Analogues of 1-[(2-Hydroxyethoxy)methyl]-6-(phenylthio)thymine," J. Med. Chem., 39:2427-2431 (1996).

Danel et al., "Anti-HIV Active Naphthyl Analogues of HEPT and DABO," Acta Chemica Scandinavica, 51:426-430 (1997).

DeClercq, "HIV Inhibitors Targeted at the Reverse Transcriptase," Aids Research and Human Retroviruses, 8(2):119-134 (1992).

Greene, "The Molecular Biology of Human Immunodeficiency Virus Type 1 Infection," New England Journal of Medicine, 324:308-317 (1991).

Gurevich et al., "Phosphorylation of Indoles with Phosphorus (III) Acid Chlorides," J. Gen. Chem. USSR (Engl. Transl.), 55(5):1121-1125 (1985).

Haikal, "Synthesis of Guanosine-3'-(5-Bromo-4-Chloroindol-3-YL)-Phosphate (G-3'-BCIP)," Collection of Czechoslovak Chemical Communications, 61(3):427-431 (1996).

Horwitz et al., "Substrates for Cytochemical Demonstration of Enzyme Activity II. Some Dihalo-3-Indolyl Phosphates and Sulfates," Journal of Medicinal Chemistry, 447 (May 1966).

Horwitz et al., "Substrates for Cytochemical Demonstration of Enzyme Activity V. Thymidine 3'-and 5'-(5-Bromo-4-Chloro-3-Indolyl) Phosphates," Journal of Medicinal Chemistry, 13(5):1024-1025 (1970).

Jakubik et al., "IDX 12899 anti-HIV-1 Activity and Resistance Profile is Superior to Efavirenz," Poster 1657 presented at the XVI International HIV Drug Resistance Workshop, Barbados, West Indies (Jun. 12-16, 2007).

Kohlstaedt et al., "Crystal Structure at 3.5 \Anstrom Resolution of HIV-1 Reverse Transcriptase Complexed with an Inhibitor," Science, 256(5065):1783-1790 (1992).

Mai et al., "Dihydro(alkylthio)(naphthylmethyl)oxopyrimidines: Novel Non-Nucleoside Reverse Transcriptase Inhibitors of the S-DABO Series," J. Med. Chem., 40:1447-1454 (1997).

March et al., "The Synthesis of Ribonucleotide-5'-(5-Iodoindol-3-ol) and (4-Methylcoumarin-7-ol) Esters for the Histochemical Demonstration of Nucleases (1A)," Journal of Heterocyclic Chemistry, 7(4):885-889 (1970).

Mitsuya et al., "Molecular Targets for AIDS Therapy," Science, 249(4976):1533-1544 (1990).

Pauwels et al., "Potent and Selective Inhibition of HIV-1 Replication in vitro by a Novel Series of TIBO Derivatives," Nature, 343:470-474 (1990).

Pauwels et al., "Potent and Highly Selective Human Immunodeficiency Virus Type 1 (HIV-1) Inhibition by a Series of α-anilinophenylacetamide Derivates Targeted at HIV-1 Reverse Transcriptase," PNAS, 90:1711-1715 (1993).

Pontikis et al., "Synthesis and Anti-HIV Activity of Novel N-1 Side Chain-Modified Analogs of 1-[(2-Hydroxyethoxy)methyl]-6-(phenylthio)thymine (HEPT)," J. Med. Chem., 40:1845-1854 (1997).

Rabiger et al., "Synthesis of 5-Iodo and 5-Nitro-3-indolyl Phosphates as Cytochemical Substrates for Acid Phosphatase," Journal of Heterocyclic Chemistry, 7:307-311 (1970).

Razumov et al., "Phosphorylation of Indoles with Phosphoramidites," J. General Chemistry, USSR (Engl. Transl.) 50(4):618-624 (1980).

Richman et al., "IDX 12899 and IDX 12989, Novel NNRTIs with Potent anti-HIV Activity, Enhanced Barrier to Resistance and Favorable Pharmacokinetic Profile," Poster 489 presented at the 14th Conference on Retroviruses and Opportunistic Infections, Feb. 25-28, 2007, Los Angeles, CA.

Romero et al., "Bis(heteroaryl)piperazine (BHAP) Reverse Transcriptase Inhibitors: Structure-Activity Relationships of Novel Substituted Indole Analogues and the Identification of 1-[(5-Methanesulfonamido-1H-indol-2-yl)-carbonyl]-4-[3-[(1-methylethyl)amino]-pyridinyl]piperazine Monomethanesulfonate (U-90152S), a Second-Generation Clinical Candidate," J. Med. Chem., 36:1505-1508 (1993).

Silvestri et al., "Computer-Assisted Design, Synthesis and Biological Evaluation of Novel Pyrrolyl Heteroaryl Sulfones Targeted at HIV-1 Reverse Transcriptase as Non-Nucleside Inhibitors," Bioorganic & Med. Chem., 8:2305-2309 (2000).

Silvestri et al., "Anti-HIV-1 NNRT Agents: Acylamino Pyrryl Aryl Sulfones (APASs) as Truncated Analogues of Tricyclic PBTDs," Med. Chem. Research 11:195-218 (2002).

Silvestri et al., "Novel Indolyl Sulfones Active Against HIV-1 Carrying NNRTI Resistance Mutations: Synthesis and SAR Studies," J. Med. Chem., 46:2482-2493 (2003).

Tanaka et al., "A New Class of HIV-1-Specific 6-Substituted Acyclouridine Derivatives: Synthesis and Anti-HIV-1 Activity of 5- or 6-Substituted Analogues of 1-[(2-Hydroxyethoxy)methyl]-6-(phenylthio)thymine (HEPT)," J. Med. Chem, 34:349-357 (1991).

Tolmachev et al., "3-Phosphorylated N-Alkylindoles," Heteroatom Chemistry, 7(6):525-531 (1996).

Tsou et al., "Synthesis of 3-Indolyl and 5-Bromo-3-Indolyl Phosphate for Histochemical Demonstration of Alkaline Phosphatase," Journal of Medicinal Chemistry, 10(4):662-664 (1967).

Tsou et al., "Synthesis of 5-Iodo-3-Indolylphosphodiesters of 5-Fluorodeoxyuridine as Possible Chromogenic Cancer Chemotherapeutic Agents," Journal of Medicinal Chemistry, 13(4):765-768 (1970).

Tsou et al., "Indigogenic Phosphodiesters as Potential Chromogenic Cancer Chemotherapeutic Agents," Journal of Medicinal Chemistry, 15(12):1221-1224 (1972).

Williams et al., "5-Chloro-3-(phenylsulfonyl)indole-2-carboxamide: A Novel, Non-Nucleoside Inhibitor of HIV-1 Reverse Transcriptase," J. Med. Chem., 36(9):1291-1294 (1993).

Zhang et al., "A Facile One-Pot Synthesis of 3-dialkoxyphosphoryl- and 3-[alkoxy(phenyl)phosphoryl]-1-hydroxyindoles," Synthesis, 9:801-802 (1990).

ISA/EP PCT International Search Report, dated Apr. 1, 2008, for International Application No. PCT/US2007/020900.

ISA/EP PCT Written Opinion, dated Apr. 1, 2008, for International Application No. PCT/US2007/020900.

ISA/EP PCT International Preliminary Report on Patentability, dated Mar. 31, 2009, for International Application No. PCT/US2007/020900.

Cahn et al., "Specification of Molecular Chirality," *Angewandte Chemie International Edition 5*: 385-415 (1966).

Quin. "A Guide to Organophosphorus Chemistry," Wiley-Interscience, New York. p. 274 (2000).

ISA/EP, International Search Report and Written Opinion dated Nov. 23, 2006 for International Patent Application No. PCT/IB2005/004063 filed Sep. 16, 2005.

ISA/EP, PCT International Preliminary Report on Patentability dated Mar. 20, 2007 for International Patent Application No. PCT/IB2005/004063 filed Sep. 16, 2005.

EPO, Communication pursuant to Article 96(2) EPC dated Jul. 6, 2007, for European Patent Application No. 05850774.0, with attached Beilstein Crossfire Search per Section V. 2.5 of the Written Opinion of International Application No. PCT/IB2005/004063.

EPO, Communication pursuant to Article 96(2) EPC dated Nov. 16, 2007 for European Patent Application No. 05850774.0.

Singapore Written Opinion dated Jul. 7, 2008, referencing Australian Patent Office Written Opinion dated Jun. 27, 2008, for Singapore Patent Application No. 200702002-7 (based on International Application No. PCT/IB2005/004063) filed Sep. 16, 2005.

EPO, European Search Report dated Jul. 25, 2008, for European Patent Application No. 08075531.7 (division of European Application Patent No. 05850774.0) filed Sep. 16, 2005.

EPO, Communication under Rule 71(3) EPC of intent to grant an European patent, dated Feb. 2, 2010, for European Patent Application No. 08075531.7 (division of European Application Patent No. 05850774.0) filed Sep. 16, 2005.

EPO, Communication pursuant to Article 94(3) EPC dated Feb. 11, 2010, for European Patent Application No. 07838974.9.

Abdou et al., 2004, "Phosphono-Substituted Isoindolines and Indoles from 2,3- and 2,4-Benzoxazin-1-1 ones," Heteroatom Chemistry, vol. 15:77-84.

Aboujaoude and Collignon, 1985, "Dialkyl Formyl-1 Methylphosphonates α-Fonctionnels-II," Tetrahedron, vol. 41(2):427-433.

Asadov et al., 2003, "Synthesis of 3-Phosphorylated Indoles from α-Chloro Aldehydes," Chemistry of Heterocyclic Compounds, vol. 39(11):1521-1522.

Benincori et al., 2000, "3,3'-Bis(diphenylphosphino)-1,1'-disubstituted-2-2'-biindoles: Easily Accessible, Electron-Rich, Chiral Diphosphine Ligands for Homogeneous Enantioselective Hydrogenation of Oxoesters," J. Org. Chem., vol. 65:8340-8347.

Blechert, 1985, "Hetero-Cope-Rearrangements. Regio-Controlled Synthesis of Indoles," Helvetica Chimica Acta., vol. 68:1835-1843.

Gonda et al., 1987, "2-Isothiocyanatobenzyltriphenyphosphonium Bromides—New Type of Functionalized Heterocumulenes Suitable for Synthesis of Indole Derivatives," Collection Czechoslovak Chem. Commun., vol. 52:2508-2520.

Gray, et al., 1996, "Carbanion-Mediated Heterocyclizations: Regiospecific, General Route to Dibenzo-[b,e]phosphininones by Synthetic Anionic Equivalents of Friedel-Crafts Reactions and Remote Fries Rearrangement," Angew. Chem. Int. Ed. Engl., vol. 35(13/14):1558-1560.

Gribble and Conway, 1992, "Palladium-Catalyzed Coupling of 3-Indolyl Triflate. Syntheses of 3-Vinyl and 3-Alkynylindoles," Synthetic Communications, vol. 22(15):2129-2141.

Gurevich et al., 1984, "Quaternization of N,N,N',N'-Tetraalkyl-P-(Indol-1-yL)-Phosphonous Diamides," The Journal of General Chemistry of the USSR, vol. 54(12):2510.

Gurevich et al., 1984, "Phosphorylated 3-Thioindoles," Pharmaceut. Chem. J. (Engl. Transl.), 18(7):431-512.

Gurevich et al., 1978, "1-3 Isomerization of Phosphorylated Indoles," The Journal of General Chemistry of the USSR (Engl. Transl.), vol. 48(7), Part 2, pp. 1513.

Haake and Ossip, 1971, "Reactions of Phosphinates in Sulfuric Acid and Oleum," Journal of the American Chemical Society, pp. 6919-6924.

Haelters et al., 1988, "Synthese D'Indole Phosphonates PAR Cyclisation Selon Fischer D'Arylhydrazones Phosphonates," Phosphorus and Sulfur, vol. 37:41-63.

Mingoia, 1932, "Su alcuni nuovi fosfossidi ed acidi fosfonici a nucleo pirrolico e indolico," Gazzetta Chimica Italiana, vol. 62:333-337.

Mingoia, 1930, "Su alcune fosfine indoliche," Gazzetta Chimica Italiana, vol. 60:144-147.

Powers, 1966, "Chloroindoles," The Journal of Organic Chemistry, vol. 31(8):2627-2631.

Razumov et al., 1974, "Phosphorylated (Aminomethyl) Indoles,", "[Hydroxy(Indol-3-Yl)Methyl]Phosphonic ESTERS," and "Synthesis of 3-Phosphorylated Indoles," The Journal of General Chemistry of the USSR, vol. 44(11) Part 2. pp. 2545-2547.

Russell and Yao, 1992, "Reactions of Ethyl Phosphites with β-Nitrostyrenes. The Role of Nitrosoalkenes as Intermediates," The Journal of Organic Chemistry, vol. 57(24):6508-6513.

Sundberg, 1965, "Deoxygenation of Nitro Groups by Trivalent Phosphorus. Indoles from o-Nitrostyrenes," The Journal of Organic Chemistry, vol. 30:3604-3610.

Tolmachev et al., 1991, "Phosphorylation of 1,2-Dimethylindole with Phosphorus Tribomide and Diphenylchlorophosphine," J. Chem. USSR (Engl. Transl.), 60(7):1488-1489.

Yaroshevskaya et al., 2001, "Reaction of $CoS_4C_4Ph_4$ with (3-Indolyl)phosphonites by ESR Data," Russian Journal of General Chemistry, vol. 71(7):1036-1037.

Yaroshevskaya et al., 2001 "Sorption Properties of Phosphorylated Indoles," Russian Journal of General Chemistry, vol. 71(7):1033-1035.

Yuan et al., 1993, "New Synthetic Methods for Carbocyclic and Heterocyclic Compounds Bearing Phosphonate Moiety with Biological Significances," Phosphorus, Sulfur, and Silicon, vol. 75:147-150.

Zbiral and Berner-Fenz, 1967, "Über die Umsetzung von Triphenyldibromphosphin mit nucleophilen Substraten Von," Reaktionen mit phosphororganichen Verbindungen, 11. Mitt., pp. 667-678.

American Heritage Medical Dictionary Second Edition, 2007, p. 692, Houghton Mifflin Company, Boston, MA, USA.

Dorland's Illustrated Medical Dictionary 31$^{st}$ Edition, 2007, p. 1593, Sauders Elsevier, Philadelphia, PA, USA.

Hawley's Condensed Chemical Dictionary Thirteenth Edition, 1997, p. 952, John Wiley & Sons, Inc. New York, NY, USA.

Mosby's Medical Dictionary Sixth Edition, 2002, p. 1455, Mosby Inc., St. Lewis, MO, USA.

Webster's New World College Dictionary Fourth Edition, 1999, p. 1181, Macmillan Company, New York, NY, USA.

USPTO, non-final Office Action, mailed Oct. 18, 2010, for U.S. Appl. No. 12/275,510.

* cited by examiner

Crystal Structure of K103N/Y181C HIV 1 RT with Cmpd I

Schematic Structure Of HIV-1 K103N/Y181C RT With Compound I

ENANTIOMERICALLY PURE PHOSPHOINDOLES AS HIV INHIBITORS

The instant application claims the benefit under 35 U.S.C. §119(e) of U.S. provisional application Nos. 60/848,584, filed Sep. 29, 2006, 60/857,980, filed Nov. 9, 2006, and 60/903,115, filed Feb. 23, 2007. The contents of these applications are hereby incorporated by reference in their entireties.

FIELD OF THE INVENTION

Provided herein are enantiomerically pure phosphoindole compounds useful for inhibiting viral replication. In certain embodiments, provided herein are pure S-phosphoindole compounds useful for inhibiting viral replication. In certain embodiments, provided herein are pure R-phosphoindole compounds useful for inhibiting viral replication. Further provided are pharmaceutically acceptable salts, derivatives and analogues of the compounds, pharmaceutical compositions comprising the compounds, methods of using the compounds, for example, in the treatment or prophylaxis of a HIV infection, and processes for preparation of the compounds.

BACKGROUND OF THE INVENTION

Indoles, nucleosides and their analogs are known in the art as having utility in the treatment of viral infections in mammals, including humans. Viruses that infect mammals and are treatable by the administration of pharmaceutical compositions comprising indoles, nucleosides or their analogues or derivatives include but are not limited to hepacivirus including HCV, human immunodeficiency virus (HIV), pestiviruses such as bovine viral diarrhea virus (BVDV), classic swine fever virus (CSFV, also known as hog cholera virus), and Border disease virus of sheep (BDV), and flaviviruses like dengue hemorrhagic fever virus (DHF or DENV), yellow fever virus (YFV), West Nile virus (WNV), shock syndrome and Japanese encephalitis virus (Moennig et al., Adv. Vir. Res. 1992, 41:53-98; Meyers, G. and Thiel, H-J., Adv. In Viral Res., 1996, 47:53-118; Moennig et al., Adv. Vir. Res. 1992, 41:53-98; S. B. Halstead, Rev. Infect. Dis., 1984, 6:251-64; S. B. Halstead, Science, 1988, 239:476-81; T. P. Monath, New Engl. J. Med., 1988, 319:641-3).

Indoles

Certain indole analogues and derivatives have been used to treat infection with human immunodeficiency virus (HIV).

For example, Williams et al. teaches substituted indoles for the treatment of HIV infection in U.S. Pat. No. 5,527,819 to Merck. The compounds disclosed in the '819 patent comprise a large class represented generically by the following broad structural Formula (III):

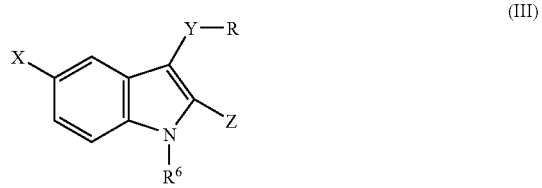

(III)

in which the variables X, Y, Z, R and $R^6$ are broadly defined to embrace about one hundred compounds. In most examples shown, Y is $SO_2$, Z is —$C(O)NH_2$, and R an optionally substituted phenyl.

U.S. Pat. No. 5,124,327 to Greenlee et al. and assigned to Merck & Co. discloses a class of optionally substituted sulfonylphenyl indole compounds. These compounds are allegedly active as reverse transcriptase inhibitors and therefore useful in the treatment of HIV infection and AIDS.

U.S. Pat. No. 6,710,068 to Idenix Pharmaceuticals, Ltd., discloses a class of phenylindoles that are substituted with at least two moieties other than hydrogen on either the phenyl ring or the benzyl ring of the indole function, or on both rings. The substituents are generally contained at the 3" and 5" positions if located on phenyl ring, and at the 4' and 5'; 5' and 6' or the 5' and 7' positions if located on the benzyl ring of the indole moiety. See also PCT Publication No. WO 02/083126.

PCT Publication No. WO 2004/014364 to Idenix Pharmaceuticals discloses yet another class of phenylindoles that display enhanced anti-HIV activity. Like their predecessors, these compounds are substituted with at least two moieties other than hydrogen on either the phenyl ring or the benzo ring of the indole functionality, or on both rings. In addition, these compounds incorporate a number of substituents having a carboxamide functionality at position-2 on the indole group of the compound, the position shown in Formula (III) above as "Z".

Idenix Pharmaceuticals disclosed still another class of phenylindole compounds, these being phospho-phenylindoles, that are useful in the treatment of HIV and/or AIDS (U.S. 2006/0074054 and WO 06/054182).

Bristol Myers Squibb is the assignee of numerous patents, published patent applications, and PCT publications that disclose various optionally substituted indoles, azaindoles, piperazines, and pyrrolidines for the treatment of HIV and/or AIDS. See U.S. Publication No. 2004/0006090 to Kadow et al.; U.S. Publication No. 2004/0063746 to Regueiro-Ren et al.; U.S. Publication No. 2003/0096825 to Wang et al.; U.S. Publication No. 2003/0236277 to Kadow et al.; and WO 03/068221 to Kadow et al.

WO 01/02388 to SmithKline Beecham S.P.A discloses optionally substituted phenylindoles with a carbamyl substituent that have utility in the treatment of HIV, AIDS, osteoporosis, cancers, and Alzheimer's disease.

Warner-Lambert Company discloses various indole-thiazepinones, oxazepinones, diazepinones, benzothiophenes, benzofurans, and indole-2-carboxamides for the treatment of HIV. (See U.S. Pat. No. 5,424,329 to Boschelli et al.; U.S. Pat. No. 5,565,446 to Boschelli et al.; U.S. Pat. No. 5,703,069 to Connor et al.; and WO 96/29077 to Warner-Lambert Company).

Shinogi & Co. disclose optionally substituted indole derivatives that are viral integrase inhibitors useful as anti-HIV drugs (U.S. Publication No. 2002/0019434 to Fujishita et al.; U.S. Pat. No. 6,716,605 to Fujishita et al.; and U.S. Pat. No. 6,506,787 to Fujishita et al.)

U.S. Pat. No. 5,945,440 to Kleinschroth et al. discloses a class of indolocarbazole amides for the treatment of a variety of diseases including cancer, viral diseases (including HIV), cardiac and vascular diseases, bronchopulmonary diseases, inflammatory disorders, degenerative diseases of the central nervous system, and other diseases.

Gunasekera et al. in U.S. Pat. No. 4,866,084 teaches certain bisindole alkaloid compounds that have antiviral and antitumor activity, including HSV (herpes simplex virus). U.S. Pat. No. 5,935,982 to Dykstra et al. reports a different class of bisindoles that have specific utility versus retroviral infections and especially HIV.

Matsunaga et al., in U.S. Pat. No. 5,852,011 (Dec. 22, 1998), discloses a class of indole derivatives substituted by a heteroaryl function and an amide function. The compounds are said generally to possess antitumor, antiviral, and antimicrobial properties.

Dykstra et al., in U.S. Pat. No. 5,935,982 discloses a class of bis-indoles and specifically propose their use for treating retroviral infections, and especially infection by HIV.

Domagala et al., in U.S. Pat. No. 5,929,114 (Jul. 27, 1999) discloses a class of arylthio and bithiobisarylamide compounds, including indole derivative, that reportedly have antibacterial and antiviral activity.

Pevear et al., in U.S. Pat. No. 5,830,894 (Nov. 3, 1998) discloses a class of triazinoindole derivatives that reportedly have anti-pestivirus activity, most notably BVDV activity.

Indoles have been used in the treatment of diseases other than HIV. U.S. Pat. No. 5,981,525 to Farina et al. discloses a complex array of indoles for use in the treatment of osteoporosis based on their ability to inhibit osteoclast $H^+$-ATPase and thus reduce bone resorption. U.S. Pat. No. 6,025,390, also to Farina et al., teaches another group of indole derivatives, termed heteroaromatic pentadienoic acid derivatives that too are useful in the treatment of osteoporosis. U.S. Pat. No. 5,489,685 to Houpis et al. discloses a series of compounds that are furo(2,3-b) pyridine carboxylic acid esters, whose utility is in the treatment of HIV.

In light of the fact that HIV infections have reached epidemic levels worldwide and have tragic effects on the infected host, there remains a strong need to provide new and effective pharmaceutical agents to treat these viral infections with low toxicity to the host.

It is an object of the invention to provide compounds, methods of use, and compositions for the treatment of a host infected with HIV or for the treatment of AIDS related symptoms.

SUMMARY OF THE INVENTION

Accordingly, provided herein are enantiomerically pure compounds useful for the treatment or prevention of a viral infection, for example, an HIV infection in a host in need thereof. Further provided are pharmaceutical compositions comprising the compounds, methods of using the compounds for treatment or prophylaxis, and methods of preparing the compounds.

As demonstrated in the examples below, much of the activity of chiral phosphoindole compounds resides in one enantiomer or stereoisomer. Further, certain compounds provided herein are potent and selective inhibitors of wild-type and non-nucleoside reverse transcriptase inhibitor (NNRTI)-resistant HIV in vitro. Certain compounds provided herein may provide a higher genetic barrier to the development of HIV resistance when compared to current therapies such as efavirenz.

In one aspect, provided herein are pure S-phosphoindole compounds and methods of their use for the treatment or prevention of a viral infection such as an HIV infection in a host in need thereof.

In one aspect, provided herein are pure R-phosphoindole compounds and methods of their use for the treatment or prevention of a viral infection such as an HIV infection in a host in need thereof.

In one aspect, provided herein are pure phosphoindole compounds according to formula (A), or pharmaceutically acceptable salts, solvates, hydrates, esters or prodrugs thereof:

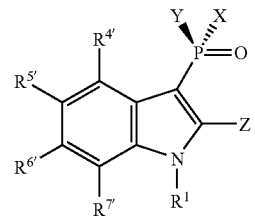

(A)

wherein, e.g.:
X is hydrogen; aryl or heterocycle, which may be substituted or unsubstituted and which may comprise a bicyclic, tricyclic or spiro structure; $C_{2-6}$ alkenyl, $C_{2-6}$ alkynyl or alkyl;
Y is hydrogen, R, O—R, NH—R, or NRR;
Z is OR, NHR, NRR, carboxamido, amido, carboxyl, carbonyl, or an amino acid residue;
$R^1$ is hydrogen, acyl, $S(O)_n$—R, carboxyl, carbonyl, or an amino acid residue;
each of $R^{4'}$, $R^{5'}$, $R^{6'}$ and $R^{7'}$ is independently hydrogen, $C_{2-6}$ alkenyl, $C_{2-6}$ alkynyl, aryl, heterocycle, halogen, CN, $CF_3$, OR, NHR, NRR, or $NO_2$;
n is 0, 1 or 2; and
each R is independently hydrogen, alkyl, $C_{2-6}$ alkenyl, $C_{2-6}$ alkynyl, aryl, or heterocycle.

In certain embodiments, according to formula (A), X is aryl or heterocycle; $C_{2-6}$ alkenyl, $C_{2-6}$ alkynyl or alkyl; and Y is hydrogen, R, O—R, NH—R, or NRR.

In another aspect, provided herein are pure phosphoindole compounds according to formula (B), or pharmaceutically acceptable salts, solvates, hydrates, esters or prodrugs thereof:

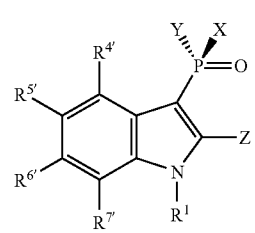

(B)

wherein, e.g.:
X is hydrogen; aryl or heterocycle, which may be substituted or unsubstituted and which may comprise a bicyclic, tricyclic or spiro structure; $C_{2-6}$ alkenyl, $C_{2-6}$ alkynyl or alkyl;
Y is hydrogen, R, O—R, NH—R, or NRR;
Z is OR, NHR, NRR, carboxamido, amido, carboxyl, carbonyl, or an amino acid residue;
$R^1$ is hydrogen, acyl, $S(O)_n$—R, carboxyl, carbonyl, or an amino acid residue;
each of $R^{4'}$, $R^{5'}$, $R^{6'}$ and $R^{7'}$ is independently hydrogen, $C_{2-6}$ alkenyl, $C_{2-6}$ alkynyl, aryl, heterocycle, halogen, CN, $CF_3$, OR, NHR, NRR, or $NO_2$;
n is 0, 1 or 2; and
each R is independently hydrogen, alkyl, $C_{2-6}$ alkenyl, $C_{2-6}$ alkynyl, aryl, or heterocycle.

In certain embodiments, according to formula (B), X is aryl or heterocycle; $C_{2-6}$ alkenyl, $C_{2-6}$ alkynyl or alkyl; and Y is hydrogen, R, O—R, NH—R, or NRR.

In another aspect, provided herein are pharmaceutically acceptable salts, solvates, hydrates, esters and prodrugs of the compounds.

In another aspect, provided are pharmaceutical compositions comprising a compound provided herein and one or more pharmaceutically acceptable carriers, excipients or diluents.

In another aspect, provided herein are methods of treating or preventing an HIV infection in a host in need thereof by administering a compound or pharmaceutical composition described herein.

In another aspect, provided herein are methods of orally administering a compound of formula (A) or formula (B) for therapy or for treatment. As shown in the examples below, certain compounds of formula (A) are orally bioavailable with favorable pharmacokinetics.

In another aspect, provided herein are methods of inhibiting a cytochrome P450. As shown in the examples below, certain compounds described herein are effective to inhibit one or more cytochrome P450s including cytochrome P450 3A4, cytochrome P450 2C8 and cytochrome P450 2C9. Accordingly, provided herein are methods of using compounds provided herein to inhibit a cytochrome P450. The methods comprise the step of contacting a cyclochrome P450 with an amount of a compound disclosed herein such as a compound of formula (A) effective to inhibit the cytochrome P450.

In another aspect, provided herein are methods of modulating the pharmacokinetics of a drug that is metabolized by a cytochrome P450. The methods comprise the step of administering the drug in combination or alternation with a compound described herein. The drug can be any pharmaceutically acceptable molecule known to those of skill in the art to be metabolized by a cytochrome P450. In certain embodiments the cytochrome P450 is cytochrome P450 3A4, cytochrome P450 2C8 or cytochrome P450 2C9.

The compounds provided herein may be administered alone or in combination or alternation with one or more other anti-viral agents. The compounds or their compositions also can be used prophylactically to prevent or retard the progression of clinical illness in individuals who carry an anti-HIV antibody, who are HIV-antigen positive, or who have been exposed to a HIV virus.

In another aspect, provided are compositions and methods for the treatment of a host co-infected with HIV and hepatitis B, comprising administering a pure compound disclosed herein in combination with one or more agents effective for the treatment of hepatitis B infection. In another aspect, provided are compositions and methods for the treatment of a host co-infected with HIV and hepatitis C, comprising administering a pure compound disclosed herein in combination with one or more agents effective for the treatment of hepatitis C infection.

In another aspect, provided are processes for the preparation of the compounds described herein, including enantiomerically pure phosphoindole compounds, pure S-phosphoindole compounds, pure R-phosphoindole compounds, pure compounds according to formula (A), and pure compounds according to formula (B).

DETAILED DESCRIPTION OF THE INVENTION

Figure 1A:
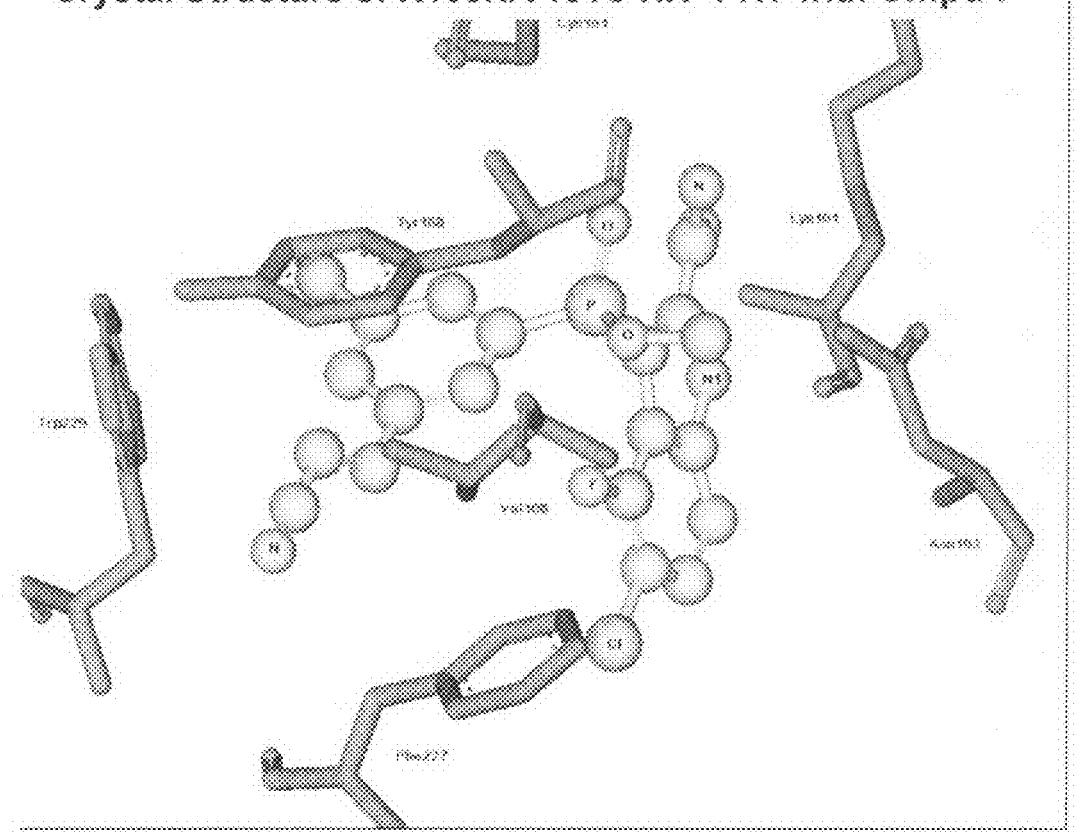
FIG. 1A shows a crystal structure of K103N/Y181C HIV Reverse Transcriptase with the 3-phosphoindole compound of Formula I.

Provided are compositions of matter, methods of use and pharmaceutical compositions for the treatment of virus infections, particularly HIV infections, in mammals. In particular, provided are pure 3-phosphoindole compounds, compositions comprising these compounds and methods of use of the compounds and compositions for the treatment or prophylaxis of an infection including an HIV infection in a host. In addition, provided herein are processes for the preparation of pure 3-phosphoindoles.

Definitions

As used herein the term "pure" when applied to a chiral compound, refers to an enantiomer of the chiral compound substantially free from its opposite enantiomer (i.e., in enantiomeric excess). For example, the pure "R" form of a compound is substantially free from the "S" form of the compound and is, thus, in enantiomeric excess of the "S" form. The term "enantiomerically pure" or "pure enantiomer" denotes that the compound comprises an excess of an enantiomer, e.g. more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of the compound, i.e. all enantiomers of the compound. In certain embodiments, one enantiomer can be in excess by 30-80%, or by 30-70%, 30-60%, 30%, 35%, 40%, 45%, 50%, 55% or 60%, or any percentage in between.

As used herein and unless otherwise indicated, the term "enantiomerically pure (S)-phosphoindole" or "(S)-phosphoindole" refers, e.g., to at least about 80% by weight (S)-phosphoindole and at most about 20% by weight (R)-phosphoindole, at least about 90% by weight (S)-phosphoindole and at most about 10% by weight (R)-phosphoindole, at least about 95% by weight (S)-phosphoindole and at most about 5% by weight (R)-phosphoindole, at least about 99% by weight (S)-phosphoindole and at most about 1% by weight (R)-phosphoindole or at least about 99.9% by weight (S)-phosphoindole and at most about 0.1% by weight (R)-phosphoindole. In certain embodiments, the weights are based upon total weight of the compound, i.e. both or all of the enantiomers of the compound.

As used herein and unless otherwise indicated, the term "enantiomerically pure (R)-phosphoindole" refers, e.g., to at least about 80% by weight (R)-phosphoindole and at most about 20% by weight (S)-phosphoindole, at least about 90% by weight (R)-phosphoindole and at most about 10% by weight (S)-phosphoindole, at least about 95% by weight (R)-phosphoindole and at most about 5% by weight (S)-phosphoindole, at least about 99% by weight (R)-phosphoindole and at most about 1% by weight (S)-phosphoindole, at least about 99.9% by weight (R)-phosphoindole or at most about 0.1% by weight (S)-phosphoindole. In certain embodiments, the weights are based upon total weight of phosphoindole, i.e., both or all enantiomers of the phosphoindole.

In the compositions provided herein, enantiomerically pure phosphoindole or a pharmaceutically acceptable salt, solvate, hydrate, ester or prodrug thereof can be present with other active or inactive ingredients. For example, a pharmaceutical composition comprising enantiomerically pure (S)-phosphoindole can comprise, for example, about 90% excipient and about 10% enantiomerically pure (S)-phosphoindole. In certain embodiments, the enantiomerically pure (S)-phosphoindole in such compositions can, for example, comprise, at least about 99.9% by weight (S)-phosphoindole and at most about 0.1% by weight (R)-phosphoindole. In certain embodiments, the active ingredient can be formulated with little or no carrier, excipient or diluent.

Whenever a range is referred to herein, it includes independently and separately every member of the range. As a non-limiting example, the term "$C_1$-$C_{10}$ alkyl" is considered to include, independently, each member of the group, such that, for example, $C_1$-$C_{10}$ alkyl includes straight, branched and where appropriate cyclic $C_1$, $C_2$, $C_3$, $C_4$, $C_5$, $C_6$, $C_7$, $C_8$, $C_9$ and $C_{10}$ alkyl functionalities. Similarly, as another non-limiting example, 1-10% includes independently, 1%, 2%, 3%, 4%, 5%, 6%, 7%, 8%, 9% and 10%, as well as ranges in between such as 1-2%, 2-3%, etc.

The term "chiral" as used herein includes a compound that has the property that it is not superimposable on its mirror image.

The term "isolated" includes a composition that includes at least 85 or 90% by weight, 95%, 98%, 99% or 100% by weight, of the compound.

The term "alkyl" as used herein unless otherwise specified, includes a saturated straight, branched, or cyclic primary, secondary or tertiary hydrocarbon of typically $C_{1-10}$, and specifically includes but is not limited to methyl, $CF_3$, $CCl_3$, $CFCl_2$, $CF_2Cl$, ethyl, $CH_2CF_3$, $CF_2CF_3$, propyl, isopropyl, cyclopropyl, butyl, isobutyl, sec-butyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups, and particularly includes halogenated alkyl groups and even more particularly, fluorinated alkyl groups. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected or protected as necessary, as known to those of skill in the art, for example, as taught by Greene et al., *Protected Groups in Organic Synthesis*, John Wiley and Sons, 2$^{nd}$ Ed., 1991.

The term "lower alkyl" as used herein and unless otherwise specified, refers to a $C_{1-6}$ saturated straight, branched, or if appropriate, a cyclic (for example, cyclopropyl) alkyl group, including both substituted and unsubstituted moieties.

The terms "alkylamino" or "arylamino" refer to an amino group that has one or two alkyl or aryl substituents, respectively. Unless otherwise specifically stated in this application, when alkyl is a suitable moiety, then it is a lower alkyl, whether substituted or unsubstituted.

As used herein, the term "nitro" means —$NO_2$; the term "sulfhydryl" means —SH; and the term "sulfonyl" means —$SO_2$.

The terms "alkenyl" and "alkynyl" includes alkyl moieties, including both substituted and unsubstituted forms wherein at least one saturated C—C bond is replaced by a double or triple bond. Thus, $C_{2-6}$ alkenyl may be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $C_{2-6}$ alkynyl may be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkylene" includes a saturated, straight chain, divalent alkyl radical of the formula —$(CH_2)_n$—, wherein "n" may be any whole integer from 1 to 10.

"Alkyl", "alkoxy", "alkenyl", "alkynyl", etc., includes both straight chain and branched groups. However, reference to an individual radical such as "propyl" embraces only that straight-chain radical, whereas a branched chain isomer such as "isopropyl" is specifically termed such.

The term "protected" as used herein and unless otherwise defined refers to a group that is added to an oxygen, nitrogen, sulfur or phosphorus atom to prevent its further reaction or for other purposes. A wide variety of oxygen, nitrogen, sulfur or phosphorus protecting groups are known to those skilled in the art of organic synthesis.

The term "aryl" as used herein and unless otherwise specified refers to any stable monocyclic, bicyclic, or tricyclic carbon ring of up to 8 members in each ring, wherein at least one ring is aromatic as defined by the Huckel 4n+2 rule, and especially phenyl, biphenyl, or naphthyl. The term includes both substituted and unsubstituted moieties. The aryl group can be substituted with any described moiety, including but not limited to one or more moieties selected from the group consisting of halogen (fluoro, chloro, bromo or iodo), hydroxyl, amino, azido, alkylamino, arylamino, alkoxy, aryloxy, nitro, cyano, sulfonic acid, sulfate, phosphonic acid, phosphate, or phosphonate, either protected or unprotected as necessary, as known to those skilled in the art, for example, as taught in Greene et al., *Protective Groups in Organic Synthesis*, John Wiley & Sons, 3$^{rd}$ Ed., 1999.

The term "alkaryl" or "alkylaryl" refers to an alkyl group with an aryl substituent or an alkyl group linked to the molecule through an aryl group as defined herein. The term "aralkyl" or "arylalkyl" refers to an aryl group substituted with an alkyl substituent or linked to the molecule through an alkyl group as defined above.

The term "cycloalkyl" includes a ring of $C_{3-8}$, including but not limited to cyclopropyl, cyclobutyl, cyclopentyl, cyclohexyl, cycloheptyl and cyclooctyl.

The term "alkoxy" means a straight or branched chain alkyl group having an attached oxygen radical, the alkyl group having the number of carbons specified or any number within this range. For example, a "—O-alkyl", $C_{1-4}$ alkoxy, methoxy, etc.

The term "halo" as used herein refers to any member of the halogen family. Specifically included are fluoro, chloro, bromo and iodo.

The term "acyl" or "O-linked ester" includes a group of the formula C(O)R', wherein R' is an straight, branched, or cyclic alkyl (including lower alkyl), carboxylate residue of an amino acid, aryl including phenyl, heteroaryl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups in the esters optimally comprise a phenyl group. In nonlimiting embodiments, acyl groups include acetyl, trifluoroacetyl, methylacetyl, cyclopropylacetyl, cyclopropyl-carboxy, propionyl, butyryl, isobutyryl, hexanoyl, heptanoyloctanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "acylamino" includes a group having a structure of "—N(R')—C(=O)—R'", wherein each R' is independently as defined above.

The term "carbonyl" includes a group of the structure "—C(=O)—X—R'" or "X—C(=O)—R'", where X is O, S, or a bond, and each R is independently as defined above.

The term "heteratom" includes an atom other than carbon or hydrogen in the structure of a heterocyclic compound, nonlimiting examples of which are nitrogen, oxygen, sulfur, phosphorus or boron.

The term "heterocycle" or "heterocyclic" as used herein except where noted, includes a stable 5- to 7-membered monocyclic or stable 8- to 11-membered bicyclic heterocyclic ring which is either saturated or unsaturated, including heteroaryl, and which consists of carbon atom(s) and from one to four heteroatoms including but not limited to O, S, N and P; and wherein the nitrogen and sulfur heteroatoms may optionally be oxidized, and/or the nitrogen heteroatom quaternized, and including any bicyclic group in which any of the above-identified heterocyclic rings is fused to a benzene ring. The heterocyclic ring may be attached at any heteroatom or carbon atom which results in the creation of a stable structure. The heteroaromatic ring may be partially or totally hydrogenated, as desired. For example, dihydropyridine may be used in place of pyridine. Functional oxygen and nitrogen groups on a heteroaryl may be protected as necessary or desired. Suitable protecting groups for oxygen or nitrogen include trimethylsilyl, dimethylhexylsilyl, t-butyldimethylsilyl, t-butyldiphenylsilyl, trityl, substituted trityl, alkyl, methanesulfonyl, p-toluenesulfonyl, or acyl groups such as acetyl and propionyl.

Non-limiting examples of heteroaryl and heterocyclic groups include furyl, pyridyl, pyrimidyl, pyridazinyl, pyrazinyl, piperidinyl, piperazinyl, thienyl, pyrrolyl, pyrrolinyl, pyrrolidinyl, imidazolyl, tetrazolyl, triazolyl, triazinyl, thiazinyl, oxazolyl, purinyl, carbazolyl, quinolinyl, pyrazolyl, morpholinyl, benzimidazolyl, and the like. Any of the heteroaromatic and heterocyclic moieties may be optionally substituted as described above for aryl, including substitution(s) with one or more hydroxyl, amino, alkylamino, arylamino, alkoxy, aryloxy, alkyl, heterocyclyl, halo, carboxy, acyl, acyloxy, amido, nitro, cyano, sulfonic acid, sulfate, phosphonic acid, phosphate, or phosphonate, either protected or unprotected as needed, as known to those skilled in the art and as taught, for example, in Greene et al., *Protective Groups in Organic Synthesis*, John Wiley and Sons, Third Ed., 1999.

The term "amino" as used herein unless otherwise specified, includes a moiety represented by the structure "—NR$_2$", and includes primary, secondary and tertiary amines optionally substituted by alkyl, aryl, heterocyclyl, and/or sulfonyl groups. Thus R$_2$ may represent two hydrogen atoms, two alkyl moieties, or one hydrogen and one alkyl moiety.

The term "amino acid" or "amino acid residue" includes naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In one embodiment, the amino acid is in the L-configuration, but can also be used in the D-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β, γ, or δ glycine, alanine, valine, leucine, isoleucine, methionine, phenylalanine, tryptophan, praline, serine, threonine, cysteine, tyrosine, asparagine, glutamine, aspartate, glutamate, lysine, arginine, and histidine in the D- and L-configurations.

The term "amido" as used herein includes an amino-substituted carbonyl, while the term "amidino" means a group having the structure "—C(=NH)—NH$_2$".

Certain sulfur and phosphorus-containing terms have the following structural significances: "sulfonate" includes a group of the structure "—S(=O)(=O)—OR'"; "sulfate" includes a group of the structure "O—S(=O)(=O)—OR'"; "sulfonamide" includes a group of the structure "N(R')—S(=O)(=O)—R'"; "sulfamoyl" includes a group of the structure "—S(=O)(=O)—N(R')(R')"; "phosphoryl" includes a group of the structure "—P(=O)—OR'"; and "phosphoroamidate" includes a group of the structure "Q-P(NR$_1$R$_2$)(=O)—OR'", where each, R' is independently as defined above.

The term "host", as used herein, refers to an unicellular or multicellular organism in which the virus can replicate, including cell lines and animals, and in certain instances, a human. Alternatively, the host can be carrying a part of the HIV viral genome, whose replication or function can be altered by the compounds of the present invention. The term host specifically refers to infected cells, cells transfected with all or part of the HIV genome and animals, in particular, primates (including chimpanzees) and humans. In most animal applications of the present invention, the host is a human patient. Veterinary applications, in certain indications, however, are clearly encompassed by embodiments of the present invention (such as chimpanzees).

The term "substituted" includes multiple degrees of substitution by one or more named substituents such as, for example, halo, hydroxyl, thio, alkyl, alkenyl, alkynyl, nitro, cyano, azido, amino, carboxamido, etc. Where multiple substituent possibilities exist, the compound can be substituted by one or more of the disclosed or claimed substituent groups, independently from one another, and taken singly or plurally.

Compounds

In certain embodiments, provided herein are pure compounds according to formula (A), or pharmaceutically acceptable salts, solvates, hydrates, esters or prodrugs thereof:

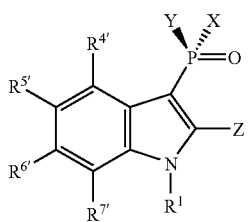

(A)

wherein, e.g.:
  X is hydrogen; aryl or heterocycle, which may be substituted or unsubstituted and which may comprise a bicyclic, tricyclic or spiro structure; $C_{2-6}$ alkenyl, $C_{2-6}$ alkynyl or alkyl;
  Y is hydrogen, R, O—R, NH—R, or NRR;
  Z is OR, NHR, NRR, carboxamido, amido, carboxyl, carbonyl, or an amino acid residue;
  $R^1$ is hydrogen, acyl, $S(O)_n$—R, carboxyl, carbonyl, or an amino acid residue;
  each of $R^{4'}$, $R^{5'}$, $R^{6'}$ and $R^{7'}$ is independently hydrogen, $C_{2-6}$ alkenyl, $C_{2-6}$ alkynyl, aryl, heterocycle, halogen, CN, $CF_3$, OR, NHR, NRR, or $NO_2$;
  n is 0, 1 or 2; and
  each R is independently hydrogen, alkyl, $C_{2-6}$ alkenyl, $C_{2-6}$ alkynyl, aryl, or heterocycle.

In certain embodiments, according to formula (A), X is aryl or heterocycle; $C_{2-6}$ alkenyl, $C_{2-6}$ alkynyl or alkyl; and Y is hydrogen, R, O—R, NH—R, or NRR.

In certain embodiments, according to formula (A), $R^{4'}$ and $R^{5'}$ are independently hydrogen or halogen and X, Y, Z, $R^1$, $R^{6'}$, $R^{7'}$, and R are as defined above.

In certain embodiments, according to formula (A):
  each of $R^{4'}$ and $R^{5'}$ is independently hydrogen or halogen;
  $R^{6'}$ and $R^{7'}$ are hydrogen;
  $R^1$ is hydrogen or $S(O)_n$—R;
  Y is hydrogen, R, or O—R;
  X is optionally substituted aryl;
  Z is carboxamido, amido, carboxyl, or carbonyl;
  n is 0, 1 or 2; and
  each R is independently hydrogen or alkyl In certain embodiments, provided herein are pure compounds according to formula (C), or a pharmaceutically acceptable salt, solvate, hydrate, ester or prodrug thereof:

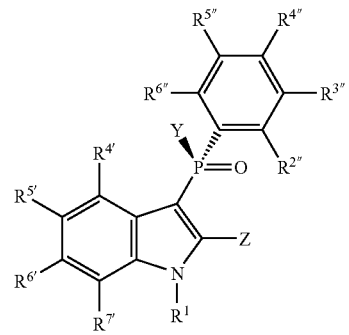

(C)

wherein $R^{2''}$, $R^{3''}$, $R^{4''}$, $R^{5''}$ and $R^{6''}$ are independently hydrogen, halogen, alkyl, or $C_{2-6}$ alkenyl;
  $R^{4'}$ and $R^{5'}$ is independently hydrogen or halogen;
  $R^{6'}$ and $R^{7'}$ are hydrogen;
  $R^1$ is hydrogen or $S(O)_n$—R;
  Y is hydrogen, R, or O—R;
  Z is carboxamido, amido, carboxyl, or carbonyl;
  n is 0, 1 or 2; and
  each R is independently hydrogen or alkyl.

In certain embodiments of formula (C):
  $R^{3''}$ and $R^{5''}$ are independently alkyl or $C_{2-6}$ alkenyl each of which independently may optionally be substituted with CN or halogen;
  $R^{2''}$, $R^{4''}$ and $R^{6''}$ are hydrogen;
  each of $R^{4'}$ and $R^{5'}$ is independently hydrogen or halogen;
  $R^{6'}$ and $R^{7'}$ are hydrogen;
  $R^1$ is hydrogen or $S(O)_n$—R;
  Y is hydrogen, R, or O—R;
  Z is carboxamido, amido, carboxyl, or carbonyl;
  n is 0, 1 or 2; and
  each R is independently hydrogen or alkyl.

In certain embodiments, according to formula (C):
  $R^{3''}$ and $R^{5''}$ are independently alkyl or $C_{2-6}$ alkenyl each of which independently may optionally be substituted with CN or halogen;
  $R^{2''}$, $R^{4''}$ and $R^{6''}$ are hydrogen;
  each of $R^{4'}$ and $R^{5'}$ is independently hydrogen or halogen;
  $R^{6'}$ and $R^{7'}$ are hydrogen;
  $R^1$ is hydrogen;
  Y is O—R;
  Z is amido, carboxyl, or carbonyl; and
  each R is independently hydrogen or alkyl.

In one embodiment, provided is a pure compound, or pharmaceutically acceptable salts, solvates, hydrates, esters or prodrugs thereof:

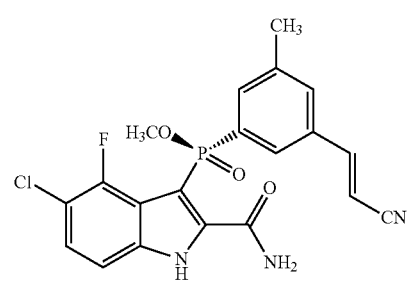

(I)

wherein the absolute configuration at the phosphorus atom is R. The chemical name of Compound I is (2-Carbamoyl-5- chloro-4-fluoro-1H-indol-3 -yl)-[3-((E)-2-cyano-vinyl)-5-methyl-phenyl]-(R)-phosphinic acid methyl ester, and the empirical formula is $C_{20}H_{16}ClFN_3O_3P$ with a molecular weight of 431.78.

In one embodiment, provided is a pure compound, or a pharmaceutically acceptable salt, solvate, hydrate, ester or prodrug thereof:

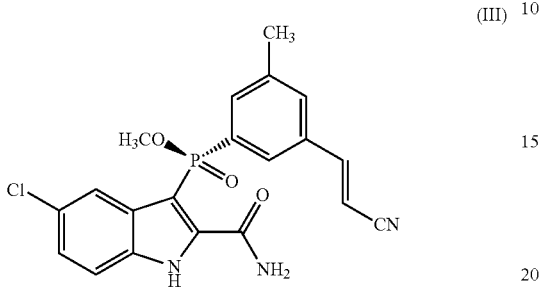

(III)

wherein the absolute configuration at the phosphorus atom is R. The chemical name of Compound III is (2-Carbamoyl-5-chloro-1H-indol-3-yl)-[3-((E)-2-cyano -vinyl)-5-methyl-phenyl]-(R)-phosphinic acid methyl ester, and the empirical formula is $C_{20}H_{17}ClN_3O_3P$ with a molecular weight of 413.79.

In one embodiment, provided is a pure compound selected from the group consisting of:
(2-carbamoyl-5-chloro-1H-indol-3-yl)-[3-((E)-2-cyano -vinyl)-5-methyl -phenyl]-(R)-phosphinic acid methyl ester; and
(2-Carbamoyl-5-chloro-4-fluoro-1H-indol-3-yl)-[3-((E) -2-cyano-vinyl)-5-methyl-phenyl]-(R)-phosphinic acid methyl ester,
or a pharmaceutically acceptable salt, solvate, hydrate, ester or prodrug thereof.

In certain embodiments, provided herein are pure compounds according to formula (B), or a pharmaceutically acceptable salt, solvate, hydrate, ester or prodrug thereof:

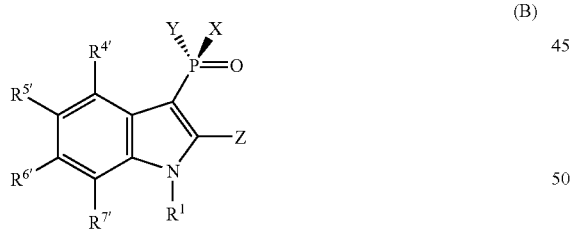

(B)

wherein, e.g.:
X is hydrogen; aryl or heterocycle, which may be substituted or unsubstituted and which may comprise a bicyclic, tricyclic or spiro structure; $C_{2-6}$ alkenyl, $C_{2-6}$ alkynyl or alkyl;
Y is hydrogen, R, O—R, NH—R, or NRR;
Z is OR, NHR, NRR, carboxamido, amido, carboxyl, carbonyl, or an amino acid residue;
$R^1$ is hydrogen, acyl, $S(O)_n$—R, carboxyl, carbonyl, or an amino acid residue;
each of $R^{4'}$, $R^{5'}$, $R^{6'}$ and $R^{7'}$ is independently hydrogen, $C_{2-6}$ alkenyl, $C_{2-6}$ alkynyl, aryl, heterocycle, halogen, CN, $CF_3$, OR, NHR, NRR, or $NO_2$;
n is 0, 1 or 2; and
each R is independently hydrogen, alkyl, $C_{2-6}$ alkenyl, $C_{2-6}$ alkynyl, aryl, or heterocycle.

In certain embodiments, according to formula (B), X is hydrogen; aryl or heterocycle; $C_{2-6}$ alkenyl, $C_{2-6}$ alkynyl or alkyl; and Y is hydrogen, R, O—R, NH—R, or NRR.

In certain embodiments, according to formula (B), $R^{4'}$ and $R^{5'}$ are independently hydrogen or halogen and X, Y, Z, $R^1$, $R^{6'}$, $R^{7'}$, and R are as defined above.

In certain embodiments, according to formula (B),
$R^{4'}$ and $R^{5'}$ each are independently hydrogen or halogen;
$R^{6'}$ and $R^{7'}$ are hydrogen;
$R^1$ is hydrogen or $S(O)_n$—R;
Y is hydrogen, R, or O—R;
Z is carboxamido, amido, carboxyl, or carbonyl;
n is 0, 1 or 2; and
each R is independently hydrogen or alkyl.

In certain embodiments, provided herein are pure compounds according to formula (D), or a pharmaceutically acceptable salt, solvate, hydrate, ester or prodrug thereof:

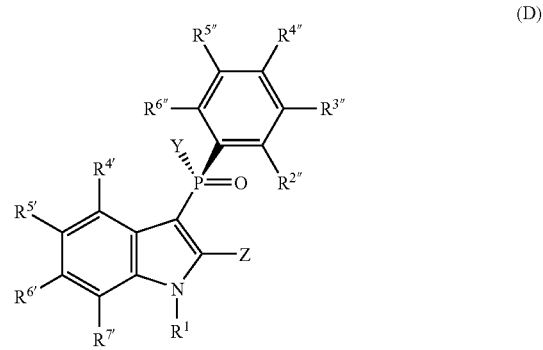

(D)

wherein $R^{2''}$, $R^{3''}$, $R^{4''}$, $R^{5''}$ and $R^{6''}$ are independently hydrogen, halogen, alkyl, or $C_{2-6}$ alkenyl;
$R^{4'}$ and $R^{5'}$ is independently hydrogen or halogen;
$R^{6'}$ and $R^{7'}$ are hydrogen;
$R^1$ is hydrogen or $S(O)_n$—R;
Y is hydrogen, R, or O—R;
Z is carboxamido, amido, carboxyl, or carbonyl;
n is 0, 1 or 2; and
each R is independently hydrogen or alkyl.
In certain embodiments of formula (D):
$R^{3''}$ and $R^{5''}$ are independently alkyl or $C_{2-6}$ alkenyl which may optionally be substituted with CN or halogen;
$R^{2''}$, $R^{4''}$ and $R^{6''}$ are hydrogen;
each of $R^{4'}$ and $R^{5'}$ is independently hydrogen or halogen;
$R^{6'}$ and $R^{7'}$ are hydrogen;
$R^1$ is hydrogen or $S(O)_n$—R;
Y is hydrogen, R, or O—R;
Z is carboxamido, amido, carboxyl, or carbonyl;
n is 0, 1 or 2; and
each R is independently hydrogen or alkyl.
In certain embodiments of formula (D):
$R^{3''}$ and $R^{5''}$ are independently alkyl or $C_{2-6}$ alkenyl which may optionally be substituted with CN or halogen; $R^{2''}$, $R^{4''}$ and $R^{6''}$ are hydrogen;
each of $R^{4'}$ and $R^{5'}$ is independently hydrogen or halogen;
$R^{6'}$ and $R^{7'}$ are hydrogen;
$R^1$ is hydrogen;
Y is O—R;
Z is amido, carboxyl, or carbonyl; and
each R is independently hydrogen or alkyl.

In one embodiment, provided is a pure compound, or a pharmaceutically acceptable salt, solvate, hydrate, ester or prodrug thereof:

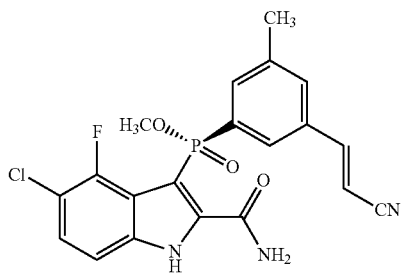

(II)

wherein the absolute configuration at the phosphorus atom is S.

In one embodiment, provided is a pure compound, or a pharmaceutically acceptable salt, solvate, hydrate, ester or prodrug thereof:

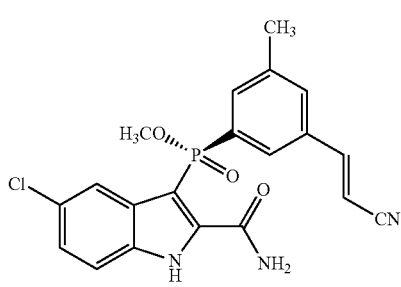

(IV)

wherein the absolute configuration at the phosphorus atom is S.

In one embodiment, provided is a pure compound selected from the group consisting of:
(2-carbamoyl-5-chloro-1H-indol-3-yl)-[3-((E)-2-cyano-vinyl)-5-methyl -phenyl]-(S)-phosphinic acid methyl ester; and
(2 Carbamoyl-5-chloro-4-fluoro-1H-indol-3-yl)-[3-((E)-2-cyano -vinyl)-5-methyl-phenyl]-(S)-phosphinic acid methyl ester,
or a pharmaceutically acceptable salt, solvate, hydrate, ester or prodrug thereof.

In certain embodiments, the compound according to (A)-(D) or (I)-(IV) is the enantiomerically pure compound or a pharmaceutically acceptable salt, solvate, hydrate, ester or prodrug thereof. In certain embodiments, the compound according to (A)-(D) or (I)-(IV) is the enantiomerically pure compound or a pharmaceutically acceptable salt thereof. In certain embodiments, the enantiomerically pure compound comprises at least about 80% by weight of the designated enantiomer and at most about 20% by weight of the other enantiomer or other stereoisomer(s), at least about 90% by weight of the designated enantiomer and at most about 10% by weight of the other enantiomer or other stereoisomer(s), at least about 95% by weight of the designated enantiomer and at most about 5% by weight of the other enantiomer or other stereoisomer(s), at least about 96.6% by weight of the designated enantiomer and at most about 3.4% by weight of the other enantiomer or other stereoisomer(s), at least about 97% by weight of the designated enantiomer and at most about 3% by weight of the other enantiomer or other stereoisomer(s), at least about 99% by weight of the designated enantiomer and at most about 1% by weight of the other enantiomer or other stereoisomer(s), or at least about 99.9% by weight of the designated enantiomer and at most about 0.1% by weight of the other enantiomer or other stereoisomer(s). In certain embodiments, the weights are based upon total weight of the compound.

Also provided are compounds that may be given as a salt, ester or prodrug that, upon administration to the recipient, and provide directly or indirectly a compound provided herein or that exhibits the desired activity itself.

Pharmaceutically Acceptable Salts, Prodrugs, Stereoisomers and Tautomers

A compound provided herein can be administered as any salt or prodrug that upon administration to the recipient is capable of providing directly or indirectly the parent compound, or that exhibits activity itself. Non-limiting examples are pharmaceutically or physiologically acceptable salts. The phrase "pharmaceutically or physiologically acceptable salt or prodrug" is used throughout the specification to describe any pharmaceutically acceptable form (such as an ester, amide, salt of an ester, salt of an amide or related group) of a compound that, upon administration to a patient, provides an active compound of the invention. Modifications like these can affect the biological activity of the compound, in some cases increasing the activity over the parent compound.

The term "pharmaceutically acceptable salt" refers to the state of a compound in which the compound carries a counterion that is pharmaceutically acceptable, and wherein the salt retains the desired biological activity of the herein-identified compounds while exhibiting minimal undesired toxicological effects. Such salts are non-toxic, therapeutically useful forms of the compounds of the present invention. Any salt that retains the desired biological activity of the compounds contained herein and that exhibits minimal or no undesired or toxicological effects is intended for inclusion here. Pharmaceutically acceptable salts include those derived from pharmaceutically acceptable organic or inorganic acids and bases. Non-pharmaceutically acceptable acids and bases also find use herein, as for example, in the synthesis and/or purification of the compounds of interest. Thus, all "salts" are intended for inclusion here.

Pharmaceutically acceptable salts include those derived from pharmaceutically acceptable inorganic or organic bases and acids, and include tosylate, methanesulfonate, acetate, citrate, malonate, tartarate, succinate, benzoate, ascorbate, alpha-ketoglutarate, alpha-glycerophosphate, formate, fumarate, propionate, glycolate, lactate, pyruvate, oxalate, maleate, salicylate, sulfate, sulfonate, nitrate, bicarbonate, hydrobromate, hydrobromide, hydroiodide, carbonate, and phosphoric acid salts. A particular embodiment is the mono- or di-hydrochloride salt. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound, including but not limited to an ester or acyl moiety. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Pharmaceutically acceptable salts may be obtained by using standard procedures well known in the art, for example, by reacting a sufficiently basic compound such as an amine with a suitable acid affording a physiologically acceptable anion. Alkali metal (such as potassium, sodium or lithium) or alkaline earth metal (such as calcium) salts of carboxylic acids also can be made.

Non-limiting examples of suitable salts include those derived from inorganic acids, such as, for example, hydrochloric acid, hydrobromic acid, sulfuric acid, phosphoric acid, nitric acid, bicarbonic acid, carbonic acid; and salts formed with organic acids, such as, for example, formic acid, acetic acid, oxalic acid, tartaric acid, succinic acid, malic acid, malonic acid, ascorbic acid, citric acid, benzoic acid, tannic acid, palmoic acid, alginic acid, polyglutamic acid, tosic acid, methanesulfonic acid, naphthalenesulfonic acid, naphthalenedisulfonic acid, α-ketoglutaric acid, α-glycerophosphoric acid and polygalacturonic acid. Suitable salts include those derived from alkali metals such as lithium, potassium and sodium, from alkaline earth metals such as calcium and magnesium, as well as from other bases well known to those of skill in the pharmaceutical art. Other suitable salts include those derived from metal cations such as zinc, bismuth, barium, or aluminum, or with a cation formed from an amine, such as ammonia, N,N-dibenzylethylenediamine, D-glucosamine, tetraethylammonium, or ethylenediamine. Moreover, suitable salts include those derived from a combination of acids and bases, such as, for example, a zinc tannate salt.

A pharmaceutically acceptable prodrug refers to a compound that is metabolized (i.e., hydrolyzed or oxidized, for example) in the host to form a compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

In one embodiment, the compounds provided herein possess antiviral activity against HIV, or are metabolized to a compound that exhibits such activity.

Methods of Treatment

In one embodiment, provided are methods for the treatment or prophylaxis of an HIV infection in a host, comprising administering an antivirally-effective amount of a compound described herein, including a compound of Formulas A-D or Compounds I-IV or a pharmaceutically acceptable salt, ester or prodrug thereof. The compounds may be combined with a pharmaceutically acceptable carrier or diluent.

In another principal embodiment, the use of a compound disclosed herein including a compound of Formula A-D or Compounds I-IV, or a pharmaceutically acceptable salt, ester or prodrug thereof, in the treatment or prophylaxis of an HIV infection in a host, optionally in combination with a pharmaceutically acceptable carrier or diluent is provided.

The use of a compound described herein, or a pharmaceutically acceptable salt, ester or prodrug thereof, in the manufacture of a medicament for the treatment or prophylaxis of an HIV infection in a host, optionally in combination with a pharmaceutically acceptable carrier or diluent also is provided.

In one embodiment, a method of treatment or prophylaxis of an HIV infection in a host is provided, comprising administering a 3-phosphoindole compound substantially in the form of one enantiomer, or a pharmaceutically acceptable salt, ester or prodrug thereof, optionally in combination with a pharmaceutically acceptable carrier, to a host in need thereof. In one embodiment, the 3-phosphoindole is of Formula A. In another embodiment, the compound is of Formula B. In one embodiment, the 3-phosphoindole is of Formula C.

In one embodiment, the 3-phosphoindole is of Formula D. In one embodiment, the 3-phosphoindole is of Formula I, wherein the absolute stereochemistry at phosphorus is R. In another embodiment, the 3-phosphoindole is of Formula II, with S absolute stereochemistry. In a further embodiment, the 3-phosphoindole may be of Formula III, with R absolute stereochemistry. In another embodiment, the 3-phosphoindole is represented by Formula IV, with S absolute stereochemistry.

In other embodiments the host can have been diagnosed by measurement of an anti-HIV antibody titer in blood. In another embodiment, the compounds are administered to reduce or prevent symptoms of AIDS (acquired immune deficiency syndrome) in a host. In yet another embodiment the compounds disclosed herein are administered to a host at risk of infection with HIV.

In another embodiment, the active compound exhibits activity against drug-resistant forms of HIV, and thus exhibits decreased cross-resistance against currently approved antiviral therapies. The phrase "activity against a drug-resistant form of HIV" means that a compound (or its prodrug or pharmaceutically acceptable salt) is active against the mutant strain with an $EC_{50}$ e.g., of less than approximately 50, 25, 10 or 1 micromolar concentration. In one embodiment, the non-nucleoside reverse transcriptase inhibitor (NNRTI) displays an $EC_{50}$ (in molar concentration) against a mutant HIV strain of less than approximately 5, 2.5, 1 or 0.1 micromolar. In one non-limiting embodiment, the HIV mutant strain has a reverse transcriptase mutation at lysine 103→asparagine and/or tyrosine 181→cysteine.

Compounds provided herein can be assessed for their ability to inhibit reverse transcriptase activity in vitro according to standard screening methods. The spectrum of activity exhibited by any particular compound is determined by evaluating the compound in assays described in this specification or with other confirmatory assays known to those skilled in the art of anti-HIV compounds. Compounds can exhibit an $EC_{50}$ of less than 10-15 µM.

In one embodiment, the efficacy of the 3-phosphoindoles is measured by the HIV-specific enzyme-linked immunosorbent assay, p24 ELISA. Drug efficacy is expressed as percent inhibition of the HIV p24 antigen in this rapid and sensitive assay. In a related embodiment useful for specific experiments, the efficacy of the anti-HIV compound is determined by a "plaque reduction assay" which measures the concentration of compound necessary to reduce the plaque number of the virus in vitro, according to the methods set forth more particularly herein, by 50% (i.e., the $EC_{50}$ of the compound). In some embodiments the compound exhibits an $EC_{50}$ of less than 15, or less that 10 micromolar to nanomolar amounts in vitro.

Combination or Alternation Therapy

In certain embodiments, the indole compound is administered in combination and/or alternation with one or more other anti-HIV agents. In another embodiment, the administration of two or more anti-HIV agents result in a synergistic effect in the inhibition of HIV. In another embodiment, the effect of administering two or more such agents in combination and/or alternation produces an additive effect in inhibiting HIV replication.

In certain embodiments, the indole compound is administered in combination and/or alternation with one or more anti-HBV or one or more anti-HCV agents. For instance, in certain embodiments, the indole compound can be administered to a host co-infected with HIV and HBV in combination with an agent effective for the treatment of HBV. The agent effective for the treatment of HBV can be any such agent known to those of skill in the art. Exemplary agents are described herein. In certain embodiments, the indole compound can be administered to a host co-infected with HIV and HCV in combination with an agent effective for the treatment of HCV. The agent effective for the treatment of HCV can be any such agent known to those of skill in the art.

In certain embodiments, the indole compound is administered in combination and/or alternation with one or more agents that are metabolized by cytochrome P450 monooxygenase. The agent can be any agent known to those of skill in the art to be metabolized by a cytochrome P450 monooxygenase. Exemplary agents are described herein. In certain embodiments, the cytochrome P450 is cytochrome P450 3A4, cytochrome P450 2C8 or cytochrome P450 2C9.

In combination therapy, effective dosages of two or more agents are administered together, whereas during alternation therapy an effective dosage of each agent is administered serially. The dosages will depend upon absorption, inactivation, and excretion rates of the drugs as well as other factors known to those of skill in the art. Dosage values also will vary with the severity of the condition to be alleviated. For any particular individual, specific dosage regimens and schedules should be adjusted over time to meet the needs of the individual and the professional judgment of the person administering or supervising the administration of the compositions.

Drug resistance most typically occurs by mutation of a gene that encodes for an enzyme used in the viral replication cycle. It has been demonstrated that the efficacy of an anti-HIV drug can be prolonged, augmented or restored by administering the compound in combination or alternation with a second, and perhaps third, antiviral compound that induces a different mutation(s) from that selected for by the principle drug. Such drug combinations simultaneously reduce the possibility of resistance to any single drug and any associated toxic effects. Alternatively, the pharmacokinetics, biodistribution, or other parameters of the drug can be altered by such combination or alternation therapy. For example, the use of a combination of drugs may permit an individual drug within that combination to be given at a dosage lower than what would be required when the drug is administered as a monotherapeutic. Likewise, when drugs that target different stages of the viral life cycle are combined, there exists the possibility for potentiating their effects. Moreover, use of combinations of drugs could lower or eliminate undesirable side-effects from a single drug while still producing anti-viral activity. In general, combination therapy is typically preferred over alternation therapy because it places multiple, simultaneous pressures on the virus.

HCV Agents

Interferons (IFNs) for the treatment of chronic hepatitis have been made available commercially for nearly a decade, and form the basis of currently available approved therapies for HCV. IFNs are glycoproteins produced by immune cells in response to viral infections. They inhibit replication of a number of viruses, including HCV, and when used as the sole treatment for hepatitis C infection, IFNs can sometimes suppress serum HCV-RNA to undetectable levels. Also, IFNs can normalize serum amino transferase levels. Unfortunately, the effect of IFNs is temporary, and a sustained response occurs in only 8-9% of patients chronically infected with HCV (Gary L. Davis, *Gastroenterology*, 2000, 118:S104-S114). Most patients, however, have difficulty tolerating interferon treatment, which causes severe flu-like symptoms, weight loss, and lack of energy and stamina.

Many patents disclose Flaviviridae, including HCV, treatments that use interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon-alpha for the treatment of infectious diseases including HCV. U.S. Pat. No. 5,849,696 to Chretien et al. discloses the use of thymosins, alone or in combination with interferon, for treating HCV. U.S. Pat. No. 5,830,455 to Valtuena et al. teaches a combination HCV therapy that employs interferon and a free radical scavenger. U.S. Pat. No. 5,738,845 to Imakawa teaches the use of human interferon-tau proteins for treating HCV. Other interferon-based treatments for HCV are given in U.S. Pat. No. 5,676,942 to Testa et al. and U.S. Pat. No. 5,372,808 to Blatt et al. A number of patents also disclose pegylated forms of interferons and their use, such as, for example, U.S. Pat. Nos. 5,747,646; 5,792,834; and 5,834,594 all to Hoffmann-LaRoche, Inc.; PCT WO 99/32139 and WO 99/32140 to Enzon; WO 95/13090 and U.S. Pat. Nos. 5,738,846 and 5,711,944 to Schering Corporation; and U.S. Pat. No. 5,908,621 to Glue et al. Interferon alpha-2a and interferon alpha-2b currently are approved as monotherapy for the treatment of HCV. ROFERON®-A from Roche is the recombinant form of interferon alpha-2a. PEGASYS® from Roche is the pegylated or polyethylene glycol modified form of interferon alpha-2a. INTRON® A from Schering Corporation is the recombinant form of interferon alpha-2b, and PEG-INTRON® from Schering Corporation is the pegylated form of interferon alpha-2b.

Other forms of interferon alpha as well as interferon beta, gamma, tau and omega currently are in development for the treatment of HCV. Examples included here are INFERGEN, interferon alphacon-1, by InterMune; OMNIFERON, a natural interferon, by Viragen; ALBUFERON by Human Genome Sciences; REBIF, interferon beta-1a, by Ares-Serono; Omega Interferon by BioMedicine; Oral Interferon Alpha by Amarillo Biosciences; and interferons gamma, tau and gamma 1-b by InterMune.

Ribavirin (1-β-D-ribofuranosyl-1-1,2,4-triazolyl-3-carboxamide) is a synthetic, non-interferon inducing, broad spectrum antiviral nucleoside analog sold under the trade name, Virazole (*The Merck Index*, $11^{th}$ Ed., 1989, Editor: Budavari, S., Merck & Co., Inc., Rahway, N.J.; p. 1304). See U.S. Pat. No. 3,798,209 and RE29,835. Structurally ribavirin is similar to guanosine and has in vitro activity against several DNA and RNA viruses including Flaviviridae (Gary L. Davis, 2000, *Gastroenterology*, 118:S104-S114).

Ribavirin reduces serum amino transferase levels to normal in 40% of patients, but it does not lower serum levels of HCV-RNA (Gary L. Davis, 2000, *Gastroenterology*, 118: S104-S114). Thus, ribavirin alone is not effective in reducing viral RNA levels. In addition, ribavirin has significant toxicity and is known to induce anemia. It is not approved for monotherapy against HCV, but has been approved in combination with interferon alpha-2a or interferon alpha-2b for the treatment of HCV.

The current standard of care for chronic hepatitis C is combination therapy with an alpha interferon and ribavirin. Studies have shown that more patients with HCV respond to pegylated interferon-alpha/ribavirin combination therapy than to combination therapy with unpegylated interferon alpha. However, as with monotherapy, significant side effects develop during combination therapy, including hemolysis, flu-like symptoms, anemia and fatigue (Gary L. Davis, 2000, *Gastroenterology*, 118:S104-S114).

Combination therapy with PEG-INTRON® (peginterferon alpha-2b) and REBETOL® (Ribivarin, USP) capsules is available from Schering Corporation. REBETOL® from Schering Corporation also has been approved in combination with INTRON® A (recombinant interferon alpha-2b from Schering Corporation). Roche's PEGASYS® (pegylated interferon alpha-2a) and COPEGUS® (ribavirin) also have been approved for the treatment of HCV infection.

PCTs WO 99/59621, WO 00/37110, WO 01/81359, WO 02/32414 and WO 03/024461 all to Schering Corporation disclose the use of pegylated interferon alpha and ribavirin combination therapy for the treatment of HCV infection. PCTs WO 99/15194, WO 99/64016 and WO 00/24355 all to Hoffmann-LaRoche, Inc., also disclose the combined use of pegylated interferon alpha and ribavirin for HCV infection treatment.

The development of new antiviral agents for treating Flaviviridae infections, especially for infections by hepacivirus HCV, are under development. Specific inhibitors of HCV-derived enzymes like protease, helicase, and polymerase are being studied. Drugs that inhibit steps in HCV replication also are being investigated and include drugs that block production of HCV antigens from RNA (IRES inhibitors), drugs that prevent the normal processing of HCV proteins (glycosylation inhibitors), drugs that block entry of HCV into cells such as by blocking its receptors, and non-specific cytoprotective agents that block cell injury caused by the viral infection. Moreover, molecular approaches to treat infection by hepatitis C virus are being investigated. For example, studies of ribozymes, enzymes that break down specific viral RNA molecules, and antisense oligonucleotides, which are small, complimentary segments of DNA that bind to and inhibit viral RNA, are being studied. A review of HCV treatments can be found in Bymock et al., *Antiviral Chemistry & Chemotherapy*, 2000, 11:2, and De Francesco et al., *Antiviral Res.*, 2003, 58:1-16.

Other classes of drugs that are being developed to treat Flaviviridae infections and hepatitis C infections in particular include:

1) Protease inhibitors:
   a. Substrate-based NS3 protease inhibitors are disclosed by Attwood et al. in WO 98/22496 and DE 19914474; by Attwood et al. in *Antiviral Chemistry and Chemotherapy*, 1999, 10:259-273; and by Tung et al. in WO 98/17679, which includes alphaketoamides and hydrazinoureas;
   b. Substrate inhibitors that terminate in an electrophile like boronic acid or phosphonate are shown by Llinas-Brunet et al. in WO 99/07734;
   c. Non-substrate based NS3 protease inhibitors such as 2,4,6-trihydroxy-3-nitro-benzamide derivatives, RD3-4082 and RD3-4078 (the former substituted on the amide with a 14-carbon chain and the latter having a para-phenoxyphenyl group), shown by Sudo et al. in *Biochemical and Biophysical Res. Comm.*, 1997, 238:643-7, and in *Antiviral Chemistry and Chemotherapy*, 1998, 9:186;
   d. Sch 68631, a phenanthrenequinone, disclosed by Chu et al. in *Tetrahedron Letters*, 1996, 37:7229-32 and Sch 351633, isolated from the fungus *Penicillium griseofulvum*, disclosed by Chu et al. in *Bioorganic and Medicinal Chem. Lett.*, 9:1949-52;
   e. Eglin c, a macromolecule isolated from leech, that exhibits nanomolar potency inhibition against several serine proteases like *S. griseus* proteases A and B, α-chymotrypsin, chymase, and subtilisin, as disclosed by Qasim et al., *Biochemistry*, 1997, 36:1598-1607;
   f. Cysteine protease inhibitors for inhibiting HCV endopeptidase 2, as disclosed in U.S. Pat. No. 6,004,933 to Spruce et al.;
   g. Synthetic inhibitors of hepatitis C virus NS3 protease or NS4A cofactor that are subsequences of substrates utilized by the protease and/or cofactor, as shown in U.S. Pat. No. 5,990,276 to Zhang et al.;
   h. Restriction enzymes to treat HCV as disclosed in U.S. Pat. No. 5,538,865 to Reyes et al.;
   i. Peptides such as NS3 serine protease inhibitors of HCV as shown in WO 02/008251 to Corvas International, Inc., and in WO 02/08187 and WO 02/008256 to Schering Corporation;
   j. HCV tripeptide inhibitors, as disclosed in U.S. Pat. Nos. 6,534,523; 6,410,531; and 6,420,380 to Boehringer Ingelheim and WO 02/060926 to Bristol Myers Squibb;
   k. Diaryl peptides like serine protease inhibitors of HCV as taught by Schering Corporation in WO 02/48172;
   l. Imidazolidinones like NS3 serine protease inhibitors of HCV as disclosed in WO 02/08198 to Schering Corporation and WO 02/48157 to Bristol Myers Squibb; and
   m. HCV protease inhibitors as taught by Vertex Pharmaceuticals in WO 98/17679 and by Bristol Myers Squibb in WO 02/48116.
2) Thiazolidine derivatives that show relevant inhibition in a reverse-phase HPLC assay with an NS3/4A fusion protein and NS5A/5B substrate, as demonstrated by Sudo et al., *Antiviral Res.*, 1996, 32:9-18, especially compounds RD4 6205, RD4 6193, and RD-1-6250 that have a fused cinnamoyl moiety substituted by a long alkyl chain;
3) Thiazolidines and benzanilides as disclosed by Kakiuchi et al., *J. EBS Letters*, 421:217-220, and Takeshita et al., *Analytical Biochemistry*, 1997, 247:242-46;
4) Helicase inhibitors as disclosed by Diana et al. in U.S. Pat. No. 5,633,358 and WO 97/36554;
5) Nucleotide polymerase inhibitors and gliotoxin as shown by R. Ferrari et al., *J. Virology*, 1999, 73:1649-54;
6) Cerulenin, a natural product shown by V. Lohmann et al., *Virology*, 1998, 249:108-118;
7) Antisense phosphorothioate oligodeoxynucleotides (S-ODN) complementary to sequence stretches in the 5'non-coding (NCR) of the Flaviviridae virus s demonstrated by M. Alt et al., *Hepatology*, 1995, 22:707-717;
8) Nucleotides 326-348 comprising the 3' end of the NCR and nucleotides 371-388 located in the core coding region of the HCV RNA, as shown by M. Alt et al., *Archives of Virology*, 1997, 142:589-599; Galderisi et al., *J. of Cellular Physiology*, 1999, 181:251-257;
9) Inhibitors of IRES-dependent translation as disclosed by Ikeda et al., JP-08268890, and Y. Kai et al., JP-10101591
10) Ribozymes, such as nuclease-resistant ribozymes as shown by D. D. Maccjak et al., *Hepatology*, 1999, 30:abstract no. 995; Barber et al. in U.S. Pat. No. 6,043,077; and Draper et al. in U.S. Pat. Nos. 5,869,253 and 5,610,054;
11) Nucleoside analogs including the use of branched nucleosides in the treatment of flaviviruses, pestiviruses, and hepacivirus, as shown by Idenix Pharmaceuticals in WO 01/92282, WO 01/90121, U.S. Pat. No. 6,812,219, and U.S. Pat. No. 6,914,054, where a method is disclosed for the treatment of hepatitis C, pestivirus and/or flavivirus infection in humans and other host animals that includes administering an effective amount of biologically active 1', 2', 3' or 4'-branched β-D or β-L nucleosides or a pharmaceutically acceptable salt or derivative thereof, administered either alone or in combination with another antiviral agent, optionally in a pharmaceutically acceptable carrier. Nucleoside analogues are also found in WO 01/32153 and WO 01/60315 to BioChem Pharma, Inc. (now Shire Biochem, Inc.); WO 02/057425 and WO 02/057287 filed by Merck & Co., Inc.; WO 02/18404 by Roche; WO 01/79246, WO 02/32920, and WO 02/48165 from Pharmasset, Ltd.; and WO 99/43691 to Emory University. At the Oral Session V, Hepatitis C Virus, Flaviviridae, 16$^{th}$ International Conference on Antiviral Research, Apr. 27, 2003, Savannah, Ga., 2'-modified nucleosides for inhibition of HCV were described by Eldrup et al.; nucleoside analogues as possible inhibitors of HCV RNA replication were taught by Bhar et al. (p. A75), wherein the author reported that 2'-modified nucleosides demonstrate potent inhibitory activity in cell-based replicon assays; the effect of 2'-modified nucleosides on HCV RNA replication was reported by Olsen et al. (p. A76).

12) Miscellaneous compounds being developed to treat Flaviviridae infections and hepatitis C infections in particular include: 1-amino-alkylcyclohexanes as described in U.S. Pat. No. 6,034,134 to Gold et al.; alkyl lipids, vitamin E and other antioxidants in U.S. Pat. No. 5,922,757 to Chojkier et al.; squalene, amantadine, and bile acids as shown in U.S. Pat. No. 5,846,964 to Ozeki et al.; N-(phosphonoacetyl)-L-aspartic acid and piperidines as found in U.S. Pat. No. 5,830,905 Diana et al.; benzenedicarboxamides as disclosed in U.S. Pat. No. 5,633,388 to Diana et al.; polyadenylic acid derivatives as described in U.S. Pat. No. 5,496, 546 to Wang et al.; 2',3'-dideoxyinosine as found in U.S. Pat. No. 5,026,687 to Yarchaon et al.; benzimidazoles as demonstrated in U.S. Pat. No. 5,891,874 to Colacino et al.; and plant extracts as shown in U.S. Pat. No. 5,837,257 to Tsai et al. and U.S. Pat. No. 5,725,859 to Omer et al.

13) Compounds currently in preclinical or clinical development for treatment of hepatitis C virus, including: Interleukin-10 by Schering Plough; IP-501 by Interneuron; Merimebodib (VX-497) by Vertex; AMANTADINE® (Symmetrel) by Endo Labs Solvay; HEPTAZYME® by RPI; IDN-6556 by Idun Pharmaceuticals; XTL-002 by XTL; HCV/MF59 by Chiron; CIVACIR® (Hepatitis C Immune Globulin) by NABI; LEVOVIRIN® by ICN/Ribapharm; VIRAMIDINE® by ICN/Ribapharm (Valeant); ZADAXIN® (thymosin alpha-1) by Sci Clone; thymosin plus pegylated interferon by Sci Clone; CEPLENE® (histamine dihydrochloride) by Maxim; VX 950/LY 570310 by Vertex/Eli Lilly; ISIS 14803 by Isis Pharmaceutical/ Elan; JTK 003 by AKROS Pharma; BILN-2061 by Boehringer Ingelheim; CellCept (mycophenolate mofetil) by Roche; T67 (β-tubulin inhibitor) by Tularik; a therapeutic vaccine directed to E2 by Innogenetics; FK788 by Fujisawa Healthcare, Inc.; IdB 1016 (Siliphos, oral silybinphosphatydylcholine phytosome); an RNA replication inhibitor VP50406 by ViroPharma/Wyeth; therapeutic vaccines by Intercell and Epimmune/Genencor; an IRES inhibitor by Anadys; ANA 245 and ANA 246 by Anadys; immunotherapy "Therapore" by Avant; protease inhibitors by Bristol Myers Squibb/Axys and Corvas/Schering; a helicase inhibitor by Vertex; a fusion inhibitor by Trimeris; T cell therapy by CellExSys; polymerase inhibitor by Biocryst; targeted RNA chemistry by PTC Therapeutics; Dication by Immtech, International; protease inhibitors by Agouron and Chiron/Medivir; antisense therapies by AVI BioPharma and Hybridon; a hemopurifier by Aethlon Medical; a therapeutic vaccine by Merix; "Chron-VacC", a therapeutic vaccine, by Tripep; UT 231B by United Therapeutics; protease, helicase and polymerase inhibitors by Genelabs Technologies; IRES inhibitors by Immusol; R803 by Rigel Pharmaceuticals; INFERGEN® (interferon alphacon-1) by InterMune; OMNIFERON® (natural interferon) by Viragen; ALBUFERON® by Human Genome Sciences; REBIF® (interferon beta-1a) by Ares-Serono; Omega Interferon by BioMedicine; Oral Interferon Alpha by Amarillo Biosciences; interferons gamma, tau and gamma-1b by InterMune; consensus interferon by Valeant; Nexavar by Onyx Pharmaceuticals; PI-88 by Progen Industries; doxorubicin transdrug by BioAlliance Pharma; JBK-122 by Jenken Biosciences; Valopicitabine by Idenix; VGX-410C by VGX Pharmaceuticals; Celgosivir by Migenix; Suvus by Bioenvision; Multiferon by Viragen; omega interferon by Intarcia; INNO0101 (E1) by Innogenetics; PF-03491390 by Pfizer; medusa interferon by Flamel Technologies; IC41 by Intercell; SCH 503034 by Schering; G126270 by GlaxoSmithKline; GV1001 by Pharmexa; R1626 by Roche; Maxygen/Roche; R7128 by Pharmasset/Roche; Belerofon by Nautilus Biotech; Alinia by Romark; Bavituximab by Peregrine; Oral Interferon alpha by Amarillo Biosciences; NOV-205 by Novelos; CGI 5005 by GlobeImmune; HCV-796 by ViroPharma/Wyeth; HCV/MF59 by Chiron/Norvartis; EMZ702 by Transition Therapeutics; AVI-4065 by Biopharma; ANA975 by ANADYS; MitoQ by Antipodean Pharmaceuticals, Inc; ACH-0137171 by Achillion Pharmaceuticals; R1626 by Roche; XTL-2125 by XTL; XTL-6865 by XTL; BLX-883 by Biolex Therapeutics/OctoPlus; DEBIO-025 by DEBIO; and UT-231B by United Therapeutics; and 14) Nucleoside prodrugs as previously described for the treatment of other forms of hepatitis, including 2'-deoxy-β-L-nucleosides and their 3'-prodrugs for the treatment of HBV as disclosed in WO 00/09531 and WO 01/96353 to Idenix Pharmaceuticals; and therapeutic esters of acyclovir as shown in U.S. Pat. No. 4,957,924 to Beauchamp.

Other examples of antiviral agents that can be used in combination and/or alternation with the compounds disclosed herein include, but are not limited to, agents such as VX-950 and interferon. Interferons that may be used include Schering-Plough's alpha interferon-2b products, Intron® A and PEG-Intron™; and Hoffman La Roche's Co-Pegasus and PEGASYS (pegylated interferon alfa-2a).

Hepatitis B Agents

The hepatitis B agent can be any agent known to those of skill in the art to be effective for the treatment of hepatitis B infection in a host in need thereof. In certain embodiments, the hepatitis B agent is interferon-alpha (Intron A, Schering-Plough), pegylated interferon (Pegasys, Roche), lamivudine (Epivir-HBV, Zeffix, or Heptodin, Glaxo-Smithkline), adefovir dipivoxil (Hepsera, Gilead), entecavir (Baraclude, Bristol-Myers-Squibb), telbivudine (Tyzeka or Sebivo, Idenix) or HBV immuneglobulin (HyperHEP S/D, Talecris; Nabi-HBV, Nabi; Hepa Gam B, Cangene).

In certain embodiments, the hepatitis B agent is FTC (Emtricitabine, Gilead), L-FMAU (Clevudine, Pharmasset; Levovir, Bukwang), tenofovir (Viread, Gilead), monoval LdC (Valtorcitabine, Idenix), DAPD (Amdoxovir, RFS Pharm LLC), Ana 380 (LB80380, Anadys), remofovir (Pradefovir, Schering-Plough), racivir (RCV, Pharmasset), BAM-205 (NOV-205, Novelos), XTL-001 (HepeX-B, XTL Biopharm, Cubist), nitoxanide (Alinia, Romark Labs), UT 231-B (United Therapeutics), Bay 41-4109 (Bayer), EHT899 (Enzo Biochem), thymosin alpha-1 (Zadaxin, SciClone), Hi-8 HBV (Oxxon), eiRNA (HepX, Nucleonics), HepaVaxx B (Virexx), HBV Core Antigen Vaccine (Emergent Europe), or SpecifEx-HepB (Chromos).

Other Antiviral Agents

Any of the viral treatments described in the Background of the Invention herein elsewhere can be used in combination or alternation with the compounds described in this specification. Non-limiting examples include a) protease inhibitors; b) thiazolidine derivatives; c) helicase inhibitors; d) benzanilides; e) phenanthrenequinones; f) polymerase inhibitors and gliotoxin; g) antisense phosphorothioate oligodeoxynucleotides (S-ODN); h) inhibitors of IRES-dependent translation; i) ribozymes; j) nucleoside analogues; k) disubstituted nucleoside analogues as disclosed by Idenix Pharmaceuticals in WO 01/90121, WO 01/92282, WO 04/00300, WO 04/002999, and WO 04/002422; l) 2'-fluoronucleoside analogues; m) 1-$NH_2$-alkylcyclohexanes; n) alkyl lipids; o) vitamin E and other antioxidants; p) squalene, amantadine and bile acids; q) N-(phosphonoacetyl)-L-aspartic acid; r) benzenedicarboxamides; s) polyadenylic acid derivatives; t) benzimidazoles; u) 2',3'-dideoxyinosine; v) plant extracts; w) piperidines; and x) other compounds currently in preclinical or clinical development for the treatment of pestiviruses, flaviviruses and/or hepacivirus, including ribavirin and the families of interferons.

The second antiviral agent for the treatment of HIV can be, for example, a protease inhibitor, an HIV-integrase inhibitor, a chemokine inhibitor, or a reverse transcriptase inhibitor ("RTI"), the latter of which can either be a synthetic nucleoside reverse transcriptase inhibitor ("NRTI") or a non-nucleoside reverse transcriptase inhibitor ("NNRTI"). In other embodiments, a second or third compound may be a pyrophosphate analog or a fusion-binding inhibitor. A list compiling resistance data collected in vitro and in vivo for certain antiviral compounds is found in Schinazi et al., Mutations in retroviral genes associated with drug resistance, *International Antiviral News*, 1997, 5(8).

In certain embodiments, the indole compound is administered in combination and/or alternation with FTC (2',3'-dideoxy-3'-thia-5-fluorocytidine); 141W94 (amprenavir, Glaxo Wellcome, Inc.); Viramune (nevirapine); Rescriptor (delavirdine); DMP-266 (efavirenz); DDI (2',3'-dideoxyinosine); 3TC (3'-thia-2',3'-dideoxycytidine); DDC (2',3'-dideoxycytidine), abacavir (1592U89), which is (1S,4R)-4-[(2-amino-6-cyclopropyl-amino)-9H-purin-9-yl]-2-cyclopentene-1-methanol succinate, Tenofovir DF (Viread), D4T, or AZT.

Other examples of antiviral agents that can be used in combination and/or alternation with the compounds disclosed herein include, but are not limited to, foscarnet; carbovir; acyclovir; interferon; fusion inhibitors such as enfuvirtide; and β-D-dioxolane nucleosides such as β-D-dioxolanylguanine (DXG), β-D-dioxolanyl-2,6-diaminopurine (DAPD), and β-D-dioxolanyl-6-chloropurine (ACP). Interferons that may be used include Schering-Plough's alpha interferon-2b products, Intron® A and PEG-Intron™; and Hoffman La Roche's Co-Pegasus and PEGASYS (pegylated interferon alfa-2a). Combinations with which the 3-phosphoindoles can be administered include Epzicom (ABC+3TC), Trizivir (ABC+3TC+AZT), Truvada (FTC+Viread) and Combivir (AZT+3TC).

Examples of protease inhibitors that can be used in combination and/or alternation with the compounds disclosed herein include, but are not limited to indinavir ({1(1S,2R),5(S)}-2,3,5-trideoxy-N-(2,3-dihydro-2-hydroxy-1H-inden-1-yl)-5-[2-[[(1,1-dimethylethyl)amino]carbonyl]-4-(3-pyridinylmethyl)-1-piperazinyl]-2-(phenylmethyl)-D-erythro-pentoamide sulfate; Merck & Co., Inc.); nelfinavir (Agouron); ritonavir (Abbott Labs), saquinavir (Roche); Amprenavir; Atazanavir; Fosamprenavir; Kaletra; and DMP-450 {[4R-4(r-a,5-a,6-b,7-6)-hexahydro-5,6-bis(hydroxy)-1,3-bis(3-amino)-phenyl]methyl-4,7-bis(phenylmethyl)-2H-1,3-diazepin-2-one}-bismesylate (Triangle Pharmaceuticals, Inc.).

Other compounds that can be administered in combination or alternation with the phosphoindole to augment its antiviral properties include (1S, 4R)-4-[2-amino-6-cyclopropyl-amino-9H-purin-9-yl]-2-cyclopentene-1-methanol succinate (1592U89, a carbovir analog, from GlaxoSmithKline); BILA 1906 (N-{1S-[[[3-[2S-{(1,1-dimethylethyl)amino]carbonyl}-4R-]3-pyrindinylmethyl)thio]-1-piperidinyl]-2R-hydroxy-1S-phenylmethyl)propyl]-amino]carbonyl]-2-methylpropyl}-2-quinolinecarboxamide) (Bio Mega/Boehringer Ingelheim); BILA 2185 (N-(1,1-dimethylethyl)-1-[2S-[[[2-2,6-dimethyl-phenoxy]-1-oxoethyl]amino]-2R-hydroxy-4-phenylbutyl]-4R-pyridinylthio-2-piperidine-carboxamide) (Bio Mega/Boehringer Ingelheim); BM+51.0836 (triazolo-iso-indolinone derivative) and BMS 186,318 (aminodiol derivative HIV-1 protease inhibitor) (Bristol-Myers Squibb); d4API (9-[2,5-dihydro-5-(phosphonomethoxy)-2-furanyl]-adenine) (Gilead); HBY097 (S-4-isopropoxycarbonyl-6-methoxy-3-[methylthio-methyl]-3,4-dihydroquinoxalin-2 (1H)-thione); HEPT (1-[(2-hydroxy-ethoxy)methyl]6-[phenylthio]-thymine); KNI-272 ((2S,3S)-3-amino-2-hydroxy-4-phenylbutyric acid-containing tripeptide); L-697, 593 (5-ethyl-6-methyl-3-(2-phthalimido-ethyl)pyridin-2 (1H)-one); L-732,524 (hydroxy-aminopentane amide HIV-1, protease inhibitor) (Merck & Co.); L-697,661 (3-{[(-4,7-dichloro-1,3-benzoxazol-2-yl)methyl]amino}-5-ethyl-6-methyl-pyridin-2(1H)-one); L-FDDC ((−)-β-L-5-fluoro-2', 3'-dideoxycytidine); L-FDOC ((−)-β-L-5-fluoro-dioxolane cytosine); PFA (phosphonoformate; "foscarnet"; Astra); PMEA (9-(2-phosphonylmethoxyethyl)adenine) (Gilead); PMPA ((R)-9-(2-phosphonylmethoxy-propyl)-adenine) (Gilead); Ro 31-8959 (hydroxyethylamine derivative HIV-1 protease inhibitor) (Roche); RPI-3121 (peptidyl protease inhibitor, 1-[(3S)-3-(n-alpha-benzyloxy-carbonyl)-1-asparginyl)-amino-2-hydroxy-4-phenylbutyryl]-n-tert-butyl-1-proline amide); 2720 (6-chloro-3,3-dimethyl-4-(isopropenyloxycarbonyl)-3,4-dihydro-quinoxalin-2(1H)thione); SC-52151 (hydroxyethylurea isostere protease inhibitor) (G.D. Searle); SC-55389A (hydroxyethyl-urea isostere protease inhibitor (G.D. Searle); TIBO R82150 ((+)-(5S)-4,5,6,7-tetrahydro-5-methyl-6-(3-methyl-2-butenyl)-imidazo-[4,5,1-jk]-[1,4]-benzodiazepin-2(1H)-thione) (Janssen Pharmaceuticals); TIBO 82913 ((+)-(5S)-4,5,6,7-tetrahydro-9-chloro-5-methyl-6-(3-methyl-2-butenyl)imidazo[4,5,1-jk]-[1,4]-benzo-diazepin-2(1H)-thione (Janssen Pharmaceuticals); TSAO-m3T ([2',5'-bis-O-(tert-butyldimethylsilyl)-3'-spiro-5'-(4'-amino-1',2'-oxathiole-2',2'-dioxide)]-β-D-pentofuranosyl-N-3-methyl-thymine); U90152 (1-[3-[(1-methylethyl-amino]2-pyridinyl]-4-[[5-[(methylsulphonyl)-amino]-1H-indol-2-yl]-carbonyl]-piperazine); UC (thiocarboxanilide derivatives) (Uniroyal); UC-781 (N-[4-chloro-3-(3-methyl-2-butenyloxy)phenyl]-2-methyl-3-furancarbothioamide); UC-82 (N-[4-chloro-3-(3-methyl-2-butenyloxy)phenyl]-2-methyl-3-thiophenecarbothioamide); VB 11,328 (hydroxyethyl-sulphonamide protease inhibitor) (Vertex/Glaxo Wellcome); XM 323 (cyclic urea protease inhibitor) (Dupont Merck); and penciclovir. In yet another embodiment, the indole compound of the invention is administered in combination with the protease inhibitor LG 1350.

The following drugs can be used in combination and/or alternation with the compounds of the present invention.

| Drug Name | Manufacturer |
|---|---|
| 3TC, Epivir ® brand lamivudine | GlaxoSmithKline |
| abacavir generic Ziagen ®, ABC, or 1592U89 | GlaxoSmithKline |
| ABC, Ziagen ® brand abacavir, or 1592U89 | GlaxoSmithKline |
| ABT-378/r, or Kaletra ® brand lopinavir/ritonavir | Abbott Laboratories |
| AG-1549, S-1153, or capravirine (CPV) | Pfizer |
| AG1661, Remune ® brand HIV-1 Immunogen, or Salk vaccine | Immune Response Corp. |
| Agenerase ® brand amprenavir (APV), 141W94, or VX-478 | GlaxoSmithKline |
| aldesleukin generic Proleukin ®, or Interleukin-2 (IL-2) | Chiron Corporation |
| amdoxovir, or DAPD | Gilead Sciences |
| amprenavir generic Agenerase ®, APV, 141W94, or VX-478 | GlaxoSmithKline |
| Aptivus ® | Boehringer Ingelheim |
| APV, Agenerase ® brand amprenavir, 141W94, or VX-478 | GlaxoSmithKline |
| atazanavir generic Reyataz ™, or BMS-232632 | Bristol-Myers Squibb |
| Atripla ® | Bristol-Myers Squibb and Gilead |
| AZT, Retrovir ® brand zidovudine (ZDV) | GlaxoSmithKline |
| Bis(POC) PMPA, Viread ® brand tenofovir DF | Gilead Sciences |
| BMS-232632, or Reyataz ™ brand atazanavir | Bristol-Myers Squibb |
| BMS-56190, or DPC-083 | Bristol-Myers Squibb |
| calanolide A | Sarawak Medichem |
| capravirine (CPV), AG-1549, or S-1153 | Pfizer |
| Combivir ® brand zidovudine + lamivudine, or AZT + 3TC | GlaxoSmithKline |
| CPV (capravirine), AG-1549, or S-1153 | Pfizer |
| Crixivan ® brand indinavir (IDV), or MK-639 | Merck & Co. |
| d4T, Zerit ® brand stavudine, or BMY-27857 | Bristol-Myers Squibb |
| DAPD, or amdoxovir | Gilead Sciences |
| ddC, or Hivid ® brand zalcitabine | Hoffmann-La Roche |
| ddI, Videx ® brand didanosine, or BMY-40900 | Bristol-Myers Squibb |
| delavirdine generic Rescriptor ®, DLV, or U-90152S/T | Pfizer |
| didanosine generic Videx ®, ddI, or BMY-40900 | Bristol-Myers Squibb |
| DLV, Rescriptor ® brand delavirdine, or U-90152S/T | Pfizer |
| DPC-083, or BMS-56190 | Bristol-Myers Squibb |
| Droxia ® brand hydroxyurea (HU) | Bristol-Myers Squibb |
| efavirenz generic Sustiva ®, or EFV | Bristol-Myers Squibb |
| EFV, Sustiva ® brand efavirenz | Bristol-Myers Squibb |
| emtricitabine generic Emtriva ™, or FTC | Gilead Sciences |
| Emtriva ® brand emtricitabine, or FTC | Gilead Sciences |
| enfuvirtide generic Fuzeon ™, or T-20 | Trimeris and Hoffmann-La Roche |
| Epivir ® brand lamivudine, or 3TC | GlaxoSmithKline |
| epoetin alfa (erythropoietin) generic Procrit ® | Ortho Biotech |
| Epzicom ® | GlaxoSmithKline |
| erythropoietin (epoetin alfa) generic Procrit ® | Ortho Biotech |
| Fortovase ® brand saquinavir (Soft Gel Cap), or SQV (SGC) | Hoffmann-La Roche |
| fosamprenavir, or GW-433908, or VX-175 | GlaxoSmithKline |
| FTC, or Emtriva ® brand emtricitabine | Gilead Sciences |
| Fuzeon ™ brand enfuvirtide, or T-20 | Trimeris and Hoffmann-La Roche |
| GW-433908, or fosamprenavir, or VX-175 | GlaxoSmithKline |
| HE2000, or alpha-epibromide | HollisEden Pharmaceuticals |
| HIV-1 Immunogen generic Remune ®, Salk vaccine, or AG1661 | Immune Response Corp. |
| Hivid ® brand zalcitabine, or ddC | Hoffmann-La Roche |
| HU, or Droxia ® brand hydroxyurea | Bristol-Myers Squibb |
| hydroxyurea generic Droxia ®, or HU | Bristol-Myers Squibb |
| IDV, Crixivan ® brand indinavir, or MK-639 | Merck & Co. |
| IL-2 (Interleukin-2), or Proleukin ® brand aldesleukin | Chiron Corporation |
| indinavir generic Crixivan ®, IDV, or MK-639 | Merck & Co. |
| Interleukin-2 (IL-2), or Proleukin ® brand aldesleukin | Chiron Corporation |
| Isentress brand raltegravir | Merck |
| Invirase ® brand saquinavir (Hard Gel Cap), SQV (HGC), or Ro-31-8959 | Hoffmann-La Roche |
| Kaletra ® brand lopinavir/ritonavir, or ABT-378/r | Abbott Laboratories |
| lamivudine generic Epivir ®, or 3TC | GlaxoSmithKline |
| Lexiva ® | GlaxoSmithKline |
| lopinavir/ritonavir generic Kaletra ®, or ABT-378/r | Abbott Laboratories |
| MK-639, Crixivan ® brand indinavir (IDV) | Merck & Co. |
| nelfinavir generic Viracept ®, NFV, or AG-1343 | Pfizer |
| nevirapine generic Viramune ®, NVP, or BI-RG-587 | Boehringer Ingelheim |
| NFV, Viracept ® brand nelfinavir, or AG-1343 | Pfizer |
| Norvir ® brand ritonavir (RTV), or ABT-538 | Abbott Laboratories |
| NVP, Viramune ® brand nevirapine, or BI-RG-587 | Boehringer Ingelheim |
| PNU-140690, or tipranavir | Boehringer Ingelheim |
| Prezista ® | Tibotec |

| Drug Name | Manufacturer |
| --- | --- |
| PRO-542 | Progenics Pharmaceuticals |
| Procrit ® brand epoetin alfa (erythropoietin) | Ortho Biotech |
| Proleukin ® brand aldesleukin, or Interleukin-2 (IL-2) | Chiron Corporation |
| Remune ® brand HIV-1 Immunogen, or Salk vaccine | Immune Response Corp. |
| Rescriptor ® brand delavirdine (DLV), or U-90152S/T | Pfizer |
| Retrovir ® brand zidovudine (ZDV), or AZT | GlaxoSmithKline |
| Reyataz ™ brand atazanavir, or BMS-232632 | Bristol-Myers Squibb |
| ritonavir generic Norvir ®, RTV, or ABT-538 | Abbott Laboratories |
| RTV, Norvir ® brand ritonavir, or ABT-538 | Abbott Laboratories |
| Salk vaccine, Remune ® brand HIV-1 Immunogen, or AG1661 | Immune Response Corp. |
| saquinavir (Hard Gel Cap) generic Invirase ®, SQV (HGC), or Ro-31-8959 | Hoffmann-La Roche |
| saquinavir (Soft Gel Cap) generic Fortovase ®, or SQV (SGC) | Hoffmann-La Roche |
| SCH-C | Schering-Plough |
| Selzentry brand maraviroc | Pfizer |
| Serostim ® brand somatropin | Serono Laboratories |
| somatropin generic Serostim ® | Serono Laboratories |
| SQV (HGC), Invirase ® brand saquinavir (Hard Gel Cap), or Ro-31-8959 | Hoffmann-La Roche |
| SQV (SGC), or Fortovase ® brand saquinavir (Soft Gel Cap) | Hoffmann-La Roche |
| stavudine generic Zerit ®, d4T, or BMY-27857 | Bristol-Myers Squibb |
| Sustiva ® brand efavirenz (EFV) | Bristol-Myers Squibb |
| T-1249 | Trimeris and Hoffmann-La Roche |
| T-20, or Fuzeon ™ brand enfuvirtide | Trimeris and Hoffmann-La Roche |
| TDF, tenofovir DF generic Viread ™, or Bis(POC) PMPA | Gilead Sciences |
| tenofovir DF (TDF) generic Viread ®, Bis(POC) PMPA | Gilead Sciences |
| tipranavir, or PNU-140690 | Boehringer Ingelheim |
| TMC-114 | Tibotec-Virco Group |
| TMC-125 | Tibotec-Virco Group |
| Trizivir ® brand abacavir + zidovudine + lamivudine (ABC + AZT + 3TC) | GlaxoSmithKline |
| Truvada ® | Gilead |
| Videx ® brand didanosine, ddI, or BMY-40900 | Bristol-Myers Squibb |
| Videx ® EC brand didanosine (ddI): delayed-release capsules | Bristol-Myers Squibb |
| Viracept ® brand nelfinavir (NFV), or AG-1343 | Pfizer |
| Viramune ® brand nevirapine (NVP), or BI-RG-587 | Boehringer Ingelheim |
| Viread ® brand tenofovir DF, or Bis(POC) PMPA | Gilead Sciences |
| VX-175, or fosamprenavir, or GW-433908 | GlaxoSmithKline |
| zalcitabine generic Hivid ®, or ddC | Hoffmann-La Roche |
| ZDV, Retrovir ® brand zidovudine, or AZT | GlaxoSmithKline |
| Zerit ® brand stavudine, d4T, or BMY-27857 | Bristol-Myers Squibb |
| Ziagen ® brand abacavir (ABC), or 1592U89 | GlaxoSmithKline |
| zidovudine generic Retrovir ®, AZT, or ZDV | GlaxoSmithKline |

Additional drugs that can be used in combination and/or alternation with the 3-phosphoindoles include:

| | | |
| --- | --- | --- |
| GW5634 (GSK) | MIV-150 (Medivir/Chiron) | Tipranavir (B-I) |
| RO033-4649 (Roche) | TMC125 (Tibotec) | |
| GW640385 (GSK/Vertex) | TMC114 (Tibotec) | |
| Elvucitabine (Achillion Ph.) | Alovudine (FLT) (B-I) | |
| MIV-210 (GSK/Medivir) | Racivir (Pharmasset) | |
| SPD754 (Shire Pharm.) | Reverset (Incyte Corp.) | |
| FP21399 (Fuji Pharm.) | AMD070 (AnorMed) | |
| GW873140 (GSK) | BMS-488043 (BMS) | |
| Schering C/D (417690) | PRO 542 (Progenics Pharm) | |
| | TAK-220 (Takeda) | |
| | TNX-355 (Tanox) | |
| | UK-427,857 (Pfizer) | |

The following drugs can be used in combination and/or alternation with the compounds of the present invention.

| Brand Name | Generic Name | Use | Manufacturer Name |
| --- | --- | --- | --- |
| Abelcet, Ambisome | Amphotericin B, ABLC | antifungal for aspergillosis | various |
| Bactrim, Septra | sulfamethoxazole and trimethoprim | antiprotozoal antibiotic for Pneumocystis carinii pneumonia treatment and prevention | various |
| Biaxin, Klacid | clarithromycin | antibiotic for *Mycobacterium avium* prevention and treatment | Abbott Laboratories |

-continued

| Brand Name | Generic Name | Use | Manufacturer Name |
| --- | --- | --- | --- |
| Cytovene | ganciclovir, DHPG | antiviral for CMV retinitis | Roche |
| DaunoXome | daunorubicin-liposomal | chemotherapy for Kaposi's sarcoma | Gilead |
| Diflucan | fluconazole | antifungal for candidiasis, cryptococcal meningitis | Pfizer |
| Doxil | doxorubicin hydrochloride-liposomal | chemotherapy for Kaposi's sarcoma | Ortho Biotech |
| Famvir | famciclovir | antiviral for herpes | Novartis |
| Foscarnet | foscavir | antiviral for herpes, CMV retinitis | Astra Pharmaceuticals |
| Gamimune N | immune globulin, gamma globulin, IGIV | immune booster to prevent bacterial infections in children | Bayer Biologicals |
| Intron A | interferon alfa-2b | Karposi's sarcoma, hepatitis C | Schering |
| Marinol | dronabinol | treat appetite loss | Roxane Laboratories |
| Megace | megestrol acetate | treat appetite, weight loss | Bristol Myers-Squibb |
| Mepron | atovaquone | antiprotozoal antibiotic for Pneumocystis carinii pneumonia treatment and prevention | GlaxoSmithKline |
| Mycobutin, Ansamycin | rifabutin | antimycobacterial antibiotic for Mycobacterium avium prevention | Adria Pharmaceuticals |
| NebuPent | pentamidine | antiprotozoal antibiotic for Pneumocystis carinii pneumonia prevention | Fujisawa |
| Neutrexin | trimetrexate glucuronate and leucovorin | antiprotozoal antibiotic for Pneumocystis carinii pneumonia treatment | MedImmune |
| Panretin gel | alitretinoin gel 0.1% | AIDS-related Karposi's sarcoma | Ligand Pharmaceuticals |
| Procrit, Epogen | erythropoetin, EPO | treat anemia related to AZT therapy | Amgen |
| Roferon A | interferon alfa-2a | Karposi's sarcoma and hepatitis C | Roche |
| Serostim | somatropin rDNA | treat weight loss | Serono |
| Sporanox | itraconazole | antifungal for blastomycosis, histoplasmosis, aspergillosis, and candidiasis | Janssen Pharmaceuticals |
| Taxol | paclitaxel | Karposi's sarcoma | Bristol Myers-Squibb |
| Valcyte | valganciclovir | antiviral for CMV retinitis | Roche |
| Vistide | cidofovir, HPMPC | antiviral for CMV retinitis | Gilead |
| Vitrasert implant | ganciclovir insert | antiviral for CMV retinitis | Bausch & Lomb |
| Vitravene intravitreal injectable | fomivirsen sodium injection | antiviral for CMV retinitis | Isis Pharmaceuticals |
| Zithromax | azithromycin | antibiotic for Mycobacterium avium | Pfizer |

Products that have been allowed to proceed as Investigational New Drugs (IND) by the FDA for the treatment of complications of HIV infection and AIDS can be used. The following drugs can be used in combination and/or alternation with the compounds of the present invention.

Trimetrexate glucuronate for the treatment of *Pneumocystis carinii* pneumonia in AIDS patients who cannot tolerate standard forms of treatment.

Ganciclovir for the treatment of cytomegalovirus retinitis in AIDS patients.

Aerosolized pentamidine for the prevention of *Pneumocystis carinii* pneumonia in AIDS patients.

Erythropoietin for the treatment of zidovudine-related anemia.

Atovaquone for the treatment of AIDS patients with *Pneumocystis carinii* pneumonia who are intolerant or unresponsive to trimethoprim-sulfamethoxazole.

Rifabutin for prophylaxis against *Mycobacterium avium* complex bacteremia in AIDS patients.

Vistide intravenous cidofovir for HIV-infected persons with relapsing cytomegalovirus (CMV) retinitis that has progressed despite treatment (Hoffmann-La Roche).

Serostim, a mammalian derived recombinat human growth hormone, for the treatment of AIDS-related wasting (Serono Laboratories).

In particular embodiments, the compounds disclosed herein can be administered in combination or alternation with one, two or more other anti-HIV agents. In one subembodiment, the additional agent is selected from:

a protease inhibitor optionally selected from amprenavir, tipranavir, indinavir, saquinavir (including saquinavir mesylate), lopinavir, ritonavir, fosamprenavir, darunavir, atazanavir (including the sulfate salt), and nelfinavir (including the mesylate salt);

a nucleoside or nucleotide reverse transcriptase inhibitor optionally selected from lamivudine, emtricitabine, abacavir, zalcitabine, zidovudine, tenofovir (including tenofovir disoproxil fumarate), didanosine, and stavudine;

a non-nucleoside reverse transcriptase inhibitor optionally selected from delavirdine, efavirenz and nevirapine;

a fixed dose combination optionally selected from Atripla, Combivir, Trizivir and Truvada;

an entry inhibitor (such as a fusion inhibitor or CCR5 co-receptor antagonist) optionally selected from maraviroc and enfuvirtide; and an integrase inhibitor such as raltegravir (MK-0518) or elvitegravir (GS-9137).

Where an additional anti-HIV agent is used it optionally may be in another form, such as a salt, solvate, hydrate, prodrug form, polymorph, enantiomer and the like. The additional anti-HIV agent also may be selected from:

a nucleoside reverse transcriptase inhibitor optionally selected from amdoxovir, apricitabine, and elvucitabine;

a protease inhibitor which is optionally brecanivir or GS-8374;

a CCR5 Receptor antagonist optionally selected from Aplaviroc, PRO2000 and Vicriviroc;

a non-nucleoside reverse transcriptase inhibitor which is optionally Etravirine (TMC-125), Rilpivirine (TMC-278), or Calanolide A;

an integrase inhibitor which is optionally Elvitegravir, GSK-364735 or raltegravir; and a maturation inhibitor that is optionally Bevirimat (PA457);

a cellular inhibitor, such as hydroxyurea;

an entry inhibitor, such as vicriviroc or TNX-355; and an immune based inhibitor such as Immunitin (alpha-epibromide), proleukin (IL-2), Remune (HIV-1 immunogen), BAY 50-4798 or IR103.

Agents Metabolized by Cytochrome P450

In certain embodiments, a compound provided herein can be administered in combination or alternation with a pharmaceutically acceptable agent that is metabolized by cytochrome P450 monooxygenase. Exemplary useful cytochrome P450 monooxygenases include cytochrome P450 2C8, cytochrome P450 2C9 and cytochrome P450 3A4. In certain embodiments, the pure compounds provided herein can inhibit cytochrome P450 monooxygenase thereby improving the pharmacokinetics of the co-administered agent. In particular embodiments, the P450 isozyme inhibited is CYP3A4. In particular embodiments, the phosphoindole compound is administered in combination with a second anti-HIV compound without the need for a ritonavir booster. In particular embodiments, the phosphoindole compound is administered in combination with one or more of Atazanavir, Fosamprenavir, Darunavir, Indinavir, Lopinavir, Nelfinavir, Saquinavir, Tipraniavir, or Enfuvirtide.

In particular embodiments, the phosphoindole compound is administered in combination therapy with one or more nucleoside reverse transcriptase inhibitors and/or one or more integrase inhibitors.

The pharmaceutically acceptable agent that is metabolized by cytochrome P450 monooxygenase can be any such agent known or identified to those of skill in the art. Exemplary, nonlimiting, compounds that may be metabolized by cytochrome P450 monooxygenase include, but are not limited to, paclitaxel, torsemide, amodiaquine, cerivastatin and repaglinide (cytochrome P450 2C8); certain NSAIDs (e.g., diclofenac, ibuprofen, lornoxicam, meloxicam, S-naproxen, piroxicam, suprofen), certain oral hypoglycemic agents (e.g., tolbutamide, glipizide), certain angiotensin II blockers (e.g., losartan, irbesartan), certain sulfonylureas (e.g., glyburide, glibenclamide, glipizide, glimepiride, tolbutamide, amitriptyline), celecoxib, fluoxetine, fluvastatin glyburide, nateglinide, phenyloin, rosiglitazone, tamoxifen, torsemide, S-warfarin (cytochrome P450 2C9); certain macrolide antibiotics (e.g., clarithromycin, erythromycin, telithromycin), certain anti-arrythmics (e.g., quinidine), certain benzodiazepines (e.g., alprazolam, diazepam, midazolam, triazolam) certain immune modulators (cyclosporine, tacrolimus), certain HIV antivirals (e.g., indinavir, nelfinavir, ritonavir, saquinavir), certain prokinetics (e.g., cisapride), certain antihistamines (e.g., astemizole, chlorpheniramine, terfenidine), certain calcium channel blockers (e.g., amlodipine, diltiazem, felodipine, lercanidipine, nifedipine, nisoldipine, nitrendipine, verapamil), certain HMG CoA reductase inhibitors (e.g., atorvastatin, cerivastatin, lovastatin, simvastatin), certain steroids (estradiol, hydrocortisone, progesterone, testosterone), alfentanyl, aprepitant, aripiprazole, buspirone, cafergot, caffeine=>TMU, cilostazol, cocaine, codeine-N-demethylation, dapsone, dexamethasone, dextromethorphan, docetaxel, domperidone, eplerenone, fentanyl, finasteride, gleevec, haloperidol, irinotecan, LAAM, lidocaine, methadone, nateglinide, odanestron, pimozide, propranolol, quetiapine, quinine, risperidone, NOT rosuvastatin, salmeterol, sildenafil, sirolimus, tamoxifen, taxol, terfenadine, trazodone, vincristine, zaleplon, ziprasidone, zolpidem (cytochrome P450 3A4). In particular embodiments, provided herein are methods in combination or alternation with HIV antivirals that are metabolized by cytochrome P450 (e.g., indinavir, nelfinavir, ritonavir, saquinavir).

Further exemplary compounds that may be metabolized by cytochrome P450 monooxygenase include, but are not limited to, CCR5 inhibitors (e.g., PRO-140, viciviroc, or SCH-417,690, and maraviroc, or UK-427,857), integrase inhibitors (e.g. JTK-303/GS-9137, 6-(3-chloro-2-fluorobenzyl)-1-[(2S)-1-hydroxy-3-methylbutan-2-yl]-7-methoxy-4-oxo-1, 4-dihydroquinoline-3-carboxylic acid, MK-0518, 5-(1,1-dioxido-1,2-thiazinan-2-yl)-N-(4-fluorobenzyl)-8-hydroxy-1, 6-naphthyridine-7-carboxamide, and those described in U.S. Pat. Nos. 6,924,282, 6,921,759, 6,919,351, 6,841,558, 6,541, 515, 6,403,347, 6,395,743, 6,380,249, 6,306,891, 6,271,402, 6,262,055, 6,245,806, 6,124,327, 6,110,716, 5,939,414, 5,858,738, 5,759,842, 7,176,220, and 7,112,600, the contents of which are hereby incorporated by reference in their entireties), protease inhibitors (e.g., saquinavir, indinavir, ritonavir, nelfinavir, amprenavir, lopinavir, ritonavir, atazanavir, fosamprenavir, tipranavir, amprenavir, and darunavir), fusion inhibitors (e.g., enfurvitide), maturation inhibitors (e.g., bevirimat, or PA-457) and nucleoside reverse transcriptase inhibitors (e.g. zidovudine, didanosine, zalcitabine, stavudine, lamivudine, abacavir, enofovir, emtricitabine, combivir, trizivir, truvada, and epzicom).

Further exemplary compounds that may be metabolized by cytochrome P450 monooxygenase include, but are not limited to, ritonavir, the immunosuppressants cyclosporine, FK-506 and rapamycin, the chemotherapeutic agents taxol and taxotere, the antibiotic clarithromycin and the HIV protease inhibitors A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), KNI-272, CGP 53437, CGP 57813 and U-103017.

In certain embodiments, provided are methods for improving the pharmacokinetics of an HIV protease inhibitor (or a pharmaceutically acceptable salt thereof) that is metabolized by cytochrome P450 monooxygenase. The methods comprise administering the HIV protease inhibitor in combination or alternation with a compound described herein. Such a combination or alternation can be useful for inhibiting HIV protease in humans and can also be useful for inhibition, treatment or prophylaxis of an HIV infection or AIDS in humans. The HIV protease inhibitor can be any HIV protease inhibitor known to those of skill in the art. In certain embodiments, the HIV protease inhibitor is amprenavir (Agenerase, Glaxo-Smithkline), tipranavir (Aptivus, Boehringer Ingelheim), indinavir (Crixivan, Merck), saquinavir (Fortovase, Hoffmann-La Roche), saquinavir mesylate (Invirase, Hoffmann-La Roche), lopinavir and ritonavir (Kaletra, GlaxoSmithkline), ritonavir (Norvir, Abott), darunavir (Prezista, Tibotec), atazanavir sulfate (Reyataz), or nelfinavir mesylate (Viracept, Agouron), or a combination thereof.

In particular subembodiments, the compounds disclosed herein can be administered in combination or alternation with one, two or more other protease inhibitor or integrase inhibitor anti-HIV agents which can potentially improve the metabolism of the second agent. In one subembodiment, the additional agent is selected from:
- a protease inhibitor optionally selected from amprenavir, tipranavir, indinavir, saquinavir (including saquinavir mesylate), lopinavir, ritonavir, fosamprenavir, darunavir, atazanavir (including the sulfate salt), nelfinavir (including the mesylate salt), brecanivir, or GS-8374; and
- an integrase inhibitor such as raltegravir (MK-0518) or elvitegravir (GS-9137), or GSK-364735.

In general, during alternation therapy, an effective dosage of each agent is administered serially. During combination therapy, effective dosages of two or more agents are administered together. Dosages administered depend upon factors such as absorption, biodistribution, metabolism and excretion rates for each drug as well as other factors known to those skilled in the art. It is to be noted that dosage amounts will vary with the severity of the condition to be alleviated, the age, weight, and general physical condition of the subject who receives the drug. It is to be understood further that for any particular subject, specific dosage regimens and schedules should be adjusted over time according to the response of the subject to the drug, the needs of the subject, and the professional judgment of the person administering or supervising the administration of the compositions. Examples of suitable dosage ranges for compounds, including nucleoside derivatives such as, for example, D4T, DDI and 3TC, 2'-branched nucleosides or protease inhibitors like nelfinavir and indinavir, can be found in the scientific literature and Physicians' Desk Reference. Suggested ranges for effective dosages of the compounds of the present invention are guidelines only, and are not intended to limit the scope or use of the invention.

The disclosed combination and alternation regimen may be useful in the treatment and prevention of retroviral infections and other related conditions, such as, for example, AIDS-related complex (ARC), persistent generalized lymphadenopathy (PGL), AIDS-related neurological conditions, anti-HIV-antibody position and HIV-positive conditions, Kaposi's sarcoma, thrombocytopenia purpurea, and opportunistic infections. In addition, these compounds or formulations may be used prophylactically to prevent or retard the progression of clinical illness in individuals who are anti-HIV antibody or HIV-antigen positive, or who have been exposed to HIV.

Assays

Compounds provided herein can be assayed for activity against HIV or HIV infection by any assay deemed suitable by one of skill in the art. Exemplary assays include those described in this section and those provided in the Examples below.

Cell Culture Systems for Determining Antiviral Activities
Amplified-Product Detection Schemes Heterogeneous Detection: Southern blotting, for example, is a heterogeneous detection technique. In Southern blotting, electrophoresis is used to separate amplification products by size and charge. The size-fractionated products are transferred to a membrane or filter by diffusion, vacuuming, or electroblotting. Labeled detection probes are hybridized to the membrane-bound targets in solution, the filters are washed to remove any unhybridized probe, and the hybridized probe on the membrane is detected by any of a variety of methods known to those skilled in the art.

Other types of heterogeneous detection are based on specific capture of the amplification products by means of enzyme-linked immunosorbent assays (ELISAs). One method used with PCR involves labeling one primer with a hapten or ligand, such as biotin, and after amplification, capturing it with an antibody- or streptavidin-coated microplate. The other primer is labeled with a reporter such as fluorescein, and detection is achieved by adding an antifluorescein antibody such as horseradish peroxidate (HRP) conjugate. This type of method is not as specific as using detection probes that hybridize to defined amplification products of interest.

The LCx probe system (Abbott Laboratories, Abbott Park, Ill.) and the Amplicor HIV-1 test (Roche Molecular Systems, Inc., Pleasanton, Calif.) are systems that use heterogeneous detection methods. In the LCx system, hapten-labeled oligonucleotide probes thermocycle in the ligase chain reaction. Either a capture hapten or a detection hapten is covalently attached to each of the four primer oligonucleotides. Upon amplification, each amplified product (amplicon) has one capture hapten and one detection hapten. When amplification is complete, the LCx system instrument transfers the reaction to a new well where antibody-coated microparticles bind the capture haptens. Each microparticle is then irreversibly bound to a glass-fiber matrix. A wash step removes the microparticle any probe that contains only the detection hapten. The LCx instrument adds an alkaline phosphatase (AP)—antibody conjugate that binds to the detection hapten. A fluorigenic substrate for AP is 4-methylumbelliferyl. Dephosphorylation of 4-methylumbelliferyl by AP converts it to 4-methylunbelliferone, which is fluorescent.

The Amplicor HIV-1 test uses an ELISA format. After amplification by PCR, the amplicon is denatured chemically. Amplicon-specific oligonucleotide probes capture the denatured strands onto a coated microplate. The operator washes away any unincorporated primers and unhybridized material in a wash step and then adds an avidin-HRP conjugate to each well. The conjugate binds to the biotin-labeled amplicon captured on the plate. The operator next adds 3,3',5,5'-tetramethylbenzidine (TMB), a chromogenic HRP substrate. When hydrogen peroxide is present, HRP oxidizes TMB. The signal is determined colorimetricallly.

Homogeneous Detection: since hybridized and nonhybridized detection probes are not physically separated in homogeneous detection systems, these methods require fewer steps than heterogeneous methods and thus are less prone to contamination. Among the commercially available kits that use homogeneous detection of fluorescent and chemiluminescent labels are the TaqMan system (Applied Biosystems, Foster City, Calif.), BDProbeTecET system (Becton Dickinson, Franklin Lakes, N.J.), QPCR System 5000 (Perkin-Elmer Corp., Norwalk, Conn.), and Hybridization Protection Assay (Gen-Probe, Inc., San Diego, Calif.).

The TaqMan system detects amplicon in real time. The detection probe, which hybridizes to a region inside the amplicon, contains a donor fluoroprobe such as fluorescein at its 5' end and a quencher moiety like rhodamine at its 3' end. When both quencher and fluorophore are on the same oligonucleotide, donor fluorescence is inhibited. During amplification the probe is bound to the target. Taq polymerase displaceds and cleaves the detection probe as it synthesizes the replacement strand. Cleavage of the detection probe results in separation of the fluorophore from the quencher, leading to an increase in the donor fluorescence signal. During each cycle of amplification the process is repeated. The amount of fluorescent signal increases as the amount of amplicon increases.

Molecular beacons also use quenchers and fluorophores. Beacons are probes that are complementary to the target amplicon, but contain short stretches (approximately 5 nucleotides) of complementary oligonucleotides at each end. The 5' and 3' ends of the beacons are labeled with a fluorophore and a quencher, respectively. A hairpin structure is formed when the beacon is not hybridized to a target, bringing into contact the fluorophore and the quencher and resulting in fluorescent quenching. The loop region contains the region complementary to the amplicon. Upon hybridization to a target, the hairpin structure opens and the quencher and fluorphore separate, allowing development of a fluorescent signal. A fluorometer measures the signal in real time.

The BDProbeTecET system uses a real-time detection method that combines aspects of TaqMan and molecular beacons. The probe has a hairpin loop structure and contains fluorescein and rhodamine labels. In this system, however, the region complementary to the target molecule is not within the loop but rather in the region 3' to the rhodamine label. Instead of containing the sequence complementary to the target, the single-stranded loop contains a restriction site for the restriction enzyme BsoBI. The single-stranded sequence is not a substrate for the enzyme. The fluorescein and rhodamine labels are near each other before amplification, which quenches the fluorescein fluorescence. Strand-displacement amplification converts the probe into a double-stranded molecule. The BsoBI restriction enzyme can cleave the molecule, resulting in separation of the labels and an increase in the fluorescent signal.

The QPCR System 5000 employs electrochemiluminescence with ruthenium labels. A biotinylated primer is used. After amplification, the biotin products are captured on streptavidin-coated paramagnetic beads. The beads are transferred into an electrochemical flow cell by aspiration and magnetically held to the surface of the electrode. Upon electrical stimulation, the ruthenium-labeled probe emits light.

The Hybridization Protection Assay is used in Gen-Probe's nonamplified PACE assays as well as in amplified *M tuberculosis* and *C. trachomatis* assays. The detection oligonucleotide probes in HPA are labeled with chemiluminescent acridinium ester (AE) by means of a linker arm. Hybridization takes place for 15 minutes at 60° C. in the same tube in which the amplification occurred. The selection reagent, a mildly basic buffered solution added after hybridization, hydrolyzes the AE on any unhybridized probe, rendering it nonchemiluminescent. The AE on hybridized probes folds inside the minor groove of the double helix, thereby protecting itself from hydrolysis by the selection reagent. The AE emits a chemiluminescent signal upon hydrolysis by hydrogen peroxide followed by sodium hydroxide. A luminometer records the chemiluminescent signal for 2 seconds (a period termed a "light off") and reports the photons emitted in terms of relative light units (RLU).

Detection-probe design is critical in all methodologies that use probes to detect amplification products. Good detection probes hybridize only to specified amplification products and do not hybridize to nonspecific products. Other key issues in optimizing detection methodologies involve the labeling of probes and the maximization of sample throughput.

Labeling Methods and Reporter Molecules. Detection probes can be labeled several different ways. Enzymatic incorporation of $^{32}$P or $^{35}$S into the probes is the most common method for isotopic labeling. Following hybridization and washing, the signal is detected on autoradiographic film.

To perform nonradioactive detection, probes can be labeled enzymatically with a variety of molecules. Biotin can be incorporated enzymatically and then detected with streptavidin-conjugated alkaline phosphatase using AP substrates like 5-bromo-4-chloro-3-indolyl phosphate (BCIP) and nitroblue tetrazolium (NBT). Chemiluminescent substrates such as Lumi-Phos 530 or Lumi-Phos Plus (Lumigen, Southfield, Mich.) also can be used with AP. In addition, digoxigenin-11-dUTP can be incorporated enzymatically into DNA or RNA, and anti-digoxigenin AP conjugates can be used with colorimetric or chemiluminescent detection.

There are numerous other types of reporter molecules including chemiluminescent moieties like acridinium esters. Many fluorescent moieties are available as well. Electrochemiluminescent compounds such as tris (2,2'-bipyridine) ruthenium (II) can be used also. Further discussions of these and similar techniques can be found in Schiff et al., *Semin. Liver Dis.*, 1999, 19. Suppl. 1:3-15).

Bioavailability Assay in Cynomolgus Monkeys

Within 1 week prior to the study initiation, the cynomolgus monkey is surgically implanted with a chronic venous catheter and subcutaneous venous access port (VAP) to facilitate blood collection and undergoes a physical examination including hematology and serum chemistry evaluations and the body weight is recorded. Each monkey (six total) receives each dose of active compound at a dose level of 10 mg/kg at a dose concentration of 5 mg/mL, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. Blood samples are collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples are analyzed by LC/MS for the maximum concentration ($C_{max}$), time when the maximum concentration is achieved ($T_{max}$), area under the curve (AUC), half life of the dosage concentration ($T_{1/2}$), clearance (CL), steady state volume and distribution ($V_{SS}$) and bioavailability (F).

Bone Marrow Toxicity Assay

Human bone marrow cells are collected from normal healthy volunteers and the mononuclear population are separated by Ficoll-Hypaque gradient centrifugation as described previously by Sommadossi J-P, Carlisle R. "Toxicity of 3'-azido-3'-deoxythymidine and 9-(1,3-dihydroxy-2-propoxymethyl)guanine for normal human hematopoietic progenitor cells in vitro" Antimicrobial Agents and Chemotherapy 1987; 31:452-454; and Sommadossi J-P, Schinazi R F, Chu C K, Xie M-Y. "Comparison of cytotoxicity of the (−)- and (+)-enantiomer of 2′,3′-dideoxy-3′-thiacytidine in normal human bone marrow progenitor cells" Biochemical Pharmacology 1992; 44:1921-1925. The culture assays for CFU-GM and BFU-E are performed using a bilayer soft agar or methylcellulose method. Drugs are diluted in tissue culture medium and filtered. After 14 to 18 days at 37° C. in a humidified atmosphere of 5% $CO_2$ in air, colonies of greater than 50 cells are counted using an inverted microscope. The results are presented as the percent inhibition of colony formation in the presence of drug compared to solvent control cultures.

Cytotoxicity Assay

Cells are seeded at a rate of between $5 \times 10^3$ and $5 \times 10^4$/well into 96-well plates in growth medium overnight at 37° C. in a humidified $CO_2$ (5%) atmosphere. New growth medium containing serial dilutions of the drugs is then added. After incubation for 4 days, cultures are fixed in 50% TCA and stained with sulforhodamine B. The optical density is read at 550 nm. The cytotoxic concentration is expressed as the concentration required to reduce the cell number by 50% ($CC_{50}$).

Cell Protection Assay (CPA)

The assay is performed essentially as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" *PNAS U.S.A.* 2000, 97(14), 7981-7986. MDBK cells (ATCC) are seeded onto 96-well culture plates (4,000 cells per well) 24 hours before use. After infection with BVDV (strain NADL, ATCC) at a multiplicity of infection (MOI) of 0.02 plaque forming units (PFU) per cell, serial dilutions of test compounds are added to both infected and uninfected cells in a final concentration of 0.5% DMSO in growth medium. Each dilution is tested in quadruplicate. Cell densities and virus inocula are adjusted to ensure continuous cell growth throughout the experiment and to achieve more than 90% virus-induced cell destruction in the untreated controls after four days post-infection. After four days, plates are fixed with 50% TCA and stained with sulforhodamine B. The optical density of the wells is read in a microplate reader at 550 nm. The 50% effective concentration ($EC_{50}$) values are defined as the compound concentration that achieved 50% reduction of cytopathic effect of the virus.

Plaque Reduction Assay

For each compound the effective concentration is determined in duplicate 24-well plates by plaque reduction assays. Cell monolayers are infected with 100 PFU/well of virus. Then, serial dilutions of test compounds in MEM supplemented with 2% inactivated serum and 0.75% of methyl cellulose are added to the monolayers. Cultures are further incubated at 37° C. for 3 days, then fixed with 50% ethanol and 0.8% Crystal Violet, washed and air-dried. Then plaques are counted to determine the concentration to obtain 90% virus suppression.

Biological Activity Against Drug Resistant Strains of HIV

In one embodiment, the efficacy of an anti-HIV compound is measured in vitro by a rapid, sensitive, and automated assay that involves the reduction of 3-(4,5-dimethylthiazol-2-yl)-2,5-diphenyltetrazolium bromide (MTT). An HIV-transformed cell line that is highly permissive and selective for HIV infection, such as, for example, the T-4 cell line, MT-4, is chosen as the target cell line (Koyanagi et al., *Int. J. Cancer*, 1985, 36:445-451). In situ reduction of 3-(4,5-dimethylthiazol-2-yl)-2,5-diphenyl-tetrazolium bromide (MTT) as assessed spectrophotometrically is the standard by which the viability of both mock-infected cells and HIV-infected cells is measured. Inhibition of the HIV-induced cytopathic effect serves as the end-point. A 50% cytotoxic concentration ($CC_{50}$ in µM) is defined as the concentration of compound that reduces the absorbance of the mock-infected control sample by 50%. The percent efficacy of an anti-HIV compound is calculated by the formula (expressed as a %):

$$(OD_{HIV\ test\ compound} - OD_{control}) / (OD_{mock\ infected\ cells} - OD_{control})$$

Here, ($OD_{HIV\ test\ compound}$) is the optical density measured for a specific amount of a test compound in HIV-infected cells; ($OD_{control}$) is the optical density measured for untreated HIV-infected, control cells; and ($OD_{mock\ infected\ cells}$) is the optical density measured for control, mock-infected cells that are untreated. Optical density values typically are assessed at 540 nm. The dosage of an anti-HIV test compound that provides 50% protection according to the preceding formula is defined as the 50% inhibitory concentration ($IC_{50}$ in µM). The selectivity index (SI) is defined as the ratio of the $CC_{50}$ to the $IC_{50}$.

In another embodiment, the p24 ELISA assay is used to determine the efficacy of an anti-HIV compound. This viral replication immunoassay measures the amount of p24 viral capsid (core) antigen present, and is available commercially from sources such as, for example, Coulter Corporation/Immunotech, Inc.® (Westbrook, Mich.).

Still other embodiments include a reverse transcriptase assay in which the amount of viral replication is measured by utilizing a homopolymer poly rA:oligo dT template primer system that quantifies the incorporation into cells of tritiated thymidine monophosphate by scintillation counting methods (Southern Research Institute, University of Alabama, Birmingham, Ala.); a syncytial inhibition assay that employs CEM-SS, HeLa-CD4, or HeLa-CD4-LTR-b-galactosidase cells having an immuno-fluorescent, chemiluminescent, or colorimetric endpoint; and an attachment- and fusion-inhibition assay that utilizes indicator cell lines and quantitation by chemiluminescent, colorimetric or microscopic evaluation (Southern Research Institute, University of Alabama, Birmingham, Ala.).

In one embodiment the indole compounds of the present invention do not exhibit cross resistance with other nonnucleoside reverse transcriptase inhibitors (NNRTIs), in that the compounds of the present invention display an $EC_{50}$ (in molar concentration) in a mutant HIV strain of less than approximately 50, 25, 10 or 1 µM concentration. In a typical embodiment, the NNRTIs display an $EC_{50}$ in a mutant HIV strain of less than approximately 5, 2.5, 1 or 0.1 µM concentration. The degree of cross-resistance against a drug resistant strain of HIV is measured by assessing the $EC_{50}$ of the desired oxo-pyrimidine compound in the target mutated, i.e., drug resistant, virus.

Pharmaceutical Compositions

Hosts, including humans, infected with a virus or any other condition described herein, can be treated by administering to the patient an effective amount of the active compound or a pharmaceutically acceptable salt or prodrug thereof optionally in the presence of a pharmaceutically acceptable carrier or diluent. The compounds can be administered to a subject in need thereof, optionally in combination or alternation with another therapeutic agent, and/or with a pharmaceutically acceptable carrier, diluent or excipient. In one embodiment, a subject infected with HIV may be treated by administering to that subject an effective amount of a compound disclosed herein, or a salt, prodrug, stereoisomer or tautomer thereof, in the presence of a pharmaceutically acceptable carrier or diluent. For subjects with multiple drug resistance, the phosphoindole compound is administered either alone or in combination with one or more other therapeutic agents. The active compounds may be administered by any appropriate route, for example, orally, parenterally, enterally, intravenously, intradermally, subcutaneously, percutaneously, transdermally, intranasally, topically or by inhalation therapy, and may be in solid, liquid or vapor form.

The active compound(s) in one embodiment are included within the pharmaceutically acceptable carrier, diluent or excipient in an amount sufficient to deliver to a patient a therapeutically effective amount of the active compound in order to e.g., inhibit viral infection, without causing serious toxic effects in a treated subject. An "inhibitory amount" includes an amount of active ingredient sufficient to halt viral replication as measured by, for example, an assay such as the ones referred to herein.

A typical dose of the compound may be in the range of from about 1 to about 50 mg/kg, from about 1 to about 20 mg/kg, of body weight per day, more generally from about 0.1 to about 100 mg/kg body weight of the recipient per day. Lower dosages may be used, for example, doses of about 0.5-100 mg, 0.5-10 mg, or 0.5-5 mg per kilogram body weight per day. Even lower doses may be useful, and thus ranges can include from about 0.1-0.5 mg/kg body weight of the recipient per day. The effective dosage range of the pharmaceutically acceptable derivatives is calculated based on the weight of the parent indole derivative compound to be delivered. If the derivative compound itself exhibits activity, then the effective dosage can be estimated as above using the weight of the derivative, or by other means known to those of skill in the art.

The compounds are conveniently administered in units of any suitable dosage form, including but not limited to one containing from about 7 to 3000 mg, from about 70 to 1400 mg, or from about 25 to 1000 mg of active ingredient per unit dosage form. For example, an oral dosage of from about 50 to 1000 mg is usually convenient, including in one or multiple dosage forms of 50, 100, 200, 250, 300, 400, 500, 600, 700, 800, 900 or 1000 mgs. Lower dosages may be preferable, for example, from about 10-100 or 1-50 mgs. Also contemplated are doses of 0.1-50 mg, 0.1-20 mgs., or 0.1-10 mgs. Furthermore, lower doses may be utilized in the case of administration by a non-oral route, as for example, by injection or inhalation.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compositions provided herein.

In certain embodiments, the compound or composition provided herein can be administered as a single once-a-day dose or preferably as divided doses throughout a day. In particular embodiments, the compound or composition is administered four times per day. In particular embodiments, the compound or composition is administered three times per day. In particular embodiments, the compound or composition is administered two times per day. In particular embodiments, the compound or composition is administered once per day.

In one embodiment, the active ingredient is administered to achieve peak plasma concentrations of the active compound of from about 0.02 to 70 µM, or from about 0.5 to 10 µM. For example, this can be achieved by intravenous injection of a 0.1 to 5% solution of active ingredient, optionally in saline, or administered as a bolus of active ingredient. It is to be understood that for any particular subject, specific dosage regimens should be adjusted over time to meet individual needs, and will vary depending upon absorption, inactivation and excretion rates of the drug. The concentrations set forth here are exemplary only and are not intended to limit the scope or practice of the claimed composition. The active ingredient may be administered all at once, or may be divided into a number of smaller doses to be administered at varying intervals of time.

One mode of administration of the active compound is oral. Oral compositions usually include an inert diluent or an edible carrier. They may be enclosed in gelatin capsules, compressed into tablets, or delivered in liquid form. For oral therapeutic administration, the active compound may be incorporated with excipients or formulated as solid dispersions or solid solutions, and used in the form of tablets, troches, or capsules. By a "solid dispersion" is meant a solid state comprising at least two components where one component is dispersed more or less evenly throughout the other component. By "solid solution" is meant a solid state comprising at least two components that are chemically and physically integrated to produce a homogeneous product. A solid solution is typical over a solid dispersion because it more easily forms a liquid solution upon contact with an appropriate liquid medium, thereby increasing the bioavailability of a drug. Pharmaceutically compatible binding agents and/or adjuvant materials also may be included as part of this composition.

The tablets, pills, capsules, troches and the like may contain any of the following ingredients or compounds of a similar nature: a binder such as microcrystalline cellulose, gum tragacanth or gelatin; an excipient such as starch or lactose; a disintegrating agent such as alginic acid, Primogel, or cornstarch; a lubricant such as magnesium stearate or Sterotes; a glidant such as colloidal silicon dioxide; a sweetening agent like sucrose of saccharin; and a flavoring agent, such as peppermint, methyl salicylate, or orange flavoring. When the dosage unit form is a capsule, it may contain a liquid carrier such as a fatty oil in addition to any material of the kinds given above. In addition, dosage unit forms may contain various other materials that modify the physical form of the dosage unit, such as, for example, coatings of sugar, shellac, or other enteric agents.

The compounds may be administered as a component of an elixir, suspension, syrup, wafer, chewing gum or the like. A syrup may contain sucrose as a sweetening agent, preservatives, dyes, colorings, and flavorings in addition to the active compounds.

The active compounds or their pharmaceutically acceptable salts or prodrugs can be mixed with other active materials that do not impair the desired action, or with materials that supplement the desired action, such as antibiotics, antifungals, anti-inflammatories, protease inhibitors, or other nucleoside or non-nucleoside antiviral agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates, and agents for the adjustment of tonicity such as sodium chloride or dextrose. A parenteral preparation normally will include sterile water and may be enclosed in ampoules, disposable syringes, or multiple dose vials made of glass or plastic.

If administered intravenously, certain carriers are physiological saline, phosphate buffered saline (PBS), a glucose solution, or a mixed solution comprising glucose and saline. In one embodiment, the active compound is prepared with a carrier that will protect the compound against rapid elimination from the body, such as a controlled release formulation, including an implant and/or microencapsulated delivery system. Biodegradable, biocompatible polymers can be used, such as ethylene vinyl acetate, polyanhydrides, polyglycolic acid, collagen, polyorthoesters and polylactic acid. The materials can be obtained commercially from Alza Corporation or prepared according to methods known to those skilled in the art. If administration is percutaneous, such as, for example, through the use of a patch or ointment, the associated carrier may comprise a penetration-enhancing agent and/or a suitable wetting agent which are not harmful to the skin. If inhalation or insufflation is the desired route of administration, then the composition of the present invention includes the compound in the form of a solution, suspension or dry powder that can be delivered through the oral and/or nasal orifices.

Liposomal suspensions, which include liposomes targeted to infected cells with monoclonal antibodies to viral antigens, also are typical as pharmaceutically acceptable carriers. These may be prepared according to methods known to those skilled in the art, for example, as described in U.S. Pat. No. 4,522,811, which is incorporated herein by reference in its entirety. For example, liposomal formulations may be prepared by dissolving appropriate lipid(s) such as stearoyl phosphatidyl ethanolamine, stearoyl phosphatidyl choline, arachadoyl phosphatidyl choline, and cholesterol, in an inorganic solvent that later is evaporated, leaving behind a thin film of dried lipid on the surface of the container. An aqueous solution of the active compound, or a salt or prodrug thereof, is then introduced into the container. The container is swirled to free lipid material from its sides and to disperse lipid aggregates, thereby forming the liposomal suspension.

Processes for Preparing the Active Compounds

An exemplary general scheme for the synthesis of phosphoindoles is provided in Scheme 1.

Scheme 1

General Scheme for Synthesis of Phosphoindoles

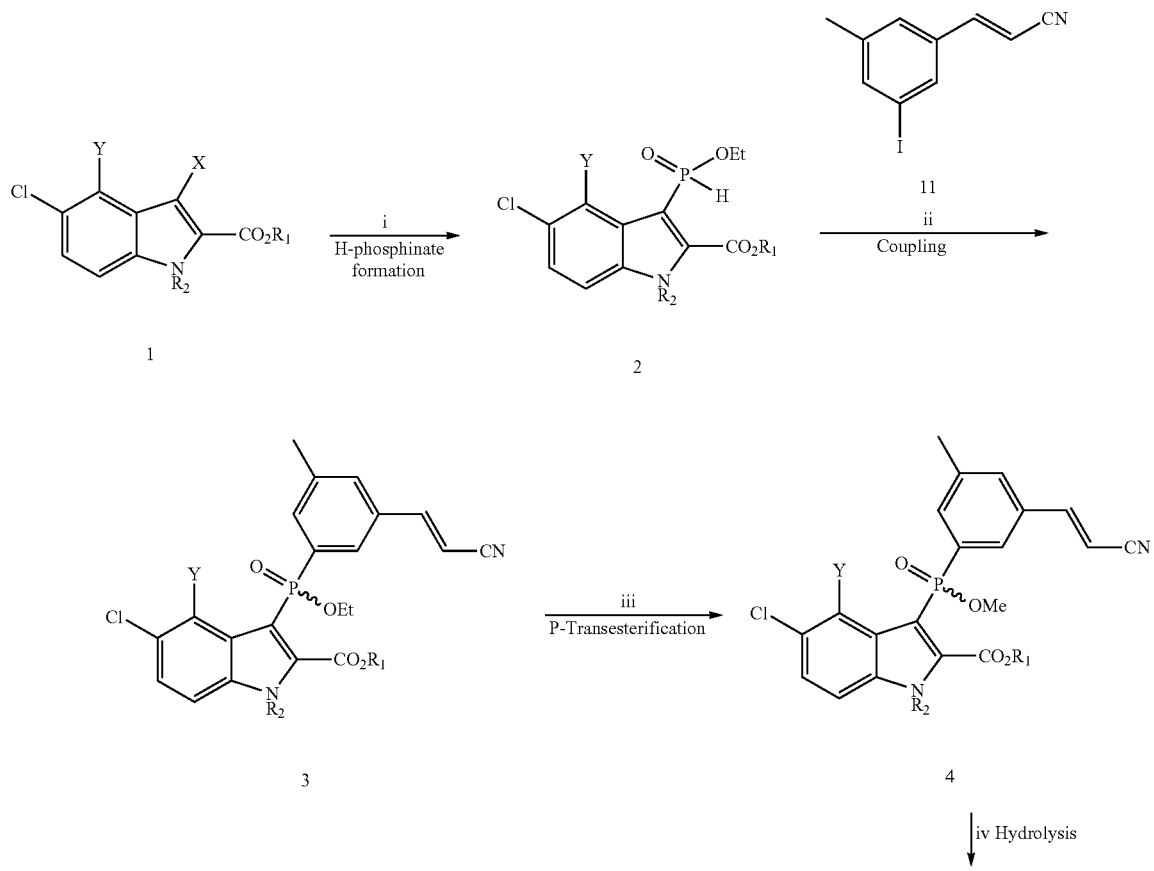

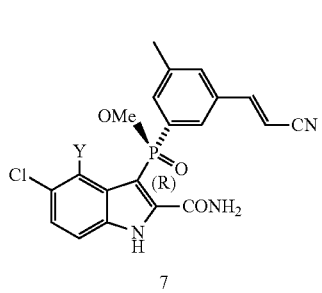
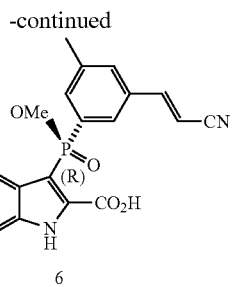
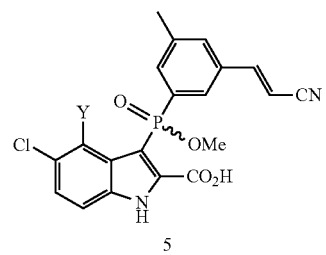

(S enantiomer recycled)

X = Br, I, OTf
Y = H, F
$R_1$ = Me, Et
$R_2$ = H, $SO_2Ph$, COMe, COPh, BOC

The synthesis involves treatment of the N-protected indole 1 with a suitable lithiating species, for example n-butyl lithium, followed by an appropriate phosphorus electrophile, for example diethylchlorophosphite, to give a P(III) intermediate which is partially hydrolyzed under acidic conditions to yield the H-phosphinate 2. Step ii consists of a palladium catalyzed coupling reaction between indole H-phosphinate 2 and iodocinnamonitrile 11. Transesterification from ethyl to methyl followed by hydrolysis of both the carboxylate ester and N-protecting groups, with for example lithium hydroxide or potassium t-butoxide at 5° C. in water-tetrahydrofuran, gives access to the indole acid 5. Chiral resolution of the enantiomers of 5, using a chiral base, followed by amide formation affords the final compound 7.

A second exemplary general scheme for the synthesis of phosphoindoles is provided in Scheme 2.

Scheme 2

General Scheme 2 for Synthesis of Phosphoindoles

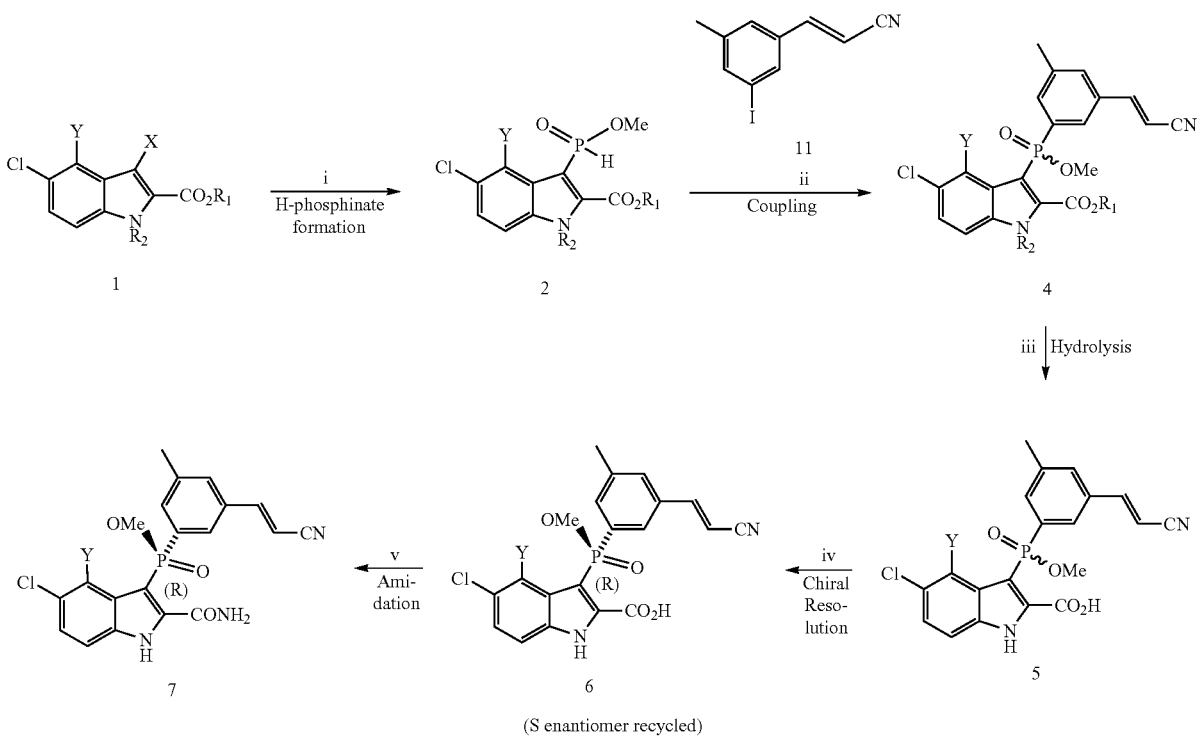

(S enantiomer recycled)

X = Br, I, OTf
Y = H, F
$R_1$ = Me, Et
$R_2$ = H, $SO_2Ph$, COMe, COPh, BOC

This synthesis involves treatment of the N-protected indole 1 with methyl phosphate under mild palladium catalysis conditions to yield the indole H-phosphinate 2. Step ii consists of a palladium catalyzed coupling reaction between indole H-phosphinate 2 and iodocinnamonitrile 11. Hydrolysis of both the carboxylate ester and N-protecting groups, with for example lithium hydroxide or potassium t-butoxide at 5° C. in water-tetrahydrofuran, gives access to the indole acid 5. Chiral resolution of the enantiomers of 5, using a chiral base, followed by amide formation affords the final compound 7.

An exemplary alternative route for the synthesis of phosphoindoles is shown in Scheme 3.

Scheme 3

Alternative Route for Synthesis of Phosphoindoles

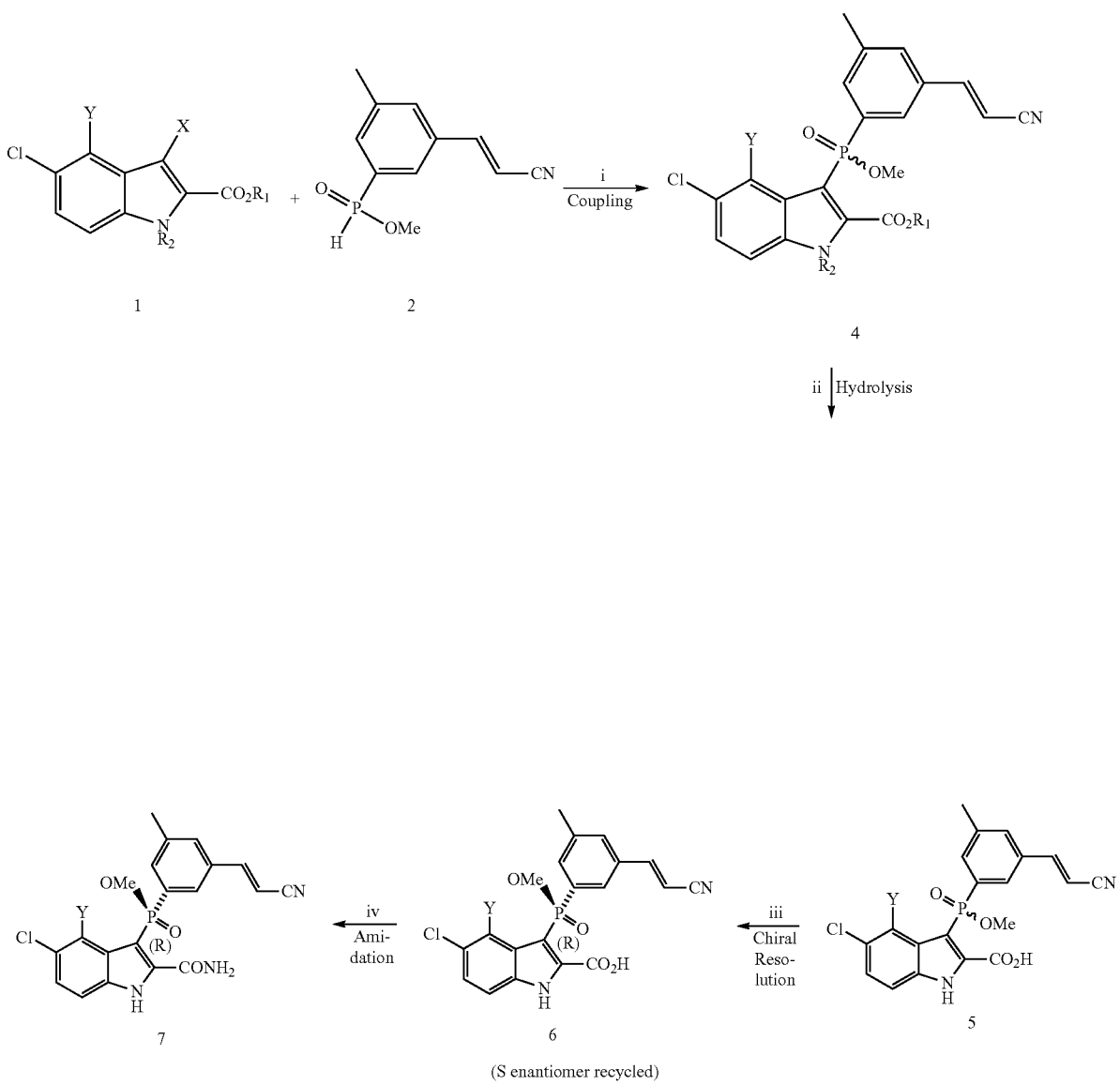

X = Br, I, OTf
Y = H, F
$R_1$ = Me, Et
$R_2$ = H, $SO_2Ph$, COMe, COPh, BOC

An alternative synthesis involves the coupling of N-protected indole 1 with aryl H-phosphinate 13 using palladium catalyst, ligand, base, in an appropriate solvent at moderate temperature to give the phosphoindole 4. Formation of aryl H-phosphinate 13 is described in Scheme 4. Hydrolysis of both the carboxylate ester and N-protecting groups, with for example lithium hydroxide or potassium t-butoxide at 5° C. in water-tetrahydrofuran, gives access to the indole acid 5. Chiral resolution of the enantiomers of 5, using a chiral base, followed by amide formation affords the final compound 7.

Exemplary iodocinnamonitrile and cinnamonitrile H-phosphinate syntheses are shown in Scheme 4.

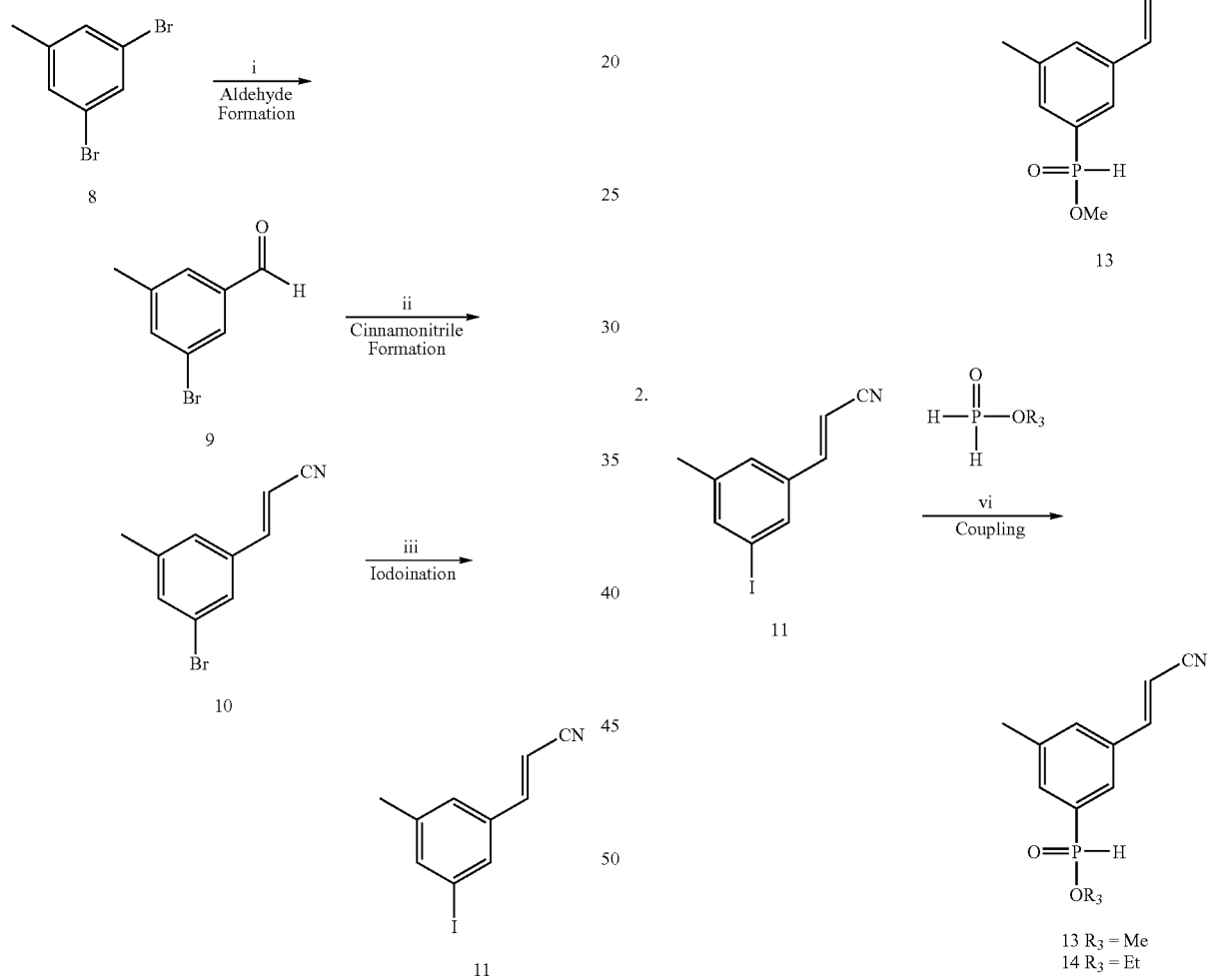

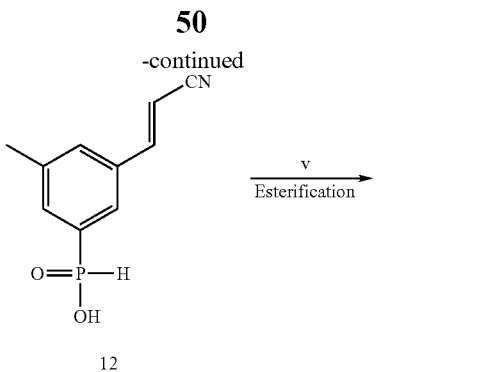

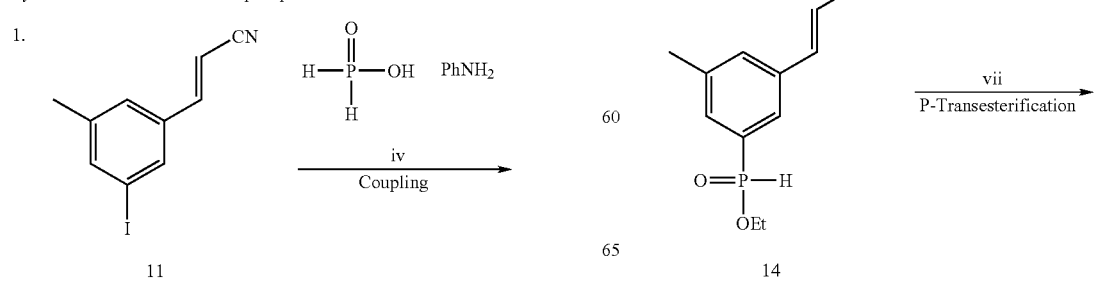

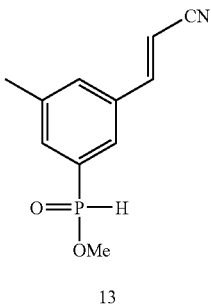

13

Iodocinnamonitrile 11 may be prepared from dibromotoluene 8. Mono-aldehyde formation of 9 is achieved by monolithiation, for example with n-butyl lithium and n-butyl magnesium chloride, and subsequent treatment with N,N-dimethylformamide. A Wittig-Horner-Emmons reaction on aldehyde 9 using, for example diethyl cyanomethylphosphonate and sodium hydride, proceeds to gives primarily the trans-isomer, which may be further enriched by crystallization to give bromocinnamonitrile 10. Iodoination is then performed to provide the desired intermediate 11.

Optionally the iodocinnamonitrile 11 may be converted into the aryl H-phosphinate 13 either by; 1. coupling with anilinium hypophosphorus acid salt followed by esterification or by 2. a direct palladium coupling with alkyl phosphinate. Additionally, the ethyl aryl H-phosphinate 14 may be transesterified to give the methyl H-phosphinate 13.

3-phosphoindoles can be prepared according to techniques known to those of skill in the art, including techniques described in U.S. Patent Application Publication No. 2006/0074054, the contents of which are hereby incorporated by reference in their entirety.

Another general synthesis for preparing the indole phosphinate is provided by the scheme below. The synthesis starts from indole 1, which is 3-halogenated and N-protected (or N-protected and 3-halogenated) to give protected indole 3. Protecting groups ("PG") can be phenylsulfonyl, tert-butylcarbamate (Boc), benzylcarbamate (Cbz), benzoyl, benzyl, paramethoxybenzyl or other substituted benzyl, tert-butyldimethylsilyl, tert-butyldiphenylsily or any N–1 indole protection. The latter 3 is either involved in a halogen-metal exchange, for example with n-Butyl lithium, and then reacts with a diethyl chlorophosphite to afford, after acidic hydrolysis, H-phosphinate 4 or involved in a palladium catalyzed reaction with hypophosphorous ester to afford same product 4. Indole H-phosphinate 4 is then involved in another palladium catalyzed reaction with an arylhalide to give indole 3-phosphinate 5. In the case of R different from Methyl group, a trans-esterification of 4 in ammonia in methanol gave H-phosphinate indolecarboxamide 6. This compound is also involved in a palladium catalysed reaction with an arylhalide to afford final compound 7.

Scheme 5

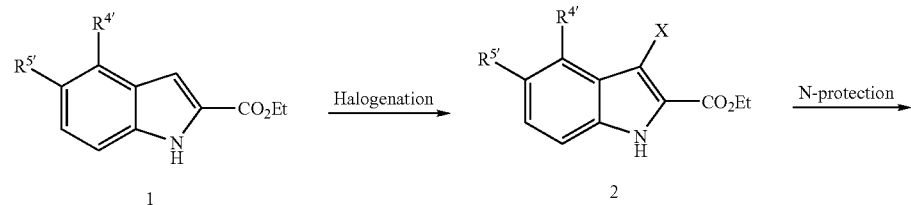

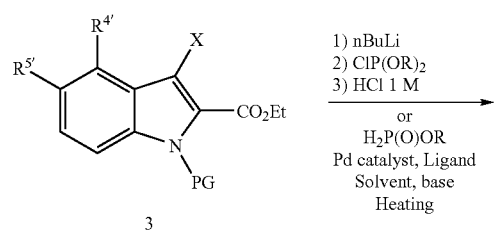

1) nBuLi
2) ClP(OR)$_2$
3) HCl 1 M
or
H$_2$P(O)OR
Pd catalyst, Ligand
Solvent, base
Heating

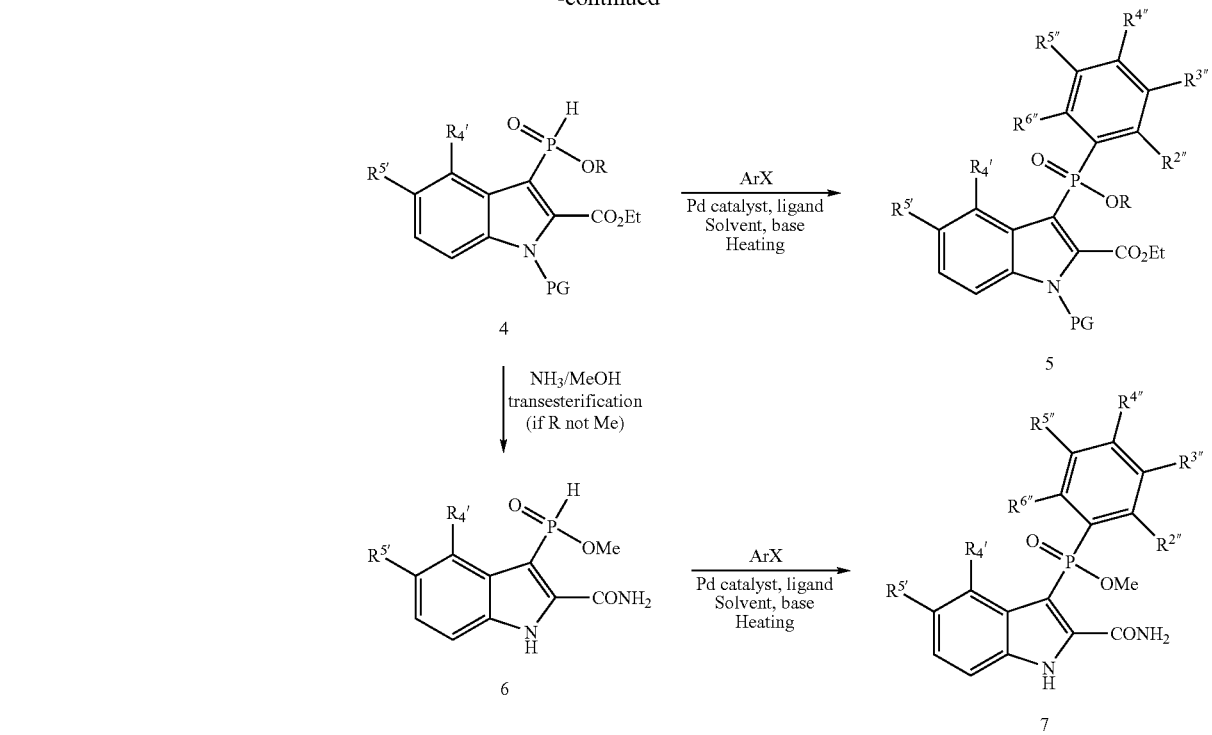

X = I, Br, OTf
R = Me, Et, Alk, Ar

Suitable palladium catalysts for the cross-coupling reaction include for example: palladium tetrakis(triphenylphosphine), palladium acetate, palladium propionate, palladium diacetonitriledichloride, dipalladium tris(dibenzylideneacetone) ($Pd_2\,dba_3$), palladium N-heterocylic carbene (NHC), or any other palladium catalyst that are known to those of skill in the art, used alone or in association with ligands such as triphenylphosphine, diphenylphosphinoferrocene, diphenylphosphinopropane or anyl phosphine or diphosphine ligands that are known to those of skill in the art. Suitable solvents for the palladium-catalyzed cross coupling reaction include for example: DMF, acetonitrile, NMP, dioxane, methanol, THF, toluene. Suitable bases for the palladium-catalyzed cross coupling reaction include for example: $Et_3N$, di-isopropylamine, $K_2CO_3$, $Na_2CO_3$, $NaHCO_3$, $Cs_2CO_3$, N-methylmorpholine, DABCO, DBU.

In further embodiments, 3-phosphoindoles can be prepared by reacting an H-arylphosphinate with a 3-iodoindole as depicted in the scheme below. The 3-iodoindole can be prepared by iodination of an indole using iodination reagents known to those of skill in the art. Optionally, the nitrogen atom of the 3-iodoindole can be protected with any protecting group deemed suitable to those of skill in the art. Reaction with an H-arylphosphinate provides the 3-phosphoindole compound. In the scheme, PG indicates the protecting group. The protecting group can be removed according to any technique known to those of skill in the art.

Scheme 6

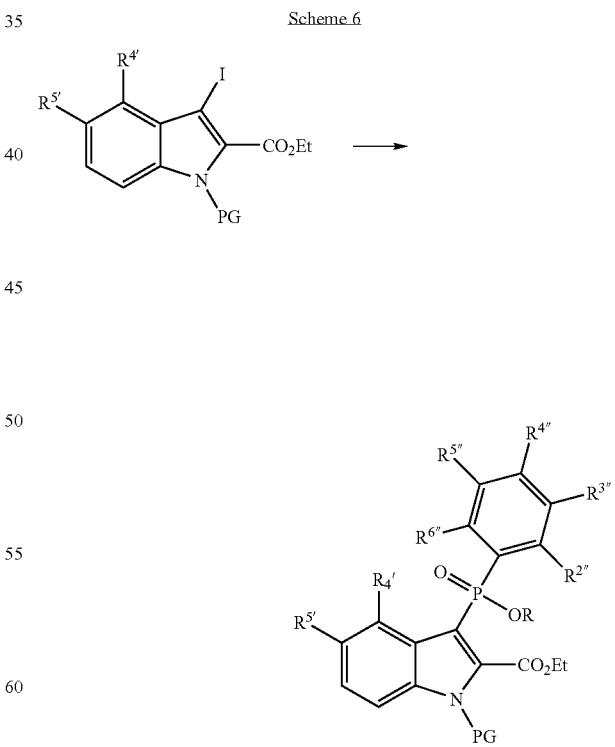

Preparation of Enantiomerically Pure 3-Phosphoindoles

The preparation of 3-phosphoindoles substantially in the form of one enantiomer may be achieved by resolution of racemic mixtures of 3-phosphoindoles prepared by any suitable method or by chiral synthesis from chiral starting materials, reagents or catalysts. The compounds may be prepared by one of the techniques described herein or by a combination of the techniques, where necessary. For example, chiral synthesis may be combined with chemical resolution to prepare an enantiomer of a 3-phosphoindole in the desired chemical and stereoisomeric purity. In addition, the stereoisomers of 3-phosphoindoles may be separated by chromatography using chiral solid phase. Chromatographic separation of diastereomeric derivates of stereoisomers of 3-phosphoindoles is also envisaged.

For resolving a mixture of chiral compounds, any method deemed suitable to those skilled in the art can be employed, e.g., formation of ionic, diastereomeric salts (or coordination complexes) with chiral compounds and separation by fractional crystallization or other methods, formation of diastereomeric compounds with chiral derivatizing reagents, separation of the diastereomers, and conversion to the pure enantiomers, separation of the enantiomers directly under chiral conditions on a variety of matrices including supercritical chromatography and enzymatic hydrolysis. See, e.g., Eliel & Wilen, 1994, *Stereochemistry of Organic Compounds*, John Wiley & Sons, Inc., New York (1994); Lochmuller, 1975, *J. Chromatogr.*, 113:(3) 283-302.

For example, diastereomeric salts can be formed by the reaction of enantiomerically pure chiral bases such as, for example, cinchonidine, brucine, quinine, ephedrine, strychnine, α-methyl-β-phenylethylamine (amphetamine), and the like with compounds provided herein. In certain embodiments, a diastereomeric salt is formed by reaction with an alkaloid such as cinchonidine. The diastereomeric salts may be induced to separate, for example, by fractional crystallization or ionic chromatography. Alternatively, a mixture of chiral compounds to be resolved can be reacted with one enantiomer of a chiral compound to form a diastereomeric pair. For example, diastereomeric compounds can be formed by reacting the compounds of the invention with enantiomerically pure chiral derivatizing reagents, such as, for example, menthyl derivatives, followed by separation of the diastereomers and hydrolysis to yield free, enantiomerically enriched compound. Alternatively, a mixture of chiral compounds can be separated by chromatography using a chiral stationary phase, see, e.g., *Chiral Liquid Chromatography*, W. J. Lough, Ed. Chapman and Hall, New York, (1989); Okamoto, 1990, *J. Chromatogr.* 513:375-378.

In certain embodiments, provided herein are methods of producing a compound of the invention by reaction of a racemic mixture with a chiral reagent followed by recovery of the resulting product and conversion to the compound of the invention. In certain embodiments, provided are methods of preparing a compound of any of Formulae A-D comprising the steps of reacting a racemic form of the compound with a chiral reagent such as cinchonidine, recovery of the reaction product and conversion to the compound of any of Formulae A-D. In particular embodiments, provided herein are methods of producing compound I comprising the step of contacting the racemic form of the 2-carboxyl derivative of compound I with (−)-cinchonidine, recovery of the reaction product, and conversion to compound I with, e.g., acid followed by amide formation. In particular embodiments, provided herein are methods of producing compound II comprising the step of contacting the racemic form of the 2-carboxyl derivative of compound II with (+)-cinchonine, recovery of the reaction product, and conversion to compound II with, e.g., acid followed by amide formation. In particular embodiments, provided herein are methods of producing compound III comprising the step of contacting the racemic form of the 2-carboxyl derivative of compound III with (−)-cinchonidine, recovery of the reaction product, and conversion to compound III with, e.g., acid followed by amide formation. In particular embodiments, provided herein are methods of producing compound IV comprising the step of contacting the racemic form the 2-carboxyl derivative of compound IV with (+)-cinchonine, recovery of the reaction product, and conversion to compound IV with, e.g., acid followed by amide formation. In further embodiments, provided herein are alternate methods with other chiral reagents such as ephedrine and ephedrine hemihydrate.

In certain embodiments, provided herein are methods of producing a compound provided herein by recycling its opposite enantiomer. In such embodiments, a racemic mixture is resolved according to a technique described herein. In addition to obtaining the desired enantiomer, the opposite enantiomer can be recycled to increase the yield of the desired enantiomer. For instance, a compound of Formula B can be recycled to yield a compound of formula A, and vice versa. A compound of formula D can be recycled to yield a compound of Formula C, and vice versa. In a recycling reaction, a compound is contacted with a reagent capable of racemizing the compound. For instance, in certain embodiments, a phosphoindole compound provided herein is contacted with a racemization reagent capable of reacting with its phospho group. In certain embodiments, the racemization reagent is, for example, an acid, a base or a halogenation reagent. In certain embodiments, the racemization reagent is, for example, oxalyl chloride. After contact with the racemization reagent, the enantiomers can be resolved according to any technique described herein. In particular embodiments, compound II can be recycled to yield compound I. In particular embodiments, compound IV can be recycled to yield compound III. Exemplary methods are provided below.

The methods below describe the synthesis of enantiomerically pure 3-phosphoindoles of Formulae A-D or Compounds I-IV as non-limiting examples of these techniques.

1. Dynamic Kinetic Resolution (DKR)

In a kinetic resolution, starting from a racemic mixture S ($S_R$ and $S_S$), one enantiomer will react preferentially to give product $P_R$ with a theoretical maximum yield of 50%. If racemization can occur concurrently with kinetic resolution, then theoretically 100% of the racemic mixture can be converted to one enantiomer (Scheme 7). This process is known as dynamic kinetic resolution (DKR).

Scheme 7: (S = substrate, P = product)

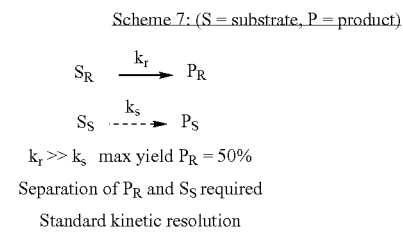

$k_r \gg k_s$  max yield $P_R$ = 50%

Separation of $P_R$ and $S_S$ required

Standard kinetic resolution

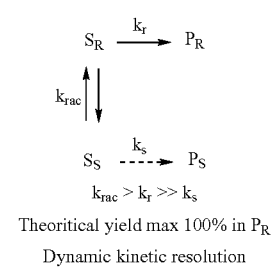

$k_{rac} > k_r \gg k_s$

Theoritical yield max 100% in $P_R$

Dynamic kinetic resolution

The problems associated with standard kinetic resolution are that only a maximum theoretical yield of 50% is possible, and the separation of the desired product from a substantial amount of the unconverted substrate is necessary. For an efficient DKR, there are some specific requirements (Strauss, U. T.; Felfer, U.; Faber, K. *Tetrahedron: Asymmetry* 1999, 10, 107):

1. The kinetic resolution should be irreversible in order to ensure high enantioselectivity.

2. The enantiomeric ratio (E=$k_R/k_S$) should be at least greater than ~20.

3. To avoid depletion of $S_R$, the rate of racemization ($k_{rac}$) should be at least equal to or greater than the reaction rate of the fast enantiomer ($k_R$).

4. In the case where the selectivities are only moderate, $k_{rac}$ should be greater than $k_R$ by a factor of ~10.

5. Any spontaneous reaction involving the substrate enantiomers as well as racemization of the product should be absent.

Scheme 8

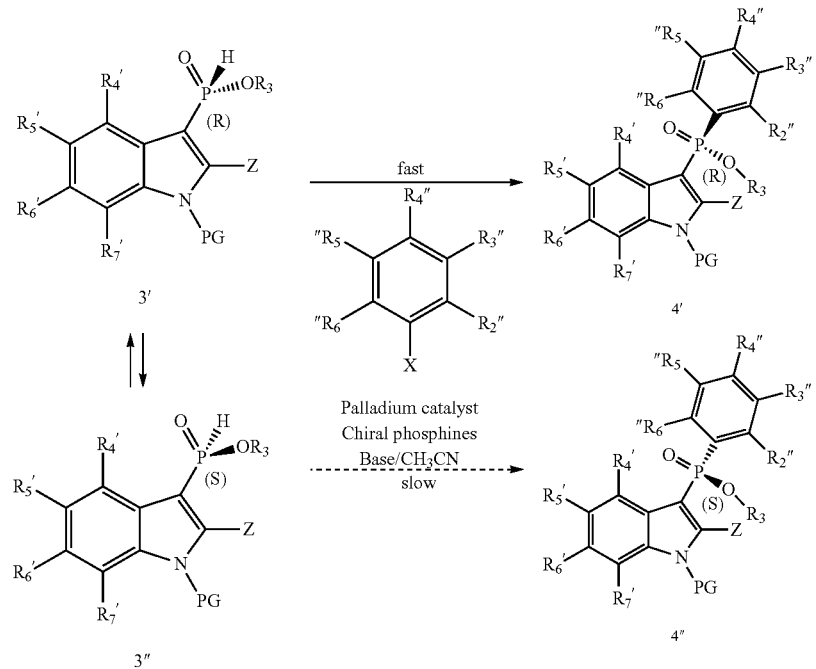

In one embodiment, the synthesis of enantiomerically pure 3-phosphoindoles, the chiral discrimination between the enantiomers in order to react with the aryl halide is realized with a chiral phosphine, which is a component of the palladium catalyst, and will produced preferentially compound 4' (Scheme 8). This palladium coupling reaction is a variation of the palladium coupling reactions described in the schemes above for the preparation of racemic mixtures of 3-phosphoindoles. The chiral phosphine ligands may be any suitable ligand that produces the required selectivity and rate of reaction in the transformation of 3-phosphoindole 3' to substituted 3-phosphoindole 4'. The chiral phosphine ligands may be monodentate or bidentate ligands. Non-limiting examples of chiral phosphine ligands include P-chiral ferrocenyl phosphines, (R)-(+)-BINAP, (S)-(−)-BINAP, (R,R)-CHIRAPHOS, and (S,S)-CHIRAPHOS.

Scheme 10

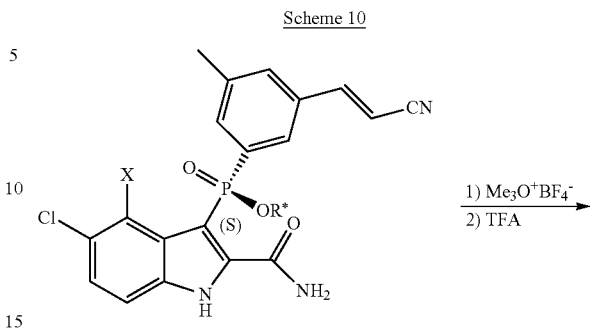

Scheme 9

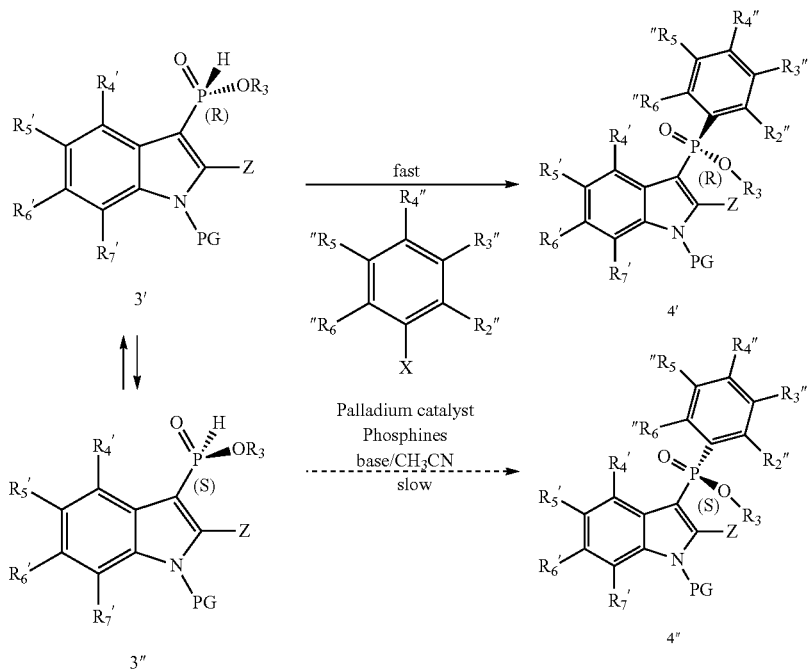

Where chirality is induced by chiral groups: $R_3$, Z or PG, or using chiral phosphines In another embodiment, the chiral discrimination may be introduced by appending a chiral group to the racemic mixture of 3-phosphoindoles, producing a mixture of diastereomers which will react at different rates with the non-chiral palladium catalyst system (Scheme 9). The second chiral center may be added as a component of the substituent $R_3$, the group Z or the protecting group PG. The chiral group is not limited, and any group that induces the desired selectivity in the reaction at a reasonable rate may be used. One non limiting example of a chiral group that may be utilized as $R_3$ in this reaction includes a chiral alcohol, for example (+) or (−)-menthol. Other non-limiting examples of groups that may be used as group Z or PG in Scheme 9 include a chiral ester or a chiral sulfone.

When $R_3$ is chiral (R*), for the transformation into target 3-phosphoindole, the chiral moiety R* may be removed using the conditions described in JOC 1975, 1523-1525 using a trialkyoxonium salt following by acidic cleavage, with inversion of configuration (Scheme 10):

-continued

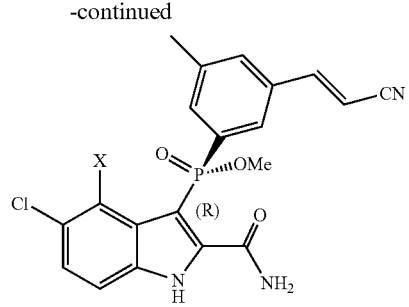

The same process of DKR may also be utilized with a racemic aryl H-phosphinate and a bromoindole in a cross coupling reaction (Scheme 11):

Scheme 11

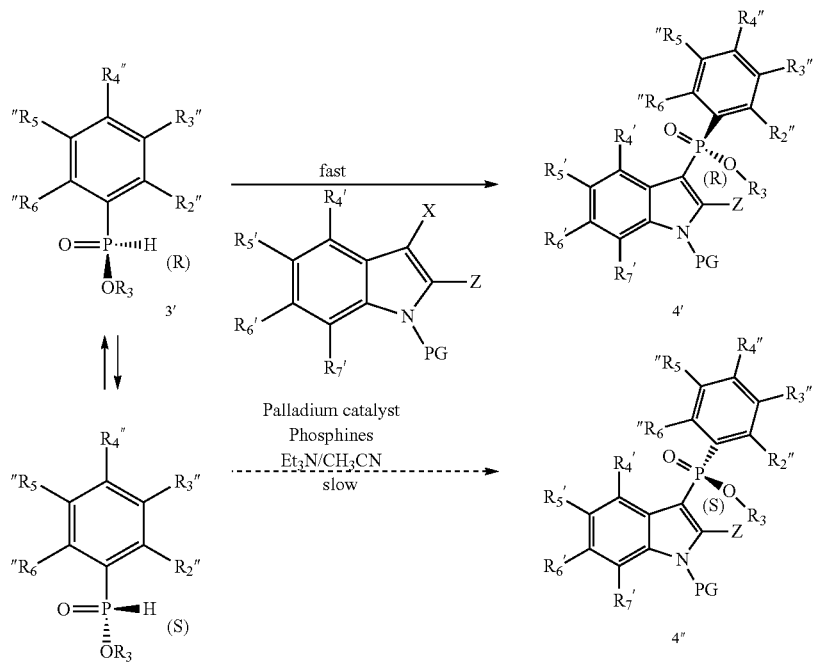

Where chirality is induced by chiral groups: $R_3$, Z, PG or using a chiral phosphines Specific DKR Scheme In the following non-limiting example of a DKR process depicted in Scheme 12, the Pd catalyst is palladium acetate, the chiral phosphine is (R)-1-[(S)-2-Di-2-furylphosphino)-ferrocenyl]ethyldi-(2-methylphenyl)phosphine, the base is diisopryl ethylamine and the solvent is acetonitrile. After heating at 100° C. the major compound is obtained with an enantiomeric excess of 40%.

Scheme 12

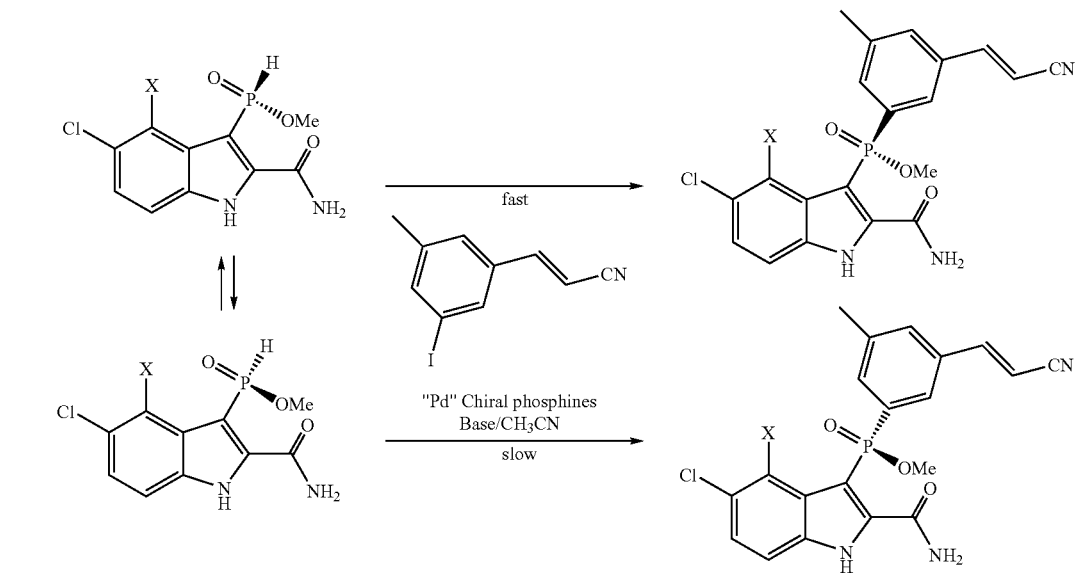

2. Chemical Resolution of 3-Phosphoindoles

The resolution of the 3-phosphoindoles free acids may be accomplished by chemical resolution using a chiral base. A chiral base will exhibit selectivity toward the free acid of one of the two enantiomers of the 3-phosphoindoles, thereby providing the means to resolving the enantiomers. As described in the Example below, chemical resolution of the 2-carboxyl derivative of 3-phosphoindoles of Formula I/II can be performed on I using (−)-Cinchonidine 2 (Scheme 13, to obtain the required enantiomer, first eluting isomer by chiral HPLC analysis) and (+)-Cinchonine 3 (which can be used to remove the undesired enantiomer from the filtrate, second eluting isomer by chiral HPLC analysis). The undesired enantiomer can be racemized to obtain more material.

A strategy could also be applied using chiral alpha-methyl substituted benzylamine as depicted in the scheme below.

Indole 1 is halogenated at position 3 then the ester function is hydrolysed to give indole 3. A chiral (where the chirality is defined S or R) alpha-methyl substituted(or unsubstituted) benzylamine is then introduced at the carboxylic function of the indole 3 via a "peptide type" coupling reaction. Alternatively 4 could be prepared via formation of acid chloride by treating acid 3 with chlorinated reagent then addition of the chiral alpha-methyl substituted (or unsubstituted) benzylamine. Intermediate 4 is then involved in a palladium catalyzed reaction to afford a mixture of diastereoisomers 5a and 5b. The mixture of 5a and 5b could be separated either by silica gel or recrystallisation. 5b (R chirality on the phosphorus) is then involved in a cleavage reaction to remove chiral moiety at position 2 and afford pure (R)-enantiomer 6. 5a could be recycled by transformation into a phosphinic acid by cleavage (eg with TMSBr) then resterified to afford a mixture of 5a and 5b, then the diastereoisomers could be re-separated.

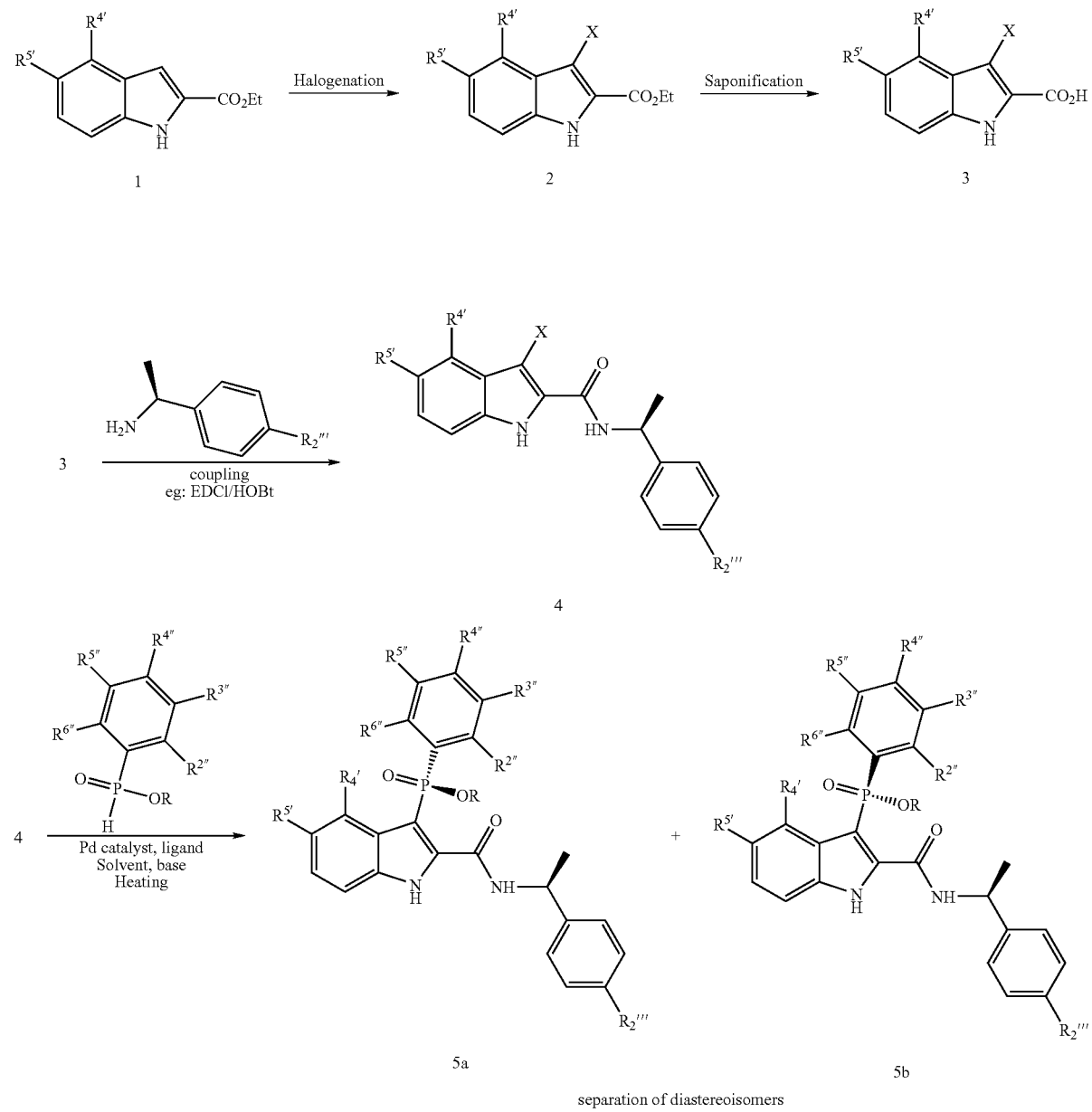

Scheme 13 separation of diastereoisomers

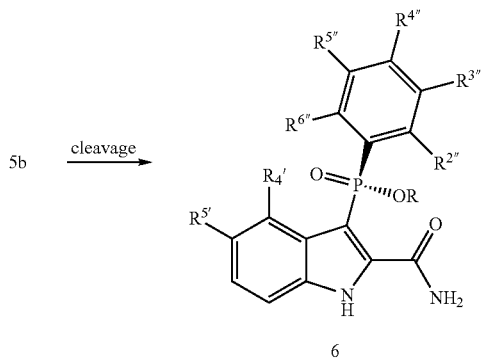
EXAMPLES
Example 1
The present example describes the preparation of compound III and compound I.
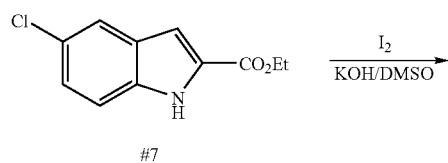
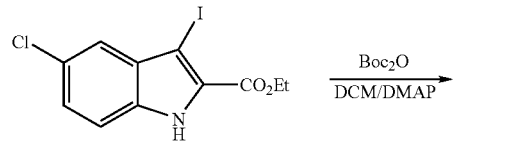
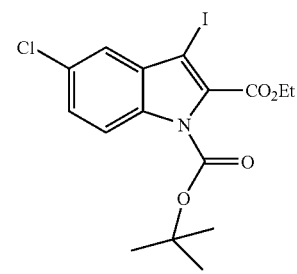
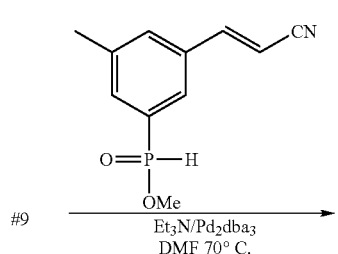
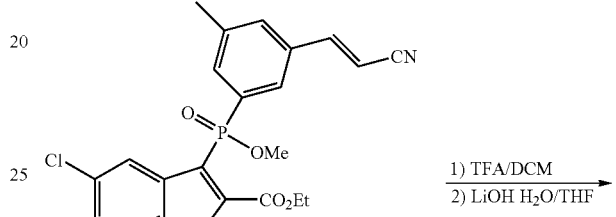
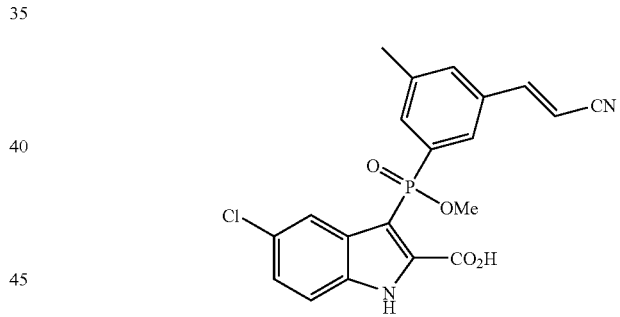
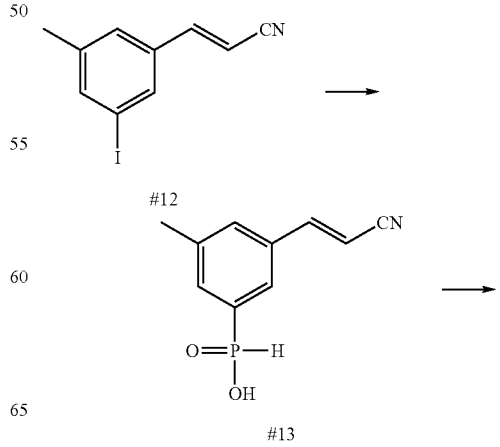

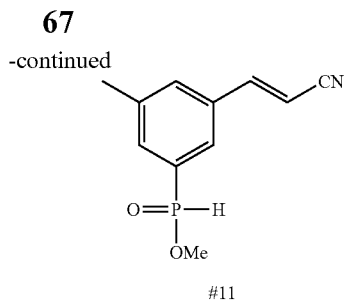

Reaction 7 to 8:

To a flask was added under argon indole 7 (1 eq) was added Iodine (1.98 eq.), solid potassium hydroxide (1 eq.) and anhydrous DMF (4.5 mL/mmol). The reaction mixture was stirred 3 hours then water was added and the slurry filtered through paper filter, the solid was dried under reduced pressure and triturated/filtered in water several times to yield after dryed under reduced pressure the 3-iodoindole 8. $^1$H NMR (CDCl3, 400 MHz) δ 1.45 (t, 3H), 4.50 (q, 2H), 7.20-7.40 (m, 2H), 7.55 (s, 1H), 9.40 (br s, 1H).

Reaction 8 to 9:

To a stirred solution of indole 8 (1 eq) in dichloromethane (3.5 mL/mmol) under nitrogen was added di-tert-butyl dicarbonate (1.8 eq.) and 4-dimethylaminopyridine (2 eq.). The reaction mixture was stirred 18 hours then phosphate buffer (pH=7) was added and extracted with dichloromethane. Combined organic layers were dried ($Na_2SO_4$) and concentrated under reduced pressure. The crude residue was purified by flash chromatography on silica gel (eluent: petroleum ether/EtOAc:1/1) to afford N-Boc-protected indole 9. Slight yellow solid. $^1$H NMR (d$_6$-DMSO, 400 MHz) δ 1.34 (t, J=8.0 Hz, 3H), 1.56 (s, 9H), 4.35 (q, J=8.0 Hz, 2H), 7.46 (d, J=4.0 Hz, 1H), 7.55 (dd, J=12.0 and 4.0 Hz, 1H), 8.0 (d, J=12.0 Hz, 1H), MS (ES$^-$) m/z=448 (M–H).

Reaction 9 to 10:

A stirred solution of degassed DMF with $N_2$, N-Boc 3-iodoindole 9 (1 eq.), H-arylphosphinate 11 (1.1 eq.), triethylamine (2 eq.) and $Pd_2 dba_3$ (0.2 eq.) was heated at 70° C. or 90° C. until reaction is finished according to TLC or HPLC analysis. Reaction mixture was cooled down to room temperature and solvent was evaporated. The crude residue was purified by flash chromatography on silica gel (eluent: petroleum ether/EtOAc:8/2) to afford indole phosphinate 10 (with also some deprotected indole). White solid. $^1$H NMR (d$_6$-DMSO, 400 MHz) δ 1.26 (t, J=7.1 Hz, 3H), 1.58 (s, 9H), 2.35 (s, 3H), 3.70 (d, J=11.5 Hz, 3H), 4.29 (m, 2H), 6.53 (d, J=16.8 Hz, 1H), 7.53 (dd, J=9.0 and 2.2 Hz, 1H), 7.65 (d, J=13.3 Hz, 1H), 7.70 (d, J=16.8 Hz, 1H), 7.76 (s, 1H), 7.84 (d, J=13.3 Hz, 1H), 7.92 (d, J=2.2 Hz, 1H), 8.06 (d, J=9.0 Hz, 1H), MS (ES$^+$) m/z=543 (MH$^+$).

Reaction 12 to 13:

The iodoaryl 12 (1 eq), dimethylformamide (1 ml/mmol), triethylamine (3 eq) and the anilinium hypophosphorous salt* (1.25 eq) were put in a pressure tube and degassed with $N_2$ for 15 min. Then palladium tetrakis was added and this mixture was stirred at 85° C. overnight.

The solvent was evaporated and water was added (pH=5-6). The mixture was basified with $NaHCO_3$ until pH=8 and extracted with diethyl ether. Aqueous layer was acidified with HCl 1N until pH=1 and extracted with ethyl acetate. Combined organic layers were dried, filtered and concentrated under reduce pressure to give the compound #13.

Anilinium salt was synthesised according to the procedure of Montchamp et al (*J. Am. Chem. Soc.*, 2001, 123, 510-511).

Off-white solid. $^1$H NMR (d$_6$-DMSO, 400 MHz) δ 6.54 (d, J=16.8 Hz, 1H), 7.46 (d, J=549.8 Hz, 1H), 7.57 (d, J=13.6 Hz, 1H), 7.71 (m, 3H), $^{31}$P NMR (d$_6$-DMSO, 121.49 MHz) δ 15.56, MS (ES$^-$) m/z=208.

Reaction 13 to 11

Pyridine (1 eq) was carefully added to a vigorously stirred solution of alkyl chloroformate (1 eq) and arylphosphinic acid 12 (1 eq) in dichloromethane (2 ml/mmol) at room temperature. Once effervescence had stopped, the solution was refluxed for 15 minutes and then allowed to cool to room temperature. The solution was poured into 0.1M hydrochloric acid (1 ml/mmol) and the organic layer was separated. After washing with water and drying over $Na_2SO_4$, the solvent was removed in vacuo to give the compound #11. White solid. $^1$H NMR (d$_6$-DMSO, 400 MHz) δ 2.40 (s, 3H), 3.71 (d, J=12.2 Hz, 3H), 6.58 (d, J=16.8 Hz, 1H), 7.52 (d, J=576, 0 Hz, 1H), 7.63 (d, J=14.0 Hz, 1H), 7.71 (d, J=16.8 Hz, 1H), 7.80 (m, 2H), MS (ES$^-$) m/z=222.

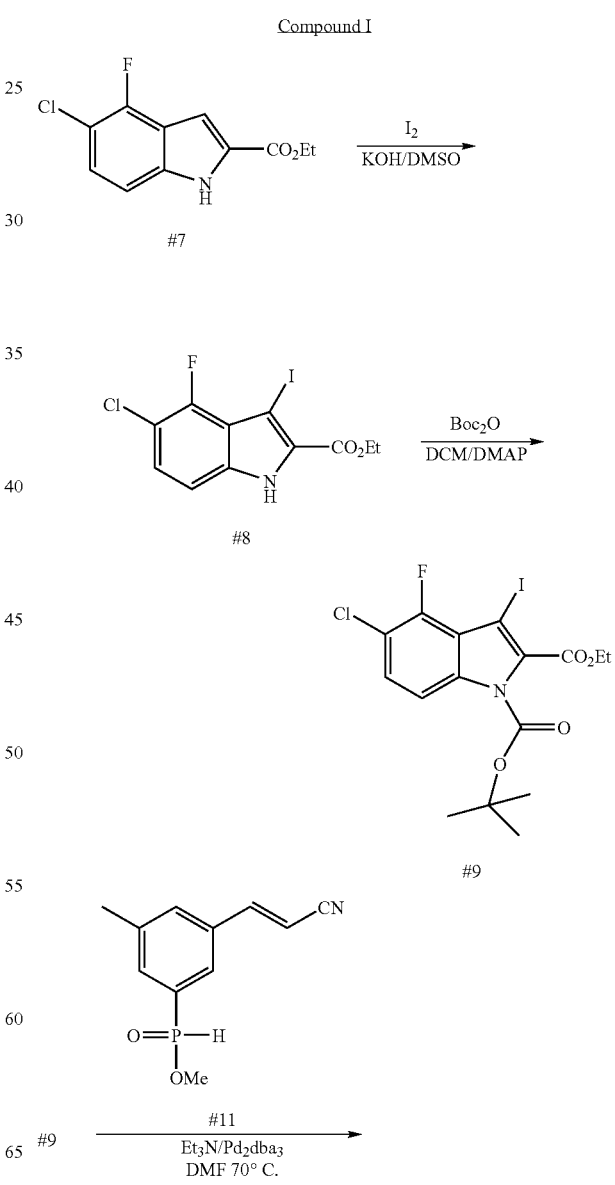

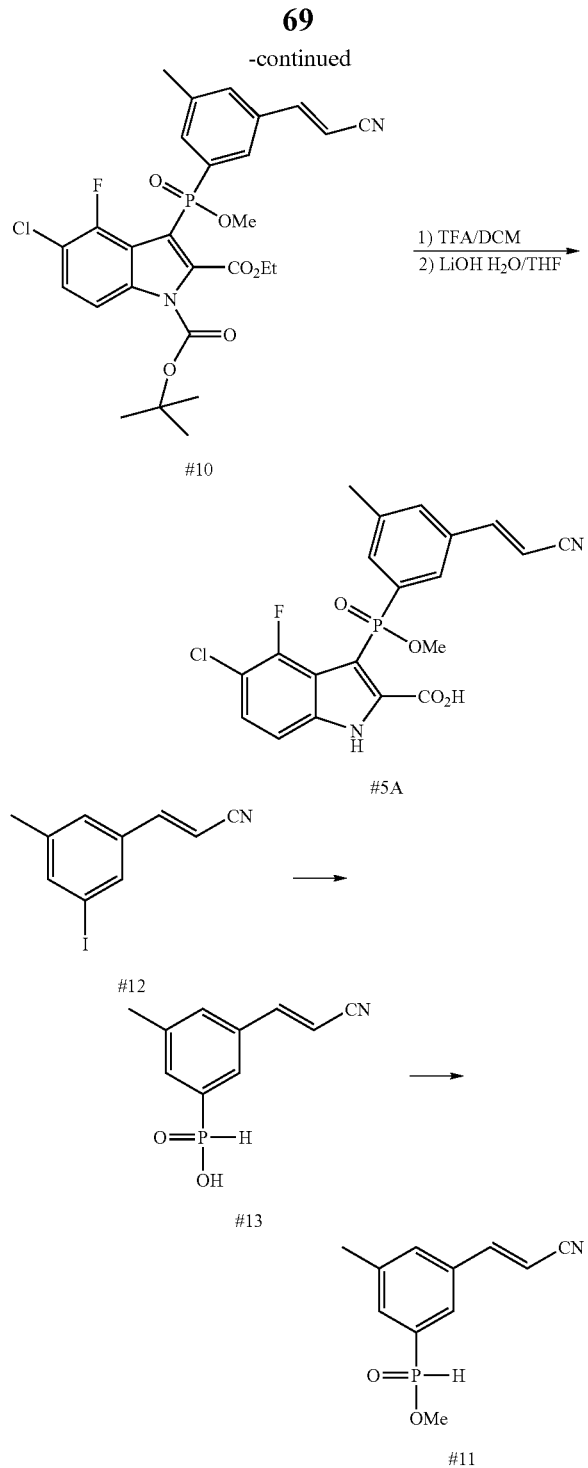

Reaction 7 to 8:

To a stirred solution of indole 7 (1.0 eq.) in dimethylformamide (4.4 mL/mmol) under argon was added iodine (1.98 eq.) and potassium hydroxide (1.0 eq.). The reaction mixture was stirred for 3 hours. The reaction mixture was quenched by addition of water (8.8 ml/mmol) and product precipitated, which was filtered and dried. The solid was resubmitted to reaction conditions (dimethylformamide (4.4 mL/mmol) under argon, iodine (0.4 eq.) and potassium hydroxide (0.2 eq.) and stirred for 1 h) to convert the remaining starting material. The reaction mixture was quenched by addition of water (8.8 ml/mmol) and product precipitated, which was filtered and dried to afford 3-iodoindole 8. Beige solid. $^1$H NMR ($d_6$-DMSO, 400 MHz) δ 1.39 (t, J=7.2 Hz, 3H), 4.40 (q, J=7.2 Hz, 2H), 7.35-7.42 (m, 2H), 12.66 (s, 1H), $^{19}$F NMR ($d_6$-DMSO, 376 MHz) δ −126.87, MS (ESI−) m/z=366.13 (M−H)$^-$ 100%, 368.15 (M−H)$^-$ 35%.

Reaction 8 to 9:

To a stirred solution of indole 8 (1 eq) in dichloromethane (3.5 mL/mmol) under nitrogen was added di-tert-butyl dicarbonate (1.8 eq.) and 4-dimethylaminopyridine (2 eq.). The reaction mixture was stirred 18 hours then phosphate buffer (pH=7) was added and extracted with dichloromethane. Combined organic layers were dried ($Na_2SO_4$) and concentrated under reduced pressure. The crude residue was purified by flash chromatography on silica gel (eluent: petroleum ether/EtOAc:1/1) to afford N-Boc-protected indole 9. White solid. $^1$H NMR ($d_6$-DMSO, 400 MHz) δ 1.35 (t, J=7.1 Hz, 3H), 1.57 (s, 9H), 4.39 (q, J=7.1 Hz, 2H), 7.64 (dd, J=7.3 and 9.1 Hz, 1H), 7.90 (d, J=9.1 Hz, 1H), $^{19}$F NMR ($d_6$-DMSO, 377 MHz) δ −126.9, MS (ESI, EI$^+$) m/z=490 (M+Na$^+$).

Reaction 9 to 10:

A stirred solution of degassed DMF with $N_2$, N-Boc 3-iodoindole 9 (1 eq.), H-arylphosphinate 11(1.1 eq.), triethylamine (2 eq.) and $Pd_2 dba_3$ (0.2 eq.) was heated at 70° C. or 90° C. until reaction is finished according to TLC or HPLC analysis. Reaction mixture was cooled down to room temperature and solvent was evaporated. The crude residue was purified by flash chromatography on silica gel (eluent: petroleum ether/EtOAc:8/2) to afford indole phosphinate 10 (with also some deprotected indole). White solid. $^1$H NMR ($d_6$-DMSO, 400 MHz) δ 1.34 (t, J=7.1 Hz, 3H), 1.62 (s, 9H), 2.35 (s, 3H), 3.66 (d, J=11.6 Hz, 3H), 4.37 (q, J=7.1 Hz, 2H), 6.51 (d, J=16.7 Hz, 1H), 7.58-7.65 (m, 2H), 7.69-7.77 (m, 3H), 7.94 (d, J=9.5 Hz, 1H), $^{19}$F NMR ($d_6$-DMSO, 377 MHz) δ −116.0 (s, 1F), $^{31}$P NMR ($d_6$-DMSO, 162 MHz) δ 23.42 (s, 1P), MS (ESI, EI$^+$) m/z=561 (M+H$^+$).

Reaction 12 to 13:

The iodoaryl 12 (1 eq), dimethylformamide (1 ml/mmol), triethylamine (3 eq) and the anilinium hypophosphorous salt* (1.25 eq) were put in a pressure tube and degassed with $N_2$ for 15 min. Then palladium tetrakis was added and this mixture was stirred at 85° C. overnight.

The solvent was evaporated and water was added (pH=5-6). The mixture was basified with $NaHCO_3$ until pH=8 and extracted with diethyl ether. Aqueous layer was acidified with HCl 1N until pH=1 and extracted with ethyl acetate. Combined organic layers were dried, filtered and concentrated under reduce pressure to give the compound #13.

Anilinium salt was synthesised according to the procedure of Montchamp et al (*J. Am. Chem. Soc.*, 2001, 123, 510-511).

Off-white solid. $^1$H NMR ($d_6$-DMSO, 400 MHz) δ 6.54 (d, J=16.8 Hz, 1H), 7.46 (d, J=549.8 Hz, 1H), 7.57 (d, J=13.6 Hz, 1H), 7.71 (m, 3H), $^{31}$P NMR ($d_6$-DMSO, 121.49 MHz) δ 15.56, MS (ES$^-$) m/z=208.

Reaction 13 to 11

Pyridine (1 eq) was carefully added to a vigorously stirred solution of alkyl chloroformate (1 eq) and arylphosphinic acid 13 (1 eq) in dichloromethane (2 ml/mmol) at room temperature. Once effervescence had stopped, the solution was refluxed for 15 minutes and then allowed to cool to room temperature. The solution was poured into 0.1M hydrochloric acid (1 ml/mmol) and the organic layer was separated. After washing with water and drying over $Na_2SO_4$, the solvent was removed in vacuo to give the compound #11. White solid. $^1$H NMR ($d_6$-DMSO, 400 MHz) δ 2.40 (s, 3H), 3.71 (d, J=12.2 Hz, 3H), 6.58 (d, J=16.8 Hz, 1H), 7.52 (d, J=576, 0 Hz, 1H), 7.63 (d, J=14.0 Hz, 1H), 7.71 (d, J=16.8 Hz, 1H), 7.80 (m, 2H), MS (ES$^-$) m/z=222.

Certain compounds of the instant example were prepared by the scheme and methods below.
Scheme 14: H-Arylphosphinate coupling with 3-iodoindole
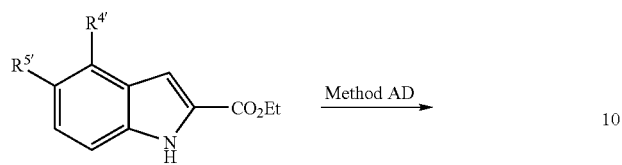
10
Method AD →
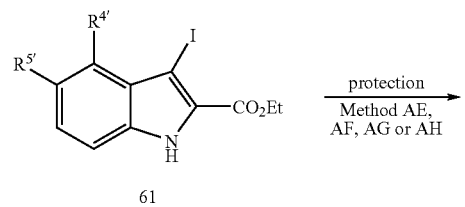
61
protection
Method AE,
AF, AG or AH
→
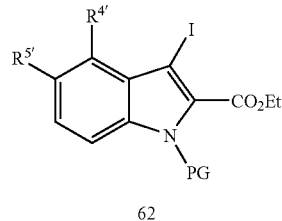
62
Method AI →
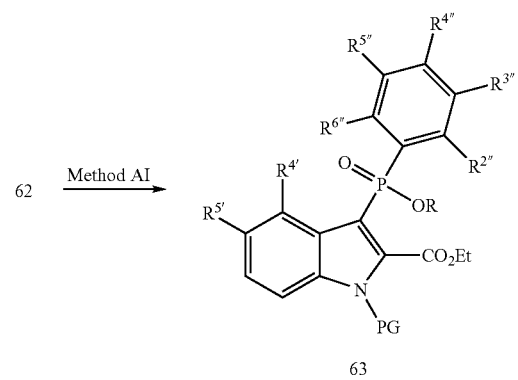
63
R = Me, Et
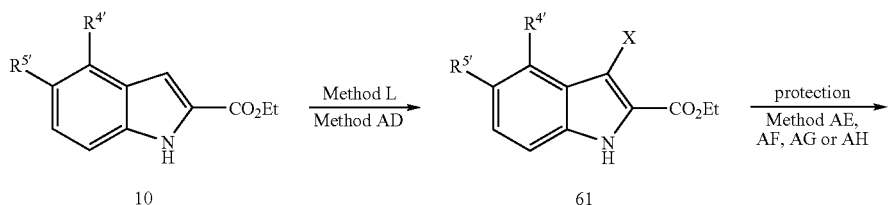
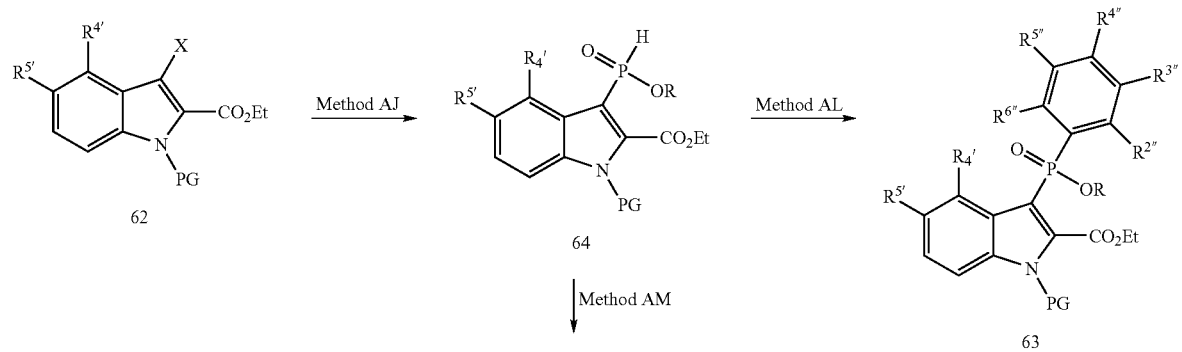
Method AM ↓

-continued

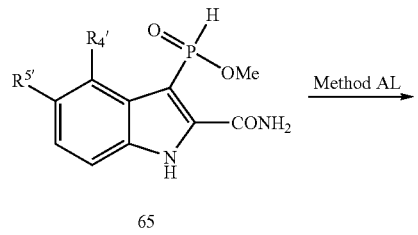 Method AL 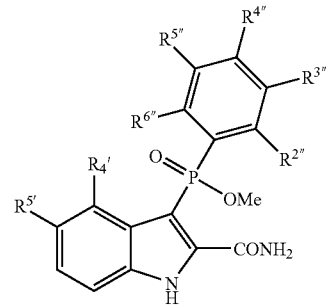

65

66

Method AD

To a flask was added under argon indole 10 (1 eq) was added Iodine (1.98 eq.), solid potassium hydroxide (1 eq.) and anhydrous DMF (4.5 mL/mmol). The reaction mixture was stirred 3 hours then water was added and the slurry filtered through paper filter, the solid was dried under reduced pressure and triturated/filtered in water several times to yield after dryed under reduced pressure the 3-iodoindole 61.

Method AE

To a stirred solution of indole 10 (1 eq.) in dichloromethane (3.5 mL/mmol) under nitrogen was added di-tert-butyl dicarbonate (1.8 eq.) and 4-dimethylaminopyridine (2 eq.). The reaction mixture was stirred 18 hours then phosphate buffer (pH=7) was added and extracted with dichloromethane. Combined organic layers were dried ($Na_2SO_4$) and concentrated under reduced pressure. The crude residue was purified by flash chromatography on silica gel (eluent: petroleum ether/EtOAc:1/1) to afford N-Boc-protected indole 62a.

Method AF

To a stirred solution of indole 10 (1 eq) in DMF (3.5 mL/mmol) under nitrogen and cooled to 0° C. (ice bath) was added sodium hydride (1.2 eq.) portionwise. Reaction mixture was stirred 15 minutes until gas evolution ceased and 4-methoxybenzyl chloride was added dropwise. The reaction mixture was stirred 18 hours then little amount of water was added at 0° C. Reaction media was diluted with water/phosphate buffer (pH=7). Aqueous layer was extracted with ethyl acetate and the organic layers were washed with water, dried ($Na_2SO_4$) and concentrated under reduced pressure. The crude residue was purified by flash chromatography on silica gel (eluent: petroleum ether/EtOAc:98/2 to 1/1) to afford N-p-methoxybenzyl-protected indole 62b.

Method AG

To a stirred and cooled (to about 0° C.) solution of ethyl indole-2-carboxylate 10 (1 eq.) in DMF (2 ml/mmol) under $N_2$, was added NaH (60% in oil, 1.2 eq.) portionwise. When gas evolution stopped, benzenesulfonyl chloride (1.2 eq.) was added. The reaction mixture was stirred for about 1 hour (TLC monitoring, eluent dichloromethane); a small amount of water then was added carefully and the DMF was evaporated. The crude residue was dissolved in ethyl acetate and washed with water and brine. After drying and evaporation of the solvents, the compound was purified by chromatography on silica gel (eluent: $C_6H_{12}$/EtOAc 9/1 to 7/3) to give the N-phenylsulfonylindole 62c.

Method AH

To a stirred solution of indole 10 (1 eq) in THF (3.5 mL/mmol) under nitrogen was added potassium tert-butoxide (1.5 eq.). Reaction mixture was stirred 15 minutes then benzoyl chloride (1.2 eq.) was added. The reaction mixture was stirred 18 hours then water was added. THF was evaporated under reduced pressure and aqueous layer was extracted three times with ethyl acetate. Combined organic layers were dried ($Na_2SO_4$) and concentrated under reduced pressure. The crude residue was purified by flash chromatography on silica gel (eluent: petroleum ether/EtOAc:3/1) to afford N-Bz-protected indole 62d.

Method AI

A stirred solution of degassed DMF with $N_2$, N-protected 3-iodoindole 62 (1 eq.), H-arylphosphinate 23 (R=Me or Et) (1.1 eq.), triethylamine (2 eq.) and $Pd_2$ $dba_3$ (0.2 eq.) was heated at 70° C. or 90° C. until reaction is finished according to TLC or HPLC analysis. Reaction mixture was cooled down to room temperature and solvent was evaporated. The crude residue was purified by flash chromatography on silica gel (eluent: typically petroleum ether/EtOAc:8/2) to afford indole phosphinate 63. (note when PG=Boc a mixture of Boc protected compound and deprotected indole compound is obtained).

Method AJ

To a −90° C. cooled solution (acetone/liquid nitrogen bath) of bromoindole 11 (1 eq.) in THF (5 mL/mmol) under nitrogen, was added n-butyllithium (2.5M in hexanes, 1.1 eq.) dropwise while maintaining the temperature around −90° C. After the end of addition, the reaction media was stirred 5 min at the same temperature and chlorodiethylphosphite (1 eq.) was added dropwise. The reaction was allowed to warm up to −20° C. and then washed quickly with a small volume of brine. The organic layer was then immediately added to a stirred solution of HCl 0.5M and the mixture stirred for 1 hour. After decantation, the aqueous layer was extracted with EtOAc several times. Combined organic layers were dried ($Na_2SO_4$) then concentrated under reduced pressure and the oily residue was purified by flash chromatography on silica gel (eluent: DCM/EtOAc:95/5) to afford indole 3-H-phosphinate 64.

Method AL

To a solution of indole 3-H-phosphinate 64 or 65 under $N_2$ in degassed acetonitrile was added 3-iodo-5-methyl-cinnamonitrile (1.1 eq.), $Et_3N$ (1 eq.) and Palladium tetrakis(triphenylphosphine) (0.2 eq.). The reaction was heated at 100° C. until the end of the reaction (monitored by HPLC). The reaction was cooled down and solvent was evaporated under reduced pressure. The crude residue was then purified by flash chromatography on silica gel to afford 3-H-phosphinate 63 or 66.

Method AM

In a pressure tube, Indole 3-H-phosphinate 64 (1 eq.) was dissolved in methanol, the solution was cooled down to 0° C. then satured with ammonia. The reaction was then heated at 50° C. under pressure for 18 hours. After cooling down the solvents were evaporated. Water was added and extraction with EtOAc was performed. Organic layers were dried (Na$_2$SO$_4$) and evaporated in vacuo. The residue was tritured in acetonitrile and gave after filtration 3-H-phosphinate indole carboxamide 65.

Intermediate 62b

Ethyl 1-(4-methoxybenzyl)-5-chloro-3-iodo-1H-indole-2-carboxylate

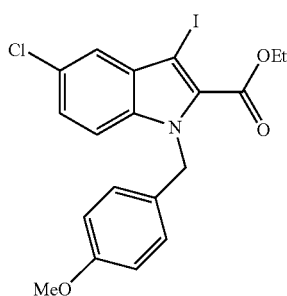

Intermediate 62b was synthesized according to method AF. White solid, $^1$H NMR (d$_6$-DMSO, 400 MHz) δ 1.33 (t, J=7.1 Hz, 3H), 3.67 (s, 3H), 4.35 (q, J=7.1 Hz, 2H), 5.73 (s, 2H), 6.82 (d, J=8.7 Hz, 2H), 6.97 (d), 7.40 (J=8.9 and 2.1 Hz, 1H), 7.45 (d, J=2.1 Hz, 1H), 7.72 (d, J=8.9 Hz, 1H).

Intermediate 62c

Ethyl 1-phenylsulfonyl-5-chloro-3-iodo-1H-indole-2-carboxylate

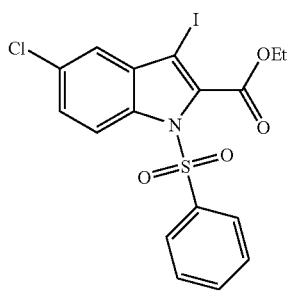

Intermediate 62c was synthesized according to method AG. $^1$H NMR (d$_6$-DMSO, 400 MHz) δ 1.40 (t, 3H), 4.50 (br q, 2H), 7.45 (s, 1H), 7.52-7.80 (m, 4H), 8.00 (m, 3H). MS (ESI, EI$^-$) m/z=488 (M–H$^+$).

Intermediate 62d

Ethyl 1-benzoyl-5-chloro-3-iodo-1H-indole-2-carboxylate

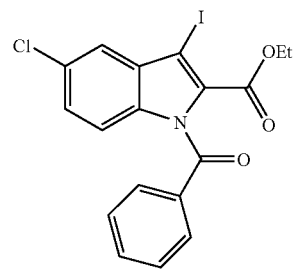

Intermediate 62d was synthesized according to method AH. Slight yellow solid, $^1$H NMR (d$_6$-DMSO, 400 MHz) δ 1.03 (t, J=9.4 Hz, 3H), 3.88 (q, J=9.4 Hz, 2H), 7.52-7.71 (m, 8H). MS (ESI, EI$^+$) m/z=476 (M+Na$^+$), MS (ES$^-$) m/z=452.

Intermediate 62e

Methyl 1-phenylsulfonyl-5-chloro-4-fluoro-3-iodo-1H-indole-2-carboxylate

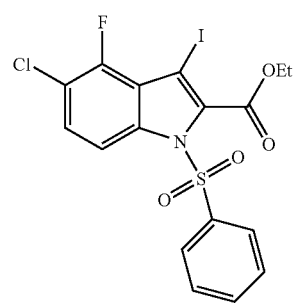

Intermediate 62e was synthesized according to method AG. Beige solid, $^1$H NMR (d$_6$-DMSO, 400 MHz) δ 1.41 (t, J=7.2 Hz, 3H), 4.51 (q, J=7.2 Hz, 2H), 7.63-7.71 (m, 3H), 7.78-7.82 (m, 1H), 7.89-7.91 (d, 1H), 8.00-8.03 (m, 2H), $^{19}$F NMR (d$_6$-DMSO, 376 MHz) δ –125.60 (d, 1F). MS (ESI–) m/z=506.12 (M–H)$^-$ 30%, 380.21 (M-I)$^-$ 100%, 382.21 (M-I)$^-$ 35%.

Intermediate 62h

Methyl 1-(4-methoxybenzyl)-4-fluoro-5-chloro-3-iodo-1H-indole-2-carboxylate

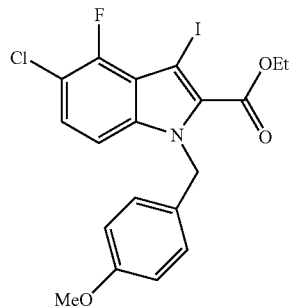

Intermediate 62h was synthesized according to method AF.
White solid, $^1$H NMR (d$_6$-DMSO, 400 MHz) δ 1.31 (t, J=7.1 Hz, 3H), 3.67 (s, 3H), 4.34 (q, J=7.1 Hz, 2H), 5.68 (s, 2H), 6.82 (d, J=8.6 Hz, 2H), 6.96 (d, J=8.6 Hz, 2H), 7.45 (dd, J=7.0 and 9.2 Hz, 1H), 7.59 (d, J=8.8 Hz, 1H), $^{19}$F NMR (d$_6$-DMSO, 377 MHz) δ −126.1 (s, 1F). MS (ESI, EI$^+$) m/z=487.

Compound 63b

1-Benzenesulfonyl-5-chloro-3-[methyl 3-((E)-2-cyanovinyl)-5-methylphenyl]phosphinoyl-1H-indole-2-carboxylic acid ethyl ester

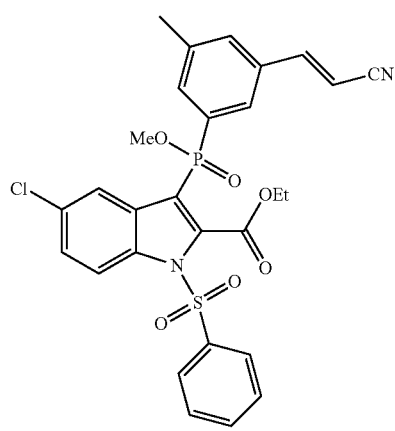

Compound 63b was synthesized according to method AI.
White solid, $^1$H NMR (d$_6$-DMSO, 400 MHz) δ 1.33 (t, J=7.1 Hz, 3H), 2.65 (s, 3H), 3.69 (d, J=11.7 Hz, 3H), 4.41 (m, 2H), 6.52 (d, J=16.7 Hz, 1H), 7.53 (dd, J=9.0 and 2.2 Hz, 1H), 7.62 (d, J=13.6 Hz, 1H), 7.60-7.71 (m, 3H), 7.76-7.81 (m, 3H), 7.85 (d, J=2.2 Hz, 1H), 8.04-8.09 (m, 3H). MS (ES$^+$) m/z=583 (MH$^+$)

Compound 63c 1-(4-methoxybenzyl)-5-chloro-3-[methyl 3-((E)-2-cyanovinyl)-5-methylphenyl]phosphinoyl-1H-indole-2-carboxylic acid ethyl ester

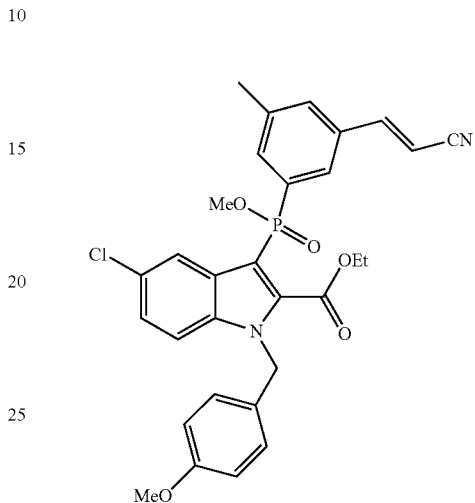

Compound 63c was synthesized according to method AI.
White solid, $^1$H NMR (d$_6$-Acetone, 400 MHz) δ 1.18 (t, J=7.1 Hz, 3H), 2.39 (s, 3H), 3.74 (s, 3H), 3.76 (d, J=11.4 Hz, 3H), 4.26 (m, 2H), 5.63 (s, 2H), 6.35 (d, J=16.8 Hz, 1H), 6.86 (d, J=8.6 Hz, 2H), 7.14 (d, J=8.6 Hz, 2H), 7.35 (dd, J=9.0 and 2.2 Hz, 1H), 7.61 (d, J=16.8 Hz, 1H), 7.67 (dd, J=8.9 and 1.9 Hz, 1H), 7.69 (s, 1H), 7.75 (d, J=13.2 Hz, 1H), 7.91 (d, J=13.2 Hz, 1H), 8.24 (d, J=2.2 Hz, 1H). MS (ES$^+$) m/z=563 (MH$^+$).

Compound 63f 1-(tert-butylcarbanate)-5-chloro-4-fluoro-3-[methyl 3-((E)-2-cyanovinyl-5-methylphenyl]phosphinoyl)-1H-indole-2-carboxilic acid ethyl ester

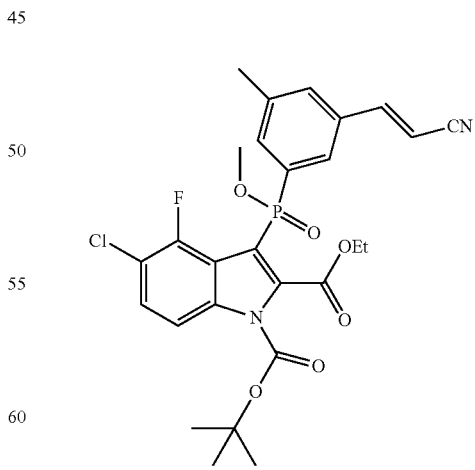

Compound 63f was synthesized according to method AI.
White solid, $^1$H NMR (d$_6$-DMSO, 400 MHz) δ 1.34 (t, J=7.1 Hz, 3H), 1.62 (s, 9H), 2.35 (s, 3H), 3.66 (d, J=11.6 Hz, 3H), 4.37 (q, J=7.1 Hz, 2H), 6.51 (d, J=16.7 Hz, 1H), 7.58-7.65 (m, 2H), 7.69-7.77 (m, 3H), 7.94 (d, J=9.5 Hz, 1H), $^{19}$F NMR (d$_6$-DMSO, 377 MHz) δ −116.0 (s, 0.1F), $^{31}$P NMR (d$_6$-DMSO, 162 MHz) δ 23.42 (s, 1P). MS (ESI, EI$^+$) m/z=561 (M+H$^+$).

Compound 63g 5-chloro-4-fluoro-3-[methyl 3-((E)-2-cyanovinyl)-5-methylphenyl]phosphinoyl-1H-indole-2-carboxilic acid ethyl ester

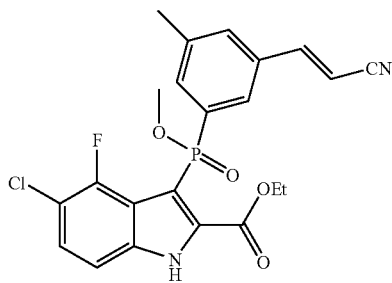

Compound 63g was synthesized according to method AI. White solid, $^1$H NMR (d$_6$-DMSO, 400 MHz) δ 1.24 (t, J=7.1 Hz, 3H), 2.35 (s, 3H), 3.58 (d, J=11.6 Hz, 3H), 4.24 (q, J=7.2 Hz, 2H), 6.49 (d, J=16.7 Hz, 1H), 7.38-7.82 (m, 6H), 13.19 (bs, 1H), $^{19}$F NMR (d$_6$-DMSO, 376 MHz) δ −115.0 (s, 1F), $^{31}$P NMR (d$_6$-DMSO, 162 MHz) δ 25.24 (s, 1P). MS (ESI, EI$^+$) m/z=461 (M+H$^+$).

Compound 63h 1-(4-methoxybenzyl)-5-chloro-4-fluoro-3-[methyl 3-((E)-2-cyanovinyl-5-methylphenyl]phosphinoyl)-1H-indole-2-carboxilic acid ethyl ester

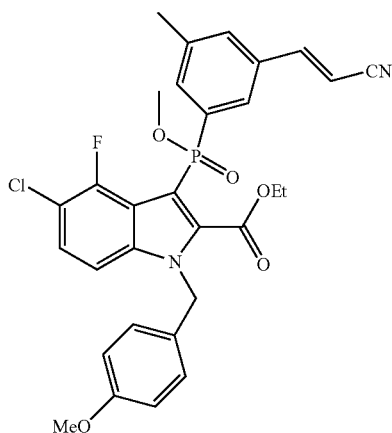

Compound 63h was synthesized according to method AI. White solid, $^1$H NMR (d$_6$-DMSO, 400 MHz) δ 1.20 (t, J=7.1 Hz, 3H), 2.35 (s, 3H), 3.61 (d, J=11.6 Hz, 3H), 3.70 (s, 3H), 4.28 (q, J=7.1 Hz, 2H), 5.43 (d, J=16.2 Hz, 1H), 5.48 (d, J=16.2 Hz, 1H), 6.48 (d, J=16.7 Hz, 1H), 6.88 (d, J=8.7 Hz, 2H), 7.12 (d, J=8.7 Hz, 2H), 7.46 (dd, J=6.8 and 8.8 Hz, 1H), 7.55-7.79 (m, 5H), $^{19}$F NMR (d$_6$-DMSO, 377 MHz) δ −116.7 (s, 1F), $^{31}$P NMR (d$_6$-DMSO, 162 MHz) δ 24.55 (s, 1P). MS (ESI, EI$^+$) m/z=581 (M+H$^+$).

Intermediate 64a

1-Benzenesulfonyl-5-chloro-3-ethoxyhydrogenophosphinyl-1H-indole-2-carboxylic acid ethyl ester

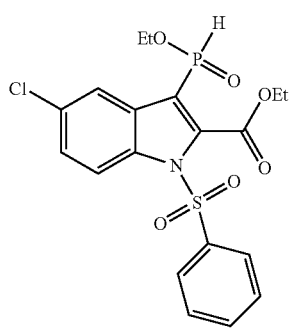

Intermediate 64a was synthesized according to method AJ. Slight yellow thick oil, $^1$H NMR (d$_6$-DMSO, 300 MHz) δ 1.25 (t, J=7.2 Hz, 3H), 1.37 (t, J=7.2 Hz, 3H), 4.1 (m, 2H), 4.46 (q, J=7.2 Hz, 3H), 7.58 (dd, J=9.0 and 2.1 Hz, 1H), 7.71 (m, 2H), 7.80 (d, J=609.6 Hz, 1H), 7.83 (m, 1H), 7.97 (d, J=2.1 Hz, 1H), 8.11 (m, 3H), $^{31}$P NMR (d$_6$-DMSO, 162 MHz) δ 13.43. MS (ES$^+$) m/z=456 (MH$^+$).

Intermediate 64b

1-Benzenesulfonyl-5-chloro-4-fluoro-3-ethoxyhydrogenophosphinyl-1H-indole-2-carboxylic acid methyl ester

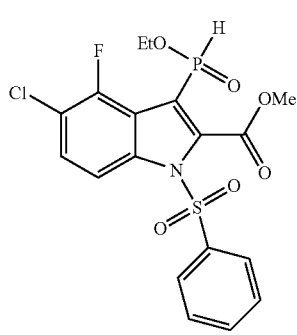

Intermediate 64b was synthesized according to method AJ. White solid, $^1$H NMR (d$_6$-DMSO, 300 MHz) δ 1.20 (t, J=6.9 Hz, 3H), 3.99 (s, 3H), 4.03 (m, 2H), 4.10 (m, 2H), 7.70 (m, 4H), 7.71 (m, 2H), 7.79 (dd, J=616.8 and 4.8 Hz, 1H), 7.84

(m, 1H), 7.96 (m, 1H), $^{31}$P NMR (d$_6$-DMSO, 121.49 MHz) δ 12.42 (J$_{P-F}$=12.6 Hz). MS (ES$^+$) m/z=460 (MH$^+$).

Compound 63f 5-chloro-3-[Ethyl 3-((E)-2-cyanovinyl)-5-methylphenyl]phosphinoyl-1H-indole-2-carboxilic acid ethyl ester

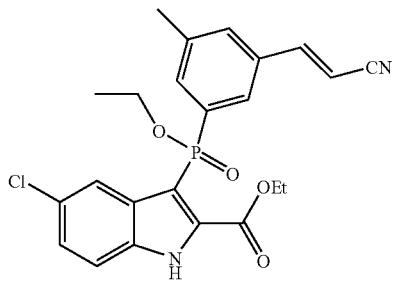

Compound 63f was synthesized according to method AL. White solid, $^1$H NMR (d$_6$-DMSO, 400 MHz) δ 1.09 (t, J=7.1 Hz, 3H), 1.26 (t, J=7.0 Hz, 3H), 2.34 (s, 3H), 3.99 (m, 2H), 4.16 (m, 2H), 6.48 (d, J=16.5 Hz, 1H), 7.39 (dd, J=8.8 and 2.2 Hz, 1H), 7.59 (m, 2H), 7.71 (m, 3H), 8.39 (d, J=2.2 Hz, 1H), 12.93 (brs, 1H). MS (ES$^+$) m/z=597 (MH$^+$).

Intermediate 65a

-5-chloro-3-methoxyhydrogenophosphinyl-1H-indole-2-carboxamide

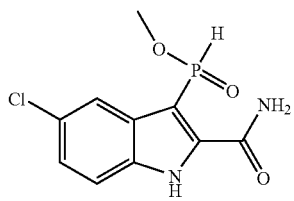

Intermediate 65a was synthesized according to method AM. White solid, $^1$H NMR (d$_6$-DMSO, 300 MHz) δ 3.71 (d, J=12.6 Hz, 3H), 7.35 (dd, J=8.7 and 2.1 Hz 1H), 7.60 (dd, J=8.7 and 1.8 Hz 1H), 7.85 (d, J=2.1 Hz 1H), 7.99 (dd, J=616.8 and 5.4 Hz 1H), 8.00 (brs, 1H), 9.28 (brs, 1H), 12.71 (brs, 1H), $^{31}$P NMR (d$_6$-DMSO, 121.49 MHz) δ 22.38. MS (ES$^-$) m/z=271 (M–H).

Intermediate 65b 5-chloro-4-fluoro-3-methoxyhydrogenophosphinyl-1H-indole-2-carboxamide

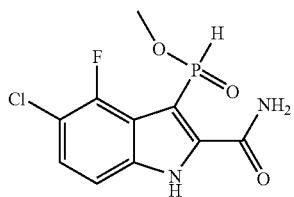

Intermediate 65b was synthesized according to method AM. White solid, $^1$H NMR (d$_6$-DMSO, 300 MHz) δ 3.72 (d, J=13.2 Hz, 3H), 7.45 (m, 2H), 7.99 (dd, J=616.8 and 5.4 Hz 1H), 8.08 (brs, 1H), 9.96 (brs, 1H), 13.0 (brs, 1H), $^{31}$P NMR (d$_6$-DMSO, 121.49 MHz) δ 22.79 (dd, J=28.8 and 4.6 Hz). MS (ES$^-$) m/z=289 (M–H).

Compound 66a 5-chloro-3-[methyl 3-((E)-2-cyanovinyl)-5-methylphenyl]phosphinoyl-1H-indole-2-carboxamide

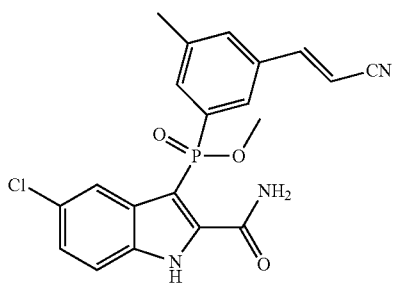

Compound 66a was synthesized according to method AL. White solid, $^1$H NMR (CDCl$_3$, 300 MHz) δ 2.40 (s, 3H), 3.88 (d, J=11.7 Hz, 3H), 5.89 (d, J=16.5 Hz, 1H), 5.97 (brs, 1H), 7.33-7.67 (m, 7H), 10.46 (s, 1H), 10.89 (brs, 1H), $^{31}$P NMR (CDCl$_3$, 121.49 MHz) δ 31.54. MS (ES$^+$) m/z=414 (MH$^+$).

Compound 66b 5-chloro-4-fluoro-3-[methyl 3-((E)-2-cyanovinyl)-5-methylphenyl]phosphinoyl-1H-indole-2-carboxamide

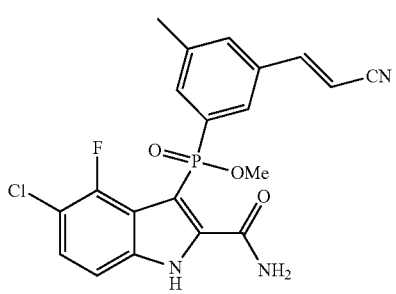

Compound 66b was synthesized according to method AL. White solid, $^1$H NMR (CDCl$_3$, 300 MHz) δ 2.42 (s, 3H), 3.88 (d, J=12.0 Hz, 3H), 6.38 (d, J=16.5 Hz, 1H), 7.20 (brs, 1H), 7.42 (dd, J=8.8 and 6.7 Hz, 1H), 7.61-7.66 (m, 2H), 7.74 (m, 2H), 7.89 (m, 1H), 11.24 (s, 1H), 12.07 (brs, 1H), $^{31}$P NMR (CDCl$_3$, 121.49 MHz) δ 30.29, $^{19}$F NMR (d$_6$-DMSO, 282.4 MHz) δ −115.0. MS (ES$^+$) m/z=432 (MH$^+$).

Intermediates 4a and 4b

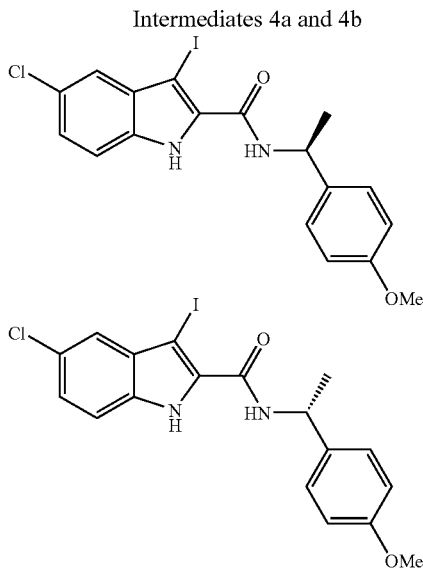

To a solution of 3-iodo-5-chloroindole 2-carboxylic acid (1 eq.) in DMF (7 mL/mmol) under nitrogen, was added HOBt (1 eq.), (R) or (S)-alpha-methyl-p-methoxybenzylamine (1 eq.) and finally EDCI (1 eq.). The reaction media was stirred for 18 hours then water was added. The precipitate solid was filtered, rinsed with water, solubilized with EtOAc, dried with Na$_2$SO$_4$ and evaporated under reduced pressure. The crude residue was purified by flash chromatography on silica gel (eluent: petroleum ether/EtOAc:95/5 to 8/2) to afford indole 4a or 4b.

4a: 5-chloro-3-iodo-N—((S)-1-(4-methoxyphenyl)ethyl)-1H-indole-2-carboxamide. Off-white solid, $^1$H NMR (d$_6$-DMSO, 400 MHz) δ 1.48 (d, J=7.0 Hz, 3H), 3.73 (s, 3H), 5.10 (m, 1H), 6.90 (d, J=8.8 Hz, 2H), 7.27 (dd, J=8.7 and 2.0 Hz, 1H), 7.35-7.38 (m, 3H), 7.45 (d, J=8.7 Hz, 1H), 8.37 (d, J=7.6 Hz, 1H), 12.15 (brs, 1H), MS (ES$^+$) m/z=455 (MH$^+$).

4b: 5-chloro-3-iodo-N—((R)-1-(4-methoxyphenyl)ethyl)-1H-indole-2-carboxamide: White solid, $^1$H NMR (d$_6$-DMSO, 400 MHz) δ 1.48 (d, J=7.0 Hz, 3H), 3.73 (s, 3H), 5.10 (m, 1H), 6.90 (d, J=8.8 Hz, 2H), 7.27 (dd, J=8.7 and 2.1 Hz, 1H), 7.35-7.38 (m, 3H), 7.45 (d, J=8.7 Hz, 1H), 8.37 (d, J=7.7 Hz, 1H), 12.20 (brs, 1H), MS (ES$^+$) m/z=455 (MH$^+$).

Intermediates 5c and 5d

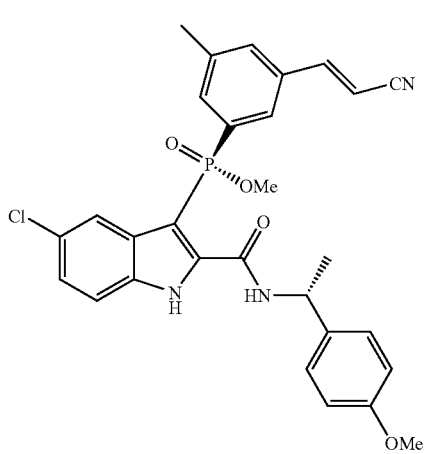

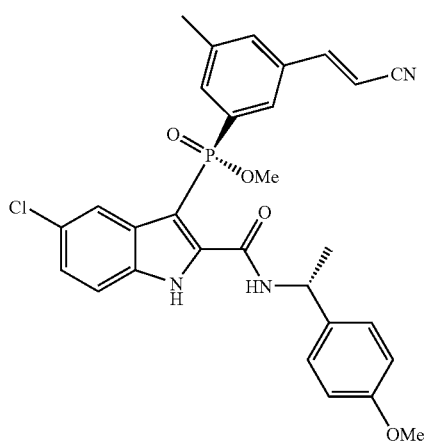

A stirred solution of degassed DMF with N$_2$, 3-iodoindole 4b (1 eq.), H-arylphosphinate #11 (1.1 eq.), triethylamine (2 eq.) and Pd$_2$dba$_3$ (0.2 eq.) was heated at 70° C. until reaction is finished according to TLC or HPLC analysis. Reaction mixture was cooled down to room temperature and solvent was evaporated. The diastereoisomers obtained are separated by flash chromatography on silica gel (eluent: petroleum ether/EtOAc:9/1 to 1/1) to afford successively phosphinate 5c and 5d.

5c: (R)-methyl 3-((E)-2-cyanovinyl)-5-methylphenyl(2-((S)-1-(4-methoxyphenyl)ethylcarbamoyl)-5-chloro-1H-indol-3-yl)-3-phosphinate: White solid, $^1$H NMR (d$_6$-DMSO, 400 MHz) δ 1.48 (d, J=6.8 Hz, 3H), 2.24 (s, 3H), 3.73 (s, 3H), 3.75 (d, J=11.8 Hz, 3H), 5.14 (m, 1H), 6.52 (d, J=16.8 Hz, 1H), 6.91 (d, J=8.5 Hz, 2H), 7.30 (dd, J=8.5 and 2.1 Hz, 1H), 7.36 (d, J=8.5 Hz, 2H), 7.56 (dd, J=8.8 and 1.5 Hz, 1H), 7.61 (m, 2H), 7.48 (dd, J=2.2 and 8.9 Hz, 1H), 7.70 (d, J=16.8 Hz, 1H), 7.77 (s, 1H), 7.80 (d, J=13.0 Hz, 1H), 11.12 (d, J=6.8 Hz, 1H), 12.76 (brs, 1H), MS (ES$^+$) m/z=548 (M+H$^+$).

5d: (S)-methyl 3((E)-2-cyanovinyl)-5-methylphenyl(2-((S)-1-(4-methoxyphenyl)ethylcarbamoyl)-5-chloro-1H-indol-3-yl)-3-phosphinate: White solid, $^1$H NMR (d$_6$-DMSO, 400 MHz) δ 1.48 (d, J=7.1 Hz, 3H), 2.24 (s, 3H), 3.72 (s, 3H), 3.79 (d, J=11.5 Hz, 3H), 5.14 (m, 1H), 6.42 (d, J=16.5 Hz, 1H), 6.85 (d, J=8.5 Hz, 2H), 7.31 (dd, J=2.1 and 8.8 Hz, 1H), 7.34 (d, J=8.5 Hz, 2H), 7.44 (d, J=13.2 Hz, 1H), 7.58 (m, 2H), 7.70 (m, 3H), 11.11 (brs, 1H), 12.77 (brs, 1H), MS (ES$^+$) m/z = 548 (M+H$^+$).

Compound (R)-66a:

To a solution of (R)-5c (1 eq.) in acetonitrile under nitrogen was cooled down to −15° C. (NaCl/ice bath), then ceric ammonium nitrate (7.5 eq.) in water was added dropwise. The reaction was stirred for 30 min at this temperature. The reaction media was diluted with EtOAc and water. The organic layer was washed with water then brine, dried (Na$_2$SO$_4$) and evaporated under reduced pressure. Chiral HPLC of the crude sample shown presence of only one enantiomer of compound 66a: (R)-methyl 3((E)-2-cyanovinyl)-5-methylphenyl(2-carbamoyl-5-chloro-1H-indol-3-yl)-3-phosphinate. Analytical data reported above.

Alternatively the indole 4 could be N-protected prior to be palladium coupled with a H-arylphosphinate as described above. After separation of the N-protected diastereoisomers, the optically pure carboxamide 6 can be obtained by sequential removal of the indole N-protecting group and of the chiral moiety.

Example 2

Chemical resolution of the 2-carboxyl derivative of 3-phosphoindoles of Formula I/II was performed on 280.82 g of 1 using (−)-Cinchonidine 2 (Scheme 15, to obtain the required enantiomer, first eluting isomer by chiral HPLC analysis) and (+)-Cinchonine 3 (which can be used to remove the undesired enantiomer from the filtrate, second eluting isomer by chiral HPLC analysis).

Scheme 15

Initial resolution on 280.82 g scale of racemic acid

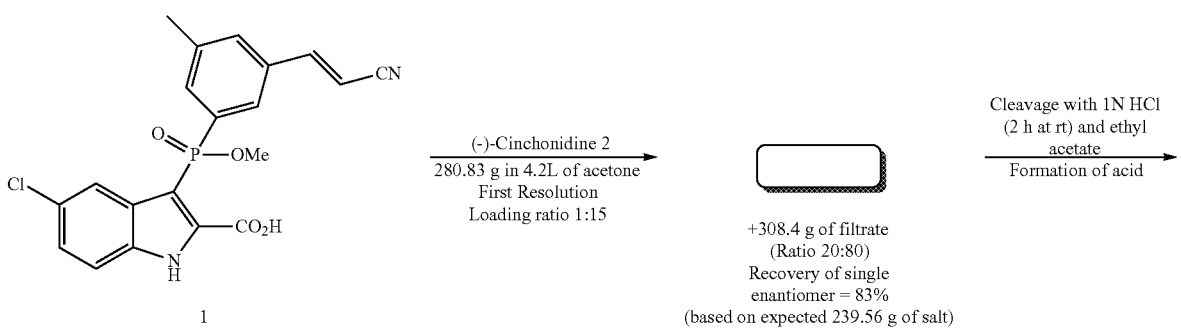

1. Initial Resolution on 280.82 g Scale of Racemic Acid
First Resolution—Using (−)-Cinchonidine 2

The free acid of indole 1 (280.83 g, 675.61 mol, Scheme 15) was suspended in acetone (4.2 L) and stirred at room temp. in a sealed flask. (−)-Cinchonidine 2 (198.89 g, 675.61 mmol) was added in one portion and after 1 h, a clear solution was observed. After a further 1 h, precipitation of a white solid was observed and the suspension was stirred at room temp. for a further 2 h (total 4 h). After this time the precipitated solid was isolated by filtration and washed with acetone (200 mL). The filtrate was concentrated in vacuo and both the precipitated solid and residue from the filtrate were dried overnight under vacuum to yield 198.5 g of solid (purity by chiral HPLC analysis, ratio=96:4) and 308.4 g of filtrate (purity by chiral HPLC analysis, ratio=20:80).

Acid Cleavage of Salt

The partially resolved salt of indole 1 (198.5 g, purity by chiral HPLC analysis 96:4) was suspended in a mixture of ethyl acetate (3 L) and 1N HCl (3 L) and vigorously stirred at room temp. for 2 h. After this time, the reaction mixture was transferred to a funnel and the layers were separated. The aqueous layer was further extracted with ethyl acetate (2 L) and the organic extracts containing product were combined, dried with sodium sulfate, filtered and concentrated in vacuo to yield the partially resolved acid as an off-white solid (107.34 g, purity by chiral HPLC analysis, ratio=95:5)

Second Resolution—Using (−)-Cinchonidine 2

The partially resolved acid indole 1 (107.34 g, 258.78 mmol, purity by chiral HPLC analysis, ratio=95:5) was suspended in acetone (1.07 L) and stirred at room temp. in a sealed flask. (−)-Cinchonidine 2 (76.18 g, 258.78 mmol) was added in one portion and after 1 h, a clear solution was observed. After a further 1 h, precipitation of a white solid was observed and the suspension was stirred at room temp. for a further 2 h (total 4 h). After this time the precipitated solid was isolated by filtration and washed with acetone (200 mL). The filtrate was concentrated in vacuo and both the precipitated solid and residue from the filtrate were dried overnight under vacuum to yield 199.07 g of solid (purity by chiral HPLC analysis, ratio=98.6:1.4) and 13.83 g of filtrate (purity by chiral HPLC analysis, ratio=55:45).

Acid Cleavage of Salt

The resolved salt (199.07 g, purity by chiral HPLC analysis, ratio=98.6:1.4) was suspended in a mixture of ethyl acetate (3 L) and 1N HCl (3 L) and vigorously stirred at room temp. for 2 h. After this time, the reaction mixture was transferred to a funnel and the layers were separated. The aqueous layer was further extracted with ethyl acetate (2 L) and the organic extracts containing product were combined, dried with sodium sulphate, filtered and concentrated in vacuo to yield the resolved acid as an off-white solid (98.08 g, purity by chiral HPLC analysis, ratio=98.6:1.4).

$^1$H NMR (d$_6$-DMSO, 400 MHz): δ 2.33 (3H, s, Ar—CH$_3$), 3.70 (3H, d, J=11.72 Hz, P—OCH$_3$), 6.50 (1H, d, J=16.84 Hz, CH=CHCN), 7.34 (1H, dd, J=1.95 Hz, J=8.79 Hz), 7.57 (1H, d, J=8.56 Hz), 7.62-7.79 (3H, m), 7.82-7.85 (1H, m or d with J 13.43 Hz), 7.98 (1H, m), 13.02 (1H, s, CO$_2$H), 14.36 (1H, br-s, NH); $^{31}$P NMR (d$_6$-DMSO, 161.8 MHz): δ 33.42; m/z (ES+) 415 (M+H)$^+$.

Recovery

Therefore, 98.08 g of required acid enantiomer was isolated (70% recovery based upon 140.42 g of available acid enantiomer from 280.83 g of racemic acid). A further 322.25 g of salt from combined filtrates of the two resolutions 4 (308.4 g+13.85 g) was further treated to recover more required enantiomer.

2. Recovery from Filtrate

Acid Cleavage of Salt

The partially resolved combined salt 4 (322.25 g) was suspended in a mixture of ethyl acetate (4.8 L) and 1N HCl (4.8 L) and vigorously stirred at room temp. for 2 h (Scheme 16). After this time, the reaction mixture was transferred to a funnel and the layers were separated. The aqueous layer was further extracted with ethyl acetate (4 L) and the organic extracts containing product were combined, dried with sodium sulfate, filtered and concentrated in vacuo to yield the partially resolved acid as an off-white solid (169.75 g, purity by chiral HPLC analysis, ratio=22:78)

Scheme 16

Recovery of required enantiomer from filtrate

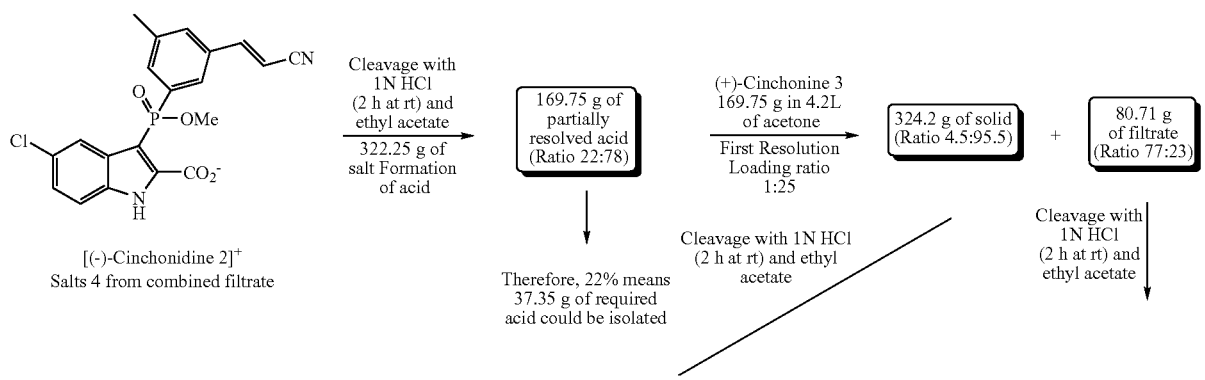

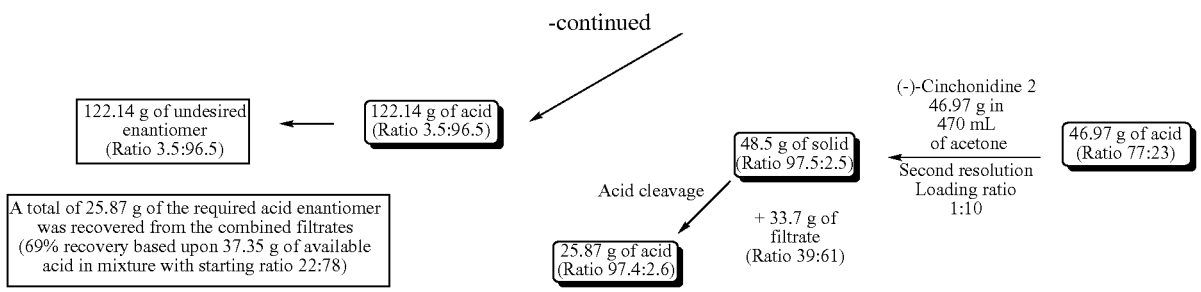

First Resolution—Using (+)-Cinchonine 3

The partially resolved acid indole (169.75 g, 409.25 mol, purity by chiral HPLC analysis, ratio=22:78) was suspended in acetone (3.06 L) and stirred at room temp. in a sealed flask. (+)-Cinchonine 3 (120.48 g, 409.25 mmol) was added in one portion and after 1 h, a clear solution was observed. After a further 5 mins, rapid precipitation of a white solid was observed and the thick suspension required additional acetone (1.14 L—total volume of acetone used=4.2 L) to allow stirring of the reaction mixture at room temp. for a further 3 h (total 4 h). After this time the precipitated solid was isolated by filtration and washed with acetone (150 mL). The filtrate was concentrated in vacuo and both the precipitated solid and residue from the filtrate were dried overnight under vacuum to yield 324.2 g of solid (purity by chiral HPLC analysis, ratio=4.5:95.5) and 80.71 g of filtrate (purity by chiral HPLC analysis, ratio=77:23).

Acid Cleavage of Salt to Obtain Undesired Enantiomer

The partially resolved salt (324.2 g, purity by chiral HPLC analysis, ratio=4.5:95.5) was suspended in a mixture of ethyl acetate (4.8 L) and 1N HCl (4.8 L) and vigorously stirred at room temp. for 2 h. After this time, the reaction mixture was transferred to a funnel and the layers were separated. The aqueous layer was further extracted with ethyl acetate (3 L) and the organic extracts containing product were combined, dried with sodium sulfate, filtered and concentrated in vacuo to yield the resolved acid as an off-white solid (122.14 g, purity by chiral HPLC analysis, ratio=3.5:96.5).

$^1$H NMR ($d_6$-DMSO, 400 MHz): δ 2.33 (3H, s, Ar—$CH_3$), 3.70 (3H, d, J=11.72 Hz, P—$OCH_3$), 6.50 (1H, d, J=16.84 Hz, CH=CHCN), 7.34 (1H, dd, J=1.95 Hz, J=8.79 Hz), 7.57 (1H, d, J=8.56 Hz), 7.62-7.79 (3H, m), 7.82-7.85 (1H, m or d with J 13.43 Hz), 7.98 (1H, m), 13.02 (1H, s, $CO_2$H), 14.36 (1H, br-s, NH); $^{31}$P NMR ($d_6$-DMSO, 161.8 MHz): δ33.42 m/z (ES+) 415 (M+H)$^+$.

Acid Cleavage of Salt to Obtain Required Enantiomer from Filtrate

The partially resolved salt (80.71 g, purity by chiral HPLC analysis, ratio=77:23) was suspended in a mixture of ethyl acetate (1.21 L) and 1N HCl (1.21 L) and vigorously stirred at room temp. for 2 h. After this time, the reaction mixture was transferred to a funnel and the layers were separated. The aqueous layer was further extracted with ethyl acetate (1 L) and the organic extracts containing product were combined, dried with sodium sulfate, filtered and concentrated in vacuo to yield the partially resolved acid as an off-white solid (46.97 g, purity by chiral HPLC analysis, ratio=77:23)

Second Resolution—Using (−)-Cinchonidine 2

The partially resolved acid indole (46.97 g, 113.24 mmol, purity by chiral HPLC analysis, ratio=77:23) was suspended in acetone (470 mL) and stirred at room temp. in a sealed flask. (−)-Cinchonidine 2 (33.34 g, 113.24 mmol) was added in one portion and after 1 h, a clear solution was observed. After a further 1 h, precipitation of a white solid was observed and the suspension was stirred at room temp. for a further 2 h (total 4 h). The precipitated solid was isolated by filtration and washed with acetone (100 mL). The filtrate was concentrated in vacuo and both the solid and residue from the filtrate were dried overnight under vacuum to yield 48.5 g of solid (purity by chiral HPLC analysis, ratio=97.5:2.5) and 33.7 g of filtrate (purity by chiral HPLC analysis, ratio=39:61).

Acid Cleavage of Salt to Obtain Required Enantiomer from Filtrate

The partially resolved salt (48.5 g, purity by chiral HPLC analysis, ratio=97.5:2.5) was suspended in a mixture of ethyl acetate (728 mL) and 1N HCl (728 mL) and vigorously stirred at room temp. for 3 h. After this time, the reaction mixture was transferred to a funnel and the layers were separated. The aqueous layer was further extracted with ethyl acetate (700 mL) and the organic extracts containing product were combined, dried with sodium sulfate, filtered and concentrated in vacuo to yield the resolved acid as an off-white solid (25.87 g, purity by chiral HPLC analysis, ratio=97.4:2.6)

$^1$H NMR ($d_6$-DMSO, 400 MHz): δ 2.33 (3H, s, Ar—$CH_3$), 3.70 (3H, d, J=11.72 Hz, P—$OCH_3$), 6.50 (1H, d, J=16.84 Hz, CH=CHCN), 7.34 (1H, dd, J=1.95 Hz, J=8.79 Hz), 7.57 (1H, d, J=8.56 Hz), 7.62-7.79 (3H, m), 7.82-7.85 (1H, m or d with J 13.43 Hz), 7.98 (1H, m), 13.02 (1H, s, $CO_2$H), 14.36 (1H, br-s, NH); $^{31}$P NMR ($d_6$-DMSO, 161.8 MHz): δ33.42; m/z (ES+) 415 (M+H)$^+$.

Recovery

Therefore, 25.87 g of required enantiomer recovered from filtrate.

Overall Recovery of Required Acid Enantiomer:—

98.08 g+25.87 g=123.95 g (out of possible 140.42 g from 280.83 g of racemic acid)=88% yield.

Example 3

Chemical Resolution of 3-Phosphoindoles of Formula III/IV

The resolution of the free acid indole of Formula III/IV has thus far been performed on 432.6 g of 5 using (−)-Cinchonidine 2. This process is depicted in Scheme 17 below.

hScheme 17

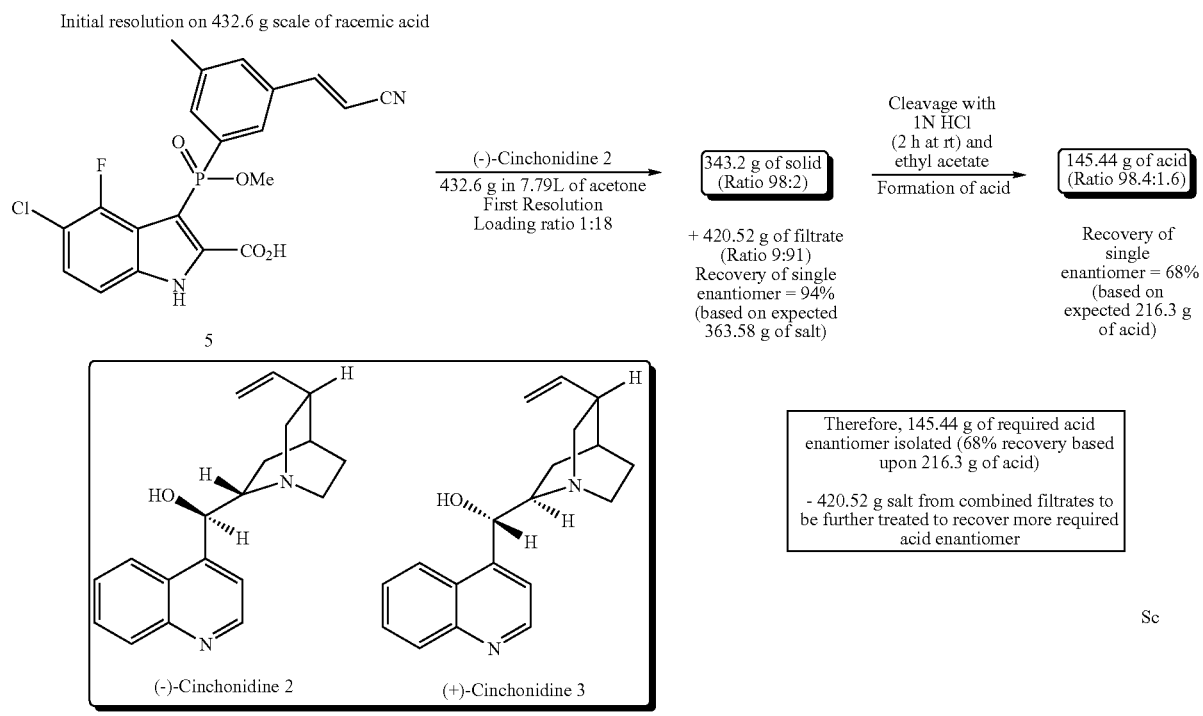

Experimental Procedure

1. Initial Resolution on 432.6 g Scale of Racemic Acid Resolution—Using (−)-Cinchonidine 2

The free acid indole 5 (432.6 g, 1.0 mol) was suspended in acetone (7.79 L) and stirred at room temp. in a sealed flask. (−)-Cinchonidine 2 (294.39 g, 1.0 mol) was added in one portion and the suspension was stirred at room temp. for 4 h. After this time the solid (no precipitation observed, a suspension was always present on this scale) was isolated by filtration and washed with acetone (300 mL). The filtrate was concentrated in vacuo and both the solid and residue from the filtrate were dried overnight under vacuum to yield 343.2 g of solid (purity by chiral HPLC analysis, ratio=98:2) and 420.52 g of filtrate (purity by chiral HPLC analysis, ratio=9:91).

Acid Cleavage of Salt

The partially resolved salt of indole 5 (343.2 g, purity by chiral HPLC analysis 98:2) was suspended in a mixture of ethyl acetate (5.2 L) and 1N HCl (5.2 L) and vigorously stirred at room temp. for 2 h. After this time, the reaction mixture was transferred to a funnel and the layers were separated. The aqueous layer was further extracted with ethyl acetate (2.7 L) and the organic extracts containing product were combined, dried with sodium sulfate, filtered and concentrated in vacuo to yield the resolved acid as an off-white solid (145.44 g, purity by chiral HPLC analysis, ratio=98.4:1.6).

$^1$H NMR $\delta_H$(400 MHz, d$_6$-DMSO): 2.35 (3H, s, Ar—CH$_3$), 3.78 (3H, d, POCH$_3$), 6.52 (1H, d, CH=CHCN), 7.46 (2H, d, Ar—H), 7.66 (1H, d, CH=CHCN), 7.69, 7.81 (2H, 2×d, H-6, H-7), 7.77 (1H, s, Ar—H), 13.63 (1H, s, N—H), 15.70 (1H, br-s, COOH); $^{31}$P NMR $\delta_P$ (162 MHz, d$_6$-DMSO): 36.44 (1P, s); $^{19}$F NMR $\delta_F$ (376 MHz, d$_6$-DMSO): −114.27 (1F, s); m/z (ESI+): 433.0 (MH$^+$, 100%), 435.0 (MH$^+$, 35%).

Recovery

Therefore, 145.44 g of required acid enantiomer was isolated (68% recovery based upon 216.3 g of available acid enantiomer from 432.6 g of racemic acid). A further 420.52 g of salt from the filtrate was further treated to recover more required enantiomer.

2. Recovery from Filtrate

Acid Cleavage of Salt

The partially resolved combined salt 4 (420.52 g) was suspended in a mixture of ethyl acetate (6.31 L) and 1N HCl (6.31 L) and vigorously stirred at room temp. for 2 h (Scheme 18). After this time, the reaction mixture was transferred to a funnel and the layers were separated. The aqueous layer was further extracted with ethyl acetate (3 L) and the organic extracts containing product were combined, dried with sodium sulfate, filtered and concentrated in vacuo to yield the partially resolved acid as an off-white solid (222.7 g, purity by chiral HPLC analysis, ratio=9:91)

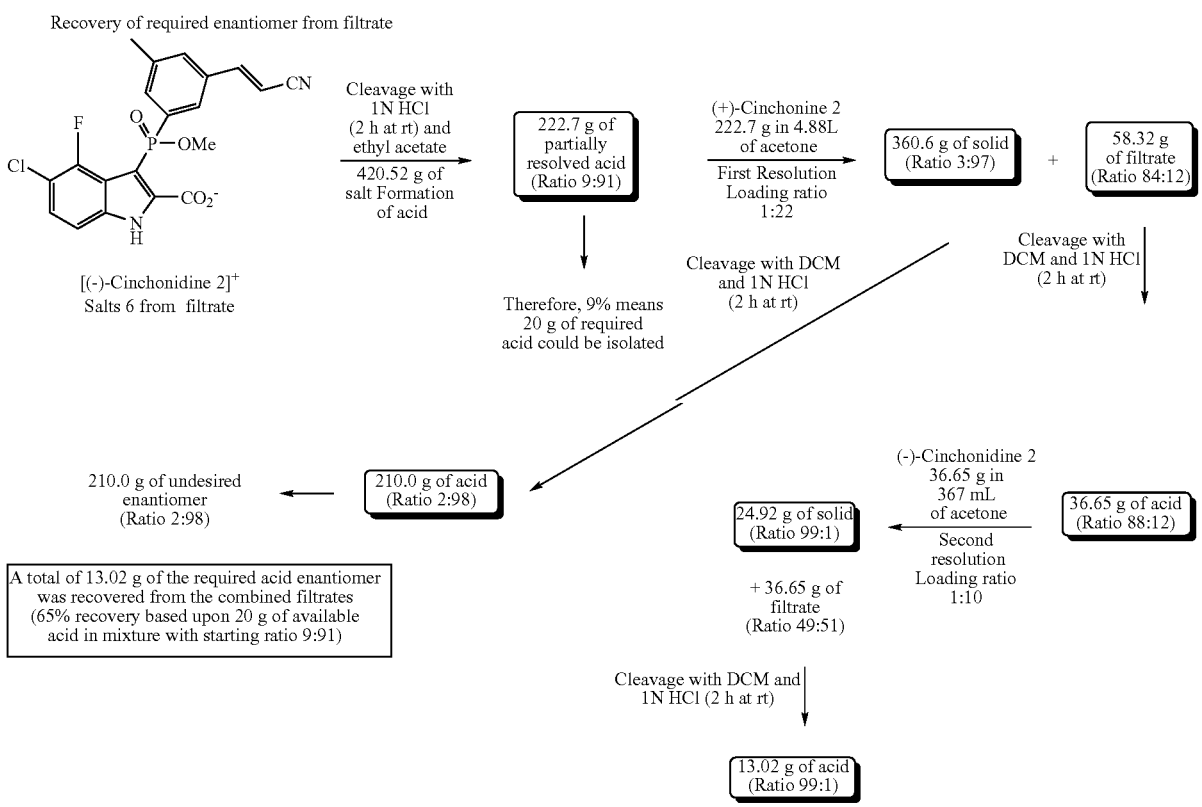

First Resolution—Using (+)-Cinchonine 3

The partially resolved acid indole (222.7 g, 409.25 mol, purity by chiral HPLC analysis, ratio=9:91) was suspended in acetone (4.38 L) and stirred at room temp. in a sealed flask. (+)-Cinchonine 3 (120.48 g, 409.25 mmol) was added in one portion and after 1 h, a clear solution was observed. After a further 5 mins, rapid precipitation of a white solid was observed and the thick suspension required additional acetone (0.5 L—total volume of acetone used=4.88 L) to allow stirring of the reaction mixture at room temp. for a further 3 h (total 4 h). After this time the precipitated solid was isolated by filtration and washed with acetone (400 mL). The filtrate was concentrated in vacuo and both the precipitated solid and residue from the filtrate were dried overnight under vacuum to yield 360.6 g of solid (purity by chiral HPLC analysis, ratio=3:97) and 58.32 g of filtrate (purity by chiral HPLC analysis, ratio=84:12).

Acid Cleavage of Salt to Obtain Undesired Enantiomer

The partially resolved salt (360.6 g, purity by chiral HPLC analysis, ratio=3:97) was suspended in a mixture of dichloromethane (5.4 L) and 1N HCl (5 L) and vigorously stirred at room temp. for 2 h. After this time, the reaction mixture was transferred to a funnel and the layers were separated. The aqueous layer was further extracted with dichloromethane (2 L) and the organic extracts containing product were combined, dried with sodium sulfate, filtered and concentrated in vacuo to yield the resolved acid as an off-white solid (210.0 g, purity by chiral HPLC analysis, ratio=2:98).

$^1$H NMR $\delta_H$ (400 MHz, $d_6$-DMSO): 2.35 (3H, s, Ar—CH$_3$), 3.78 (3H, d, POCH$_3$), 6.52 (1H, d, CH=CHCN), 7.46 (2H, d, Ar—H), 7.66 (1H, d, CH=CHCN), 7.69, 7.81 (2H, 2×d, H-6, H-7), 7.77 (1H, s, Ar—H), 13.63 (1H, s, N—H), 15.70 (1H, br-s, COOH); $^{31}$P NMR $\delta_P$ (162 MHz, $d_6$-DMSO): 36.44 (1P, s); $^{19}$F NMR $\delta_F$ (376 MHz, $d_6$-DMSO): −114.27 (1F, s); m/z (ESI+): 433.0 (MH$^+$, 100%), 435.0 (MH$^+$, 35%).

Acid Cleavage of Salt to Obtain Required Enantiomer from Filtrate

The partially resolved salt (58.32 g, purity by chiral HPLC analysis, ratio=84:12) was suspended in a mixture of dichloromethane (875 mL) and 1N HCl (875 mL) and vigorously stirred at room temp. for 2 h. After this time, the reaction mixture was transferred to a funnel and the layers were separated. The aqueous layer was further extracted with dichloromethane (400 mL) and the organic extracts containing product were combined, dried with sodium sulfate, filtered and concentrated in vacuo to yield the partially resolved acid as an off-white solid (36.65 g, purity by chiral HPLC analysis, ratio=88:12).

Second Resolution—Using (−)-Cinchonidine 2

The partially resolved acid indole (36.65 g, 85.0 mmol, purity by chiral HPLC analysis, ratio=88:12) was suspended in acetone (367 mL) and stirred at room temp. in a sealed flask. (−)-Cinchonidine 2 (25.02 g, 85.0 mmol) was added in one portion and after 1 h, a clear solution was observed. After a further 1 h, precipitation of a white solid was observed and the suspension was stirred at room temp. for a further 2 h (total 4 h). The precipitated solid was isolated by filtration and washed with acetone (100 mL). The filtrate was concentrated in vacuo and both the solid and residue from the filtrate were dried overnight under vacuum to yield 24.92 g of solid (purity by chiral HPLC analysis, ratio=99:1) and 36.65 g of filtrate (purity by chiral HPLC analysis, ratio=49:51).

Acid Cleavage of Salt to Obtain Required Enantiomer from Filtrate

The partially resolved salt (24.92 g, purity by chiral HPLC analysis, ratio=99:1) was suspended in a mixture of dichloromethane (374 mL) and 1N HCl (374 mL) and vigorously stirred at room temp. for 2 h. After this time, the reaction mixture was transferred to a funnel and the layers were separated. The aqueous layer was further extracted with dichloromethane (200 mL) and the organic extracts containing product were combined, dried with sodium sulfate, filtered and concentrated in vacuo to yield the resolved acid as an off-white solid (13.02 g, purity by chiral HPLC analysis, ratio=99:1).

$^1$H NMR $\delta_H$ (400 MHz, $d_6$-DMSO): 2.35 (3H, s, Ar—CH$_3$), 3.78 (3H, d, POCH$_3$), 6.52 (1H, d, CH=CHCN), 7.46 (2H, d, Ar—H), 7.66 (1H, d, CH=CHCN), 7.69, 7.81 (2H, 2×d, H-6, H-7), 7.77 (1H, s, Ar—H), 13.63 (1H, s, N—H), 15.70 (1H, br-s, COOH); $^{31}$P NMR $\delta_P$ (162 MHz, $d_6$-DMSO): 36.44 (1P, s); $^{19}$F NMR $\delta_F$ (376 MHz, $d_6$-DMSO): −114.27 (1F, s); m/z (ESI+): 433.0 (MH$^+$, 100%), 435.0 (MH$^+$, 35%).

Recovery

Therefore, 13.02 g of required enantiomer recovered from filtrate.

Overall Recovery of Required Acid Enantiomer:—

145.44 g+13.02 g=158.46 g (out of possible 216.3 g from 432.6 g of racemic acid)=73% yield.

The resolution of the free acid of 3-phosphoindole 6 has been performed on 1.02 g of the compound using (1R,2S)-Ephedrine 7 and (1S,2R)-Ephedrine hemihydrate 8 in 95% EtOH (Scheme 19). The principle of this resolution is the same as that described above utilizing the Cinchonidine bases.

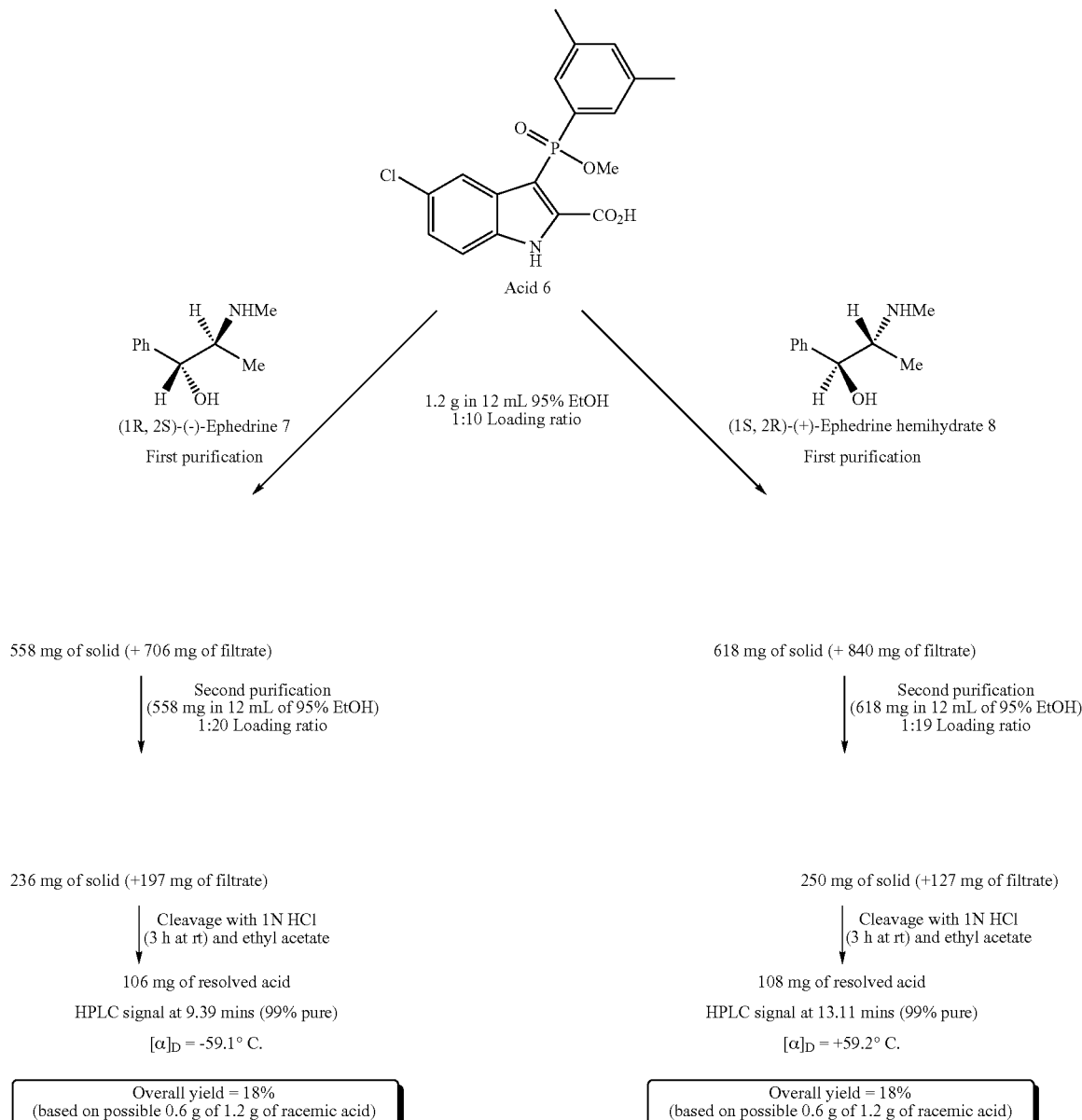

Scheme 19

Example 4

1. First Resolution—Using (1R,2S)-(−)-Ephedrine 7

The free acid 3-phosphoindole 6 (1.2 g, 3.17 mmol) was suspended in 95% ethanol (12 mL) and stirred at room temp. in a sealed flask. (1R,2S)-(−)-Ephedrine 7 (0.52 g, 3.17 mmol) was added in one portion and after 5 mins, a clear solution was observed. After a further 5 mins, rapid precipitation of a white solid was observed and stirring was continued at room temp. for 3 h. After this time the precipitated solid was isolated by filtration and washed with 95% ethanol (2 mL). The filtrate was concentrated in vacuo and both the precipitated solid and residue from the filtrate were dried overnight under vacuum to yield 558 mg of precipitated solid (purity by chiral HPLC analysis, ratio=14:86) and 706 mg of filtrate (purity by chiral HPLC analysis, ratio=74:26).

Second Resolution

The partially resolved salt of 6 (558 mg, purity by chiral HPLC analysis 14:86) was suspended in 95% ethanol (12 mL) and stirred at room temp. in a sealed flask for 3 h. After this time the solid was isolated by filtration and washed with 95% ethanol (2 mL). The filtrate was concentrated in vacuo and both the solid and residue from the filtrate were dried overnight under vacuum to yield 236 mg of solid (purity by chiral HPLC analysis, ratio=1:99) and 197 mg of filtrate (purity by chiral HPLC analysis, ratio=25:75).

Acid Cleavage of Salt

The resolved salt of 6 (236 mg, purity by chiral HPLC analysis 1:99) was suspended in a mixture of ethyl acetate (7 mL) and 1N HCl (7 mL) and vigorously stirred at room temp. for 3 h. After this time, the reaction mixture was transferred to a funnel (additional ethyl acetate (3 mL) and 1N HCl (3 mL) were required to transfer material from the flask) and the layers were separated. The aqueous layer was further extracted with ethyl acetate (2×6 mL) and the organic extracts were combined, dried with sodium sulfate, filtered and concentrated in vacuo to yield the resolved acid as a white solid (106 mg, purity by chiral HPLC analysis, ratio=1:99, $[\alpha]_D$=−59.1°).

$^1$H NMR (d$_6$-DMSO, 400 MHz): δ 2.27 (6H, s, 2×Ar—CH$_3$), 3.71 (3H, d, J 11.72 Hz, P—OCH$_3$), 7.2-7.30 (1H, m), 7.35-7.45 (m, 3H), 7.57-7.6 (m, 1H), 7.78-7.79 (m, 1H), 12.99 (1H, s, CO$_2$H), 14.73 (1H, br-s, NH); $^{31}$P NMR (d$_6$-DMSO, 161.8 MHz): δ35.41; m/z (ES+) 378 (M+H)$^+$.

2. First Resolution—Using (1S,2R)-(+)-Ephedrine 8

The free acid indole 6 (1.2 g, 3.17 mmol) was suspended in 95% ethanol (12 mL) and stirred at room temp. in a sealed flask. (1S,2R)-(+)-Ephedrine 8 (0.55 g, 3.17 mmol) was added in one portion and after 5 mins, a clear solution was observed. After a further 5 mins, rapid precipitation of a white solid was observed and stirring was continued at room temp. for 3 h. After this time the precipitated solid was isolated by filtration and washed with 95% ethanol (0.5 mL). The filtrate was concentrated in vacuo and both the precipitated solid and residue from the filtrate were dried overnight under vacuum to yield 618 mg of precipitated solid (purity by chiral HPLC analysis, ratio=94:6) and 840 mg of filtrate (purity by chiral HPLC analysis, ratio=25:75).

Second Resolution

The partially resolved salt (618 mg, purity by chiral HPLC analysis 94:6) was suspended in 95% ethanol (12 mL) and stirred at room temp. in a sealed flask for 3 h. After this time the solid was isolated by filtration and washed with 95% ethanol (0.5 mL). The filtrate was concentrated in vacuo and both the precipitated solid and residue from the filtrate were dried overnight under vacuum to yield 250 mg of solid (purity by chiral HPLC analysis, ratio=100:0) and 127 mg of filtrate (purity by chiral HPLC analysis, ratio=85:15).

Acid Cleavage of Salt

The resolved salt of 6 (250 mg, purity by chiral HPLC analysis 100:0) was suspended in a mixture of ethyl acetate (7 mL) and 1N HCl (7 mL) and vigorously stirred at room temp. for 3 h. After this time, the reaction mixture was transferred to a funnel (additional ethyl acetate (3 mL) and 1N HCl (3 mL) were required to transfer material from the flask) and the layers were separated. The aqueous layer was further extracted with ethyl acetate (2×6 mL) and the organic extracts were combined, dried with sodium sulfate, filtered and concentrated in vacuo to yield the resolved acid as a white solid (108 mg, purity by chiral HPLC analysis, ratio=100:0, $[\alpha]_D$=+59.2°)

$^1$H NMR (d$_6$-DMSO, 400 MHz): δ 2.27 (6H, s, 2×Ar—CH$_3$), 3.71 (3H, d, J 11.72 Hz, P—OCH$_3$), 7.2-7.30 (1H, m), 7.35-7.45 (m, 3H), 7.57-7.6 (m, 1H), 7.78-7.79 (m, 1H), 12.99 (1H, s, CO$_2$H), 14.73 (1H, br-s, NH); $^{31}$P NMR (d$_6$-DMSO, 161.8 MHz): δ35.41; m/z (ES+) 378 (M+H)$^+$.

Recovery

Overall recovery is 18% from racemic acid 6 using either (1R,2S)-ephedrine 7 or (1S,2R)-ephedrine hemihydrate 8 but without any optimization of the process.

Example 5

Chiral Synthesis of 3-Phosphoindoles

Synthesis with optically pure intermediates, where the chiral center is completely preserved or completely inverted. In this case the base used for the cross-coupling (e.g. Et$_3$N) is not strong enough to allow racemization of the starting H—P phosphate to occur (in contrary to DKR process). Cross-coupling reaction proceeds with retention of configuration. Cleavage of the menthyl phosphinate using trialkyloxonium salt, followed by acidic treatment, proceed with inversion of configuration (J. Org. Chem. 1975, 1523-1525). This process is depicted in Scheme 20.

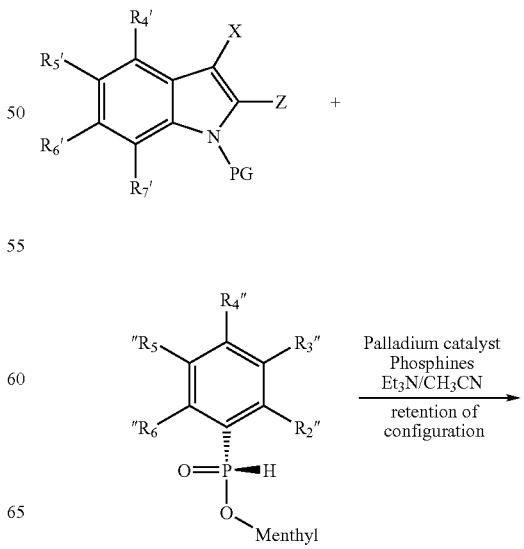

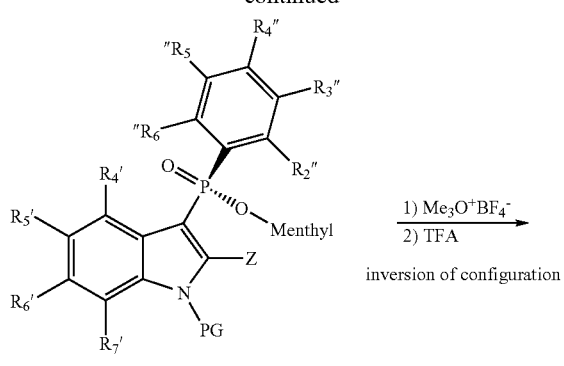
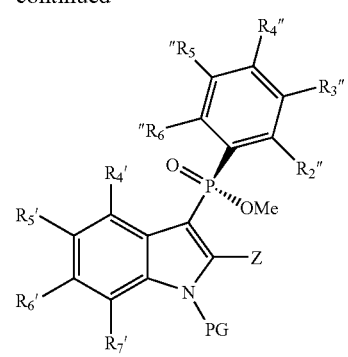

Preparation of menthyl phosphinate compound is realized in two steps from aryl halides or triflates (Scheme 21). First step is the preparation of H-phosphinic acid according methods described such as the work of Montchamp et al, *J. Am. Chem. Soc.* 2001, 123:510-511 and Montchamp et al., *J. Organomet. Chem.* 2002, 643-644:154-163. Second step is a Hewitt reaction such as described *Tetrahedron Lett.* 2003, 781-783.

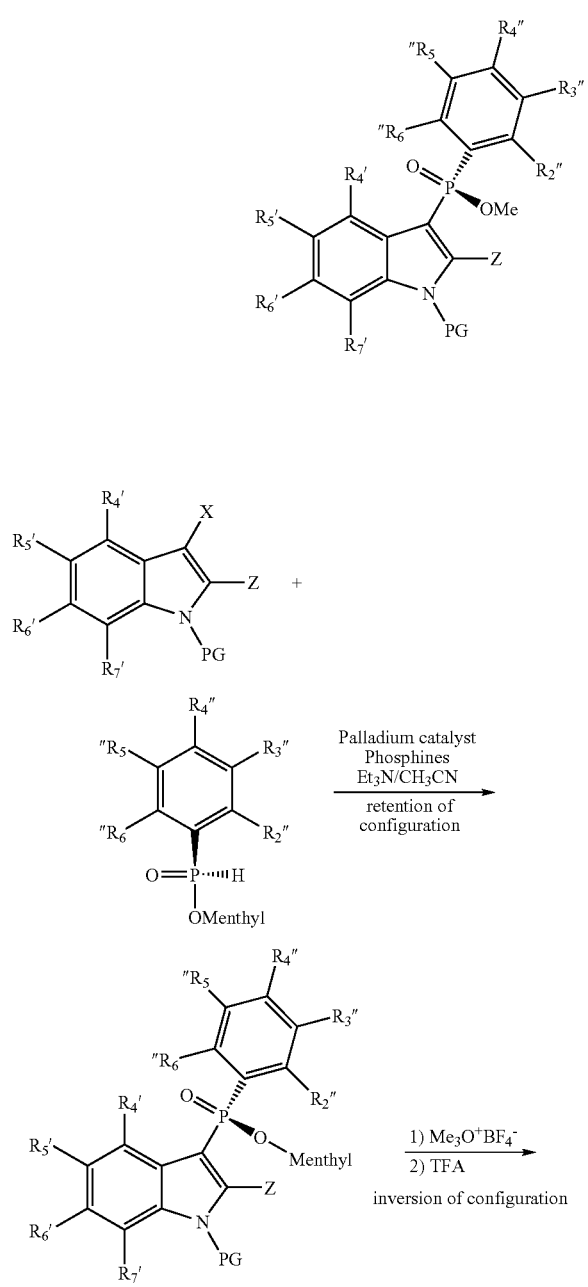
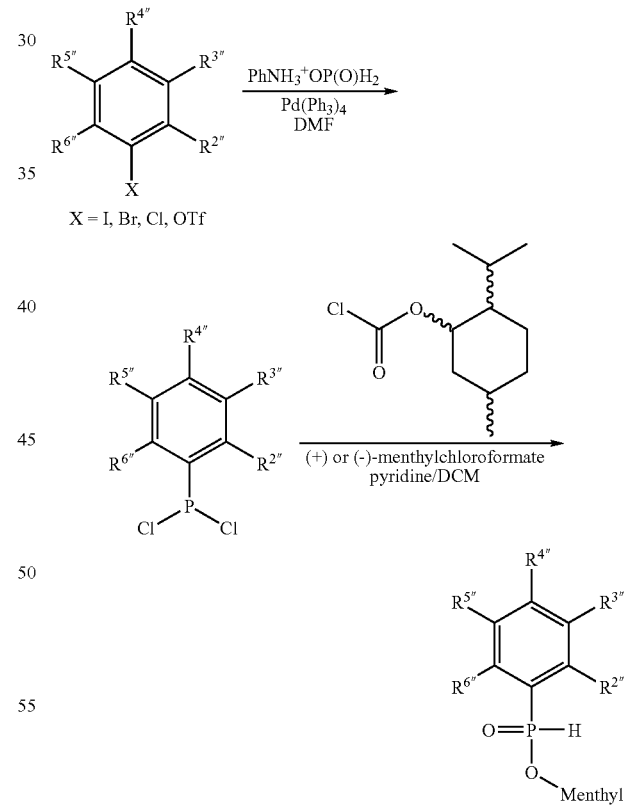

A second approach for synthesizing menthyl phosphinate starts also from an aryl halide to produce dichlorophosphite with method available in literature (Scheme 22). Then attack of (−) or (+)-menthol gives menthylphosphinate as a diastereomeric mixture as described in *J. Am. Chem. Soc.* 1967, 90, 3459-3465.

Scheme 22
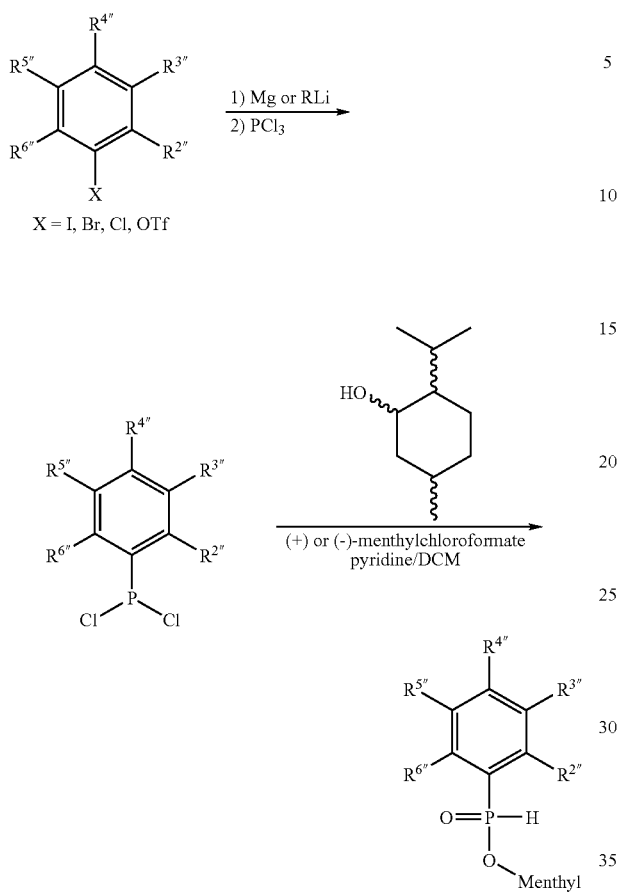
The separation of the diastereoisomers is realized by crystallization using or adapting the conditions described in *J. Am. Chem. Soc.* 1970, 92, 5809-5810, *Heteroatom Chemistry* 1995, 6, 365-70, *Russ. J. Gen. Chem.* 2005, 75, 656-657 (Scheme 23).
Scheme 23
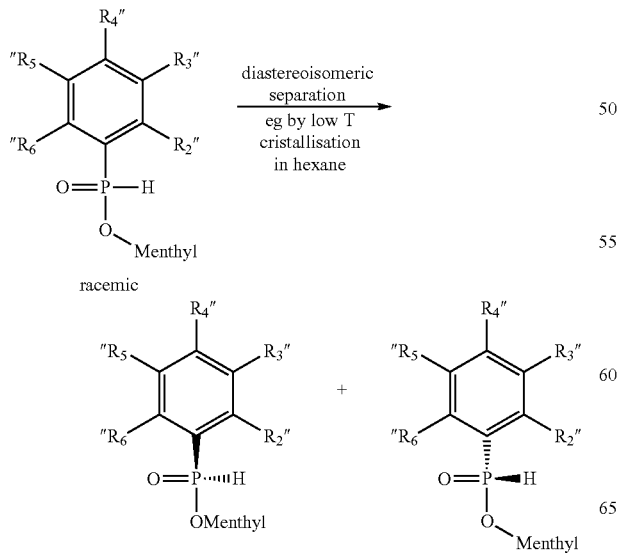
Schemes 24 and 25 depict the chiral synthesis of 3-phosphoindoles of Formula I and III using this approach:
Scheme 24
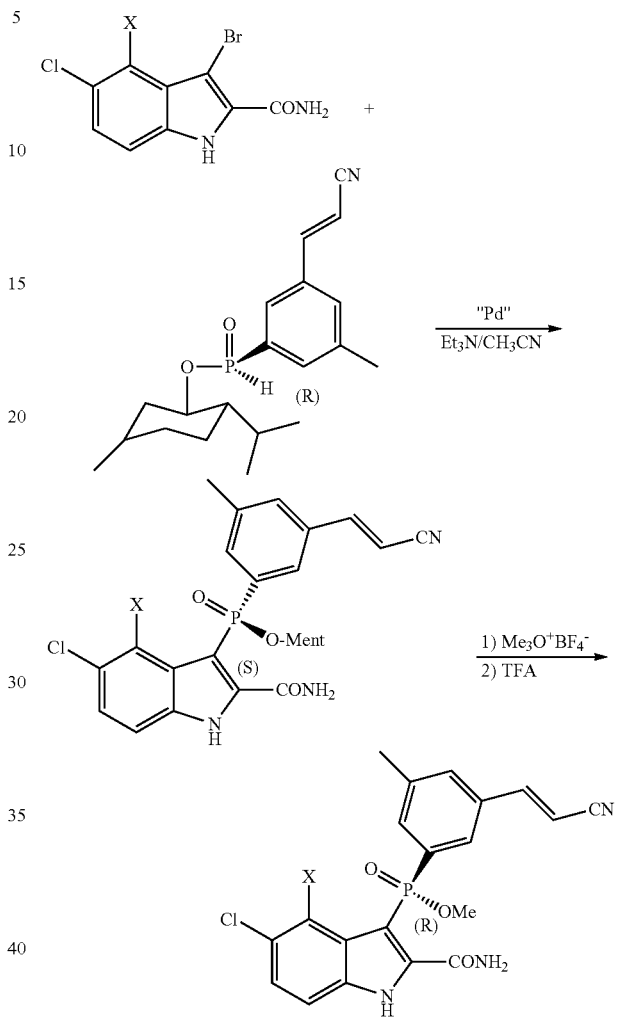
Scheme 25
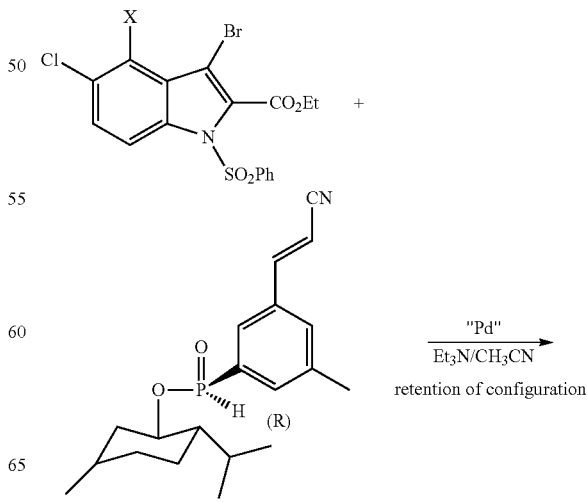

103
-continued

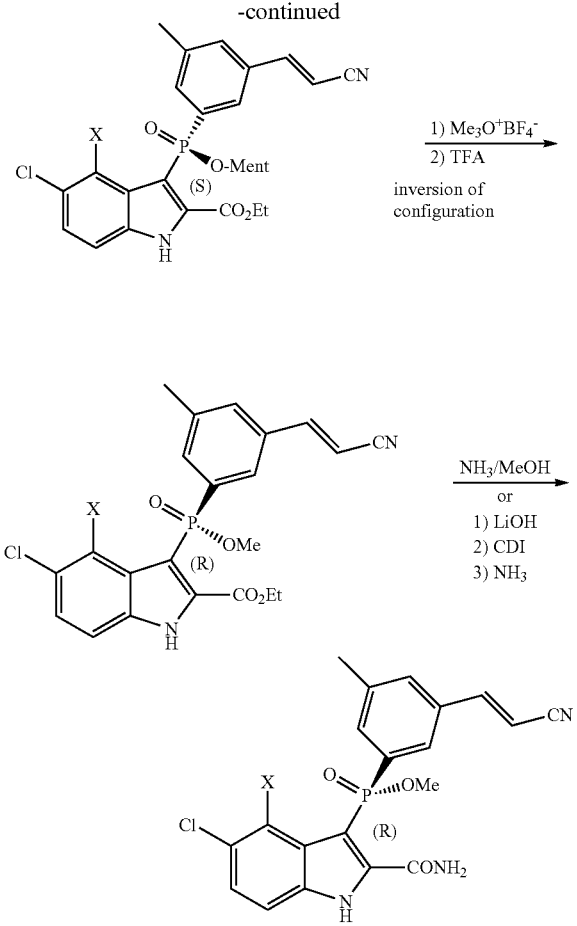

For the analytical separation of enantiomers, the conditions for chiral HPLC analysis are:
Column: DAICEL CHIRALPAK® AD-H 5 um, 250×4.6 mm I.D.
Mobile Phase A: Methanol
Mobile Phase B: IPA+0.05 wt % TFA
Isocratic: A/B (25/75)
Flow Rate: 0.4 ml/min
Detection: PDA max plot 210-400 nm
Enantiomer 1 RT=13.4 min; Enantiomer 2 RT=19.6 min.
Preparative Method:
Injection of 2 g of racemic mixture (IM403):
Column: DAICEL CHIRALPAK® AD 20 um, 260×50 mm I.D.
Mobile Phase: 50 ethanol/50 methanol/0.1 diethylamine (v/v/v)
Flow Rate: 120 ml/min
Detection: UV 320 nm
Enantiomer 1 RT=7.0 min; Enantiomer 2 RT=25.3 min.

Another approach to the synthesis of enantiomerically pure 3-phosphoindoles is depicted in schemes 49 and 50.

Determination of the stereocontrol efficiency for each step should be performed by 31P NMR and HPLC in order to confirm if the retention or inversion predicted are complete or if mixture of diastereomers are observed. The most sensitive step might be the borane deprotection which required heat. From this stage, the enantiomeric excess measurement requires the use of a chiral analytical HPLC column.

104

If the configuration at the phosphorus is 100% controlled at each step, the single precursor 4 can lead too the two different enantiomers 8 or 12 depending on the chemical pathway selected.

Example 6

Resolution of Diastereomeric Intermediates

A further method for the preparation of enantiomerically pure 3-phosphoindoles relies on the preparation of diastereomers by the functionalization of the indoles with chiral reagents. The use of chiral amino acids to prepare diastereomeric 3-phosphoindoles is depicted in Scheme 26. The S-chirality at alpha-amino-acid carbon is unchanged. The synthesis is done as follows:

Scheme 26

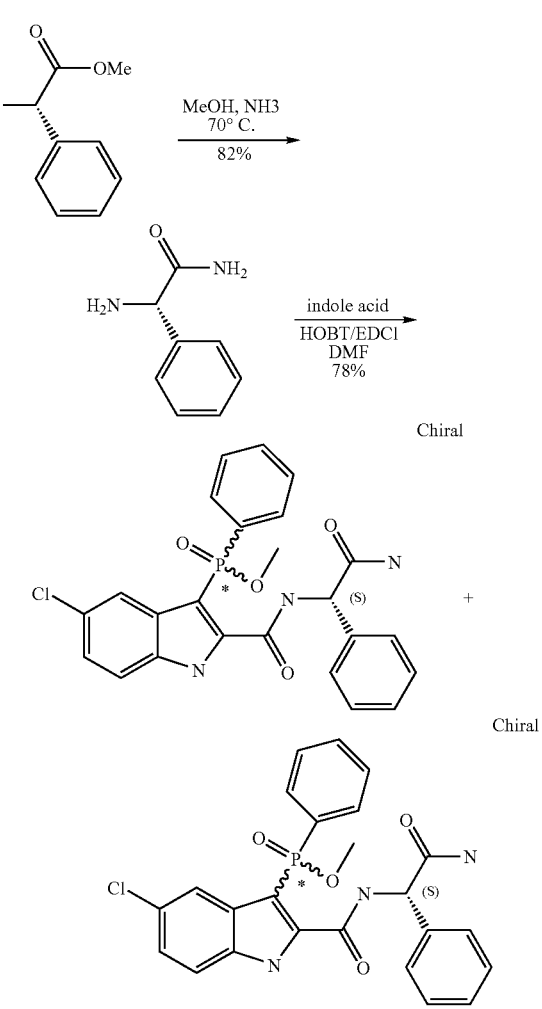

The 2 diastereomers are separated using a standard silica column.

This strategy can be applied to prepare other diastereomeric amides with enantiomerically pure benzylamines for example or to prepare diastereomeric esters rather than amides which could be cleaved after diastereomeric separation to release the separated enantiomer. This approach is shown in Scheme 27 below.

Scheme 27
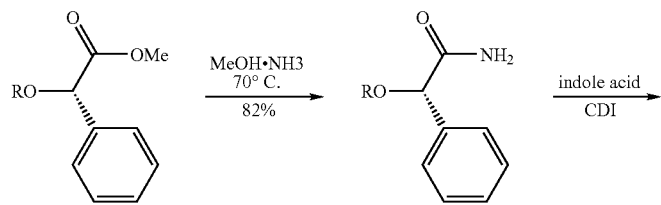
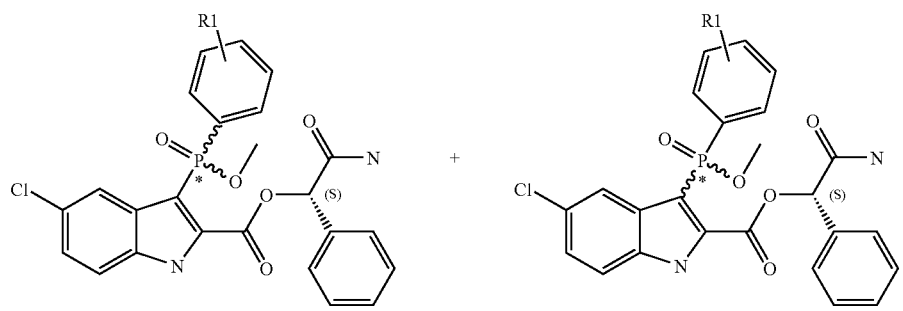
diastereomeric separation
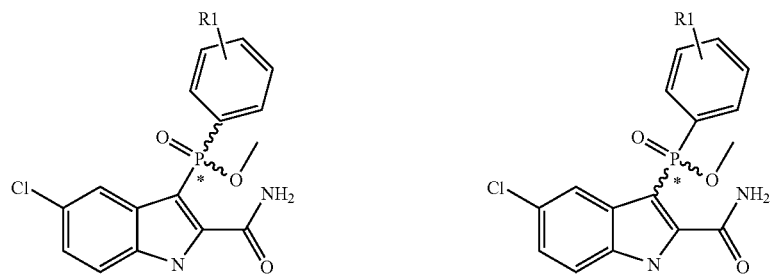
enantiomers separated

107 108
Example 7
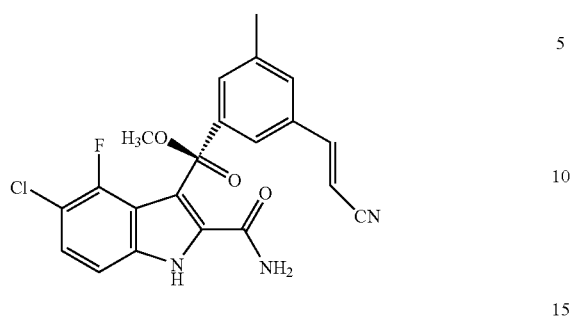
Preparation of Compound I
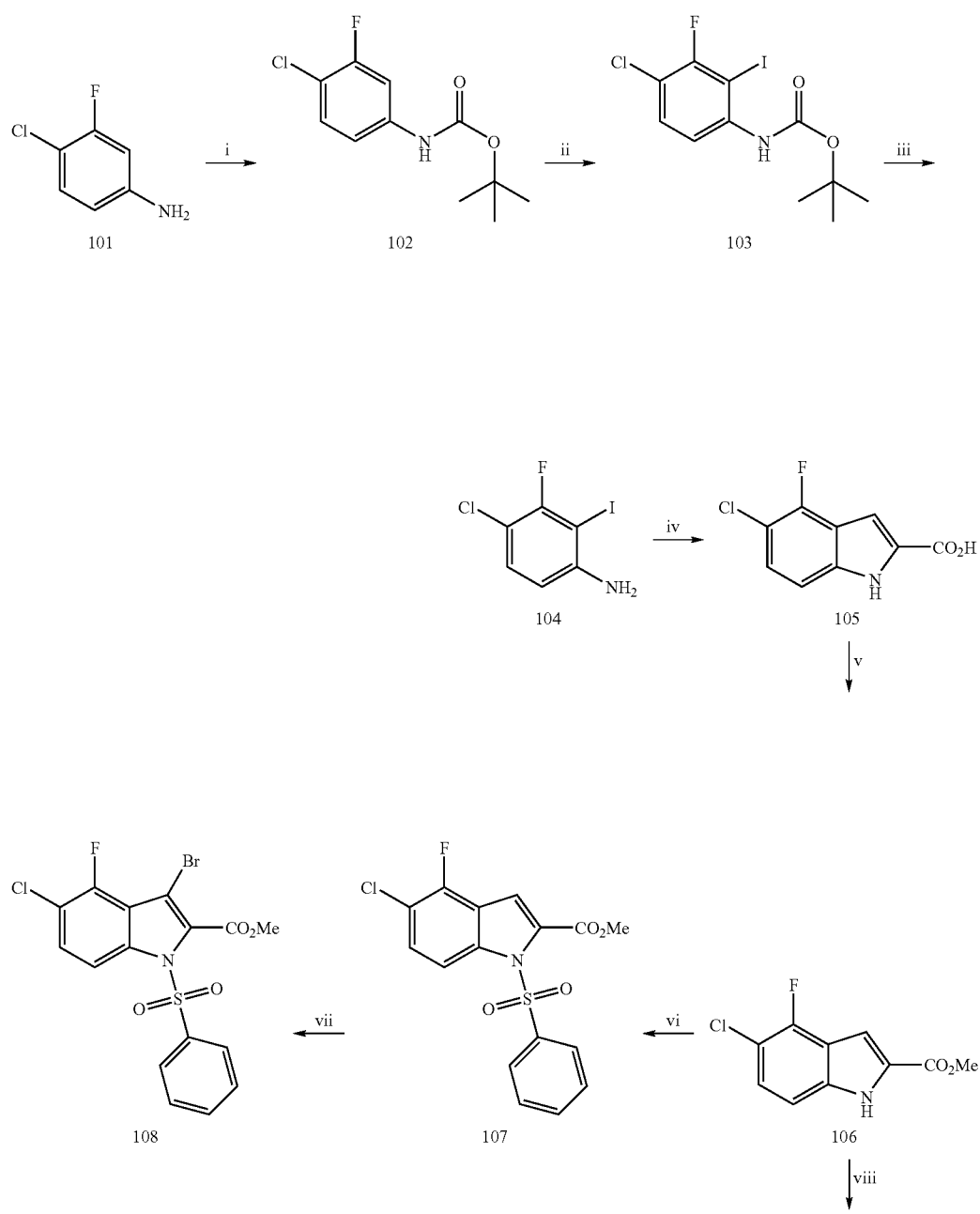

-continued

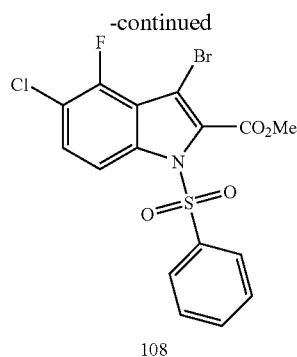
108

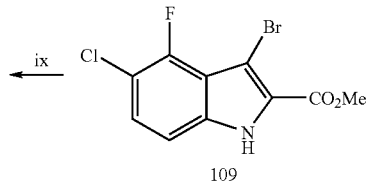
109

Alternatively ethyl ester

Conditions:
i. Boc₂O 3.0 eq, n-heptane, 90° C., 4 h
ii. n-BuLi 3.1 eq, I₂ 3.5 eq, -80° C. < T< -75° C.
iii. 1. c. HCl 6.0 eq, 55° C.; 2. 2M NaOH, 15° C.
iv. DABCO, Pyruvic acid, Pd(OAc)₂
v. 1. CDI, DMF; 2. MeOH or EtOH
vi. 1. NaH, DMF; 2. PhSO₂Cl
vii. Br₂, DCM
viii. DBDMH, THF
ix. 1. NaH, DMF; 2. PhSO₂Cl Part A: Synthesis of 3-bromo-indole intermediate Compound 102

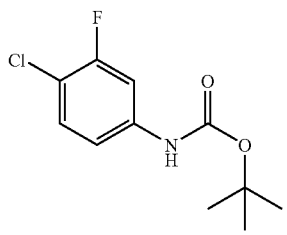

4-Chloro-3-fluoroaniline (250.3 g, 1.719 mol) was added to a 5 L four-neck round bottom flask equipped with overhead stirrer, reflux condenser, heating mantle, temperature controller, an internal temperature probe and an argon inlet. n-Heptane (2000 ml) and di-t-butyl-dicarbonate (450.3 g, 2.064 mol) were charged to the flask. The mixture was stirred under argon at room temperature for 15 min allowing dissolution of the majority of the solids. The mixture was heated to reflux for 4 h under argon (care: generation of CO₂ g). Analysis of the reaction mixture by HPLC method Test 20 (THF:MeCN 1:1) indicated complete conversion of starting material (Rt 4.57 min) to one product (Rt 6.17 min).

The reaction was allowed to cool to 50-55° C. and transferred in two portions to a 3 L one-neck RBF. A total of 1500 ml of distillate was removed by concentration in vacuo at 45° C. to give a peach colored solution with white crystals. The slurry was allowed to cool to room temperature, whilst stirring, for 1.5 h. The flask was stored at 4° C. for 15 h after which time the crystals were filtered under vacuum and washed with cold n-heptane (400 ml).

After drying at 35° C. under vacuum for 7 h, very fine, white crystals of Compound 102 (393.1 g, 93% yield) were obtained. Compound 102: $C_{11}H_{13}ClFNO_2$ 245.68 gmol⁻¹.

HPLC analysis (Test 20, MeCN): $R_t$ 6.16 min; 99% purity @ 254 nm. m.p.: 103-104° C. ¹H NMR $\delta_H$ (400 MHz, CDCl₃): 1.51 (9H, s, 3×CH₃), 6.56 (1H, br-s, N—H), 6.94, 7.25, 7.35 (3×1H, 3×m, 3×Ar—H).

Compound 103

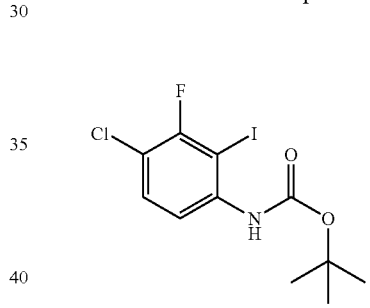

Compound 102 (80.2 g, 0.326 mol) was added to a 3 L four-neck round bottom flask equipped with overhead stirrer, an internal temperature probe, 500 ml addition funnel and an argon inlet. Anhydrous tetrahydrofuran (640 ml) was charged to the flask and cooled using a dry ice bath plus liquid nitrogen, ensuring an internal temperature of -80° C.<T<-75° C. at all times during the reaction. n-Butyl lithium (405 ml, 1.011 mol) was transferred via cannula to the argon filled funnel and added dropwise to the solution with minimal splashing over 2 h. After aging for 40 min, a solution of iodine (289.9 g, 1.142 mol) in anhydrous tetrahydrofuran (430 ml+100 ml rinse) was added dropwise to the cold reaction mixture, ensuring an internal temperature of -80° C.<T<-75° C. over 3 h.

The reaction mixture was allowed to warm slowly to -30° C. over 14 h after which time analysis by HPLC method Test 20 (sample quenched with NaHSO₃ aq, diluted with MeCN then MeCN layer diluted with MeOH) indicated nearly complete conversion of starting material (Rt 6.17 min, 1.6% @ 254 nm) to one product (Rt 6.73 min).

A solution of NH₄Cl (41.6 g in 160 ml water) was added gradually, followed by a solution of NaHSO₃ (184.8 g in 560 ml water) ensuring T<-10° C. The quenching mixture was allowed to warm to 10° C. whilst stirring for 1.5 h.

After transferring the mixture to a one-neck flask, 1370 ml of THF distillate was removed and water (500 ml) was added.

The mixture was stirred vigorously at 4° C. for 15 h and filtered. After washing with water (400 ml) a beige solid was obtained with a colorless filtrate which contained no product by HPLC.

The solid was dissolved in hot (65° C.) ethanol (700 ml) and filtered whilst hot to remove insoluble material (3.5 g, no product by HPLC). The filtrate obtained was concentrated at 45° C. under vacuum to 150 ml at which point solids began to precipitate. Water (32 ml) was added dropwise to the mixture which was then cooled slowly to 4° C. over 1.5 h. Filtration under vacuum, washing with 4° C. ethanol:water 2:1 (250 ml) and drying under vacuum at 40° C. gave Compound 103 as a pale yellow solid (114.1 g, 94% yield). Compound 103: $C_{11}H_{12}ClFINO_2$ 371.57 gmol$^{-1}$. HPLC analysis (Test 20, MeOH): R$_t$ 6.73 min; 99% purity @ 272 nm. m.p.: 66-67° C. $^1$H NMR $\delta_H$ (400 MHz, CDCl$_3$): 1.45 (9H, s, 3×CH$_3$), 7.27 (1H, dd, Ar—H), 7.55 (1H, t, Ar—H), 8.70 (1H, s, CON—H). $^{13}$C NMR $\delta_C$ (100 MHz, CDCl$_3$): 28.04 (C(CH$_3$)$_3$), 79.73 (C(CH$_3$)$_3$), 86.23, 86.49 (C—I), 115.11, 115.32 (C—Cl), 122.35, 122.38 (C—N), 129.89 (C—H), 140.99, 141.02 (C—H), 152.94 (C═O), 155.47, 157.87 (C—F).

Compound 104

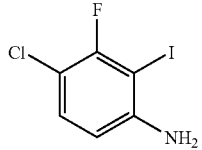

Compound 103 (110.0 g, 0.296 mol) was added to a 3 L four-neck round bottom flask equipped with overhead stirrer, reflux condenser, water bath, 250 ml addition funnel, an internal temperature probe and an argon inlet. Ethanol (900 ml) was charged to the flask and cooled to 5° C. Hydrochloric acid (37%, 145.9 ml) was added dropwise keeping the internal temperature below 15° C.

The mixture was warmed to 50-55° C. for 2 h after which time analysis by HPLC method Test 20 (MeOH) indicated complete conversion of starting material (Rt 6.73 min) to one product (Rt 5.44 min). The reaction was cooled to 5° C. and a solution of NaOH (80.0 g in 1000 ml water prepared, 865 ml added) was added gradually keeping the temperature below 15° C., monitoring the pH until neutral. The mixture was transferred to a one-neck flask and stored at 4° C. for 15 h.

A total of 970 ml of distillate was removed by concentration in vacuo at 35° C. to give a colorless solution with precipitated solids. The slurry was allowed to cool to 4° C. for 1 h after which time the solid was filtered under vacuum and washed with 4° C. ethanol:water 1:4 (200 ml). After drying at 35° C. under vacuum for 72 h, impure Compound 104 (80 g, 99% yield, 95% purity at 254 nm) was obtained.

The solid was dissolved in hot (60° C.) ethanol (450 ml) and filtered whilst hot to remove the fine insoluble material. The filtrate obtained was concentrated at 35° C. under vacuum to 175 ml at which point water (70 ml) was added dropwise to the mixture over 3-4 h, which was then cooled slowly to 4° C. and stirred for a further 0.5 h. Filtration under vacuum, washing with 4° C. ethanol:water 3:2 (100 ml) and drying under vacuum at 35° C. gave Compound 104 as orange needles (70.5 g, 88% yield, 98% purity @ 272 nm). A second crop of material was obtained from the mother liquor as a pale yellow solid (4.6 g, 5%, 98% purity at 272 nm). Combined yield=93%. Compound 104: $C_6H_4ClFIN$ 271.45 gmol$^{-1}$.

HPLC analysis (Test 20, MeCN): R$_t$ 5.44 min; 98% purity @ 272 nm. m.p.: 80.5-81° C.

ESI +ve: m/z 271.9 [M+H]$^+$ 65%; 312.9 [M+MeCN+H]$^+$ 100%. $^1$H NMR $\delta_H$ (400 MHz, d6-DMSO): 5.69 (2H, s, 2×N—H), 6.55 (1H, d, Ar—H), 7.18 (1H, t, Ar—H). $^{13}$C NMR $\delta_C$ (100 MHz, d6-DMSO): 70.97, 71.24 (C—I), 104.03, 104.25 (C—Cl), 110.14, 110.17 (C—H), 129.90 (C—H), 150.09, 150.14 (C—N), 155.45, 157.82 (C—F). $^{19}$F NMR $\delta_F$ (376 MHz, d6-DMSO): −91.60 (1F, d)

Compound 105

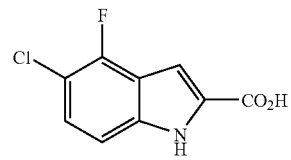

Compound 104 (74.5 g, 0.275 mol) was added to a 2 L four-neck round bottom flask equipped with overhead stirrer, reflux condenser, heating mantle, temperature controller, 250 ml addition funnel, an internal temperature probe and an argon inlet. N,N-Dimethylformamide (575 ml) was charged to the flask at room temperature. DABCO (95.5 g, 0.851 mol) was added in one portion and the internal temperature dropped to 15° C. The mixture was stirred for 20 min to effect dissolution and the solution was degassed by bubbling argon through it vigorously for 10 min. Pyruvic acid (57.33 ml, 0.824 mol) was added to the brown solution over 10 min and the internal temperature rose to 36° C. The solution was again degassed with argon for 10 min and palladium acetate (678 mg, 0.0030 mol) was added in one portion.

The mixture was heated to 100° C. for 3 h after which time analysis by HPLC method Test 20 (MeCN, filtered) indicated complete conversion of starting material (Rt 5.44 min) to one product (Rt 3.64 min). The reaction was cooled to room temperature for 15 h and subsequently to 5° C. A solution of hydrochloric acid (1.15N, 575 ml then 0.115N, 280 ml) was added gradually keeping the temperature below 10° C., monitoring the "pH" until pH=3.5. A tan solid precipitated from the solution and the mixture was stirred for an additional 0.5 h at 5° C. The solid was filtered under vacuum and washed with 10° C. water (3×200 ml). After drying at 40° C. under vacuum for 36 h, Compound 105 (55.9 g, 95% yield) was obtained. Compound 105: $C_9H_5ClFNO_2$ 213.59 gmol$^{-1}$ HPLC analysis (Test 20, MeCN): R$_t$ 3.63 min; 99% purity @ 272 nm ESI −ve: m/z 212.1 [M−H]$^-$ 10%; 168.1 [M-COOH]$^-$ 100% $^1$H NMR $\delta_H$ (400 MHz, d6-DMSO): 7.10, 7.11 (1H, d, Ar—H), 7.25-7.32 (2H, m, 2×Ar—H), 12.30, 13.33 (2×1H, 2×s, N—H, COO—H) $^{13}$C NMR $\delta_C$ (100 MHz, d6-DMSO): 102.45 (C-3), 108.76, 108.92 (C-9), 110.20, 110.24 (C-6), 116.88, 117.09 (C-5), 125.46 (C-7), 130.34 (C-2), 137.90, 138.00 (C-8), 149.76, 152.25 (C-4), 162.12 (C=O) $^{19}$F NMR $\delta_F$ (376 MHz, d6-DMSO): −121.35 (1F, d).

Compound 106

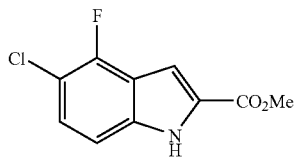

Compound 105 (55.9 g, 0.262 mol) was added to a 5 L four-neck round bottom flask equipped with overhead stirrer, addition funnel, an internal temperature probe and an argon inlet. N,N-Dimethylformamide (695 ml) was charged to the flask at room temperature under argon, stirring for 20 min to obtain a brown solution. Carbonyldiimidazole (51.0 g, 0.314 mol) was added in one portion giving a brown suspension. The mixture was stirred for 1 h under argon at room temperature after which time analysis by HPLC method Test 20 (MeOH to give Me ester, filtered) indicated incomplete conversion of starting material (Rt 3.64 min, 0.5%) to major product (Rt 5.48 min) plus intermediate (Rt 4.77 min). Additional carbonyldiimidazole (0.43 g, 0.0026 mol) and N,N-dimethylformamide (45 ml) were added and the reaction was stirred for a further 2 h after which time analysis by HPLC method Test 20 (MeOH to give Me ester, filtered) indicated complete conversion of starting material (Rt 3.64 min) to product (Rt 5.48 min). Methanol (297 ml, 7.34 mol) was added to the stirred reaction mixture under argon at 24° C. to give a cloudy brown suspension. After 3 h analysis by HPLC method Test 20 (MeCN, filtered) indicated one product (Rt 5.48 min). The reaction mixture was cooled using an ice bath and water (2000 ml) was added over 0.5 h keeping the internal temperature 15-20° C. to precipitate a tan solid. The solid was filtered under vacuum and washed with 5° C. water (2×400 ml). After air drying, the solid was taken up in dichloromethane (800 ml) and ethyl acetate (1600 ml) and dried with anhydrous sodium sulfate (400 g). Filtration through Celite and elution with dichloromethane (1000 ml) yielded a clear orange solution. The solution was concentrated under vacuum at 30° C. leaving a slurry of crystals in the remaining ethyl acetate (160 ml). The slurry was cooled to 5° C. with an ice bath for 15 min. Filtration under vacuum, washing with 4° C. ethyl acetate:n-heptane 1:1 (2×100 ml) then 1:3 (100 ml) and drying under vacuum at 35° C. gave Compound 6 as long, white needles (37.3 g, 63% yield, 99% purity @ 272 nm). A second crop of material was obtained from the mother liquor as less white needles (5.3 g, 9%, 98% purity at 272 nm). Combined yield=72%. Compound 106: $C_{10}H_7ClFNO_2$ 227.62 gmol$^{-1}$ HPLC analysis (Test 20, MeCN): $R_t$ 5.48 min; 99% purity @ 272 nm m.p.: 216.5-218° C. $^1$H NMR $\delta_H$ (400 MHz, d6-DMSO): 3.88 (3H, s, CH$_3$), 7.16 (1H, s, Ar—H), 7.27-7.35 (2H, m, 2×Ar—H), 12.48 (1H, s, N—H) $^{13}$C NMR $\delta_C$ (100 MHz, d6-DMSO): 52.15 (CO$_2$CH$_3$), 102.90 (C-3), 108.97, 109.12 (C-9), 110.27, 110.31 (C-6), 116.77, 116.98 (C-5), 125.84 (C-7), 128.82 (C-2), 138.00, 138.09 (C-8), 149.77, 152.26 (C-4), 161.05 (C=O) $^{19}$F NMR $\delta_F$ (376 MHz, d6-DMSO): −121.11 (1F, d)

Compound 107

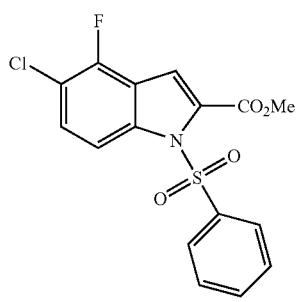

Compound 106 (46.5 g, 0.204 mol) was added to a 2 L four-neck round bottom flask equipped with overhead stirrer, ice bath, an internal temperature probe and an argon inlet. Anhydrous N,N-dimethylformamide (450 ml) was charged to the flask at room temperature under argon, stirring to obtain an orange solution. Sodium hydride (95%, 7.30 g, 0.290 mol) was added in portionwise over 45 min keeping the internal temperature below 5° C. No further gas evolution was observed. Phenylsulfonyl chloride (35.8 ml, 0.280 mol) was added dropwise over 15 min keeping the internal temperature below 10° C. The reaction was stirred for 1 h after which time analysis by HPLC method Test 20 (MeCN) indicated incomplete conversion of starting material (Rt 5.48 min, 4% at 272 nm) to product (Rt 6.42 min). Further portions of sodium hydride (95%, 1.1 g) and phenylsulfonyl chloride (4.0 ml) were added and the mixture was stirred for a further 1.5 h. Analysis by HPLC method Test 20 (MeCN) indicated incomplete conversion of starting material (Rt 5.48 min, 3% at 272 nm) to product (Rt 6.43 min). The reaction was worked up by the slow addition of water (770 ml) over 25 min, ensuring the internal temperature remained below 20° C., allowing a yellow solid to precipitate. The solid was filtered under vacuum, washed with 5° C. water (770 ml) and dried at 37° C. for 15 h. The solid was taken up in ethanol (700 ml) and warmed to 55° C. with stirring for 1 h. The hot suspension was concentrated under vacuum at 40° C. removing 350 ml of distillate, then allowed to cool to 5° C. for 0.5 h. Filtration under vacuum, washing with 4° C. ethanol (150 ml) and drying under vacuum at 40° C. gave Compound 107 as a pale yellow solid (68.5 g, 91% yield). Compound 107: $C_{16}H_{11}ClFNO_4S$ 367.78 gmol$^{-1}$ HPLC analysis (Test 20, MeCN): $R_t$ 6.43 min; 98% purity @ 272 nm m.p.: 163° C. expanded, 166-167° C. melted $^1$H NMR $\delta_H$ (400 MHz, d6-DMSO): 3.88 (3H, s, CH$_3$), 7.51 (1H, s, Ar—H), 7.62-7.68 (3H, m, 3×Ar—H), 7.77 (1H, t, Ar—H), 7.92 (1H, d, Ar—H), 8.04 (2H, d, Ar—H) $^{13}$C NMR $\delta_C$ (100 MHz, d6-DMSO): 53.21 (CO$_2$CH$_3$), 110.60 (C-3), 112.30, 112.34 (C-6), 114.02, 114.17 (C-9), 117.93, 118.14 (C-5), 127.14 (2×Ar—C), 128.78 (C-7), 129.85 (2×Ar—C), 132.29 (C-2), 135.24 (C-para), 136.82 (C-ipso), 136.88, 136.96 (C-8), 149.37, 151.89 (C-4), 160.51 (C=O) $^{19}$F NMR $\delta_F$ (376 MHz, d6-DMSO): −119.42 (1F, d)

Compound 108

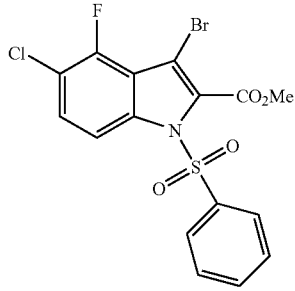

Compound 107 (68.4 g, 0.186 mol) was added to a 2 L four-neck round bottom flask equipped with overhead stirrer, addition funnel, ice bath, an internal temperature probe and an argon inlet. Anhydrous dichloromethane (685 ml) was charged to the flask at room temperature under argon, stirring to obtain a partial suspension. Bromine (11.5 ml, 0.223 mol) was added dropwise over 20 min keeping the internal temperature below 10° C. giving a deep red mixture. The reaction mixture was allowed to warm to room temperature for 1 h after which time analysis by HPLC method Test 20 (sample quenched with NaHSO$_3$ aq, diluted with MeOH then MeOH filtered and diluted with MeCN) indicated incomplete conversion of starting material (Rt 6.43 min, 78% @ 272 nm) to a minor product (Rt 6.76 min). Additional bromine (12.4 ml) was added in portions over the course of the next 6 h and the reaction was left to stir at room temperature for 14 h at which point analysis by HPLC method Test 20 (sample quenched with NaHSO$_3$ aq, diluted with MeOH then MeOH filtered and diluted with MeCN) indicated complete conversion of starting material (Rt 6.43 min) to one major product (Rt 6.76 min). The reaction was quenched by the addition of a solution of NaHSO$_3$ (132 g in 400 ml water) ensuring T<15° C. dropwise over 30 min. The layers were separated and the organic layer was washed with saturated aqueous sodium bicarbonate (400 ml×2). The aqueous layers were extracted with dichloromethane (400 ml) and the combined organic layers were washed with water (1000 ml), and dried with anhydrous sodium sulfate (500 g). Filtration and concentration under vacuum at 28° C. gave a crude yellow solid (78 g). The solid was triturated in hot ethanol (650 ml) at 50° C. for 1 h. The hot suspension was concentrated under vacuum at 40° C. removing 450 ml of distillate, then allowed to cool to 5° C. for 0.5 h. Filtration under vacuum, washing with 4° C. ethanol (150 ml) and drying under vacuum at 25° C. gave Compound 108 as a pale yellow powder (72.6 g, 88% yield, 93% purity at 272 nm). This solid was dissolved in hot ethyl acetate (500 ml) at 50° C. for 1 h. Ethanol (200 ml) was added slowly at 50° C. and stirred for 15 min. Precipitation began and the hot suspension was concentrated under vacuum at 40° C. removing 475 ml of distillate, then allowed to cool to 5° C. for 0.5 h. Filtration under vacuum, washing with 4° C. ethanol (150 ml) and drying under vacuum at 25° C. gave Compound 108, methyl 3-bromo-5-chloro-4-fluoro-1-benzenesulfonyl-indole-2-carboxylate, as a pale yellow powder (57.4 g, 69% yield, 97% purity at 272 nm). A second crop of material was obtained from the mother liquor as a yellow solid (9.6 g, 12%). Combined yield=81%. Methyl 3-bromo-5-chloro-4-fluoro-1-benzenesulfonyl-indole-2-carboxylate Compound 108: C$_{16}$H$_{10}$BrClFNO$_4$S 446.68 gmol$^{-1}$ HPLC analysis (Test 20, MeCN): R$_t$ 6.76 min; 97% purity @ 272 nm ESI +ve: m/z 447.8 [M+H]$^+$ 90%; 464.8 [M+NH$_4$]$^+$ 100%

ESI −ve: m/z 445.9 [M−H]$^-$ 100% $^1$H NMR $\delta_H$ (400 MHz, d6-DMSO): 3.99 (3H, s, CH$_3$), 7.66 (3H, t, 3×Ar—H), 7.78 (1H, t, Ar—H), 7.90 (1H, d, Ar—H), 7.98 (2H, d, 2×Ar—H) $^{13}$C NMR $\delta_C$ (100 MHz, d6-DMSO): 53.88 (CO$_2$CH$_3$), 96.66 (C-3), 111.87, 111.90 (C-6), 115.36, 115.51 (C-9), 117.29, 117.45 (C-5), 127.16 (2×Ar—C), 129.40 (C-7), 130.15 (2×Ar—C), 130.45 (C-2), 134.63, 134.69 (C-8), 135.46 (C-para), 135.81 (C-ipso), 149.31, 151.85 (C-4), 160.30 (C=O) $^{19}$F NMR $\delta_F$ (376 MHz, d6-DMSO): −124.00 (1F, d)

Part B: Synthesis of Compound I

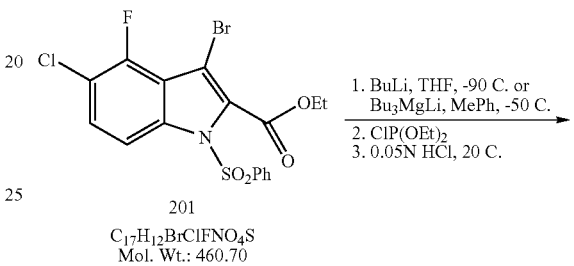

201
C$_{17}$H$_{12}$BrClFNO$_4$S
Mol. Wt.: 460.70

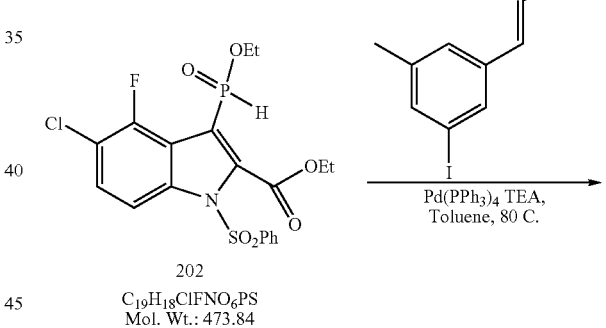

202
C$_{19}$H$_{18}$ClFNO$_6$PS
Mol. Wt.: 473.84

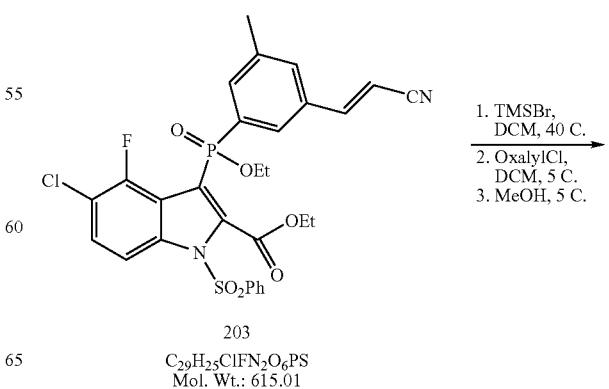

203
C$_{29}$H$_{25}$ClFN$_2$O$_6$PS
Mol. Wt.: 615.01

-continued

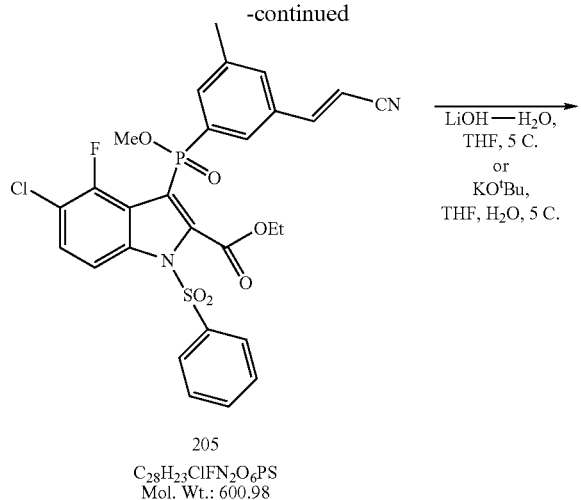

205
$C_{28}H_{23}ClFN_2O_6PS$
Mol. Wt.: 600.98

LiOH—$H_2O$,
THF, 5 C.
or
KO$^t$Bu,
THF, $H_2O$, 5 C.

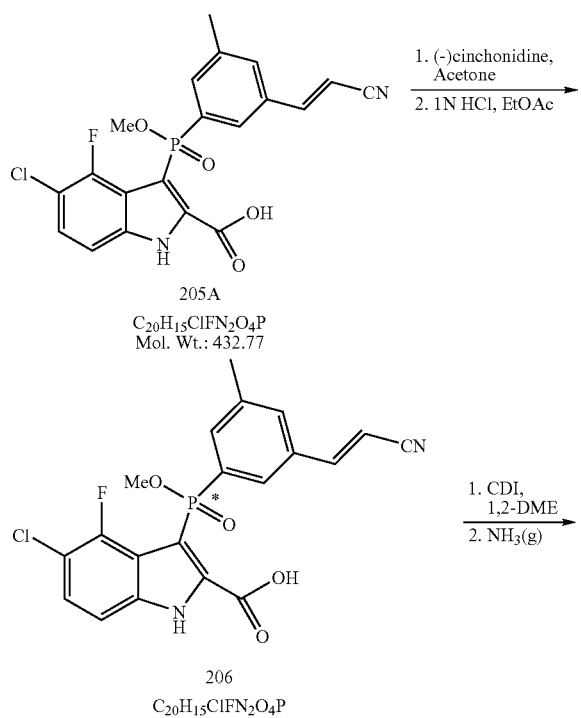

205A
$C_{20}H_{15}ClFN_2O_4P$
Mol. Wt.: 432.77

1. (-)cinchonidine, Acetone
2. 1N HCl, EtOAc

206
$C_{20}H_{15}ClFN_2O_4P$
Mol. Wt.: 432.77

1. CDI, 1,2-DME
2. $NH_3$(g)

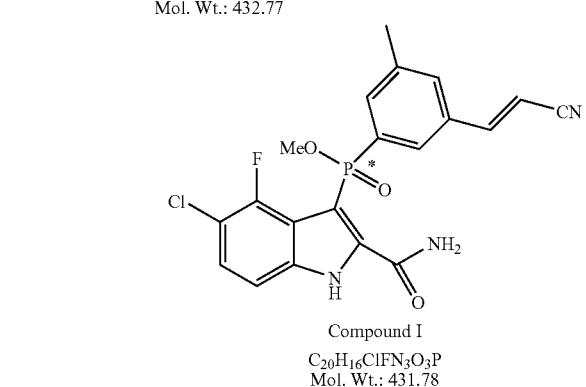

Compound I
$C_{20}H_{16}ClFN_3O_3P$
Mol. Wt.: 431.78

Compound 202

A suitable reactor was charged Compound 201 (57 g, 0.12 mol) and tetrahydrofuran (570 ml.) The resulting solution was chilled to −90° to −100° C. under nitrogen using an LN$_2$/IPA slush bath, then was treated with n-butyl lithium (2.5M in Hexanes, 52 ml, 0.13 mol) added over 10 minutes. To this was added diethyl chlorophosphite (20.5 g, 0.13 mol) over 10 minutes. HPLC (Method 001, RT=17.7 min) showed no starting material and ca. 70% product. The reaction was then diluted with ethyl acetate (570 ml) and was allowed to warm to −40° C. The mix was then treated with hydrochloric acid (0.5M, 400 ml) and was allowed to warm to ambient temperature and stir for 30 minutes. The resulting layers were separated and the aqueous extracted with ethyl acetate (500 ml). The organics were combined and washed with brine (500 ml) dried over sodium sulfate, filtered and concentrated to an oil. 78% HPLC AUC (Method 20, RT=5.6 min)>100% yield due to impurities and solvent. Used as is in the next step. Data for C-2-Methyl Ester: #2x: $C_{18}H_{16}ClFNO_6PS$ 459.81 gmol$^{-1}$ m/z (ESI+): 460.0 (MH$^+$, 100%), 462.0 (MH$^+$, 35%).

Compound 203

A suitable reactor was charged with Compound 202 (56 g, estimated 0.10 mol) iodocinnamonitrile (27 g, 0.10 mol) triethylamine (17 ml, 0.12 mol) and toluene (475 ml). The resulting mix was degassed by sparging with a stream of nitrogen for 10 minutes at ambient temperature, after which time tetrakis(triphenylphosphine) palladium(0) (6.0 g, 0.005 mol) was added. The mix was sparged for an additional 5 minutes, then was heated to 80° C. for 2 hours. HPLC (Method 20, RT=6.2 min) showed a complete reaction. The mix was cooled to ambient and was filtered through celite and washed with ethyl acetate (1000 ml.). The combined organics were washed with brine (2×500 ml) then dried over sodium sulfate, filtered and concentrated to a volume of 170 ml. The concentrate was cooled to 0° C. and was stirred for 1 hour, during which time the product crystallized. The solids were filtered and washed with hexane:toluene (2:1, 150 ml.) Dried to leave 54 g, HPLC AUC 85% (Method 20.)

The crude solid was then purified by column chromatography eluted w/25% ethyl acetate in methylene chloride. Pure fractions were collected and combined to give Compounds 203, 41 g, 67% yield, 96% HPLC AUC (method Test 20, RT=6.2 min).

Data for C-2-Ethyl Ester: #3: $C_{29}H_{25}ClFN_2O_6PS$ 615.01 gmol$^{-1}$ $^1$H NMR $\delta_H$ (400 MHz, CDCl$_3$): 1.35 (3H, t, PO$_2$CH$_2$CH$_3$), 1.52 (3H, t, CO$_2$CH$_2$CH$_3$), 2.40 (3H, s, Ar—CH$_3$), 4.08-4.20 (2H, m, PO$_2$CH$_2$CH$_3$), 4.61 (2H, q, CO$_2$CH$_2$CH$_3$), 5.90 (1H, d, CH═CHCN), 7.33-7.37 (3H, m, 2×Ar—H, CH═CHCN), 7.55 (2H, a-t, 2×Ar—H), 7.67 (1H, a-t, Ar—H), 7.74-7.79 (3H, m, 3×Ar—H), 8.13 (2H, d, 2×Ar—H)

Data for C-2-Methyl Ester: #3x: $C_{28}H_{23}ClFN_2O_6PS$ 600.98 gmol$^{-1}$ m/z (ESI+): 601.1 (MH$^+$, 100%), 603.0 (MH$^+$, 35%) $^1$H NMR $\delta_H$ (400 MHz, d6-DMSO): 1.18 (3H, t, CH$_3$CH$_2$OP), 2.34 (3H, s, Ar—CH$_3$), 4.02 (5H, m, CH$_3$CH$_2$OP, CO$_2$CH$_3$), 6.47 (1H, d, CH═CHCN), 7.54 (1H, d, Ar—H), 7.62 (1H, t, Ar—H), 7.72 (1H, d, CH═CHCN), 7.70-7.76 (4H, m, 4×Ar—H), 7.82 (1H, t, Ar—H), 7.91 (1H, d, Ar—H), 8.13 (2H, d, 2×Ar—H). Multiple $\delta_C$ values indicate splitting of carbon signal due to F and/or P. $^{13}$C NMR $\delta_C$ (100 MHz, d6-DMSO): 15.97, 16.03 (CH$_3$CH$_2$OP), 20.79 (Ar—CH$_3$), 53.88 (CO$_2$CH$_3$), 61.73, 61.79 (CH$_3$CH$_2$OP), 98.39 (CH═CHCN), 107.50, 107.54 (C), 108.95, 108.99 (C), 111.37, 111.42 (C), 115.47, 115.63 (C), 116.82, 116.91, 117.01, 117.10 (C), 118.43 (CN), 127.44 (SO$_2$Ph, 2×C$_{ortho}$), 127.91, 128.02 (C—H), 128.67 (C—H), 130.27 (SO$_2$Ph, 2×C$_{meta}$), 131.21, 131.41 (C—H), 132.68 (C), 133.29, 133.40 (C—H), 134.12, 134.27 (C), 134.55, 134.63, 134.72 (C), 135.49 ($SO_2Ph$, $C_{ipso}$), 136.09 ($SO_2Ph$, $C_{para}$), 139.10, 139.25 (C), 149.06, 151.60 (C-4), 149.51 (CH=CHCN), 161.10 (C=O). $^{19}F$ NMR $\delta_F$ (376 MHz, d6-DMSO): −112.36 (1F, d). $^{31}P$ NMR $\delta_P$ (162 MHz, d6-DMSO): 23.49 (1P, s)

Compound 204

A suitable reactor was charged with Compound 203 (41 g, 0.067 mol) and methylene chloride (175 ml.) The resulting solution was cooled to 0° C., and was treated with bromotrimethylsilane (46 g, 0.30 mol) added over 15 minutes. The reaction was then warmed to 40° C. for 1.5 hours. HPLC (Method 20, RT=4.3 min) indicated a complete reaction. The excess TMSBr was stripped under vacuum (40-45° C.) and the resulting sticky solid was resuspended in DCM (200 ml) and chilled to 0° C. Oxalyl chloride (12 ml, 0.13 mol) were added over 15 minutes, followed by N,N-dimethylformamide (1.0 ml) both added at 0° C. Gas evolution was observed during the DMF addition. After 1 hour at ambient, HPLC (Method 20, RT=6.0 min, sample quenched with methanol prior to injection) showed a complete reaction. The solvents were stripped again to remove residual oxalyl chloride and the mix resuspended methylene chloride (100 ml). The solution was chilled to 0°-5° C., and then was treated with methanol (300 ml) and was allowed to warm to ambient. After two hours, HPLC indicated a complete reaction (HPLC Method 20, RT=6.0 min.) The solvents were stripped and the crude solid was used as is in the next step. Compound 204 48 g, HPLC AUC 91%, >100% yield due to solvents and impurities.

Data for C-2-Ethyl Ester: 204: $C_{28}H_{23}ClFN_2O_6PS$ 600.98 gmol$^{-1}$ $^1H$ NMR $\delta_H$ (400 MHz, $CDCl_3$): 1.53 (3H, t, $CO_2CH_2CH_3$), 2.40 (3H, s, Ar—$CH_3$), 3.79 (3H, d, $POCH_3$), 4.61 (2H, q, $CO_2CH_2CH_3$), 5.90 (1H, d, CH=CHCN), 7.33-7.37 (3H, m, 2×Ar—H, CH=CHCN), 7.55 (2H, a-t, 2×Ar—H), 7.67 (1H, a-t, Ar—H), 7.73-7.79 (3H, m, 3×Ar—H), 8.13 (2H, d, 2×Ar—H)

Data for C-2-Methyl Ester: 204x: $C_{27}H_{21}ClFN_2O_6PS$ 586.96 gmol$^{-1}$ m/z (ESI+): 587.1 (MH$^+$, 100%), 589.0 (MH$^+$, 35%) $^1H$ NMR $\delta_H$ (400 MHz, d6-DMSO): 2.33 (3H, s, Ar—$CH_3$), 3.66 (3H, d, $POCH_3$), 4.02 (3H, s, $CO_2CH_3$), 6.47 (1H, d, CH=CHCN), 7.53 (1H, d, Ar—H), 7.61 (1H, dd, Ar—H), 7.70 (1H, d, CH=CHCN), 7.68-7.76 (4H, m, 4×Ar—H), 7.82 (1H, t, Ar—H), 7.90 (1H, d, Ar—H), 8.13 (2H, d, 2×Ar—H). Multiple $\delta_C$ values indicate splitting of carbon signal due to F and/or P. $^{13}C$ NMR $\delta_C$ (100 MHz, d6-DMSO): 20.81 (Ar—$CH_3$), 52.07, 52.13 ($CH_3OP$), 53.99 ($CO_2CH_3$), 98.46 (CH=CHCN), 106.99 (C), 108.41 (C), 111.45 (C—H), 115.51, 115.67 (C), 116.77, 116.86, 117.07 (C), 118.48 (CN), 127.51 ($SO_2Ph$, $2×C_{ortho}$), 127.92, 128.04 (C—H), 128.71 (C—H), 130.32 ($SO_2Ph$, $2×C_{meta}$), 131.56 (C—H), 132.20 (C), 133.35, 133.46 (C—H), 134.19, 134.34 (C), 134.55, 134.63, 134.72 (C), 135.47 ($SO_2Ph$, $C_{ipso}$), 136.16 ($SO_2Ph$, $C_{para}$), 139.20, 139.35, 139.39, 139.54 (C), 149.09, 151.63 (C-4), 149.51 (CH=CHCN), 161.15 (C=O). $^{19}F$ NMR $\delta_F$ (376 MHz, d6-DMSO): −113.93 (1F, d). $^{31}P$ NMR $\delta_P$ (162 MHz, d6-DMSO): 25.42 (1P, s)

Compound 205

A suitable reactor was charged with Compound 204 (48 g, ca. 0.072 mol) and tetrahydrofuran (800 ml.) The resulting solution was then cooled to 5° C. and was treated with lithium hydroxide monohydrate (12 g, 028 mol) and water (180 ml) added over 15 minutes. The reaction was allowed to warm to ambient, during which time the color lightened. After overnight stirring, HPLC indicated a complete reaction (Method Test 20, product RT=4.5, major impurity RT=3.7). The reaction was cooled to 5° C. and was acidified with hydrochloric acid (5N, 300 ml). The excess THF was removed by evaporation under reduced pressure and the resulting sticky solids were slurried in acetone (200 ml). The mix was warmed to 40° C. for 30 minutes, and then left to cool to ambient. The solids were allowed to granulate for 2 hours, then were filtered and washed with acetone/water (2:1, 100 ml.) Dried to leave Compound 205, 21 g, 67% yield. HPLC AUC 93% (method Test 20). Used as is in the next step.

Compound 206 (Chiral Resolution)

A suitable reactor was charged with Compound 205 (432.6 g, 1.0 mol) and acetone (7.79 L). (−)-Cinchonidine (294.39 g, 1.0 mol) was added in one portion and the resulting suspension was stirred for four hours. The solids were isolated by filtration and washed with acetone (300 ml) to leave 343.2 g of the salt after drying under vacuum. Chiral HPLC analysis ratio=98:2.

The salt was suspended in a mixture of ethyl acetate (5.2 L) and 1N HCl (5.2 L) and was vigorously stirred at ambient for 2 hours. After this time, the layers were separated. The aqueous layer was further extracted with ethyl acetate (2.7 L) and the organic extracts were combined, dried with sodium sulfate, filtered and concentrated under reduced pressure to yield the resolved Compound 206 as a white solid. 145.44 g, 68% overall yield, chiral HPLC analysis, ratio=98.4:1.6. Used as is in the next step. #6: $C_{20}H_{15}ClFN_2O_4P$ 432.77 gmol$^{-1}$ m/z (ESI+): 433.0 (MH$^+$, 100%), 435.0 (MH$^+$, 35%)

$^1H$ NMR $\delta_H$ (400 MHz, d6-DMSO): 2.35 (3H, s, Ar—$CH_3$), 3.78 (3H, d, $POCH_3$), 6.52 (1H, d, CH=CHCN), 7.46 (2H, d, Ar—H), 7.66 (1H, d, CH=CHCN), 7.69, 7.81 (2H, 2×d, H-6, H-7), 7.77 (1H, s, Ar—H), 13.63 (1H, s, N—H), 15.70 (1H, br-s, COOH). $^{19}F$ NMR $\delta_F$ (376 MHz, d6-DMSO): −114.27 (1F, s). $^{31}P$ NMR $\delta_P$ (162 MHz, d6-DMSO): 36.44 (1P, s).

Compound I

A suitable reactor was charged with Compound 206 (0.63 g, 0.0014 mol) and 1,2-dimethoxyethane (10 ml). The mix was treated with 1,1-carbonyldiimidazole (0.47 g, 0.0028 mol) added in one portion, and the mix was allowed to stir at ambient temperature until gas evolution ceased (ca. 1.5 hours). The solution was then cooled to 5° C., and was sparged with ammonia gas for 5 minutes. HPLC (Method 20, product RT=5.0 min) showed a complete reaction after one hour at ambient. The reaction was quenched by the addition of 10 g crushed ice, and was concentrated under reduced pressure to remove the DME. The resulting slurry was stirred for one hour at 5° C. to granulate the product. The solids were filtered and dried to leave pure Compound I ((2-Carbamoyl-5-chloro-4-fluoro-1H-indol-3-yl)-[3-((E)-2-cyano-vinyl)-5-methyl-phenyl]-(R)-phosphinic acid methyl ester). 0.56 g, 89% yield. HPLC (Method 20) chemical purity 98.5%. Chiral purity 97%.

A suitable reactor was charged with Compound 206 (10 g, 0.024 mol) and 1,2-dimethoxyethane (150 ml.) The mix was treated with 1,1-carbonyldiimidazole (7.8 g, 0.048 mol) added in one portion, and the mix was allowed to stir at ambient temperature until gas evolution ceased. The solution was then cooled to 5° C., and was sparged with ammonia gas for 5minutes. HPLC (Method 20, product RT=5.0 min) showed a complete reaction after one hour. The reaction was quenched by the addition of 100 g crushed ice, and was concentrated under reduced pressure to remove the DME.

The resulting oily solid (in water) was diluted with methanol (20 ml) and stirred for one hour at 5° C. to granulate the product. The solids were filtered and dried to leave pure Compound I ((2-Carbamoyl-5-chloro-4-fluoro1H-indol-3-yl)-[3-((E)-2-cyano-vinyl)-5-methyl-phenyl]-(R)-phosphinic acid methyl ester). 9.8 g, 98% yield.

HPLC (Method 20) chemical purity 99.5%. Chiral purity 94.3%. White solid.

Compound I: $C_{20}H_{16}ClFN_3O_3P$ 431.78 gmol$^{-1}$ m/z (ESI+): 432.1 (MH$^+$, 100%), 434.0 (MH$^+$, 35%) $v_{max}$ (KBr disc) (cm$^{-1}$) 1619.0 (amide I), 1672.5 (amide II), 2218.4 (CN), 3063.0, 3286.0 (N—H) $[\alpha]_D^{20}$: +33.42 (c, 10.04 mgml$^{-1}$ in CHCl$_3$) m.p.: 177° C. glistens, 181° C. softens, 183-185° C. melts Elemental analysis: $C_{20}H_{17}ClN_3O_3P$ calculated C, 55.63%; H, 3.73%; N, 9.73%; C, 18.21%; F, 4.40%; P, 7.17%. Found C, 55.56%; H, 3.74%; N, 9.72%; C, 18.24%; F, 4.21%; P, 7.11%. $^1$H NMR $\delta_H$ (400 MHz, d6-DMSO): 2.32 (3H, s, Ar—CH$_3$), 3.70 (3H, d, CH$_3$OP), 6.49 (1H, d, CH═CHCN), 7.37 (1H, dd, H-6), 7.43 (1H, dd, H-7), 7.54 (1H, d, H-6'), 7.66 (1H, d, CH═CHCN), 7.69 (1H, d, H-2'), 7.73 (1H, s, H-4'), 8.05, 10.63 (2×1H, 2×s, NH$_2$), 13.02 (1H, s, N—H) Multiple $\delta_C$ values indicate splitting of carbon signal due to F and/or P. $^{13}$C NMR $\delta_C$ (100 MHz, d6-DMSO): 20.77 (Ar—CH$_3$), 51.70, 51.76 (CH$_3$OP), 96.03, 96.07, 97.52, 97.56 (C-3), 98.29 (CH═CHCN), 110.70 (C-7), 111.66, 111.83 (C-5), 118.04, 118.13, 118.22, 118.32 (C-9), 118.56 (CN), 125.84 (C-6), 127.11, 127.22 (C-2'), 131.05 (C-4'), 132.57, 132.67 (C-6'), 132.96, 134.50 (C-1'), 134.03, 134.18 (C-3'), 136.40, 136.51, 136.61 (C-8), 138.95, 139.10 (C-5'), 141.71, 141.91 (C-2), 149.19, 151.70 (C-4), 149.65 (CH═CHCN), 160.46 (C═O). $^{19}$F NMR $\delta_F$ (376 MHz, d6-DMSO): −113.11 (1F, d). $^{31}$P NMR $\delta_P$ (162 MHz, d6-DMSO): 33.39 (1P, s)

Example 8

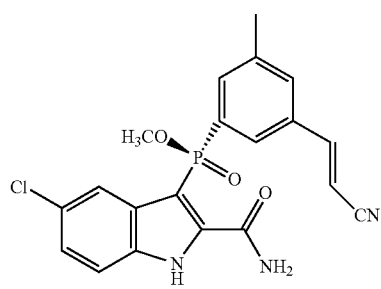

Preparation of Compound III

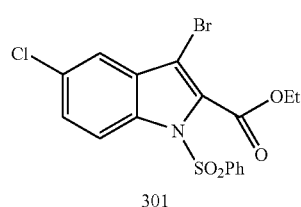

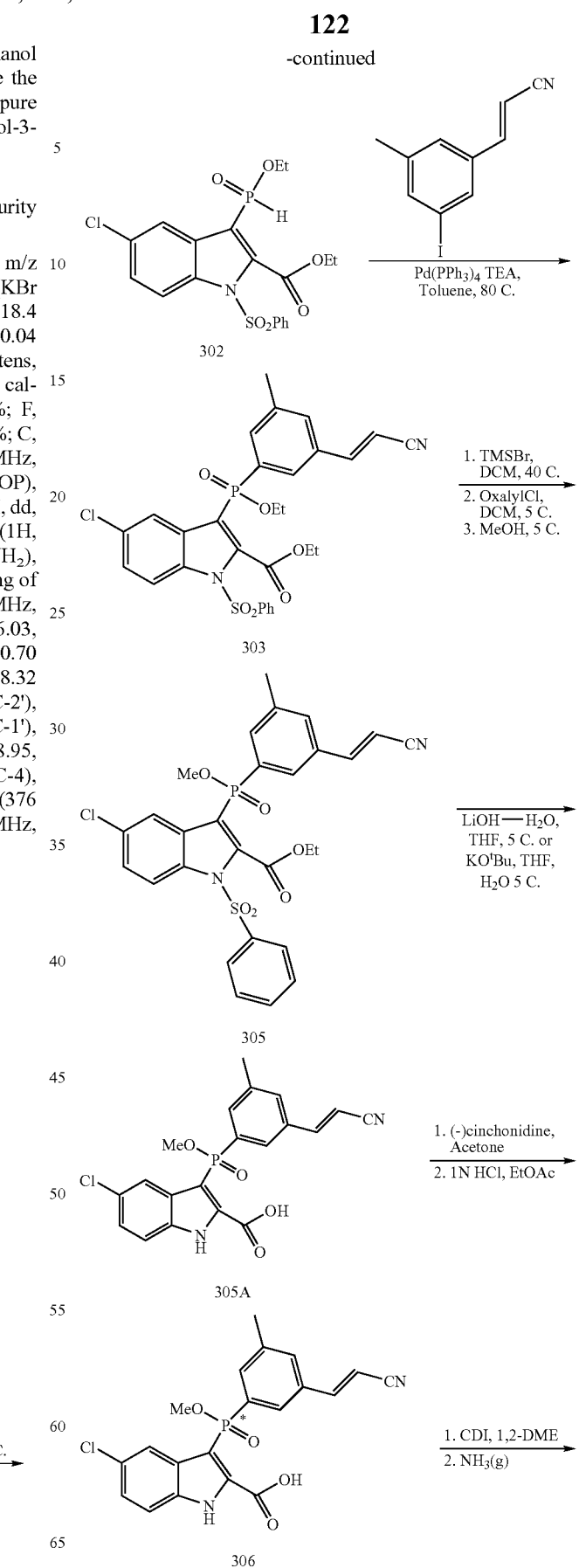

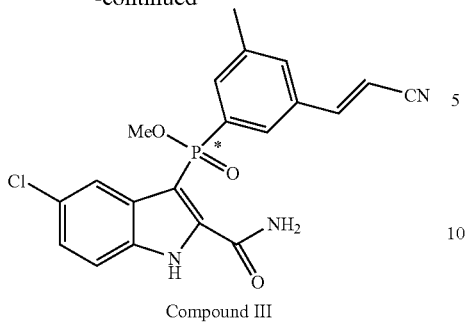

Compound III

Compound 302

A suitable reactor was charged Compound 301 (100 g, 0.23 mol) and tetrahydrofuran (1 L). The resulting solution was chilled between −90° to −100° C. under nitrogen using a LN$_2$/IPA slush bath, then was treated with n-butyl lithium (2.5M in Hexanes, 99 ml, 0.25 mol) added over 10 minutes. To this was added diethyl chlorophosphite (37.1 g, 0.24 mol) over 10 minutes. HPLC (Method 001, RT=18.9 min) showed no starting material and ca. 85% product. The reaction was then diluted with ethyl acetate (1 L) and was allowed to warm to −40° C. The mix was then treated with hydrochloric acid (0.5M, 590 ml) and was allowed to warm to ambient temperature and stir for 30 minutes. The resulting layers were separated and the aqueous extracted with ethyl acetate (500 ml). The organics were combined and washed with brine (500 ml) dried over sodium sulfate, filtered and concentrated to an oil. 88% HPLC AUC (Method 20, RT=5.8 min) 115 g, >100% yield due to impurities and solvent. Used as is in the next step.

Compound 303

A suitable reactor was charged with Compound 302 (111 g, estimated 0.18 mol), iodocinnamonitrile (47.1 g, 0.175 mol), triethylamine (29.3 ml, 0.21 mol) and toluene (800 ml). The resulting mix was degassed by sparging with a stream of nitrogen for 10 minutes at ambient temperature, after which time tetrakis(triphenylphosphine) palladium(0) (10.1 g, 0.0088 mol) was added. The mix was sparged for an additional 5 minutes, then was heated to 80° C. for 2 hours. HPLC (Method 20, RT=6.5 min) showed a complete reaction. The mix was cooled to ambient and was filtered through celite and washed with ethyl acetate (400 ml). The combined organics were washed with brine (2×500 ml) then dried over sodium sulfate, filtered and concentrated to a volume of 350 ml. The concentrate was cooled to 0° C. and was stirred for 1 hour, during which time the product crystallized. The solids were filtered and washed with hexane:toluene (2:1, 150 ml). Dried to leave 95 g, 90% yield, HPLC AUC 98% (Method 20). Used as is in the next reaction.

303: C$_{29}$H$_{26}$ClN$_2$O$_6$PS 597.02 gmol$^{-1}$ m/z (ESI+): 597.0 (MH$^+$, 100%), 599.0 (MH$^+$, 35%) $^1$H NMR $\delta_H$ (400 MHz, CDCl$_3$): 1.38, 1.48 (2×3H, 2xt, COOCH$_2$CH$_3$, POOCH$_2$CH$_3$), 2.41 (3H, s, Ar—CH$_3$), 4.09-4.16 (2H, m, POOCH$_2$CH$_3$), 4.52 (2H, q, COOCH$_2$CH$_3$), 5.93 (1H, d, CH═CHCN), 7.33-7.38 (3H, m, CH═CHCN, 2×Ar—H), 7.52 (2H, t, 2×Ar—H), 7.64 (1H, t, Ar—H), 7.74, 7.77 (2×1H, 2xd, 2×Ar—H), 7.85 (1H, d, Ar—H), 7.94 (1H, dd, Ar—H), 8.08 (2H, d, 2×Ar—H) $^1$H NMR $\delta_H$ (400 MHz, d6-DMSO): 1.26, 1.33 (2×3H, 2xt, COOCH$_2$CH$_3$, POOCH$_2$CH$_3$), 2.34 (3H, s, Ar—CH$_3$), 3.95-4.10 (2H, m, POOCH$_2$CH$_3$), 4.40 (2H, q, COOCH$_2$CH$_3$), 6.52 (1H, d, CH═CHCN), 7.52 (1H, dd, Ar—H), 7.60-7.84 (8H, m, CH═CHCN, 7×Ar—H), 8.07 (3×1H, m, 3×Ar—H)

Compound 304

A suitable reactor was charged with Compound 303 (537 g, 0.90 mol) and methylene chloride (2.0 L). The resulting solution was cooled to 0° C., and was treated with bromotrimethylsilane (450 g, 2.9 mol) added over 15 minutes. The reaction was then warmed to 40° C. for 1.5 hours. HPLC (Method 20, RT=4.4 min) indicated a complete reaction. The excess TMSBr was stripped under vacuum (40-45° C.) and the resulting sticky solid was resuspended in DCM (2.5 L) and chilled to 0° C. Oxalyl chloride (156 ml, 1.8 mol) was added over 15 minutes, followed by N,N-dimethylformamide (13.7 ml, 0.18 mol) both added at 0° C. Gas evolution was observed during the DMF addition. After 1 hour, HPLC (Method 20, RT=6.2 min, sample quenched with anhydrous methanol prior to injection) showed a complete reaction. The solvents were stripped again to remove residual oxalyl chloride and the mix resuspended in chilled methanol (3.0 L) at 0°-5° C., and then was allowed to warm to ambient. After two hours, HPLC indicated a complete reaction (HPLC Method 20, RT=6.2 min). The solution was concentrated to a volume of 1.5 L, and the resulting thin slurry was cooled to 0° C., and was diluted with an aqueous solution of sodium bicarbonate (126 g, 3 L water). After 2 hours at 5° C., the product was filtered and washed with cold water/methanol (2:1, 1.5 L) then dried to leave 500 g Compound 304. HPLC (Method 20) purity 92% used as is.

Compound 305

A suitable reactor was charged with Compound 304 (ca. 280 g, 0.48 mol) and tetrahydrofuran (2.8 L). The resulting solution was then cooled to 5° C. and was treated with lithium hydroxide monohydrate (45 g, 1.07 mol) added in one portion. The reaction was allowed to warm to ambient, during which time the color lightened and a white precipitate formed. After overnight stirring, HPLC indicated an incomplete reaction (Method 20, product RT=4.3, partially deprotected RT=5.1, major impurity RT=3.8). An additional 10% LiOH—H$_2$O was added, but after 10 hours, the partially deprotected intermediate remained at 5%, and the impurity peak at 3.8 minutes had increased to ca. 25%. The reaction was cooled to 5° C. and was acidified with hydrochloric acid (5N, 280 ml) then was diluted with ethyl acetate (2 L). The layers were separated and the aqueous extracted with ethyl acetate (500 ml). The combined organics were washed with brine (1 L) and dried with sodium sulfate, then concentrated to leave a crude oily solid, Compound 305. Ca. 300 g, HPLC AUC 57%.

The crude product was taken up in acetonitrile (1.2 L) at 40° C., and the product triturated w/water (1.2 L). The resulting slurry was cooled to 5° C. and was allowed to granulate for 30 minutes, after which time the product was filtered and washed with ACN:H$_2$O (1:1, 100 ml). Ca. 103 g, 88% by HPLC. The product was then recrystallized from 360 ml ACN at 40° C. and 360 ml water as before. Filtered, washed and dried to leave 75 g Compound 305. HPLC AUC 97%. Used as is in the next step.

Compound 306 (Chiral Resolution)

A suitable reactor was charged with Compound 305 (280 g, 0.66 mol) and acetone (4.2 L). The resulting thin slurry was then treated with (−)-cinchonidine (199 g, 0.66 mol) added in one portion. After one hour, a solution had formed, and after an additional hour, a white solid precipitated, and the mix was left to stir for an additional two hours (four hours total) after which time the solids were filtered, washed with acetone (200 ml) and dried to leave 199 g Crude Compound 306 cinchonidine salt. HPLC showed an isomer ratio of 96:4.

The crude salt was then slurried in ethyl acetate (3 L) and hydrochloric acid (1N, 3 L). The two phase solution was vigorously stirred for 2 hours at ambient temperature. The layers were separated, and the aqueous extracted with ethyl acetate (3 L). The organics were combined, dried with sodium sulfate, and concentrated to leave the free base Compound 306, 107 g, 95:5 by chiral HPLC.

The crude Compound 306 was then suspended in acetone (1.07 L) and treated with (−)-cinchonidine (76 g, 0.26 mol.) After 4 hours total stir time (as above) the solids were filtered, washed with acetone (200 ml) and dried to leave 199 g of the salt. HPLC 98.6:1.4.

The salt was broken by dissolving in ethyl acetate (3 L) and hydrochloric acid (1N, 3 L). The two phase solution was stirred for 2 hours at ambient temperature. The layers were separated, and the aqueous extracted with ethyl acetate (2 L). The organics were combined, dried with sodium sulfate, and concentrated to leave the free base Compound 306, 98 g, 98.6:1.4 by chiral HPLC. 70% recovery of the desired isomer, 35% yield from the racemic Compound 306. #6: $C_{20}H_{16}ClN_2O_4P$ 414.78 gmol$^{-1}$ m/z (ESI+): 415.1 (MH$^+$, 100%), 417.0 (MH$^+$, 35%) $[\alpha]_D^{25}$: −47.51 (c, 10.66 mgml$^{-1}$ in EtOAc) [Opposite enantiomer $[\alpha]_D^{25}$: +47.26 (c, 9.60 mgml$^{-1}$ in EtOAc)] $^1$H NMR $\delta_H$ (400 MHz, d6-DMSO): 2.33 (3H, s, Ar—CH$_3$), 3.71 (3H, d, CH$_3$OP), 6.50 (1H, d, CH=CHCN), 7.36 (1H, dd, H-6), 7.57 (1H, d, H-7), 7.66-7.71 (2H, m, H-4, Ar—H$_{ortho}$), 7.67 (1H, d, CH=CHCN), 7.84 (1H, d, Ar—H$_{ortho}$), 7.98 (1H, s, Ar—H$_{para}$), 12.97 (1H, s, N—H), 14.38 (1H, br-s, COOH) Multiple $\delta_C$ values indicate splitting of carbon signal due to P. $^{13}$C NMR $\delta_C$ (100 MHz, d6-DMSO): 20.68 (Ar—CH$_3$), 51.70 (CH$_3$OP), 98.15 (CH=CHCN), 102.33, 103.85, 114.98, 120.91 (3×C), 118.47 (CN), 125.39 (C), 126.78 (C), 127.74, 127.86 (C—H$_{ortho}$), 129.78, 129.88 (C), 131.25 (C), 132.06 (C), 133.44, 133.55 (C), 133.89, 134.05 (C), 134.62, 134.75 (C), 135.47, 135.66 (C), 138.78, 138.91 (C), 149.62 (CH=CHCN), 160.40 (C=O) $^{31}$P NMR $\delta_P$ (162 MHz, d6-DMSO): 33.50 (1P, s)

Compound III

A suitable reactor was charged with Compound 306 (0.63 g, 0.0014 mol) and 1,2-dimethoxyethane (10 ml.) The mix was treated with 1,1-carbonyldiimidazole (0.47 g, 0.0028 mol) added in one portion, and the mix was allowed to stir at ambient temperature until gas evolution ceased (ca. 1.5 hours.) The solution was then cooled to 5° C., and was sparged with ammonia gas for 5 minutes. HPLC (Method 20, product RT=5.0 min) showed a complete reaction after one hour at ambient. The reaction was quenched by the addition of 10 g crushed ice, and was concentrated under reduced pressure to remove the DME. The resulting slurry was stirred for one hour at 5° C. to granulate the product. The solids were filtered and dried to leave pure Compound III 2 Carbamoyl-5-chloro-1H-indol-3-yl)-[3-((E)-2-cyano-vinyl)-5-methyl-phenyl]-(R)-phosphinic acid methyl ester) as a white solid 0.56 g, 89% yield. HPLC (Method 20) chemical purity 98.5%. Chiral purity 97%.

A suitable reactor was charged with Compound 306 (10 g, 0.024 mo1) and 1,2-dimethoxyethane (150 ml). The mix was treated with 1,1-carbonyldiimidazole (7.8 g, 0.048 mol) added in one portion, and the mix was allowed to stir at ambient temperature until gas evolution ceased. The solution was then cooled to 5° C., and was sparged with ammonia gas for 5 minutes. HPLC (Method 20, product RT=5.0 min) showed a complete reaction after one hour. The reaction was quenched by the addition of 100 g crushed ice, and was concentrated under reduced pressure to remove the DME. The resulting oily solid (in water) was diluted with methanol (20 ml) and stirred for one hour at 5° C. to granulate the product. The solids were filtered and dried to leave pure Compound III ((2-Carbamoyl-5-chloro-1H-indol-3-yl)-[3-((E)-2-cyano-vinyl)-5-methyl-phenyl]-(R)-phosphinic acid methyl ester). 9.8 g, 98% yield. HPLC (Method 20) chemical purity 99.5%. Chiral purity 94.3%. Compound III: $C_{20}H_{17}ClN_3O_3P$ 413.79 gmol$^{-1}$ m/z (ESI+): 414.1 (MH$^+$, 100%), 416.1 (MH$^+$, 35%) $v_{max}$ (KBr disc) (cm$^{-1}$) 1620.0 (amide I), 1670.6 (amide II), 2218.7 (CN), 3125.5, 3291.9 (N—H) $[\alpha]_D^{20}$: −75.08 (c, 9.04 mgml$^{-1}$ in CHCl$_3$) m.p.: 144-148° C. transition to opaque semi-solid, 209-210° C. melts Elemental analysis: $C_{20}H_{17}ClN_3O_3P$ calculated C, 58.05%, H, 4.14%, N, 10.15%, Cl, 8.57%, P, 7.49%. Found C, 58.13%, H, 4.08%, N, 10.16%, Cl, 8.69%, P, 7.44% $^1$H NMR $\delta_H$ (400 MHz, d6-DMSO): 2.32 (3H, s, Ar—CH$_3$), 3.74 (3H, d, CH$_3$OP), 6.52 (1H, d, CH=CHCN), 7.30 (1H, dd, H-6), 7.53-7.58 (3H, m, H-4, H-7, H-6'), 7.68 (1H, d, CH=CHCN), 7.73 (1H, s, H-4'), 7.75 (1H, d, H-2'), 8.02, 10.15 (2×1H, 2×s, NH$_2$), 12.80 (1H, s, N—H) Multiple $\delta_C$ values indicate splitting of carbon signal due to P. $^{13}$C NMR $\delta_C$ (100 MHz, d6-DMSO): 20.77 (Ar—CH$_3$), 51.75, 51.81 (CH$_3$OP), 98.39, 98.91 (C-3), 98.44 (CH=CHCN), 115.05 (C-7), 118.53 (CN), 119.96 (C-4), 124.73 (C-6), 126.68 (C-5), 127.15, 127.26 (C-2'), 129.25, 129.35 (C-9), 131.37 (C-4'), 132.45, 134.04 (C-1'), 132.69, 132.80 (C-6'), 133.92 (C-8), 134.30, 134.44 (C-3'), 139.33, 139.46 (C-5'), 139.96, 140.17 (C-2), 149.55 (CH=CHCN), 160.65 (C=O) $^{31}$P NMR $\delta_P$ (162 MHz, d6-DMSO): 33.72 (1P, s).

Example 9

Recycling of the S enantiomer of Compound I-2-carboxylic acid 2(S):

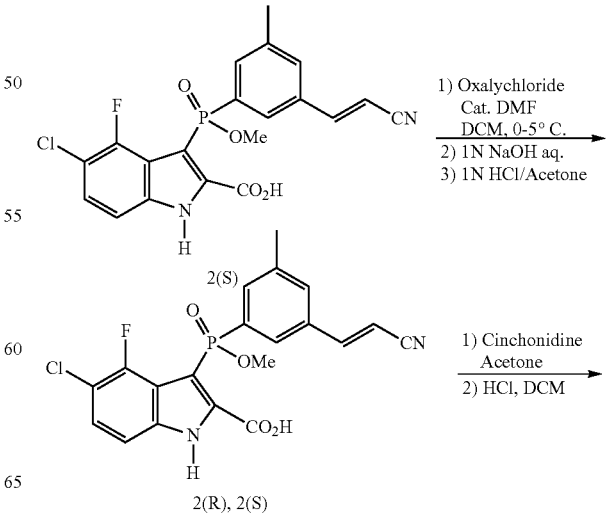

-continued

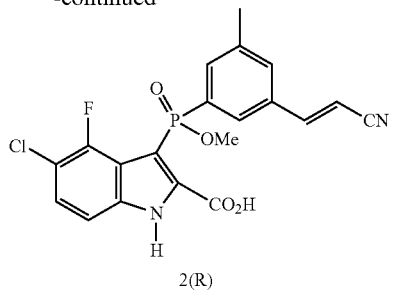

2(R)

To a cold (0-5° C.) solution of the starting enantiomer 2(S) (50.0 g, 120.8 mmol) in anhydrous DCM (300 ml), was added oxalylchloride (15.2 ml, 174.2 mmol, 1.5 eq) dropwise over a period of 5 minutes. Anhydrous DMF (1.43 ml, 18.5 mmol) was added using a syringe over a period of 2 minutes. Gas evolution was observed. The resulting yellow solution was kept stirring under argon atmosphere at 0-5° C. After 60 minutes, HPLC result of methanol quenched reaction aliquot indicted only 10% of staring acid was unreacted. After stirring for 10 more minutes, the reaction mixture was diluted with cold (0-5° C.) DCM (300 ml). The diluted mixture was quickly transferred to an addition funnel and was added to a stirring aqueous NaOH solution (1N, 695 ml) over a period of 7 minutes. Temperature of the quenching mixture went up (from 26.5° C., starting temperature of NaOH aqueous) to 33° C. when the addition was completed. After continuous stirring for additional 3 minutes, upper layer liquid was decanted. The lower layer (containing precipitated salt) was concentrated under reduced pressure to remove DCM. The residue was taken into acetone (300 ml) and was acidified using 1N HCl (total 275 ml was added) to pH 4. The resulting mixture was stirred at room temperature for 30 minutes. Collected solid product by filtration, washed the solid with 1:1 acetone/DI water (100 ml). The solid obtained was dried in a vacuum oven at 45° C. over 18 hrs. Net weight of this $1^{st}$ crop material=31.4 g. Chemical purity=98.4% by HPLC (AUC). Chiral HPLC result indicated a mixture of 2(R) (51.7%) and 2(S) (47.5%). $^1$H-NMR spectrum indicated clean product with trace of DCM.

Recovery of $2^{nd}$ crop product from mother liquor of the $1^{st}$ crop product: two layers were presence in the mother liquor. The layers were separated. The upper layer was extracted with DCM (400 ml). The lower layer of the $1^{st}$ crop mother liquor (brown oil, mainly product by HPLC) was taken into toluene (30 ml) and was washed with a mixture of 1N HCl (5 ml) and brine (15 ml). Combined the toluene layer with the DCM extract, washed with DI water (400 ml), dried over anhydrous sodium sulfate. Solvents were removed under reduced pressure. The $2^{nd}$ crop material was dried under high vacuum for 16 hours. Net weight=15.1 g. Chemical purity=90% by HPLC (AUC). Chiral HPLC result indicated a mixture of 2(R) (91.4%) and 2(S) (8.6%). $^1$H-NMR spectrum indicated mainly product with residue Toluene (5.3 Wt %) and trace of minor impurities. Total recovery of free acid (mixture of 2 enantiomers)=92%.

Recycling of the S enantiomer of Compound III-2-carboxylic acid 1 (S):

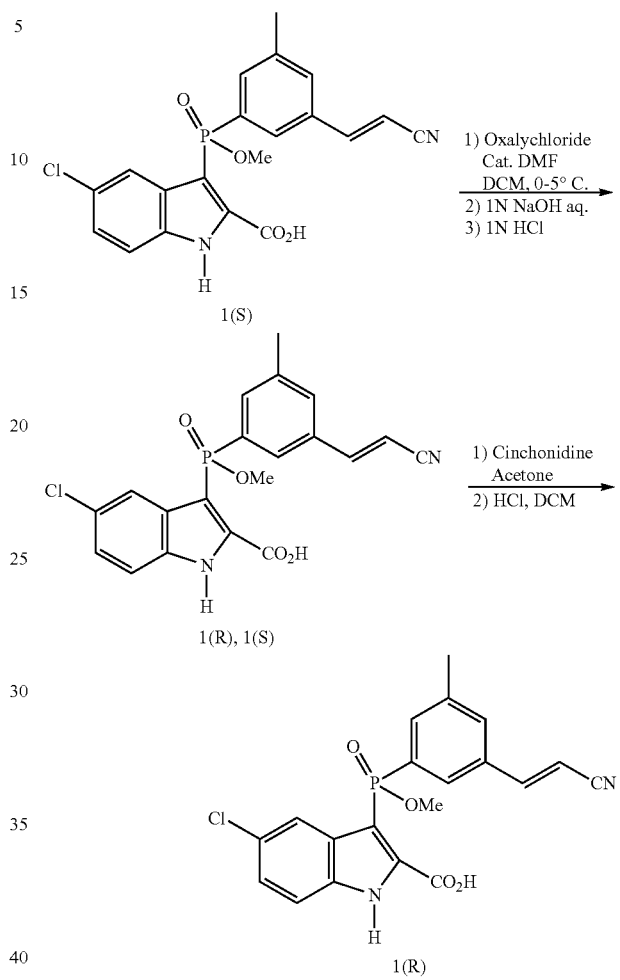

To a cold (0-5° C.) turbid solution of the starting enantiomer 1(S) (50.0 g, 120.8 mmol) in anhydrous DCM (300 ml), was added oxalylchloride (15.7 ml, 180 mmol, 1.5 eq) dropwise over a period of 5 minutes. Anhydrous DMF (1.45 ml, 18.8 mmol) was added using a syringe over a period of 2 minutes. Gas evolution was observed. The resulting yellow solution was kept stirring under argon atmosphere at 0-5° C. for 30 minutes. The reaction mixture was then diluted with DCM (300 ml) and was quickly transferred to an addition funnel. The diluted reaction mixture was added to a stirring aqueous NaOH solution (1N, 725 ml) over a period of 6 minutes. Temperature of the quenching mixture went up (from 24.5° C., starting temperature of NaOH aqueous) to 33° C. when the addition was completed. After continuous stirring for additional 5 minutes, the quenched mixture was placed on an ice bath. 1N HCl (365 ml) was added through an addition funnel over 2 minute. The resulting acidified mixture (pH=2) was stirred for 5 minutes. Layers were separated using a separation funnel. The aqueous was further extracted with DCM (200 ml×2). Combined the organic layer and DCM extracts. Washed with DI water (200 ml), dried over anhydrous sodium sulfate. DCM was removed under reduced pressure. The crude was dried in a vacuum oven for 42 hours. Net weight=52.4 g. Chemical purity>97% by HPLC (AUC). Chiral HPLC result indicated a mixture of 1(R) (64.1%) and 1(S) (35.9%). $^1$H-NMR spectrum indicated clean product with residue DCM (4.3 Wt %) and trace of DMF. Recovery of free acid (mixture of 2 enantiomers)=100%.

Example 10

Preparation of Iodo Cinnamonitrile

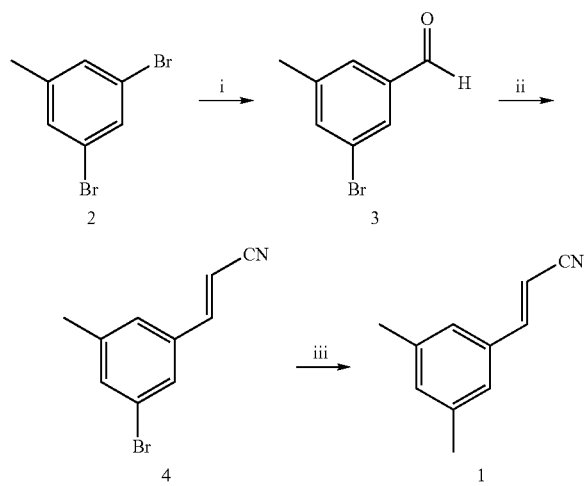

3-Bromo-5-methyl-benzaldehyde (3)

Anhydrous toluene (365 ml) was added to a 3 L four-neck round bottom flask equipped with overhead stirrer, one 250 ml and one 1 L addition funnel, an internal temperature probe and an argon inlet. The flask was immersed in an ice/methanol bath in order to keep the internal temperature in the region of −15° C. n-Butyl lithium (2.5M in hexane, 232 ml, 0.581 mol) was added to the flask via syringe, under argon at a moderate stirring rate. n-Butyl magnesium chloride (2.0M in THF, 145 ml, 0.290 mol, light brown solution) was introduced into the 250 ml addition funnel via syringe, under argon. Addition of this solution was performed dropwise over 22 minutes during which time the internal temperature rose from −16° C. to −13° C. and the mixture turned from clear to light, opaque yellow. The solution was stirred for a further 0.5 h at −13° C.

A solution of 3,5-dibromotoluene (196 g, 0.784 mol; Aldrich) in anhydrous toluene (1458 ml) was prepared in a 2 L one-neck round bottom flask under argon. This pale yellow solution was transferred in two portions to the 1 L addition funnel. Addition of this solution was performed dropwise over 50 minutes during which time the internal temperature was kept between −13° C. and −17° C. and the mixture became a darker, opaque, orange-brown color. The suspension was stirred for a further 2.75 h between −13° C. and −17° C. under argon. An HPLC sample was taken after 2 h and prepared by addition of 2 drops of methanol, followed by solvent removal under reduced pressure. HPLC method Test 20 indicated no starting material remaining ($R_t$ 6.64 min) and a mixture of intermediates ($R_t$ 4.94 min, 6.15 min, 7.40 min). This suspension was labeled 'Mixture A'.

During the 3,5-dibromotoluene addition, anhydrous N,N-dimethylformamide (78.7 ml, 1.016 mol) was added via syringe to a 5 L four-neck round bottom flask equipped with overhead stirrer, a 1 L addition funnel, an internal temperature probe and an argon inlet. The flask was immersed in an ice/methanol bath in order to keep the internal temperature in the region of −15° C. Anhydrous toluene (91 ml) was added to the flask via syringe, under argon at a moderate stirring rate. This solution was labeled 'Mixture B'.

Mixture A was transferred in two portions (2×950 ml) to the 1 L addition funnel of the 5 L flask containing Mixture B. The addition funnel was wrapped with aluminum foil to avoid excessive heat influx. Addition of Mixture A was performed dropwise over 38 minutes during which time the internal reaction temperature was kept between −16° C. and −12° C. and the reaction became an orange solution. The solution was stirred for a further 1 h between −13° C. and −16° C. under argon after which time an HPLC sample was prepared by removing toluene under reduced pressure, dissolving in MeOH and filtering off any insoluble material. HPLC method Test 20 indicated one major product ($R_t$ 5.42 min).

The reaction was deemed to be complete and ready to be quenched.

A prepared solution of citric acid (341.54 g) in water (650 ml) in a 1 L conical flask was added slowly over 20 minutes to the reaction mixture in 50 ml portions, keeping the internal temperature below 0° C. This yellow solution was stirred at 0° C. for a further 20 minutes.

After this time, the quenched reaction mixture was transferred to 4 L separating funnel and the two phases were separated. The organic layer was washed with water (650 ml) and saturated brine (550 ml) prior to being dried by addition of anhydrous sodium sulfate (500 g). The drying agent was removed by vacuum filtration. The dried organic layer was transferred in two portions to a 3 L round bottom flask and the solvents were removed under high vacuum at 35° C. A low viscosity, red-orange oil 3-bromo-5-methyl-benzaldehyde (159.1 g, 102% yield) was obtained. $C_8H_7BrO$ 199.04 gmol$^{-1}$; HPLC: $R_t$ 5.42 min; 96% purity @ 272 nm; $^1$H NMR $\delta_H$ (400 MHz, CDCl$_3$): 2.41 (3H, s, CH$_3$), 7.58, 7.60, 7.81 (3×1H, 3×s, 3×Ar—H), 9.92 (1H, s, CHO); $^{13}$C NMR $\delta_C$ (100 MHz, CDCl$_3$): 21.17 (CH$_3$), 123.27 (C-3), 129.15, 129.93 (C-2, C-6), 138.06 (C-1), 138.11 (C-4), 141.33 (C-5), 191.20 (CHO).

3-Bromo-5-methyl-cinnamonitrile (4)

Sodium hydride (60% dispersion in mineral oil, 39.2 g, 0.980 mol) was added to a 5 L four-neck round bottom flask equipped with overhead stirrer, 250 ml addition funnel, an internal temperature probe and an argon inlet. Anhydrous tetrahydrofuran (2.6 L) was added to the flask under argon and stirring commenced at a moderate rate to give a white, opaque suspension. Diethyl cyanomethylphosphonate (152.1 ml, 0.941 mol, slightly viscous pale yellow liquid) was introduced into a 250 ml addition funnel, under argon. Addition of the phosphonate was performed dropwise over 56 minutes during which time the internal temperature rose from 21° C. to 29° C. and the mixture became a less opaque, very pale yellow suspension. The solution was stirred for a further 1 h during which time the internal temperature fell from 29° C. to 22° C. and the mixture became a pale yellow, clear solution.

3-Bromo-5-methyl-benzaldehyde (159 g, 0.784 mol, assumed quantitative, red oil) was transferred from its 3 L round bottom flask to the 250 ml addition funnel by pouring. The flask was rinsed with anhydrous tetrahydrofuran (3×5 ml). The three rinses were also poured into the addition funnel, which was then flushed with argon. Addition of the aldehyde was performed dropwise under argon, over 71 minutes during which time the internal temperature rose from 20° C. to 33° C. and the mixture became a dark orange solution.

The solution was stirred for a further 2 h during which time the internal temperature fell from 32° C. to 19° C. An HPLC sample of the dark brown solution was prepared at 1 h by diluting with THF. HPLC method Test 20 indicated complete conversion of starting material ($R_t$ 5.42 min) to one major product with a 10:1 mixture of E:Z isomers (272 nm, $R_t$ 5.76 min Z; $R_t$ 5.83 min E).

Hydrochloric acid (6N, 21.66 ml) and water (2578.33 ml) were mixed in a 4 L conical flask to give an aqueous solution of 0.05M HCl (2.6 L).

The reaction mixture was diluted with tert-butyl methyl ether (0.5 L) and quenched with aqueous 0.05M HCl (0.5 L), after which the internal temperature rose to 22° C. The partially quenched reaction mixture was transferred to a 22 L separating funnel. Residue from the reaction vessel was transferred to the separating funnel by consecutive rinsing with tert-butyl methyl ether (1.5 L), aqueous 0.05M HCl (1.0 L), tert-butyl methyl ether (2.0 L), aqueous 0.05M HCl (1.1 L), tert-butyl methyl ether (1.2 L). The layers were agitated for 30 seconds, allowing gases to escape periodically and the aqueous layer was separated into a 22 L flask. The organic layer was washed with water (2.0 L) and the aqueous layers were combined. The organic layer was dried with anhydrous sodium sulfate (500 g) for 10 minutes and the drying agent was then filtered off under vacuum. The solvents were removed under reduced pressure to give pale yellow solid, which was dried overnight under vacuum at 30° C. The resulting crude material (200.2 g) was a yellow, powdery but slightly sticky solid.

The crude yellow solid (200 g), in a 2 L three-neck round bottom flask equipped with internal temperature probe, 500 ml addition funnel and overhead stirrer, was dissolved in methanol (700 ml) by immersion in a water bath at 50° C. On dissolution, the yellow solid became a red-orange solution. The water bath was removed and water (250 ml) was introduced into the 500 ml addition funnel. Addition of the water was performed dropwise with a moderate stirring rate, over 3 h during which time the internal temperature fell from 50° C. to 25° C. A yellow solid began to precipitate out of the red-orange solution after five minutes and the addition of 50 ml of water. The mother liquor was checked periodically by HPLC to determine the ratio of E:Z isomers still in solution. After adding 250 ml of water the E:Z ratio was 1:1.2 and determined to be favorable. The suspension was cooled in an ice bath for 10 minutes allowing the internal temperature to fall to 17° C., before being filtered through a 3 L sintered glass funnel under reduced pressure. The resulting solid was washed with a cold methanol:water solution (1:1, 2×50 ml, 5-10° C.). The solid was dried to constant weight in a vacuum oven at 35° C. A pale yellow solid, 3-bromo-5-methyl-cinnamonitrile (144.1 g, 83% yield) was obtained. This material was, however, contaminated with the unremoved mineral oil, as observed in the proton and carbon NMR spectra. 3-Bromo-5-methyl-cinnamonitrile: $C_{10}H_8BrN$ 222.08 gmol$^{-1}$; HPLC: E-isomer $R_t$ 5.83 min; 97% purity @ 272 nm. Z-isomer $R_t$ 5.76 min; ~1.7% @ 272 nm; $^1H$ NMR $\delta_H$ (400 MHz, CDCl$_3$): 2.36 (3H, s, CH$_3$), 5.86 (1H, d, $J_{H,H}$ 16.7, CH=CHCN), 7.17 (1H, s, Ar—H), 7.28 (1H, d, $J_{H,H}$ 16.7, CH=CHCN), 7.39 (2×1H, s, 2×Ar—H); $^{13}C$ NMR $\delta_C$ (100 MHz, CDCl$_3$): 21.23 (CH$_3$), 97.86 (CH=CHCN), 117.89 (CN), 123.19 (C-3), 127.03, 127.38 (C-4, C-6), 134.85 (C-2), 135.38 (C-1), 141.16 (C-5), 149.31 (CH=CHCN).

3-Iodo-5-methyl-cinnamonitrile (1)

Three 500 ml screw-top, sealable, pressure flasks (labeled A, B and C) were individually equipped with a magnetic stirrer and arranged over oil baths heated to 115° C. Separately and sequentially added to each flask were; 3-bromo-5-methyl-cinnamonitrile (3×47.5 g, 3×0.214 mol); m-xylene (3×171 ml), giving an orange solution; diethylene glycol dimethyl ether (3×43 ml); sodium iodide (3×64.12 g, 3×0.428 mol); copper (I) iodide (3×4.08 g, 3×0.0214 mol); and lastly N,N-dimethylethylenediamine (3×4.60 ml, 3×0.0427 mol) at which point the color became dark green-black. The threaded top of each flask was rinsed with m-xylene (3×1 ml). The hardened, insoluble solid sodium iodide was mobilized with a spatula, whilst the solution was degassed: Steady streams of argon were bubbled through the solutions in each flask for 10 minutes.

The three flasks were sealed under an argon atmosphere and lowered into their respective oil baths at 115° C., ensuring a moderate stirring rate in each. The reactions were left to stir at 115° C., behind a blast shield for 14 h overnight.

After this time, flask C was found to have stopped stirring. The flasks were allowed to cool in air for 5 minutes prior to opening. HPLC samples of the three reactions were prepared by removing the m-xylene under reduced pressure and dissolving in MeCN. Analysis was performed using HPLC method Test 20;

Flask A: Major product ($R_t$ 5.97 min), 2.5% starting material ($R_t$ 5.83 min).

Flask B: Major product ($R_t$ 5.97 min), 1.0% starting material ($R_t$ 5.83 min).

Flask C: Major product ($R_t$ 5.97 min), 20% starting material ($R_t$ 5.83 min).

All three flasks were degassed by bubbling steady streams of argon through the respective reaction mixtures for 10 minutes. The three flasks were sealed under an argon atmosphere and lowered into their respective oil baths at 120° C., ensuring a moderate stirring rate in each. The reactions were left to stir at 120° C., behind a blast shield for 2 h.

After this time, the flasks were allowed to cool in air for 5 minutes prior to opening. HPLC samples of the three reactions were prepared by removing the m-xylene under reduced pressure and dissolving in MeCN. Analysis was performed using HPLC method Test 20;

Flask A: Major product ($R_t$ 5.97 min), 1.9% starting material ($R_t$ 5.83 min).

Flask B: Major product ($R_t$ 5.97 min), 0.9% starting material ($R_t$ 5.83 min).

Flask C: Major product ($R_t$ 5.97 min), 7.5% starting material ($R_t$ 5.83 min).

Reactions A and B were deemed to be complete and left to cool to room temperature. Flask C was again degassed by bubbling a steady stream of argon through the reaction mixture for 10 minutes. The flask was sealed under an argon atmosphere and lowered into the oil bath at 125° C., ensuring a moderate stirring rate. The reaction was left to stir at 125° C., behind a blast shield, for a further 4 h.

After this time, the Flask C was allowed to cool in air for 5 minutes prior to opening. An HPLC sample of the reaction was prepared by removing the m-xylene under reduced pressure and dissolving in MeCN. Analysis was performed using HPLC method Test 20;

Flask C: Major product ($R_t$ 5.97 min), 2.0% starting material ($R_t$ 5.83 min).

Reaction C was deemed to be complete and left to cool to room temperature.

Flask A was diluted with tert-butyl methyl ether (2×150 ml) and the mixture was filtered under vacuum, to remove the insoluble materials, through a 3 L sintered glass funnel containing Celite (1.5 L), pre-washed with tert-butyl methyl ether. Flasks B and C were similarly diluted and filtered through the same Celite sinter funnel combining the three filtrates A, B and C in a 12 L conical flask. The flasks were rinsed and the Celite was eluted with tert-butyl methyl ether (3 L).

The combined filtrates were re-filtered under vacuum through a clean 3 L sintered glass funnel containing fresh Celite (1.5 L), pre-washed with tert-butyl methyl ether, to remove the remaining cloudy particulates. Elution was performed with tert-butyl methyl ether (4 L). The resulting clear, red-brown color filtrate was stable being stored at 4° C. for 48 h.

The filtrate was concentrated under reduced pressure at 40° C. and the high boiling solvents were then removed under high vacuum at 45° C. Co-evaporation with methanol (2×50 ml) yielded a crude brown solid (203 g).

The crude brown solid (200 g), in a 2 L three-neck round bottom flask equipped with internal temperature probe, 500 ml addition funnel and overhead stirrer, was dissolved in methanol (700 ml) by immersion in a water bath at 53° C. On dissolution, the brown solid became a red-brown solution. The water bath was removed and water (300 ml) was introduced into the 500 ml addition funnel. Addition of the water was performed dropwise with a moderate stirring rate, over 3 h during which time the internal temperature fell from 50° C. to 24° C. A yellow-brown solid began to precipitate out of the red-brown solution after ten minutes and the addition of 80 ml of water. The mother liquor was checked periodically by HPLC to determine the ratio of E:Z isomers still in solution. After adding 300 ml of water the E:Z ratio was 1:1.1 and determined to be favorable. The suspension was cooled for 14 h allowing the internal temperature to fall to 4° C., before being filtered through a 3 L sintered glass funnel under reduced pressure. The resulting solid was washed with a cold methanol:water solution (1:4, 100 ml then 200 ml, 5° C.). The solid was dried to constant weight in a vacuum oven at 35° C. A pale brown solid, 3-iodo-5-methyl-cinnamonitrile (149.4 g, 86% yield) was obtained. This material was, however, contaminated with the unremoved mineral oil, as observed in the proton and carbon NMR spectra.

The slightly sticky, brown solid (148.8 g), in a 2 L conical flask, was dissolved in acetonitrile (1.5 L) to give a dark orange-brown solution with insoluble globules of mineral oil. This mixture was filtered under gravity through filter paper (Whatman, 541) removing the majority of the mineral oil (10.6 g). The filtrate was transferred to a 4 L separating funnel and washed with heptane (0.5 L). The heptane layer was extracted with acetonitrile (250 ml) and concentrated under reduced pressure to give more mineral oil (3.2 g). The acetonitrile layers were combined, concentrated under reduce pressure and dried in a vacuum oven at 35° C. yielding 3-iodo-5-methyl-cinnamonitrile (132.5 g, 77% yield) as a light brown solid. This material was observed to be free of all mineral oil by proton and carbon NMR spectra. 3-Iodo-5-methyl-cinnamonitrile: $C_{10}H_8IN$ 269.08 gmol$^{-1}$; M.P.: 98° C. softens, 99-100° C. melts; HPLC (Acetonitrile): E-isomer $R_t$ 5.97 min; 97% purity @ 272 nm (3-Bromo-5-methyl-cinnamonitrile, E-isomer $R_t$ 5.83 min; ~1.4% @ 272 nm.); $^1$H NMR $\delta_H$ (400 MHz, CDCl$_3$): 2.33 (3H, s, CH$_3$), 5.85 (1H, d, $J_{H,H}$ 16.7, CH=CHCN), 7.20 (1H, s, Ar—H), 7.25 (1H, d, $J_{H,H}$ 16.7, CH=CHCN), 7.59, 7.60 (2×1H, 2×s, 2×Ar—H); $^{13}$C NMR $\delta_C$ (100 MHz, CDCl$_3$): 21.09 (CH$_3$), 94.93 (C-3), 97.70 (CH=CHCN), 117.91 (CN), 127.61 (C-6), 133.37 (C-2), 135.44 (C-1), 140.81 (C-4), 141.15 (C-5), 149.18 (CH=CHCN).

Example 11

Figure 2A:
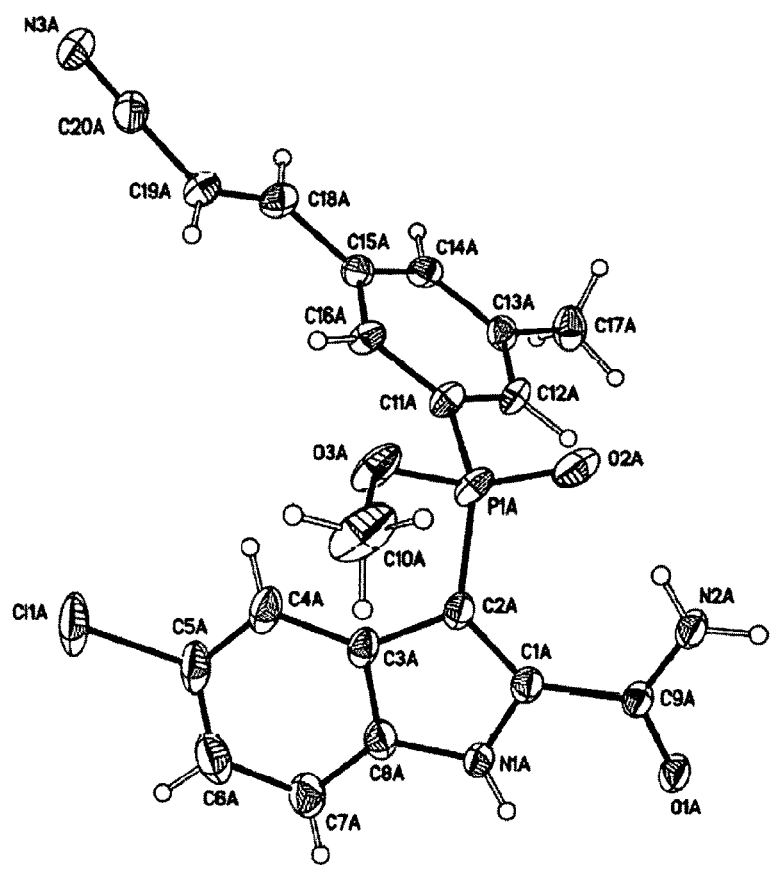
FIG. 2A shows a crystal structure of a molecule of Compound III.
Figure 2B:
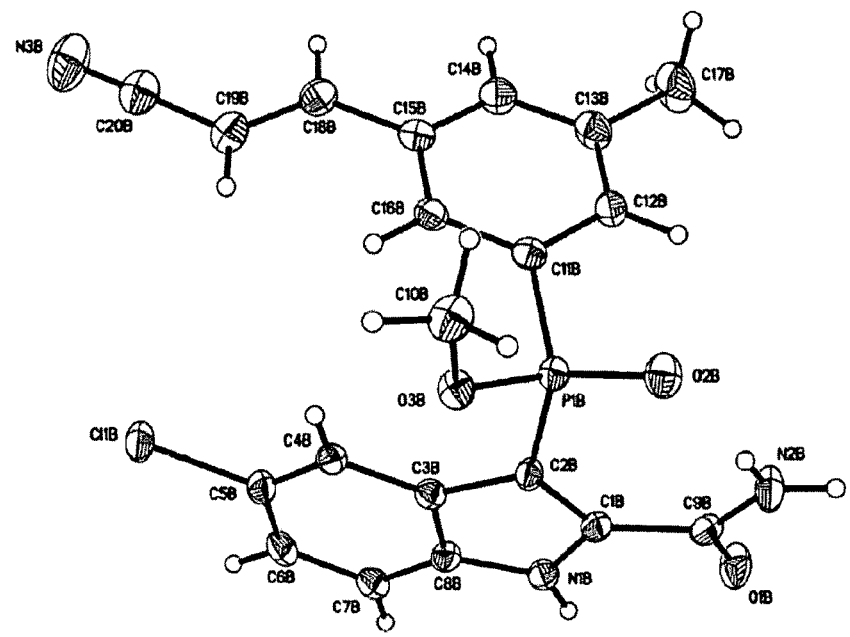
FIG. 2B shows a crystal structure of a molecule of Compound III.

Absolute Configuration of Compound III (2-Carbamoyl-5-chloro-1H-indol-3-yl)-[3-((E)-2-cyano-vinyl)-5-methyl-phenyl]-(R)-phosphinic acid methyl ester 5mg of Compound III was suspended in 50 ml of anisole. Crystals suitable for single crystal X-ray analysis formed after 2 days. The crystals were monoclinic with a space group of P21 and unit cell dimensions of a=13.0983 Å, b=10.9625 Å, c=16.4266 Å, α=90°, β=103.6063° and γ=90°. In the crystal, the asymmetric unit contained two independent molecules of compound III (molecule A and molecule B), and a single, partially occupied, (ca 86%), molecule of anisole as solvent. The Flack parameter was determined as –0.04(7) for molecule A and 1.04(7) for molecule B. On the basis of the former determination the absolute stereochemistry was assigned, and the chiral centers at P1A and P1B are both in the R configuration. FIG. 2A provides a view of molecule A including stereochemistry at P1A, and FIG. 2B provides a view of molecule B including stereochemistry at P1B.

Example 12

Pharmacology of Compound I (2-Carbamoyl-5-chloro-4-fluoro-1H-indol-3-yl)-[3-((E)-2-cyano-vinyl)-5-methyl-phenyl]-(R)-phosphinic acid methyl ester)

and

Compound III (2-Carbamoyl-5-chloro-1H-indol-3-yl)-[3-(E)-2-cyano-vinyl)-5-methyl-phenyl]-(R)-phosphinic acid methyl ester)

The following Tables show the in vitro anti-HIV activity of enantiomerically pure 3-phosphoindoles of compounds I and III in assays, including analysis of resistance to the drugs tested. Table 1 shows the activity of the compounds against a panel of mutant HIV-1 Reverse Transcriptase enzymes. The anti-viral activity of 3-phosphoindole compounds of compound I and compound III are compared with the activity of compounds control compound EFV (efavirenz, 6-chloro-4-cyclopropylethynyl-4-trifluoromethyl-1,4-dihydro-2H-3,1-benzoxazin-2-one) with various viruses.

As shown in Table 1, Compound I inhibited HIV-1 reverse transcriptase (RT) enzyme (subtype B, BH10 strain) with mean 50% inhibitory concentration (IC$_{50}$) values ranging from 0.366±0.251 µM (wild-type RT) to 1.411±0.873 µM (K103N/Y181C). Similarly, Compound III IC$_{50}$s ranged from 0.343±0.083 µM (wild-type RT) to 1.614±0.279 µM (K103N/Y181C). Compound I and Compound III were not inhibitory to human polymerases alpha (IC$_{50}$s≧145 µM), beta (IC$_{50}$s≧422 µM) or gamma (IC$_{50}$s≧60 µM) as seen in Table 5, demonstrating the test compounds' selectivity. Crystollographic studies with Compound I and the HIV RT K103N/Y181C double mutant revealed that Compound I binds to the known hydrophobic NNRTI pocket in the enzyme.

In HIV-1 cell culture assays, using MT-4 cells and a subtype B HIV-1 (BH-10 strain), Compound I and Compound III inhibited HIV production with mean 50% effective concentration (EC$_{50}$) values of 1 nM and 1.2 nM, respectively (see Table 6). In assays performed in human PBMC, Compound I and Compound III inhibited HIV-1 production with a mean $EC_{50}$ of 0.4 nM (BH-10 strain) or 1.5 nM (NL4-3 strain). Against 3 different HIV-1 viral strains in 5 different host human cell lines, the $EC_{50}$ range determined for Compound I was 0.5-2.0 nM and for Compound III was 0.5-1.7 nM. Compound I and Compound III were active against a panel of 9 different HIV-1 subtypes with respective potency ranges of 0.25 to 3.2 nM and 0.2 to 2.14 nM. The activities of Compound I and Compound III were reduced 24.8 and 19.5 fold, respectively, in the presence of alpha-1 acid glycoprotein and 45% human serum.

In 4 day cytotoxicity testing in 6 human HIV-1 host cell lines, Compound I and Compound III showed mean 50% cytotoxic concentration ($CC_{50}$) values of 16.6 to 32.9 μM and 14.8 to 50.0 μM, respectively. In PBMC, $CC_{50}$ values of 52.6 (Compound I) and 66.9 μM (Compound III) were determined. In 9-12 day testing in HeLa, HuH7 and HepG2 cell lines, the $CC_{50}$ values of Compound I and Compound III were in the 23.5 to 31.5 μM range. Based on the $CC_{50}/EC_{50}$ ratios determined in MT-4 cells, Selectivity Index (SI) values of >22,000 and >18,000 were calculated for Compound III and Compound I, respectively.

In cross resistance testing using a variety of cell lines and HIV-1 strains, Compound I and Compound III retained good potency against NNRTI resistant viruses bearing K103N, Y181C or K103N/Y181C mutations (respective $EC_{50}$ values remained below 4.5 and 14.5 nM), while EFV showed considerable resistance against the double mutant in particular ($EC_{50}$ values 36 to 116 nM).

The resistance profile of Compound I and Compound III was examined in greater depth using 3 different panels of viruses in testing performed by Monogram BioSciences (formerly ViroLogic): a screening panel of low to moderate EFV resistant viruses; a panel of 8 highly EFV resistant viruses and a broad spectrum panel of 64 viruses including 40 NNRTI resistant viruses with single, double and triple NNRTI resistance mutants. Compound I and Compound III, were highly active against a sub-panel of mutants bearing NRTI and PI mutations. Compound I and Compound III were superior to EFV against essentially all EFV resistant viruses, including viruses with double and triple mutants. Compound I was 2-3 more potent than Compound III against EFV resistant viruses with double and triple mutants In a series of in vitro interaction studies, there was no negative interaction observed between the Compound I and Compound III and 7 NRTIs or 6 PIs approved for the therapy of HIV-1 in the clinic.

Primary Pharmacodynamics
List of Abbreviations
IIIB Commonly used HIV-1 laboratory strain
A98 Alanine at position 98 of RT
AAG Alpha-1 acid glycoprotein
AIDS Acquired immunodeficiency syndrome
AZT Zidovudine
BH10 Laboratory adapted strain of human immunodeficiency virus type 1
$CC_{50}$ 50% cytotoxic concentration
CPE Cytopathic effect
DNA Deoxyribonucleic acid
DSA Drug susceptibility assay
E138K Glutamate to lysine change at position 138 of RT
$EC_{50}$, $EC_{50}$s 50% effective concentration
EFV Efavirenz
ELISA Enzyme-linked immunosorbent assay
F227F/L Phenylalanine/leucine at position 227 of RT
FBS Fetal bovine serum
G190A Glycine to alanine change at position 190 of RT
G190A/G Glycine/alanine change at position 190 of RT
G190S Glycine to serine change at position 190 of RT
GLP Good laboratory practices
H9 Human T cell line derived a patient with T cell lymphoma
HepG2 Human hepatoma cell line
HeLa Human cell line isolated from a patient with adenocarcinoma
HIV, HIV-1 Human immunodeficiency virus type 1
HIV-2 Human immunodeficiency virus type 2
HS Human serum
HuH7 Human hepatoma cell line
$IC_{50}$, $IC_{50}$s 50% inhibitory concentration
IND Investigational New Drug Application
K101E Lysine to glutamate change at position 101 of RT
K103N Lysine to asparagine change at residue 103 of RT
K103R Lysine to arginine change at residue 103 of RT
K103S Lysine to serine change at position 103 of RT
L100I Leucine to isoleucine change at position 100 of RT
M184V Methionine to valine change at position 184 of RT
mg Milligram
MOLT-4 Human T cells isolated from a patient with leukemia
MT-2 Human T cell line isolated from a patient with adult T cell leukemia
MT-4 Human T cell line isolated from a patient with adult T cell leukemia
MTS (3-(4,5-dimethylthiazol-2-yl)-5-(3-carboxymethoxyphenyl)-2-(4-sulfophenyl)-2H-tetrazolium, inner salt)
MTT 3-[4,5-dimethylthiazol-2-yl]-2,5-diphenyl tetrazolium bromide
NAM Nucleoside associated mutation
NL4-3, 4595 Commonly used HIV-1 laboratory strain
nM Nanomolar
NNRTI, NNRTIs Non-nucleoside reverse transcriptase inhibitor(s)
NRTI Nucleoside/Nucleotide reverse transcriptase inhibitor
P225H Proline to histidine change at residue 225 of RT
P227L Proline to leucine change of position 227 of RT
P236L Proline to leucine change at position 236 of RT
p24 HIV p24 core protein
p28 SIV p28 core protein
PI Protease inhibitor
PBMC Peripheral blood mononuclear cells
RC Replication capacity
ROD Commonly used HIV-2 laboratory strain
RT Reverse transcriptase
SD Standard deviation
SI Selectivity index
SIV Simian immunodeficiency virus
U937 Human monocyte cell line isolated from a patient with lymphoma
V106A Valine to alanine change at position 106 of RT
V106M Valine to methionine change at position 106 of RT
V108I Valine to isoleucine change at position 108 of RT
V179D Valine to aspartic acid change at residue 179 of RT
WT, W.T., wt Wild-type
Y181C Tyrosine to cysteine change at residue 181 of RT
Y181V Tyrosine to valine change at position 181 of RT
Y188L Tyrosine to leucine change at position 188 of RT
μg Microgram
μM Micromolar
In Vitro Antiviral Activity Against the HIV RT Enzyme The activity profiles of Compound I, Compound III, and EFV against HIV RT were determined using a panel of in vitro HIV reverse transcriptase (RT) assays as shown in Table 1. These studies employed wild-type HIV RT enzyme derived from HIV subtype B (BH-10 strain), along with a standard panel of NNRTI-resistant, site-directed, mutant enzymes with K103N and Y181C substitutions alone or in combination.

When tested in vitro, Compound I inhibited HIV reverse transcription with $IC_{50}$ values ranging from 0.366±0.251 µM (wild-type RT) to 1.411±0.873 µM (K103N/Y181C). Similarly, Compound III—derived $IC_{50}$s ranged from 0.343±0.083 µM (wild-type RT) to 1.614±0.279 µM (K103N/Y181C). EFV yielded the expected in vitro inhibition profile exhibiting wild-type activity against Y181C enzyme but strongly impaired activity against K103N and K103N/Y181C mutant enzymes.

TABLE 1

Activity Against HIV-1 RT in Enzyme Assay

Average $IC_{50}$ Values (µM) ± Standard Deviation

| Compound | N | W.T.[a] | Y181C[b] | K103N[b] | Y181C/K103N[b] |
|---|---|---|---|---|---|
| I | 4 | 0.366 ± 0.251 | 0.526 ± 0.285 | 0.782 ± 0.801 | 1.411 ± 0.873 |
| III | 5 | 0.343 ± 0.083 | 0.361 ± 0.086 | 2.203 ± 1.259 | 1.614 ± 0.279 |
| EFV | 4 | 0.055 ± 0.019 | 0.0765 ± 0.047 | 1.7973 ± 0.19 | 1.4313 ± 0.31 |

$IC_{50}$ = inhibitor concentration that reduces enzyme activity by 50%
N = number of replicate experiments performed.
[a] wild-type HIV-1 RT enzyme in BH10 backbone The relative activity of the test and comparator agents against the different viruses can be seen from the fold-resistance data presented in Table 2.

TABLE 2

Fold Change

| Compound | W.T. | Y181C | K103N | Y181C/K103N |
|---|---|---|---|---|
| I | 1 | 1.6 ± 0.7 | 3.2 ± 3.5 | 5.0 ± 3.4 |
| III | 1 | 3.2 ± 1.1 | 1.2 ± 0.4 | 12.7 ± 4.3 |
| EFV | 1 | 2.3 ± 1.5 | 34.3 ± 17.5 | 36.8 ± 20.5 |

Fold-Change = $EC_{50}$ for the mutant HIV divided by the $EC_{50}$ for the wild-type HIV virus.
Average fold-change was calculated as the mean of the individual fold-changes tested in parallel.

The calculated drug concentrations required to block 50% of enzyme (IC50) and data shown in Tables 1-4 were measured in the presence of detergent (which increases the IC50 value) however lower values were generally obtained in the absence of detergent.

In Vitro Antiviral Activity Against Additional Mutant HIV RT Enzymes

Compounds I and III were tested against a broader panel of RT enzymes carrying common NNRTI-resistance mutations. The efficacy data are shown in Table 3 and the corresponding fold-changes are summarized in Table 4. The studies are summarized in the text that follows.

TABLE 3

Antiviral in vitro activity against site-directed mutant HIV-1 RT enzymes

| RT Mutation | N | Cpd I | Cpd III | EFV |
|---|---|---|---|---|
| | | IC50 III ± Standard Deviation | | |
| W.T.[b] | 10 | 0.23 ± 0.05 | 0.21 ± 0.02 | 0.04 ± 0.006 |
| L1001[c] | 3 | 0.16 ± 0.03 | 0.13 ± 0.06 | 0.26 ± 0.09 |

TABLE 3-continued

Antiviral in vitro activity against site-directed mutant HIV-1 RT enzymes

| RT Mutation | N | Cpd I | Cpd III | EFV |
|---|---|---|---|---|
| V106M[c] | 3 | 0.23 ± 0.06 | 0.20 ± 0.06 | 0.37 ± 0.07 |
| V1081[c] | 3 | 1.20 ± 0.71 | 0.83 ± 0.35 | 0.30 ± 0.05 |

TABLE 3-continued

Antiviral in vitro activity against site-directed mutant HIV-1 RT enzymes

| RT Mutation | N | Cpd I | Cpd III | EFV |
|---|---|---|---|---|
| E138K[c] | 3 | 4.67 ± 0.91 | 2.99 ± 0.18 | 0.6 ± 0.16 |
| M184V[d] | 4 | 0.29 ± 0.08 | 0.17 ± 0.08 | 0.02 ± 0.00 |
| | | Average IC50 Values (µM) ± Standard Deviation | | |
| V188L[c] | 3 | 1.25 ± 0.38 | 1.15 ± 0.36 | 1.73 ± 0.22 |
| L1001/K103N[c] | 4 | 0.43 ± 0.33 | 0.40 ± 0.26 | >2 |
| Mean Activity Range (µM) | | 0.16-4.67 | 0.13-2.99 | 0.02->2 |

$IC_{50}$ = inhibitory concentration that reduces enzyme activity by 50%
[a] Number of replicate experiments performed per enzyme except where indicated otherwise
[b] wild-type HIV-1 RT enzyme in BH10 backbone
[c] BH10-derived RT enzymes with site-directed NNRTI drug resistance mutations
[d] BH10 derived RT enzyme with site-directed NRTI drug resistance mutations
[e] 2 data sets used for $IC_{50}$ calculations As can be seen from the data, Compound III and Compound I retained substantial in vitro efficacy against HIV RT enzymes with substitutions at codons 100, 106, 184, and 134. The only significant loss of efficacy was seen for mutants at codons 108, 138 and 188.

TABLE 4

Fold-resistance Against a Panel of Site-Directed Mutant HIV-1 RT

Average Fold Changes ± Standard Deviation

| RT Mutation | N | Cpd I | Cpd III | EFV |
|---|---|---|---|---|
| W.T.[b] | 10 | 1 | 1 | 1 |
| L1001[c] | 3 | 0.5 ± 0.2 | 0.6 ± 0.6 | 3.3 ± 4.0 |
| V106M[c] | 3 | 1.2 ± 0.5 | 1.0 ± 0.3 | 13.4 ± 8.2 |
| V1081[c] | 3 | 4.0 ± 5.3 | 3.8 ± 3.8 | 3.7 ± 2.3 |
| E138K[c] | 3 | 15.5 ± 6.8 | 13.7 ± 1.9 | 7.6 ± 7.5 |
| M184V[d] | 4 | 1.7 ± 0.5 | 0.8 ± 0.3 | 0.8 ± 0.4 |
| Y188L[c] | 3 | 6.0 ± 1.7 | 7.0 ± 5.9 | 59.6 ± 25.8 |

TABLE 4-continued

Fold-resistance Against a Panel of Site-Directed Mutant HIV-1 RT

| RT Mutation | N | Average Fold Changes ± Standard Deviation | | |
|---|---|---|---|---|
| | | Cpd I | Cpd III | EFV |
| L100I/K103N[c] | 4 | 2.4 ± 1.2 | 1.8 ± 0.8 | >101 ± 43.2 |
| Mean Activity Range (µM) | | 0.5-15.5 | 0.6-13.7 | 0.8-101 |

Fold-resistance = $IC_{50}$ for the mutant HIV-1 RT divided by the $IC_{50}$ for the wild-type enzyme in corresponding assay.
Average fold change was calculated as the means of the individual fold changes tested in parallel.
N = number of replicate sets of experiments performed except where indicated by footnote.
[a]Two data set used for calculation of average fold-resistance.

Overall, the Compounds I and III gave fold changes ranging from 0.5±0.2 to 15.50±6.8.

Effect on Human DNA Polymerases Alpha, Beta and Gamma

HIV RT, like other viral polymerase, shares limited structural homology with the cellular DNA polymerases responsible for normal nuclear and mitochondrial DNA synthesis and repair. This raises the formal possibility that inhibitors of HIV RT might inhibit cellular polymerases, resulting in cellular toxicity. In particular, inhibition of polymerase gamma has the potential to result in mitochondrial toxicity. The ability of Compound I and Compound III to inhibit cellular DNA polymerases was assessed using standard in vitro assays (Table 5).

When tested in vitro, Compound III, Compound I, and EFV did not reach an $IC_{50}$ with human cellular DNA polymerase alpha or beta at concentrations ranging from 100->450 µM. Similarly, preliminary data (n=1) showed that the IC50's of Compound I, and EFV were >100 µM against human DNA polymerase gamma activity in vitro, while Compound III had an $IC_{50}$ of 60.1 µM against this enzyme.

TABLE 5

In vitro activity against human cellular DNA-dependent polymerases alpha, beta and gamma

| Compound | N | Average $IC_{50}$ Values (µM) ± Standard Deviation | | |
|---|---|---|---|---|
| | | DNA Pol Alpha[a] | DNA Pol Beta[b] | DNA Pol Gamma[c] |
| I | 4/4/1 | 145.7 ± 44.5 | ≧422.2 ± 149.6 | 118.5 |
| III | 4/4/1 | 159.3 ± 84.3 | ≧479.0 ± 41.9 | 60.1 |
| EFV | 4/4/1 | 108.6 ± 40.9 | 314.2 ± 177.2 | 116.3 |
| Act.D | 4/4/1 | 16.1 ± 11.2 | 23.0 ± 10.4 | 16.9 |

$IC_{50}$ = effective concentration that inhibits enzyme activity by 50% in vitro.
N = number of replicate experiments performed for each polymerase
Act. D = actinomycin D used as a positive assay control
[a]human DNA polymerase alpha
[b]human DNA polymerase beta
[c]human DNA polymerase gamma; preliminary data from a single experiment Direct Demonstration of Binding to HIV RT The structural determination of the K103N/Y181C double mutant HIV RT (the same BH-10 strain enzyme used in the activity assays) co-crystallized with the Compounds I and III was performed.

NNRTIs are usually small and have a strong affinity for a hydrophobic pocket located close to the catalytic site of RT. The binding of the inhibitor restricts the flexibility of the enzyme and interferes with proper DNA synthesis (Clavel and Hance, HIV drug resistance. N Engl J Med; 350:1023-35 (2004)).

Crystallization of K103N/Y181C mutant protein in the presence of Compound I was performed. Recombinant HIV-1 K103N/Y181C RT protein was concentrated in the presence of Compound I, then used in successive crystal micro-seeding experiments to yield protein crystals sufficient in size to allow X-ray data collection. A single crystal was used for X-ray diffraction and modelling. At 3 Å, the schematic shows Compound I bound to the NNRTI pocket of HIV-1 RT.

Figure 1B:
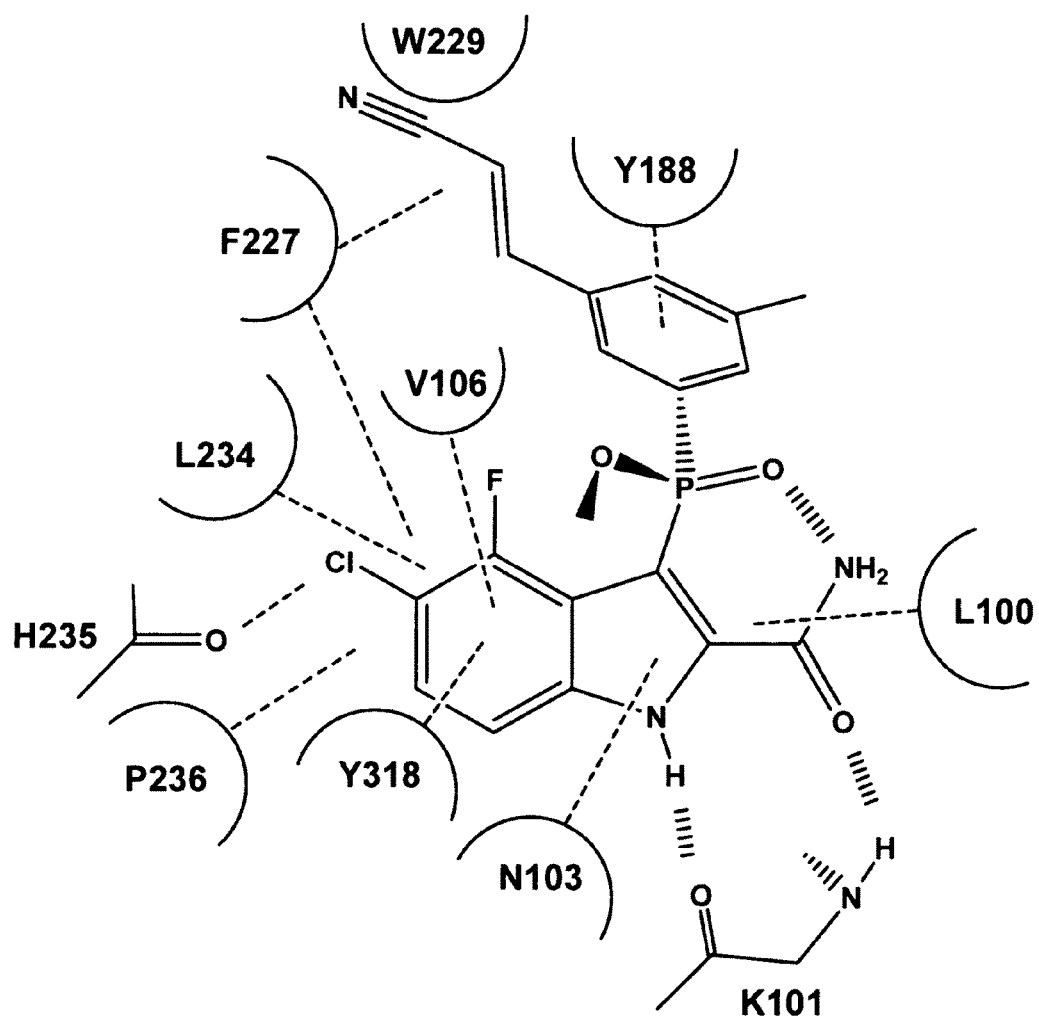
FIG. 1B shows a schematic of the crystal structure of K103N/Y181C HIV Reverse Transcriptase with the 3-phosphoindole compound of Formula I.

The X-ray crystal structure of Compound I in a co-complex with enzymatically active K103N/Y181C HIV-1 double mutant enzyme is shown in FIG. 1A and a schematic is shown at FIG. 1B. The structure shows Compound I binding to the NNRTI pocket in HIV RT, in a manner similar to the approved drug efavirenz (Bacheler, et al., J Virol; 75:4999-5008 (2001)). The indole ring of Compound I can be seen in close proximity to codons 101 and 103 of HIV-1 RT.

Cellular Activity

This section summarizes the antiviral activity profiles of Compound I and Compound III against HIV-1 and HIV-2 in cell culture systems. These activities were measured with a broad variety of assays and endpoints, using multiple HIV strains and human cell types that support HIV replication.

Example 13

Activity Against HIV-1 BH10 Strain

The standard HIV cell-based assay employed is a 4 day assay in MT-4 cells with a p24 ELISA readout. The in vitro anti-HIV-1 activity (EC50 value) of IDX12899 was determined in a standard cell based drug susceptibility assay (DSA) essentially as described in Devine D, Mathews N, Kinchington D (2000), Antiviral Meth and Prot. Human Press Inc., Totowa, N.J. 185-199. The HIV-1 test virus is of subtype B, BH10 strain origin. The standard test panel included wild-type virus, as well as Y181C, K103N, and K103N/Y181C site-directed mutant derivatives. Data from this assay are summarized in Table 6 below. Against the wild-type BH10 virus, the inhibitory activities of Compound I and Compound III, and EFV were all closely similar with $EC_{50}$s around 1 nM. Control values were in good agreement with previously published results (Young et al., 1995, Antimicrob Agents Chemother: 39(12):2602-5; Andries et al., 2004, Antimicrob Agents Chemother; 48(12):4680-6; Janssen et al., 2004, J Med Chem; 48(6):1901-9; Boone 2006, Curr. Opin Investig Drugs; 7(2):128-35) and those obtained utilizing the PhenoScreen™ assay.

TABLE 6

| Compound | N | Mean $IC_{50}$ Values (µM) ± Standard Deviation | | |
|---|---|---|---|---|
| | | DNA Pol Alpha[a] | DNA Pol Beta[b] | DNA Pol Gamma[c] |
| I | 4 | 145.7 ± 44.5 | 422.2 ± 149.6 | 118.5 |
| II | 4 | 159.3 ± 84.3 | ≧479.0 ± 41.9 | ≧95.2 ± 9.5 |
| EFV | 4 | 108.5 ± 40.9 | 314.2 ± 177.2 | ≧100 |
| Act. D | 4 | 16.1 ± 11.2 | 23.0 ± 10.4 | 11.8 ± 1.9 |
| ddCTP | 4 | N/A | N/A | 1.5 ± 0.6 |

$IC_{50}$ = effective concentration that inhibits enzyme activity by 50% in vitro.
N = number of replicate experiments performed for each polymerase
Act. D = actinomycin D used as a positive assay control inhibitor
ddCTP = dideoxycytidine triphosphate used as a positive control inhibitor in DNA pol gamma assay
N/A = not applicable
[a]human DNA polymerase alpha
[b]human DNA polymerase beta
[c]human DNA polymerase gamma
[d]visible precipitates observed Against the mutant viruses, EFV exhibited the expected antiviral profile; it efficiently inhibited Y181C virus growth ($EC_{50}$=2.5 nM) but was significantly less active against the K103N or Y181C/K103N mutant viruses (mean $EC_{50}$ values of 41 to 42 nM).

The activities of the different test articles against the mutant viruses are apparent from the corresponding fold-resistance values summarized in Table 7. All 5 compounds showed similarly decreased activity against the Y181C mutant (mean fold shifts ranged from 2.3 to 3.7). Whereas EFV showed a mean 34.3 fold shift against the K103N virus, the remaining compounds showed essentially unchanged activity (0.8-1.2 fold)

TABLE 7

Fold-resistance of Compounds Against HIV-1 BH10 Virus

| Compound | W.T. | Fold Change Y181C | K103N | K103N/V181C |
|---|---|---|---|---|
| Cmpd I | 1 | 3.4 ± 1.7 | 0.9 ± 0.4 | 4.5 ± 2.5 |
| Cmpd III | 1 | 3.2 ± 1.1 | 1.2 ± 0.4 | 12.7 ± 4.3 |
| EFV | 1 | 2.3 ± 1.5 | 34.3 ± 17.5 | 36.8 ± 20.5 |

Fold-Change = $EC_{50}$ for the mutant HIV divided by the $EC_{50}$ for the wild-type HIV virus. Average fold-change was calculated as the mean of the individual fold-changes tested in parallel.

The activity of the compounds was also assessed with the same virus and cell type using a different assay readout based on cytopathic effect (CPE). This assay measures cell viability following HIV-1 infection rather than capsid protein production and also differs from the standard assay in terms of assay set up and execution and hence provides a useful corroboration of results obtained by the latter method. The data from 5 independent experiments are summarized in Table 8 below.

In the CPE assay, replication of WT BH10 virus was potently inhibited by Compound I, Compound III, and EFV as shown by the subnanomolar mean $EC_{50}$ values (range 0.1 to 0.7 nM).

The Y181C, K103N and K103N/Y181C BH10 panel viruses were inhibited effectively by Compound I, Compound III, with mean $EC_{50}$ values ranging from 0.1 to a maximum of 6.6 nM. As expected, EFV efficiently inhibited the Y181C virus growth but was far less active against the other mutant viruses ($EC_{50}$ values 41 to 53 nM). Control values were in good accord with previously described results (Young et al., 1995, Antimicrob Agents Chemother: 39(12): 2602-5; Andries et al., 2004, Antimicrob Agents Chemother; 48(12):4680-6; Janssen et al., 2004, J Med Chem; 48(6): 1901-9; Boone 2006, Curr. Opin Investig Drugs; 7(2):128-35).

In terms of fold changes compared to the BH10 WT strain, Compound I, Compound III, and EFV showed a 2.7 to 11.9 fold range of increase against the Y181C mutant, while Compound I and Compound III showed no change (<1.8 fold) against the K103N mutant. The K103N/Y181C mutant gave greater variability and fold changes of 12.7 (Compound I) and 55.6 (Compound III). EFV showed respective mean fold-shifts of 66.8 and 88.0 against the K103N and K103N/Y181C mutants, respectively.

TABLE 8

Activity against HIV-1 BH10 viruses in MT-4 cell assay by CPE

| Compound | $N^a$ | Average $EC_{50}$ Values (µM) ± Standard Deviation W.T.$^b$ | Y181C$^b$ | K103N$^b$ | K103N/Y181C$^b$ |
|---|---|---|---|---|---|
| Cmpd I | 5 | 0.0003 ± 0.0001 | 0.0018 ± 0.0003 | 0.0003 ± 0.0001 | 0.0035 ± 0.0015 |
| Cmpd III | 5 | 0.0002 ± 0.0001 | 0.0015 ± 0.0006 | 0.0001 ± 0.0001 | 0.0066 ± 0.0010 |
| EFV | 5 | 0.0006 ± 0.0001 | 0.0016 ± 0.0001 | 0.0410 ± 0.0130 | 0.0530 ± 0.0120 |

$^a$= number of replicate experiments performed.
$^b$= Laboratory adapted wild-type and site-directed mutant BH10 viruses.

TABLE 9

Fold-resistance

| Compound | W.T. | Fold Change Y181C | K103N | K103N/Y181C |
|---|---|---|---|---|
| Cmpd. I | 1 | 6.5 ± 0.9 | 1.0 ± 0.3 | 12.7 ± 5.0 |
| Cmpd. III | 1 | 11.9 ± 4.7 | 1.1 ± 0.3 | 55.6 ± 21.8 |
| EFV | 1 | 2.7 ± 0.7 | 66.8 ± 14.8 | 88.0 ± 20.5 |

Fold-Change = $EC_{50}$ for the mutant HIV divided by the $EC_{50}$ for the wild-type HIV virus. Average fold-change was calculated as the mean of the individual fold-changes tested in parallel.

Activity Against HIV-1 NL4-3 Strain

The activities of the Compound I and Compound III were also determined in a cell-based assay employing subtype B HIV-1 viruses with a NL4-3 backbone. The standard panel of NL4-3 viruses (w.t., Y181C, K103N and K103N/Y181C) were assayed as with the test compounds as described for the BH-10 virus panel above using the ELISA readout. The results of these assays are summarized in Table 10.

The results of this study are generally comparable to those seen with the BH10 viruses. In the NL4-3 background, the compounds are potent against the w.t. NL4-3 virus ($EC_{50}$s ranged from 0.7 to 2.3 nM) and the Y181C virus ($EC_{50}$s ranged from 0.7 to 2.3 nM).

TABLE 10

Activity against HIV-1 NL4-3 viruses in MT-4 cell assay

| | | Average EC$_{50}$ Values (uM) ± Standard Deviation | | | |
|---|---|---|---|---|---|
| Compound | N[a] | W.T.[b] | Y181C[b] | K103N[b] | K103N/Y181C[b] |
| Cmpd. I | 5 | 0.0020 ± 0.0001 | 0.0039 ± 0.0016 | 0.0014 ± 0.0004 | 0.0028 ± 0.0008 |
| Cmpd. III | 5 | 0.0017 ± 0.0003 | 0.0036 ± 0.0020 | 0.0015 ± 0.0003 | 0.0065 ± 0.0023 |
| EFV | 5 | 0.0023 ± 0.0002 | 0.0057 ± 0.0019 | 0.0612 ± 0.0338 | 0.0619 ± 0.0183 |

EC$_{50}$ = effective concentration that reduces virus production by 50% in cell culture.
[a]N = number of replicate experiments performed.
[b]Laboratory adapted wild-type and site-directed mutant BH10 viruses.

TABLE 11

Fold-resistance

| | | Fold Change | | |
|---|---|---|---|---|
| Compound | W.T. | Y181C | K103N | K103N/Y181C |
| Cmpd. I | 1 | 2.0 ± 0.8 | 0.7 ± 0.2 | 1.4 ± 0.4 |
| Cmpd. III | 1 | 2.1 ± 1.1 | 0.9 ± 0.2 | 3.9 ± 1.7 |
| EFV | 1 | 2.5 ± 0.7 | 34.6 ± 7.8 | 27.4 ± 8.6 |

Fold-Change = EC$_{50}$ for the mutant HIV divided by the EC$_{50}$ for the wild-type HIV virus.
Average fold-change was calculated as the mean of the individual fold-changes tested in parallel.

Activity Against HIV-1 Clinical Isolates in MT-2 Cells

The antiviral efficacy of Compound I and Compound III was next measured against two MT-2 cell line-adapted HIV-1 clinical isolates alongside the comparator drugs. The virus test panel consisted of clinical isolate mutants expressing Y181C (#3350) and K103N/Y181C (#5054) compared to a sensitive WT virus. The data are summarized in Table 12 below.

TABLE 12

Activity against HIV-1 clinical isolates in MT-2 cell assay

| | | Average EC$_{50}$ Values (uM) ± Standard Deviation | | |
|---|---|---|---|---|
| Compound | N | W.T. (BH10)[a] | Y181C[b] | K103N/Y181C[c] |
| Cmpd. I | 5 | 0.0009 ± 0.0006 | 0.0014 ± 0.0006 | 0.0020 ± 0.0003 |
| Cmpd. III | 5 | 0.0011 ± 0.0004 | 0.0015 ± 0.0005 | 0.0057 ± 0.0035 |
| EFV | 5 | 0.0008 ± 0.0002 | 0.0018 ± 0.0003 | 0.0724 ± 0.0217 |

EC$_{50}$ = effective concentration that reduces virus production by 50% in cell culture.
[a]Laboratory adapted wildtype strain.
[b]Clinical isolate 3350 is resistant to Nevirapine. This mutant also possesses a M184V mutation.
[c]Clinical isolate 5054.

TABLE 13

Fold-resistance

| | | Fold Change | |
|---|---|---|---|
| Compound | W.T. | Y181C | K103N/Y181C |
| Cmpd. I | 1 | 2.2 ± 1.3 | 3.2 ± 2.1 |
| Cmpd. III | 1 | 1.7 ± 0.9 | 6.2 ± 4.3 |
| EFV | 1 | 2.2 ± 0.6 | 93.1 ± 31.4 |

Fold-change = EC$_{50}$ for the mutant HIV divided by the EC$_{50}$ for the wild-type HIV. Note that fold-change was not determined from the mean EC$_{50}$ values in Table 12, but was first calculated for individual experiments. Then the mean fold-change +/− SD was taken from all experiments.

Activity Against HIV-1 Strains in Human PBMC

The antiviral activity of Compound I and Compound III and comparators was next measured against an HIV-1 panel in peripheral blood mononucleocyte cells (PBMC). The full virus panel consisted of 3 clinical isolate mutants expressing K103N (#4937 and #5002) and K103N/Y181C (#5004) viruses, along with two NNRTI-sensitive WT viruses (BH10 and NL4-3). The results from five independent data sets are summarized in Table 14.

TABLE 14

Activity against HIV-1 viruses in PBMC cell assay

| | Average EC$_{50}$ Values (uM) ± Standard Deviation | | | |
|---|---|---|---|---|
| Compound | W.T. (BH10)[a] | W.T. (NL4-3)[a] | K103N[b] | K103N/Y181C[c] |
| Cmpd. I | 0.0004 ± 0.0001 | 0.0015 ± 0.0007 | 0.0007 ± 0.0003 | 0.0027 ± 0.0016 |
| Cmpd. III | 0.0004 ± 0.0001 | 0.0015 ± 0.0005 | 0.0009 ± 0.0004 | 0.0088 ± 0.0044 |
| EFV | 0.0009 ± 0.0003 | 0.0021 ± 0.0007 | 0.0414 ± 0.0369 | 0.0687 ± 0.0487 |

EC$_{50}$ = effective concentration that reduces virus production by 50% in cell culture.
Numbers represent mean values +/− standard deviation derived from 5 independent experiments.
[a]Laboratory adapted wildtype virus strain.
[b]Results used clinical isolates 4937 (n = 3) and 5002 (n = 2).
[c]Clinical isolate 5004.

All 5 compounds were extremely potent against the wt BH10 virus in PBMC, with $EC_{50}$ values of 0.4 to 0.9 nM. The agents were typically 2 to 4 fold less efficacious against the NL4-3 virus in the same cells. Compound I and Compound III inhibited replication of the K103N viruses effectively, with only a 1 to 2 fold loss of activity (versus the BH10 virus), but were less 6 to 22 fold less inhibitory to the K103N/Y181C isolate. In contrast, EFV exhibited roughly 40 to 70 fold less activity against the single and double mutant isolates, respectively. Control and test article values were in good agreement with previously published results (Young et al., 1995, Antimicrob Agents Chemother: 39(12):2602-5; Andries et al., 2004, Antimicrob Agents Chemother; 48(12):4680-6; Janssen et al., 2004, J Med Chem; 48(6):1901-9) and with other values reported in this section.

Activity Against HIV-1 IIIB Viruses in MT-4 Cells by CPE Assay

The test articles were next profiled against a panel of HIV-1 IIIB laboratory cultivated mutants as summarized in the text below. Antiviral efficacy was determined via a CPE assay with an MTS read-out for cell viability. The viruses tested in this assay included the standard IIIB w.t., as well as culture-selected Y181C and Y181C/K103N viruses, but the usual K103N was replaced by a selected K103R/V179D/P225H triple mutant virus which is described further below. Averaged efficacy data are shown in Table 15.

0.0099±0.0016. EFV, however, was far less effective as seen by the mean $EC_{50}$ value (in μM) of 0.1120±0.0330.

The K103R/V179D/P225H triple mutant IIIB virus showed more variable results and much greater resistance to EFV, although it remained relatively sensitive to Compound I and Compound III. The mean $EC_{50}$ values (in μM) were: 0.0100±0.0015 (Compound I), 0.0250±0.0060 (Compound III), and >1.0 (EFV). Note that a K103R mutant RT enzyme is not NNRTI resistant (data not shown).

In terms of fold changes in drug susceptibility for the IIIB mutant panel, the mean fold-resistance values for Compound I, Compound III, and EFV were generally little changed (2.9±0.8 to 7.7±2.8 fold) against the Y181C virus. Fold-resistance against the K103N/Y181C mutant was more variable but within the range of changes seen in this section overall: the fold changes were 4.8±1.6 (Compound I) and 19.5±4.3 (Compound III). The mean fold-resistance values seen for the K103R/V179D/P225H mutant were: 11.1±4.1 (Compound I), 53.5±12.8 (Compound III), and >711.7±255.3 (EFV).

In summary, these tests in the IIIB virus CPE assay generally confirm findings presented elsewhere in this section, with

TABLE 15

Activity against HIV-1 IIIB viruses in MT-4 cells by CPE

| | | Average $EC_{50}$ Values (μM) ± Standard Deviation | | | |
|---|---|---|---|---|---|
| Compound | $N^a$ | W.T.$^b$ | Y181C$^b$ | K103R/V179D/P225H$^b$ | K103N/Y181C$^b$ |
| Cmpd I | 5 | 0.0010 ± 0.0004 | 0.0028 ± 0.0003 | 0.0100 ± 0.0015 | 0.0047 ± 0.0009 |
| Cmpd III | 5 | 0.0005 ± 0.0001 | 0.0021 ± 0.0003 | 0.0250 ± 0.0060 | 0.0091 ± 0.0019 |
| EFV | 5 | 0.0015 ± 0.0006 | 0.0069 ± 0.0020 | >1.0 | 0.1120 ± 0.0330 |

$^a$ = number of replicate experiments performed.
$^b$ = Laboratory adapted wild-type and site-directed mutant BH10 viruses.

TABLE 16

Fold-resistance

| | | Fold Change | | |
|---|---|---|---|---|
| Compound | W.T. | Y181C | K103R/V179D/P225H | K103N/Y181C |
| Cmpd. I | 1 | 2.9 ± 0.8 | 11.1 ± 4.1 | 4.8 ± 1.6 |
| Cmpd. III | 1 | 4.5 ± 1.0 | 53.5 ± 12.8 | 19.5 ± 4.3 |
| EFV | 1 | 4.6 ± 0.5 | >711.7 ± 255.3 | 74.2 ± 17.2 |

Fold-Change = $EC_{50}$ for the mutant HIV divided by the $EC_{50}$ for the wild-type HIV virus.
Average fold-change was calculated as the mean of the individual fold-changes tested in parallel.

W.T. IIIB virus was inhibited effectively by all 5 drugs with mean $EC_{50}$ values (in μM) ranging from 0.0004±0.0002 to 0.0017±0.0004.

Replication of the culture-selected IIIB Y181C virus was also inhibited effectively by each drug with mean $EC_{50}$ values (in μM) ranging from 0.0021±0.0003 to 0.0120±0.0026. These values agree well with other results presented throughout this section.

The IIIB K103N/Y181C virus was generally inhibited effectively by Compound I and Compound III as implied by the mean $EC_{50}$ values (in μM) ranging from 0.0026±0.0004 to the exception of the K103R/V179D/P225H triple mutant virus. Compound I was most active against this mutant ($EC_{50}$=10 nM), followed by Compound III with reasonable activity ($EC_{50}$=21 to 25 nM), while EFV was essentially inactive ($EC_{50}$>1000 nM). Although the K103R/V179D/P225H mutant genotypic pattern is not commonly recognized in clinical samples, the combination of K103R/V179D is known to confer large reductions in susceptibility to all three approved NNRTIs (Harrigan et al., 2005, AIDS; 19:549-54; Parkin et al., 2006, Antimicrob Agents Chemother; 50(1): 351-4).

Activity Against Various HIV-1 Strains in Different Human Cell Lines

The virus and host-cell dependency of Compound I, Compound III and control drugs was further examined in drug susceptibility assays performed across 3 different subtype B wild-type HIV-1 strains and 5 different cell lines. The HIV-1 strains used were BH10, NL4-3 and IIIB: the cell lines were U-937 cells (human monocytes derived from a histiocytic lymphoma); MOLT-4 cells (a human T lymphoblastic leukemia cell line); H-9 cells (human lymphoblastic T cells); and MT-2 and MT-4 human leukemia T cells.

The mean $EC_{50}$ values and standard deviations from three independent experiments are summarized in Table 17. Under the experimental conditions of this study, Compound I, Compound III, and EFV retained largely unchanged potencies across each wild-type virus and host cell combination tested. The activities seen ranged from 0.4 to 3.2 nM.

TABLE 17

Activity Against HIV-1 W.T. Strains in Established Human Host Cell Lines
Average $EC_{50}$ Values (uM) ± Standard Deviation

| Host | Virus | Cmpd I | Cmpd III | EFV |
|---|---|---|---|---|
| U937 | IIIB | 0.0005 ± 0.0001 | 0.0005 ± 0.0001 | 0.0015 ± 0.0008 |
| MOLT-4 | IIIB | 0.0007 ± 0.0001 | 0.0006 ± 0.0001 | 0.0009 ± 0.0002 |
| H9 | IIIB | 0.0006 ± 0.0001 | 0.0005 ± 0.0002 | 0.0015 ± 0.0006 |
| U937 | BH10 | 0.0006 ± 0.0002 | 0.0013 ± 0.0006 | 0.0019 ± 0.0008 |
| MT-2 | BH10 | 0.0009 ± 0.0006 | 0.0011 ± 0.0004 | 0.0008 ± 0.0002 |
| MT-4 | BH10 | 0.0010 ± 0.0004 | 0.0012 ± 0.0006 | 0.0012 ± 0.0008 |
| MT-4 | NL4-3 | 0.0020 ± 0.0001 | 0.0017 ± 0.0003 | 0.0023 ± 0.0002 |
| Mean Activity Range (uM) | | 0.0005 ± 0.0020 | 0.0005 ± 0.0017 | 0.0008 ± 0.0023 |

$EC_{50}$ = effective concentration that reduces virus production by 50% in cell culture.
Numbers represent mean values +/– standard deviation derived from 3 independent experiments.

The mean activity ranges seen for each of the drugs across each of the virus strains and cell types are summarized in the last row of the table. Compound I and Compound III displayed potent in vitro antiviral activity (0.5 to 2 nM range) across three HIV-1 strains and morphologically distinct human T and monocytic cell lines. All 5 compounds showed fairly comparable activity.

Activity Against a Panel of Different HIV-1 Subtypes

The activities of the test and control compounds were next tested against a subtype panel which covers all major HIV-1 subtypes or clades (A, B, C, D, F1, G, H, AE and AG). This panel was part of a 64 virus panel selected from the large library of clinical isolates Monogram BioSciences (formerly ViroLogics). Each of the subtypes in the panel was represented by 2 distinct viruses which share many sequence similarities, but also some key differences and therefore could respond differently to one or more of the drugs included in this study.

From the PhenoSense™ testing of the test articles Compound I, Compound III and the control drug EFV, the activity of compound I, compound III and EFV against a subtype panel (18 viruses) comprising 9 different HIV-1 subtypes (A, B, C, D, F1, G, H, AE, AG) were all within 2-fold of the wild type activity values (data not shown).

Among the different subtypes, the overall potency ranges were: Compound I, 0.25 to 3.20 nM; Compound III=0.2 to 2.14 nM; EFV=0.40 to 3.10 nM. Not surprisingly, the range of potency was somewhat greater across subtypes (10 to 11 fold) than within subtypes, but this variability was primarily due to just two virus isolates: the second subtype C HIV-1 isolate was, across the board, the least susceptible to all the drugs tested; conversely, the two subtype H isolates appeared highly susceptible to all the drugs ($EC_{50}$ values 0.17 to 0.55 nM). However, these viruses also had reduced replication capacity of 42% and 10%, respectively, which could contribute to their apparent hypersensitivity. The remaining subtype viruses generally showed a <2.5-fold divergence in potency from the CNDO reference strain.

Activity Against HIV-2 ROD in H9 Cells

The susceptibility of HIV type 2 ROD in H9 cells to Compound I and Compound III was determined against zidovudine (AZT) as a control. Averaged data were derived from two independent antiviral activity experiments and shown in Table 18.

Compound I and Compound III failed to suppress HIV-2 ROD replication at the highest concentration assayed (1.25 μM), while the AZT control displayed activity (0.1619±0.0767 μM) comparable to published values (Witvrouw, et al 2004, Antiviral Therapy 9:57-65).

TABLE 18

Activity against HIV-2 ROD WT in H9 cell assay

| Compound | $EC_{50}$ Values (uM) |
|---|---|
| Compound I | >1.25 |
| Compound III | >1.25 |
| AZT | 0.1619 ± 0.0767 |

$EC_{50}$ = effective concentration that reduces virus production by 50% in cell culture.
Numbers represent mean values +/– standard deviation from 2 independent experiments.

Activity Against HIV-1 in the Presence of Human Serum and Alpha-1 Acid Glycoprotein The prior studies typically measured the $EC_{50}$ of each drug against HIV-1 grown in cell culture in the presence of 10% fetal bovine serum (FBS). To estimate a serum-adjusted $EC_{50}$ for the test articles, additional experiments were performed in the presence of 45% human serum, or 1 mg/mL alpha-1 acid glycoprotein, or both. Averaged results from 3 to 7 antiviral activity experiments are shown in Table 19.

TABLE 19

Anti-HIV-1 BH10 W.T. activity in presence of HS or AAG

| | | Average $EC_{50}$ Values (μM) ± Standard Deviation | | | |
|---|---|---|---|---|---|
| Compound | N | 10% Fetal Bovine Serum | 10% Fetal Bovine Serum + AAG[a] | 45% Human Serum[b] | 45% Human Serum + AAG |
| Cmpd I | 5 | 0.0011 ± 0.0004 | 0.0029 ± 0.0012 | 0.0146 ± 0.0063 | 0.0190 ± 0.0017 |
| Cmpd III | 5 | 0.0012 ± 0.0004 | 0.0028 ± 0.0004 | 0.0219 ± 0.0117 | 0.0326 ± 0.0073 |
| EFV | 7 | 0.0016 ± 0.0005 | 0.0050 ± 0.0023 | 0.0115 ± 0.0039 | 0.0116 ± 0.0074 |

$EC_{50}$ = effective concentration that reduces virus production by 50% in cell culture.
[a]α-1 acid glycoprotein at 1 mg/ml.
[b]Human Serum - AB+ lacks antibodies against the A and B blood type antigens.

TABLE 20

Fold-resistance

| Compound | N | 10% Fetal Bovine Serum | 10% Fetal Bovine Serum + AAG[a] | 45% Human Serum | 45% Human Serum + AAG |
|---|---|---|---|---|---|
| Cmpd I | 5 | 1 | 2.7 ± 0.7 | 15.9 ± 11.1 | 19.5 ± 7.6 |
| Cmpd III | 5 | 1 | 2.1 ± 0.5 | 17.0 ± 6.3 | 24.8 ± 3.8 |
| EFV | 7 | 1 | 2.4 ± 0.8 | 8.4 ± 3.2 | 5.4 ± 3.2 |

Fold change = $EC_{50}$ obtained with fetal bovine Serum + AAG or human serum +/− AAG divided by $EC_{50}$ obtained with fetal bovine serum only. Note that fold-change was not determined from the mean $EC_{50}$ values in Table 19, but was first calculated for individual experiments. Then the mean fold change +/− standard deviation was taken from all experiments.
[a]α-1 acid glycoprotein at 1 mg/ml.

The 5 drugs inhibited the replication of WT virus in the presence of 10% FBS with the anticipated potencies, with $EC_{50}$ values ranging from 1.0 to 1.6 nM. The addition of 1 mg/mL AAG generally decreased drug potency by 2 to 3 fold for each drug, shifting the mean $EC_{50}$ values to the 2 to 5 nM range.

The potencies of the 5 drugs were reduced to a greater extent by 45% human serum (HS), leading to mean $EC_{50}$ values from 11.5 to 21.9 nM and fold-shifts of 8.4 to 17.0 fold. The presence of 45% HS+AAG in culture experiments gave more variable results and mean $EC_{50}$ values (in nM) of 19.0 (Compound I), 32.6 (Compound III, and 11.6 (EFV). The values seen for the controls were in good agreement with published results (Young et al., 1995, Antimicrob. Agents Chemother: 39(12):2602-5; Andries et al., 2004, Antimicrob. Agents Chemother; 48(12):4680-6; Janssen et al., 2004, J. Med. Chem.; 48(6):1901-9; Boone 2006, Curr. Opin Investig Drugs; 7(2):128-35). The corresponding mean fold changes were 19.5 (Compound I), 24.8 (Compound III), and 5.4 (EFV).

In summary, no significant protein binding interaction was observed with AAG alone (<3-fold change) for the Compound I and Compound III. A moderate elevation of $EC_{50}$ (16 to 25 fold change) was estimated in HS or HS+AAG. Overall, the data suggest that protein binding is a little higher for Compound I and Compound III than for EFV.

Example 14

In Vitro Cytotoxicity

Conventional cell-based assays using proliferating cells were used to assess the cytotoxicity of Compound I and Compound III. These 3 to 12 day cytotoxicity studies focused on human cell lines which are either (i) susceptible to infection with HIV-1 virus in vitro (e.g. primary blood monocytes; MT-2 and MT-4 leukemia T cells), or (ii) commonly used to evaluate drug induced in vitro cytotoxicity (e.g. HepG2, HuH7 or HeLa) (Divi R L, Haverkos K J, Humsi J A, et al (2006) Morphological and molecular course of mitochondrial pathology in cultured human cells exposed long-term to zidovudine. Environ Mol Mutagen; 47). Cell viability was measured by standard MTT or MTS staining.

Cytotoxic Effect in PBMC Cells

The in vitro cytotoxicity of the test articles was assessed in 4 independent experiments in stimulated human primary blood mononuclear cells (PBMC). PBMC were exposed to Compound I and Compound III along with control drug EFV for 3 days at concentrations ranging from 0.005 μM to 100 μM. Cell viability was determined via MTT staining. The results are presented as the mean effective drug concentrations that reduced cell viability by 50% ($CC_{50}$).

Mean $CC_{50}$ values (in μM) determined for the test articles in PBMC were: Compound I=52.6±15.2 and Compound III=66.9±19.6. For the control article mean $CC_{50}$ value (in μM) determined was: EFV=70.9±7.6.

Cellular Cytotoxicity in HIV-1 Human Host Cells

The in vitro cytopathic effects of the test articles Compound I and Compound III and control drug EFV were next tested in the following six HIV-1 susceptible human host cell lines: U-937 cells (human monocytes derived from a histiocytic lymphoma); MOLT-4 cells (a human T lymphoblastic leukemia cell line); H9 cells (human lymphoblastic T cells); IM9 cells (a human B lymphoblastic cell line); and MT-2 and MT-4 human leukemia T cells.

Following drug exposure for 4 days, cell viability was measured by MTS staining and $CC_{50}$ values were determined. Drug concentrations ranged from 0.005 μM to 100 μM. The results from 3 independent experiments (unless indicated otherwise) are summarized in Table 21.

TABLE 21

Cellular Cytotoxicity in HIV-1 Human Host Cell Lines

| Compound | Average $CC_{50}$ Values (μM) ± Standard Deviation[a,b] | | | | | | Mean $CC_{50}$ Range (μM) |
|---|---|---|---|---|---|---|---|
| | U937[d] | MOLT-4[e] | H9[f] | IM9[g] | MT-2[h] | MT-4[h] | |
| I | 26.5 ± 0.5 | 16.6 ± 0.4 | 20.0 ± 1.6 | 32.9 ± 2.6 | 23.5 ± 1.0 | 18.6 ± 3.1 | 16.6-32.9 |
| III | 24.6 ± 1.9 | 14.8 ± 1.0 | 31.3 ± 5.2 | 50.0 ± 17.4 | 25.9 ± 2.1 | 27.3 ± 12.9 | 14.8-50.0 |
| EFV | 23.2 ± 1.0 | 41.7 ± 3.4 | 50.0 ± 9.0 | 51.0 ± 1.3 | 24.6 ± 4.5 | 44.1 ± 18.2 | 23.2-51.0 |

[a]$CC_{50}$ = effective concentration that reduces cell viability by 50%.
[b]Numbers represent mean values +/− standard deviation derived from 3 independent experiments unless noted otherwise.
[c]Values were derived from 2 independent experiments.
[d]Human monocyte histiocytic lymphoma; plated at $5 \times 10^3$ cells per well.
[e]Human T lymphoblastic leukemia; plated at $2 \times 10^4$ cells per well.
[f]Human lymphoblastic T cell lymphoma; plated at $4 \times 10^4$ cells per well.
[g]Human B lymphoblastoid cell line; plated at $2 \times 10^4$ cells per well.
[e]Human T cell leukemia; plated at $1.25 \times 10^4$ (MT-2) and $2.5 \times 10^4$ (MT-4) cells per well.

The test articles Compound I and Compound III and the control compounds exhibited measurable in vitro cytotoxicity in the 6 human HIV-1 susceptible host cell lines. Depending on cell type, the mean $CC_{50}$ values for Compound I ranged from 16.6 to 32.9 µM versus 14.8 to 50.0 µM for Compound III (Table 21), similar to the mean $CC_{50}$ ranges determined for EFV (23.2 to 51.0 µM).

Among the 6 cell lines, the MOLT-4 cell line was the most sensitive to cytotoxicity for Compound I and Compound III. EFV showed the most cytotoxicity in U937 and MT-2 cells.

Example 15

Selectivity Index of Compound I and Compound III Against HIV-1

The preceding data, allows us to calculate selectivity index (SI) values, based on the ratio of $CC_{50}$ to $EC_{50}$ in MT-4 cells (the standard assay used in this work).

The $CC_{50}$ of Compound I in MT-4 T cells was 27 µM versus an $EC_{50}$ of 1.2 nM, giving an SI>22,000. The $CC_{50}$ of Compound III was 18.6 µM versus an $EC_{50}$ of 1.0 nM, for an SI of >18,000. Similarly, the selectivity index of control drug was estimated to be: EFV=37,000. These values are in good agreement with previously reported SI values (Young et al., 1995. Antimicrob Agents Chemother: 39(12):2602-5; Andries et al., 2004, Antimicrob Agents Chemother; 48(12): 4680-6; Janssen et al., 2004, J Med Chem; 48(6):1901-9; Boone 2006, Curr. Opin Investig Drugs; 7(2):128-35).

Using cytotoxicity and activity data derived in PBMC, SI values of >100,000 could be computed for Compound I and Compound III.

Longer Term Cellular Cytotoxicity in Other Human Cell Types

Lastly, the in vitro cytotoxicity of the test articles was determined in other human cell lines with toxicologic relevance; HuH7 and HepG2 liver cells (Knowles et al., 1980, Science; 209(25):497-9) and HeLa epithelial cells (Gey et al., 1952, Cancer Research; 12:264-5) via MTS viability staining. Cells were repeatedly treated with a range of drug concentrations (0.005 to 100 µM) for 9 (HeLa) or 12 days (HuH7, HepG2). The mean $CC_{50}$ values and standard deviations derived from 3 to 5 independent experiments are summarized in Table 22.

TABLE 22

Cellular Cytotoxicity in Select Human Cell Lines

| Compound | Average $CC_{50}$ Values (µM) ± Standard Deviation | | |
|---|---|---|---|
| | HeLa[a,d] | HuH7[b,e] | HepG2[c,e] |
| I | 27.88 ± 1.14 | 23.49 ± 1.61 | 25.69 ± 3.26 |
| III | 29.86 ± 2.09 | 31.46 ± 3.37 | 23.50 ± 1.51 |
| EFV | 48.57 ± 2.50 | 75.72 ± 12.43 | 80.56 ± 12.12 |

$CC_{50}$ = effective concentration that reduces cell viability by 50%.

Numbers represent mean values +/− standard deviation derived from 3 to 5 independent experiments as indicated; [a] = 3-4; [b] = 4-5; [c] = 3-5.

[d]HeLa cells were plated at 1 × 10³ cells/well and incubated in the presence of drug for 9 days. Drug and media were replaced every 3 days.

[e]HuH7 and HepG2 cells were plated at 1 × 10³ and 7 × 10³ cells/well respectively and incubated for 12 days in the presence of drug. Drug and media were replaced every 3 days.

The trends observed in this longer term cytotoxicity testing mirror those seen in the preceding studies. In general, Compound I and Compound III gave similar $CC_{50}$ values in the 3 cell lines, ranging from 23 to 32 µM. EFV was again the least cytotoxic of the compounds ($CC_{50}$ range 48-81 µM).

Example 16

In Vitro Comparative Data

Compounds I and III, the corresponding enantiomers (i.e., compounds II and IV) and the corresponding racemates were evaluated in the standard BH10 HIV cell-based assays described above. The standard test panel included wild-type virus, as well as Y181C, K103N, and K103N/Y181C site-directed mutant derivatives.

The table below provides data for compound I, compound II and their corresponding racemate. Against wild-type BH10 virus and the Y181C, K103N, and K103N/Y181C mutant viruses, the racemate had $EC_{50}$s from 2.4 to 6.2 nM. Against wild-type BH10 virus and the Y181C, K103N, and K103N/Y181C mutant viruses, compound I had $EC_{50}$s from 0.6 to 3.5 nM. Against wild-type BH10 virus and the Y181C and K103N mutant viruses, compound II had $EC_{50}$s from 129 to 920 nM.

| Activity against HIV-1 BH10 viruses in cell assay | | | | | | | | |
|---|---|---|---|---|---|---|---|---|
| Cpd | BH10 | n | K103N | n | Y181C | n | Y181C/K103N | n |
| I | 0.001 ± 0.0005 | 8 | 0.0006 ± 0.0002 | 3 | 0.0026 ± 0.0011 | 3 | 0.0035 ± 0.0014 | 3 |
| I | 0.0007 ± 0 | 1 | 0.0009 ± 0 | 1 | 0.0024 ± 0 | 1 | 0.003 ± 0 | 1 |
| II | 0.1917 ± 0 | 1 | 0.9201 ± 0 | 1 | 0.3637 ± 0 | 1 | | |
| rac | 0.0025 ± 0.0004 | 3 | 0.0024 ± 0.0007 | 3 | 0.0032 ± 0.0006 | 3 | 0.0062 ± 0.0036 | 3 |

$EC_{50}$ = effective concentration that reduces virus production by 50% in cell culture.

[a]N = number of replicate experiments performed.

[b]Laboratory adapted wild-type and site-directed mutant BH10 viruses.

The table below provides data for compound III, compound IV and their corresponding racemate. Against wild-type BH10 virus and the Y181C, K103N, and K103N/Y181C mutant viruses, the racemate had $EC_{50}$s from 1.6 to 24.4 nM. Against wild-type BH10 virus and the Y181C, K103N, and K103N/Y181C mutant viruses, compound III had $EC_{50}$s from 0.6 to 23.1 nM. Against wild-type BH10 virus and the Y181C, K103N, and K103N/Y181C mutant viruses, compound IV had $EC_{50}$s from 89.2 to 824 nM.

| Activity against HIV-1 BH10 viruses in cell assay | | | | | | | |
|---|---|---|---|---|---|---|---|
| Cpd | BH10 | n | K103N | n | Y181C | n | Y181C/K103N | n |
| III | 0.001 ± 0.0005 | 10 | 0.0013 ± 0.0005 | 5 | 0.0028 ± 0.0005 | 5 | 0.0114 ± 0.0023 | 5 |
| III | 0.0018 ± 0.0003 | 3 | 0.0016 ± 0.0005 | 3 | 0.0040 ± 0.0005 | 3 | 0.0231 ± 0.0121 | 3 |
| III | 0.0006 ± 0 | 1 | 0.0006 ± 0 | 1 | 0.0029 ± 0 | 1 | 0.0045 ± 0 | 1 |
| IV | 0.1902 ± 0.0038 | 2 | 0.3776 ± 0.2047 | 2 | 0.8241 ± 0.3636 | 2 | | 0 |
| IV | 0.0892 ± 0.1068 | 2 | 0.1053 ± 0.0579 | 2 | 0.2286 ± 0.0605 | 2 | 0.5167 ± 0 | 1 |
| IV | 0.0976 ± 0 | 1 | 0.3123 ± 0 | 1 | 0.331 ± 0 | 1 | | 0 |
| rac | 0.031 ± 0.0002 | 2 | 0.0031 ± 0.0005 | 2 | 0.0049 ± 0.0011 | 2 | 0.0167 ± 0.0088 | 2 |
| rac | 0.0017 ± 0 | 1 | 0.0017 ± 0 | 1 | 0.0016 ± 0 | 1 | 0.0042 ± 0 | 1 |
| rac | 0.0025 ± 0.0007 | 3 | 0.0025 ± 0.0013 | 3 | 0.005 ± 0.0037 | 3 | 0.0244 ± 0.0188 | 3 |

$EC_{50}$ = effective concentration that reduces virus production by 50% in cell culture.
[a]N = number of replicate experiments performed.
[b]Laboratory adapted wild-type and site-directed mutant BH10 viruses.

As shown in the tables above, in these assays most if not all of the activity of the racemic mixture lies in the R enantiomers compounds I and III.

Cell Protection Assay

Compounds I and III, the corresponding enantiomers (i.e., compounds II and IV) and the corresponding racemates were evaluated in a cell protection assay. The standard test panel included wild-type virus, as well as Y181C, K103N, and K103N/Y181C site-directed mutant derivatives.

Test compounds were dissolved in DMSO at 15 mM and then diluted in culture medium RPMI 1640+2 g/L $NaHCO_3$+ 1% kanamycin solution 100×(10000 μg/mL)+10% FCS+/− 1.2% DMSO MT-4 cells (Source: NIH Catalog #120) were seeded onto 96-well cell culture plates (1×10⁴ cells per well in 50 μL).

Serial 2-fold dilutions of test compounds in 50 μL (0.29 μM to 75 μM) were added to cells in complete growth media (RPMI, 10% Foetal Bovine Serum, Penicillin-streptomycin) and the cells were infected with a 20 μL-aliquot of an HIV suspension (HIV-1 strain BH10 wild-type and resistant viruses Y181C, K103N and Y181C/K103N) at a dilution that gives 90% cytopathic effect. The final DMSO concentration in the assay was 0.5% in 120 μL. Cell cultures were then incubated at 37° C./5% $CO_2$ for 4 days. Then, Cell Titer 96 $AQ_{ueous}$ One Solution Cell Proliferation Assay (Promega) was used to measure cell viability. Briefly, the One Solution Reagent was added directly to culture wells (20 μL/well), incubated for 5 hours, and the absorbance was recorded at 492 nm using the Sunrise Tecan Spectrophotometer.

The $EC_{50}$ values were determined from the percent inhibition versus concentration data using a sigmoidal non-linear regression analysis based on four parameters with Tecan Magellan software.

The table below provides data for compound I, compound II and their corresponding racemate. Against wild-type BH10 virus and the Y181C, K103N, and K103N/Y181C mutant viruses, the racemate had $EC_{50}$s from 1.5 to 7.0 nM. Against wild-type BH10 virus and the Y181C, K103N, and K103N/Y181C mutant viruses, compound I had $EC_{50}$s from 0.26 to 3.5 nM. Against wild-type BH10 virus and the Y181C and K103N mutant viruses, compound III had $EC_{50}$S from 62 to over 1000 nM.

| Activity against HIV-1 BH10 viruses in Cell Protection Assay | | | | |
|---|---|---|---|---|
| Cpd | BH10 | K103N | Y181C | Y181C/K103N |
| I | 0.00028 ± 0.000072 | 0.00026 ± 0.000057 | 0.0018 ± 0.00029 | 0.0035 ± 0.0015 |
| II | 0.062 ± 0.019 | 0.277 ± 0.099 | 0.424 ± 0.21 | >1 |
| rac | 0.0015 ± 0.0007 | 0.001 ± 0 | 0.0045 ± 0.0007 | 0.007 ± 0.0028 |

$EC_{50}$ = compound concentration that achieved 50% reduction of cytopathic effect of the virus.

The table below provides data for compound III and its corresponding racemate. Against wild-type BH10 virus and the Y181C, K103N, and K103N/Y181C mutant viruses, the racemate had $EC_{50}$s from 0.2 to 9.0 nM. Against wild-type BH10 virus and the Y181C, K103N, and K103N/Y181C mutant viruses, compound III had $EC_{50}$s from 0.14 to 6.6 nM.

| | Activity against HIV-1 BH10 viruses in Cell Protection Assay | | | |
|---|---|---|---|---|
| Cpd | BH10 | K103N | Y181C | Y181C/K103N |
| III | 0.00015 ± 0.00011 | 0.00014 ± 0.000052 | 0.0015 ± 0.0006 | 0.0066 ± 0.00097 |
| IV rac | 0.0002 ± 0.0001 | 0.0003 ± 0 | 0.0023 ± 0.0005 | 0.009 ± 0.0048 |

$EC_{50}$ = compound concentration that achieved 50% reduction of cytopathic effect of the virus.

Cytochrome P450 Binding, Inhibition and Induction

Compounds I and III, the corresponding enantiomers (i.e., compounds II and IV) and the corresponding racemates were evaluated in assays for cytochrome P450 binding.

Inhibition studies were conducted to assess the potential of compounds I and III to inhibit the catalytic activity of CYP450 isoenzymes of human liver microsomal proteins. The rate of metabolite formation of CYP450-specific probe substrates by human liver microsomes was determined in the presence and absence of Compound I or III. Direct inhibition as well as time-dependent inhibition, also referred to as mechanism-based inhibition or MBI, was also evaluated. Initial studies determined $IC_{50}$ values with subsequent determination of $k_i$ or $k_{inact}$ and $k_i$ for MBI, when marked inhibition ($IC_{50}$<10 µM) was noted. In addition, the type of inhibition was also evaluated.

Compounds were assayed using recombinant human microsomal proteins with fluorometric substrates. Signal was measured with a Fusion plate reader utilizing the appropriate excitation and emission wavelength set to detect the specific metabolite:

| Enzyme | Substrate | Excitation (bandwidth) | Emission (bandwidth) |
|---|---|---|---|
| CYP1A2 | CEC | 400 nm (20 nm) | 535 nm (25 nm) |
| CYP2B6 | EFC | 400 nm (20 nm) | 535 nm (25 nm) |
| CYP2D6 | AMMC | 400 nm (20 nm) | 460 nm (35 nm) |
| CYP3A4 | BFC | 400 nm (20 nm) | 535 nm (25 nm) |

CYP2C9 inhibition was performed by incubating a luminogenic CYP450 substrate Luciferin-H with CYP2C9 and an NADPH regeneration system. Luminescence measured using a Fusion plate reader.

| | In vitro recombinant cytochrome P450 isozyme inhibition | | | | | | |
|---|---|---|---|---|---|---|---|
| CYP450 isozyme | Highest concentration tested (µM) | IC50 (µM) rac (I + II) | $IC_{50}$ (µM) I | $IC_{50}$ (µM) II | $IC_{50}$ (µM) rac (III + IV) | $IC_{50}$ (µM) III | $IC_{50}$ (µM) IV |
| CYP1A2 | 20 | NA | 17.5% | NA | NA | 17.6 ± 2.06 | NA |
| CYP2B6 | 20 | NA | 21.6% | NA | NA | 22.9% | NA |
| CYP2C9 | 10 | NA | 8.40 ± 0.67 | NA | 5.99 | 6.85 ± 0.48 | 3.38 |
| CYP2D6 | 10 | NA | 11.2% | NA | 16-23% | 15.2% | 29.1% |
| CYP3A4 | 10 | 1.608 | 1.46 ± 0.39 | 3.21 | 2.269 | 2.86 ± 0.78 | 2.962 |

Inhibition studies $IC_{50}$ = 50% inhibitory concentration (µM) or percentage of inhibition at the highest concentration tested Values represent the average ± SD of three independent experiments NA not available Enzyme kinetic studies of cytochrome P450 isozyme inhibition were conducted using human liver microsomes. The rate of metabolite formation of CYP450-specific probe substrates by pooled human liver microsomes was determined in the presence and absence of standard inhibitors or compound I or III (0, 0.01, 0.1, 1, 10 and 50 µM). Time-dependent inhibition was also investigated by evaluating the effect of compound I or III pre incubation (30 minutes) on inhibition of CYP450 enzymes (at concentrations as noted above) with microsomes. $IC_{50}$ values for both direct and time-dependent inhibition were determined when inhibition reached levels of greater than 50%. Furthermore, direct inhibition of CYP2C8 and CYP2C9 by compound I or III (at concentrations of 0, 1, 3, 6, 9, and 12 µM) was examined by determining the $K_i$ value and inhibition type.

In addition to $K_i$ values for CYP2C8 and CYP2C9 direct inhibition, $K_{inact}$ and $K_i$ values for time dependent inhibition of CYP3A4 (testosterone and midazolam) by compound I or compound III were determined. Compound I and compound III at 0, 0.0125, 0.125, 1.25, 12.5 and 62.5 µM for CYP3A4 (midazolam and testosterone) were pre-incubated with human liver microsomes and NADPH for 0, 1, 5, 10, 20, and 30 minutes at 37° C. Control incubations included test article at a single concentration pre-incubated without NADPH and a positive control inhibitor. Metabolite formation was monitored by validated LC-MS/MS methods and the percent remaining activity in addition to $k_{inact}$ and $K_i$ values were determined.

Compound I exhibited limited inhibition ($IC_{50}$>20 µM) of CYP1A2, CYP2B6, CYP2D6, and CYP2C19 ($IC_{50}$=10.2 µM) and marked inhibition ($IC_{50}$<10 µM) of CYP2C8, CYP2C9 and CYP3A4. Compound I exhibited competitive inhibition of CYP2C8 and CYP2C9 with $k_i$ values of 1.1 and 1.4 µM, respectively. Because CYP3A4 has multiple binding sites, inhibition is typically evaluated with two structurally unrelated probe substrates, testosterone and midazolam. Compound I exhibited marked mechanism-based inhibition of CYP3A4-testosterone and CYP3A4-midazolam with $k_i$ values of 0.14 and 0.18 µM, respectively.

| In vitro human microsomal cytochrome P450 isozyme inhibition with Compound I | | | |
|---|---|---|---|
| CYP450 isozyme | $K_i$ (µM) | $K_{inact}$ (min$^{-1}$)$^c$ | Type of inhibition |
| CYP1A2 (Phenacetin)$^a$ | ND$^b$ | | |
| CYP2B6 (Bupropion) | ND | | |
| CYP2C8 (Paclitaxel) | 1.1 | | Competitive |
| CYP2C9 (Diclofenac) | 1.4 | | Competitive |
| CYP2C19 (S-Mephenytoin) | ND | | |
| CYP2D6 (Dextromethorphan) | ND | | |
| CYP3A4 (Midazolam) | 0.36 | 0.072 | Mechanism based inhibition |
| CYP3A4 (Testosterone) | 0.14 | 0.033 | Mechanism based inhibition |

$^a$= CYP450 specific probe substrate
$^b$= not determined. $k_i$ values determined for $IC_{50}$ values <10 µM
$^c$= maximum rate constant for inactivation. Relevant only for time-dependent inhibition.

Compound III exhibited limited inhibition ($IC_{50}$>20 µM) of CYP1A2, CYP2B6, CYP2D6, marginal inhibition of CYP2C19 ($IC_{50}$=10.2 µM) and marked inhibition ($IC_{50}$<10 µM) of CYP2C8, CYP2C9 and CYP3A4. Compound III exhibited competitive inhibition of CYP2C8 and CYP2C9 with $k_i$ values of 0.66 and 0.93 µM, respectively. Because CYP3A4 has multiple binding sites, inhibition is typically evaluated with two structurally unrelated probe substrates, testosterone and midazolam. Compound III exhibited marked mechanism-based inhibition of CYP3A4-testosterone and CYP3A4-midazolam with $k_i$ values of 0.21 and 0.06 µM, respectively.

| In vitro human microsomal cytochrome P450 isozyme inhibition with Compound III | | | |
|---|---|---|---|
| CYP450 isozyme | $K_i$ (µM) | $K_{inact}$ (min$^{-1}$)$^c$ | Type of inhibition |
| CYP1A2 (Phenacetin)$^a$ | ND$^b$ | | |
| CYP2B6 (Bupropion) | ND | | |
| CYP2C8 (Paclitaxel) | 0.66 | | Competitive |
| CYP2C9 (Diclofenac) | 0.93 | | Competitive |
| CYP2C19 (S-Mephenytoin) | ND | | |
| CYP2D6 (Dextromethorphan) | ND | | |
| CYP3A4 (Midazolam) | 0.06 | 0.06 | Mechanism based inhibition |
| CYP3A4 (Testosterone) | 0.21 | 0.05 | Mechanism based inhibition |

$^a$= CYP450 specific probe substrate
$^b$= not determined. $IC_{50}$ values were ≧10 µM. $k_i$ values only determined for $IC_{50}$ values <10 µM
$^c$= maximum rate constant for inactivation. Relevant only for time-dependent inhibition.

The potential for in vitro induction of CYP3A4 was screened in DPX2 cells. The DPX2 cell line is a derivative of a human hepatocellular carcinoma cell line (HepG2) transformed with the human pregnane x receptor (PXR) and a reporter gene vector containing the enhancer region of CYP3A4. The potential for in vitro induction of CYP1A2 was screened in CYP1A2-DRE cells. The CYP1A2-DRE cell line is a stably transformed HepG2 cells with dioxin response elements (DRE) and reporter gene containing CYP1A2 promoter elements. The extent of CYP3A4 induction was determined by comparing the activation of PXR obtained with test article to that obtained with rifampicine (potent inducer), mifepristone (moderate inducer) and androstanol (weak inducer). The extent of CYP1A2 induction was determined by comparing the activation of the aryl hydrocarcon receptor (AhR) obtained with test article to that obtained with TCDD (potent inducer), omeprazole (moderate inducer), and 2-acetylaminofluorene (weak inducer).

| | Induction | |
|---|---|---|
| Compound | DPX2 (CYP3A4) | CYP1A2-DRE (CYP1A2) |
| rac (I + II) | NA | NA |
| I | Moderate (n = 2) | Not inducer (n = 1) |
| II | NA | NA |
| rac (III + IV) | Moderate (n = 1) | NA |
| III | Moderate (n = 2) | Not inducer (n = 1) |
| IV | Moderate (n = 1) | NA |

NA = not available

As shown in the table above, compounds I and III are moderate inducers of CYP3A4 and CYP1A2.

In Vitro Plasma Protein Binding

The in vitro plasma protein binding of compound I and compound III in rat, dog, monkey and human plasma was determined by equilibrium dialysis. Protein binding was assessed by equilibrium dialysis using rat, dog, monkey and human plasma. Samples were assayed by HPLC with LC-MS/MS detection. Plasma protein binding was high (>99%) for all species and for both compounds.

Protein binding of Compound I and Compound III

| Species | Percentage Plasma Protein Binding | |
| --- | --- | --- |
| | Compound I | Compound III |
| Rats | 99.1 | 99.4 |
| Dogs | 99.0 | 99.4 |
| Monkeys | 99.9 | 99.9 |
| Humans | 99.8 | 99.9 |

Example 17

In vitro Cytochrome P450 Inhibition
Effects of Compound I and Compound III in Combination with Other Agents In vitro drug-drug interaction studies involving Compound I and Compound III and compounds of the NRTI and PI classes active against HIV were carried out.

The in vitro effect of each antiretroviral drug on the antiviral activity of either test article was tested in triplicate on wild-type HIV-1 virus infection of MT-4 human T cells using a standard drug susceptibility assay (DSA) performed in 45% human serum (HS) to provide a better estimate of interactions that would occur under protein binding conditions found in vivo. Compound I or Compound III were titrated alone or in combination with each NRTI or PI.

The impact of each NRTI or PI on the efficacy of Compound I or Compound III was tested at two different drug concentrations, a "low" (1×) and a "high" (5×) concentration; the high concentration used for each compound was determined from pilot experiments conducted to ensure that measurable inhibition values could still be obtained in the presence of 45% HS.

These in vitro drug-drug interaction studies were powered primarily to determine the potential for negative interactions between the different classes of HIV drugs, rather than to examine the potential for synergy between the different agents.

In summary, none of the seven HIV NRTI drugs or the six HIV PI drugs tested exhibited a measurable negative or antagonistic interaction with Compound I or Compound III against HIV in these in vitro experiments.

Example 18

Metabolism

The metabolism of compounds I and III was evaluated in rat, dog, monkey and human cells, and inhibition of cytochrome P450 was evaluated in human liver microsomes.

Methods

Fresh hepatocytes were plated onto collagen-coated plates and exposed to test compounds at 1 µM for up to 2 hours. Tissue culture medium was assayed for compound depletion by LC/MS detection. Values in Table 23 represent independent experiments from 5 to 7 donors.

Inhibition of CYP450 activity was determined by monitoring changes in the metabolism of CYP450-specific substrates by human liver microsomes with varying concentrations of compound I or III. Probe substrate for 2C8 was paclitaxel, probe substrate for 2C9 was diclofenac and for 3A4 probe substrates were midazolam and testosterone. Two substrates are used to assess 3A4 interactions due to multiple binding sites on the enzyme.

Results

TABLE 23

| Compound Depletion in Hepatocytes | | |
| --- | --- | --- |
| | t½ (min) | |
| Species | Compound I | Compound III |
| Rat | 33 ± 26 | 17 ± 15 |
| Dog | 28 ± 14 | 21 ± 10 |
| Monkey | 63 ± 40 | 52 ± 24 |
| Human | 215 ± 48 | 125 ± 55 |

As shown in the above table, both compound I and compound III exhibited limited in vitro metabolism in human hepatocytes.

| CYP450 Isozyme Inhibition | | |
| --- | --- | --- |
| | Ki (mM) | |
| | Compound I | Compound III |
| 2C8 | 1.10 | 0.66 |
| 2C9 | 1.45 | 0.93 |
| 3A4 | 0.36 | 0.06 |

As shown in the above table, both compound I and compound III showed competitive inhibition of CYP2C8 and CYP2C9. Further, both compound I and compound III showed mechanism based inhibition of CYP3A4. Mechanism based inhibition is characterized by time-dependent loss of enzyme activity, associated with covalent binding between the enzyme and a reactive metabolic intermediate. Mechanism based inhibition is also associated with CYP450 induction as new enzyme is required to restore enzyme activity. Inhibition of CYP 2D6, 1A2, 2B6 and 2C19 was not observed.

Metabolism of Compound I and III Versus Corresponding Racemates

In vitro metabolism was assessed using liver microsomes for all species. Compounds were incubated at 1 µM with liver microsomes for up to one hour. Reported half-lives greater than the total incubation time are extrapolated values. Extracts were assayed for disappearance of parent compound by LC-MS/MS detection.

Data represents one independent experiment conducted.

| In vitro half-life of Compounds I & III and Racemates in Liver Microsomes | | | | |
| --- | --- | --- | --- | --- |
| Species | I | rac (I + II) | III | rac (III + IV) |
| | | Half-life (min) | | |
| Rat | 100 | 146 | 88.8 | 105 |
| Dog | 19.3 | 287 | 13.2 | 257 |
| Monkey | 15.4 | 18.4 | 12.6 | 16.3 |
| Human | 120.6 | 115 | 154 | 91.2 |

As shown in the table above, pure enantiomeric compounds I and III had significantly shorter half-lives in liver microsomes when compared to their corresponding enantiomers.

Example 19

In Vivo Pharmacokinetics

The pharmacokinetics of compounds I and III were evaluated in rats (compound III only), dogs and monkeys.

Methods

All animals received a single oral or intravenous dose of compound in either polyethylene glycol 400 (PEG400) or a mixture of 10% ethanol (EtOH), 10% dimethylacetamine (DMA) and 80% PEG400 at the indicated dose level. Plasma concentration data were acquired using sensitive and specific LC-MS/MS methods. Pharmacokinetic data from the toxicity study included aspects of gender differences, variability and exposure.

Blood samples (1.5-2.5 mL) were collected in heparinized tubes at 0 (pre-dose), 5 (IV only), 10, 20, 30 min, 1, 2, 4, 6, 8, 12 (PO only) and 24 hr after dosing. Plasma was separated and stored at −70° C. until analysis.

Concentrations of unlabeled compound I and compound III within plasma samples and excreta from rat, dog and monkey PK studies were identified through high performance liquid chromatographic (HPLC) methods that incorporated tandem mass spectrometric detection (LC-MS/MS).

The absolute oral bioavailability was determined in pharmacokinetic by comparison of AUC values of parent compound following single intravenous and oral doses of in rats (compound III only), dogs and monkeys.

The oral bioavailability of both compounds (5 mg/kg) from the exploratory PK studies was 38% in rats (compound III only), 4-9% in dogs and 42-58% in monkeys. Although the bioavailability of compound III in rats was higher than dogs and comparable to monkeys, rats had much lower plasma AUC exposure compared to dogs and monkeys.

The absolute bioavailability was also estimated for both compounds from monkey studies at 5 mg/kg. The absolute bioavailability of compound III was 42% in males and 76% in females suggesting a potential gender difference in systemic exposure. The bioavailability of compound I, calculated using mean $AUC_t$ values was 54% in males and 61% in females. However, the value for males may have been underestimated, as the absorption in one animal was slow and the plasma concentrations appeared to be still increasing at 8 hours post-dose. Based on AUC values, and excluding this animal for which AUC could not be calculated, bioavailability in males was 75%.

Following a 5 mg/kg oral dose, plasma concentrations at 24 hours post-dose were 12 ng/mL for compound III and 17.9 ng/mL for compound I. A 5 mg/kg oral dose in the monkey is equivalent (based on body surface area) to a human dose of approximately 100 mg (see *Guidance for Industry: Estimating the Maximum Safe Starting Dose in Initial Clinical Trials for Therapeutics in Adult Healthy Volunteers*, U.S. Department of Health and Human Services, Food and Drug Administration, Center for Drug Evaluation and Research, July 2005). This level of compound at 24 hours post-dose is supportive of once-a-day dosing.

| Oral bioavailability of Compounds I and III | | | | | |
|---|---|---|---|---|---|
| Species | Dose (mg/kg)[a] | Route of administration | No. animals/ Gender | $T_{max}$ (hr) | BA (%) |
| Compound I | | | | | |
| Dog | 5 | PO-Fed | 2M, 1F | 0.3[b] | 9 |
| Monkey | 5 | PO-Fed | 3M | 2.7[b] | 58 |
| Monkey | 5 | PO-Fed | 3M | 4.0[c] | 54 |
| Monkey | 5 | PO-Fed | 3F | 4.0[c] | 61 |
| Compound III | | | | | |
| Rat | 10 | PO-Fasted | 3M | 0.4[b] | 38 |
| Dog | 5 | PO-Fed | 1M, 1F | 1.5[b] | 4 |
| Dog | 20 | PO-Fed | 1M, 1F | 2.2[b] | 23 |
| Monkey | 5 | PO-Fed | 2M | 3.0[b] | 42 |
| Monkey | 5 | PO-Fed | 3M | 2.0[c] | 42 |
| Monkey | 5 | PO-Fed | 3F | 2.0[c] | 76 |
| Monkey | 20 | PO-Fed | 2M | 2.5[b] | 61 |

BA = absolute oral bioavailability
[a] = Rats, dogs and monkeys received a single oral dose of either Compound I or Compound III. Additionally, rats received a 2 mg/kg IV dose and dogs and monkeys received a 1 mg/kg IV dose.
[b] = Mean
[c] = Median value

Example 20

Toxicology

The potential toxicities of compounds I and III were evaluated in vivo in rats and monkeys.

Methods

Sprague-Dawley rats and cynomolgus monkeys were dosed once daily for 14 days via oral gavage with compound I or compound III or dose vehicle (68% Capmul PG-8, 20% PEG 400, 2% Tween 20, and 10% Labrasol) according to GLP. There were 10 male and 10 female rats, and there were 3 male and 3 female monkeys. Rats and monkeys were dosed with 0, 50, 150 or 500 mg/kg/day compound I or with 0, 50, 150, 450 mg/kg/day compound III.

Toxicity was assessed using clinical observations, body weights, food consumption, and clinical pathology (hematology, coagulation, and serum chemistry).

A comprehensive necropsy and gross pathological examination was performed on all animals and selected organs and tissues were collected for histological evaluation.

Determinations of hematocrit, hemoglobin concentration, erythrocyte count, total leukocyte count, and platelet count were conducted on all samples. Leukocyte differential and morphologic assessments were performed.

Clinical biochemistry determinations included activities of alanine aminotransferase (ALT), aspartate aminotransferase (AST), gamma-glutamyltranspeptidase (GGT), and alkaline phosphatase (ALP) and concentrations of blood urea nitrogen (BUN), creatinine, total protein, albumin, globulin, glucose, cholesterol, triglycerides, total bilirubin, and electrolyte levels (Na, K, P, Cl, Ca).

Urine samples (monkeys only) were evaluated macroscopically and microscopically and tested for pH, bilirubin, glucose, protein, ketones, blood, urobilinogen, nitrites, leukocytes, and specific gravity.

Results

No effects on food consumption or body weight differences were associated with dosing compound I or compound III. No treatment related clinical findings were observed, and no toxicologically meaningful changes in hematological or serum chemistry parameters or urinalysis findings were observed.

No toxicologically significant effect on organ weights (absolute or relative) with the exception of increased liver weights in compound III--treated rats (females only) and monkeys at the mid and high doses. However, these livers were microscopically unremarkable.

In compound I and compound III-treated rats, minimal to mild thyroid follicular cell hypertrophy/hyperplasia was observed in all dose groups except low dose compound III-treated females. The impact upon thyroid function could not be assessed since circulating thyroid hormone and TSH levels were not examined.

No other macroscopic lesions, microscopic findings or histopathology findings were observed in rats or monkeys All publications and patent applications cited in this specification are herein incorporated by reference as if each individual publication or patent application were specifically and individually indicated to be incorporated by reference. This invention has been described with reference to certain embodiments. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Variations and modifications of the invention, will be obvious to those skilled in the art from the foregoing detailed description of the invention.

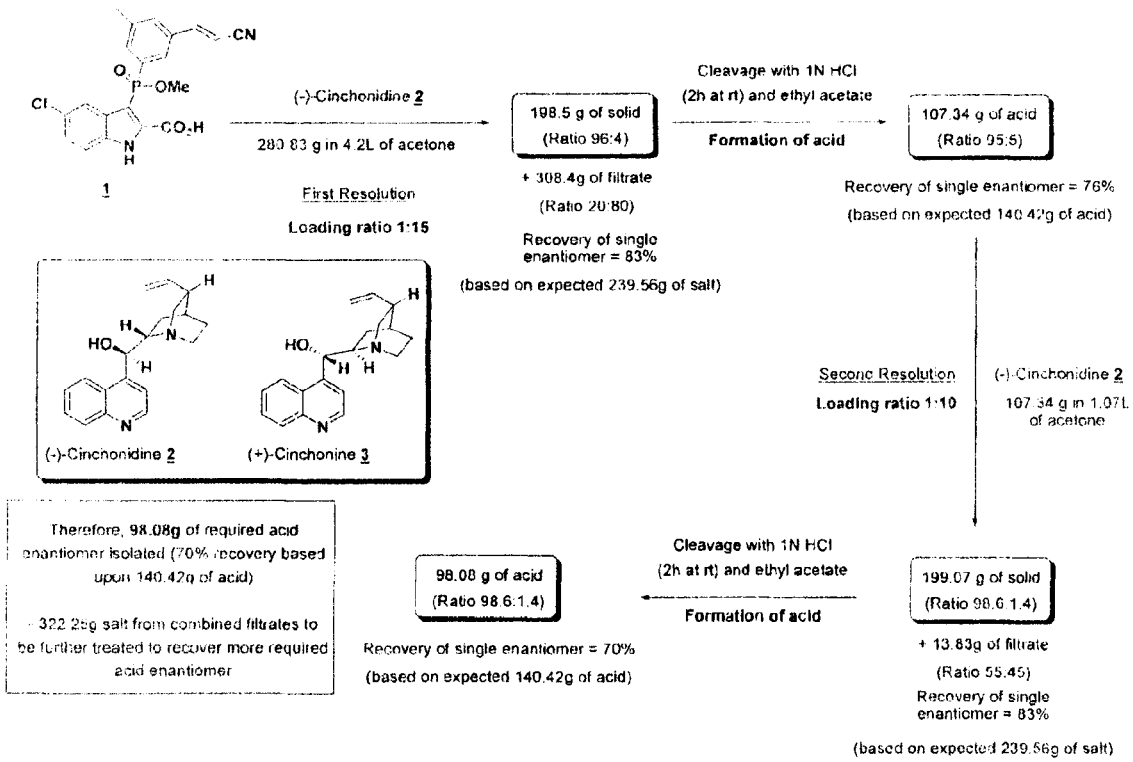

What is claimed is:

1. A pure compound of the following formula, or a pharmaceutically acceptable salt thereof:

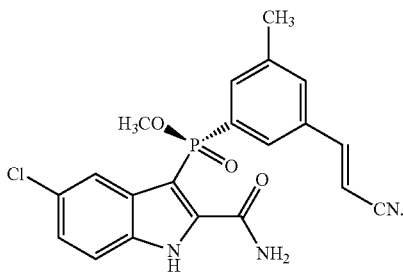

2. A pure compound of the following formula, or a pharmaceutically acceptable salt thereof:

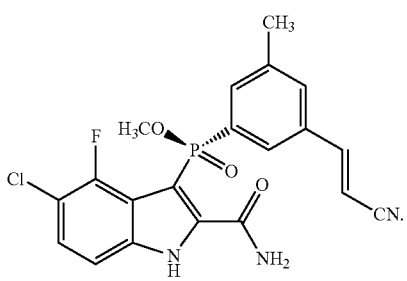

3. The compound of claim 1 that is enantiomerically pure.
4. The compound of claim 1 that is substantially free of its opposite enantiomer.
5. The compound of claim 1 that comprises at least 80%, 90%, 95%, or 99% by weight of the designated enantiomer.
6. A pharmaceutically acceptable salt of the compound of claim 1.
7. A pharmaceutical composition comprising the compound of claim 1 and a pharmaceutical carrier, excipient or diluent, wherein said composition is substantially free of the opposite enantiomer of said compound.
8. The pharmaceutical composition of claim 7, which is in a pharmaceutically acceptable oral dosage form.
9. The pharmaceutical composition of claim 8, wherein the oral dosage form is a capsule or tablet.
10. The pharmaceutical composition of claim 8 wherein the compound is enantiomerically pure.
11. A pharmaceutical composition comprising a compound of claim 1 and a second anti-HIV agent, wherein said composition is substantially free of the opposite enantiomer of said compound.
12. The pharmaceutical composition of claim 11 wherein the second anti-HIV agent is a protease inhibitor or an integrase inhibitor.
13. The pharmaceutical composition of claim 11 wherein the second anti-HIV agent is amprenavir, tipranavir, indinavir, saquinavir, lopinavir, ritronavir, fosamprenavir, darunavir, atazanavir, nelfinavir, brecanivir, GS-8374, Elvitegravir, GSK-364735, or raltegravir.
14. A method of treating an HIV infection comprising administering to a subject in need thereof an effective amount of a compound of claim 1.
15. The method of claim 14, wherein the compound is in a pharmaceutically acceptable oral dosage form.
16. The method of claim 15, wherein the oral dosage form is a capsule or tablet.
17. The method of claim 14, wherein the compound is enantiomerically pure.
18. The method of claim 14, wherein the compound is administered orally.
19. The method of claim 18, wherein the compound is administered orally once per day.
20. A method of inhibiting HIV replication comprising the step of contacting a cell infected with HIV with a compound of claim 1.
21. A pharmaceutical composition comprising the compound of claim 1 and a pharmaceutical carrier, excipient or diluent, wherein said composition comprises at least about 10%, 20%, 30%, 40%, 50%, 60%, 70%, 80%, 90% , or 99% by weight of the designated enantiomer, wherein the remaining weight percentage is made up by the pharmaceutical carrier, excipient or diluent, and wherein the weight is based upon the total weight of the composition.
22. A pharmaceutical composition comprising the compound of claim 1 and a pharmaceutical carrier, excipient or diluent, wherein said composition comprises at least about 80%, 90%, 95%, or 99% by weight of the designated enantiomer, and wherein the weight is based upon the total weight of the compound.
23. The compound of claim 2 that is enantiomerically pure.
24. The compound of claim 2 that is substantially free of its opposite enantiomer.
25. The compound of claim 2 that comprises at least 80%, 90%, 95%, or 99% by weight of the designated enantiomer.
26. A pharmaceutically acceptable salt of the compound of claim 2.
27. A pharmaceutical composition comprising the compound of claim 2 and a pharmaceutical carrier, excipient or diluent, wherein said composition is substantially free of the opposite enantiomer of said compound.
28. The pharmaceutical composition of claim 27, which is in a pharmaceutically acceptable oral dosage form.
29. The pharmaceutical composition of claim 28, wherein the oral dosage form is a capsule or tablet.
30. The pharmaceutical composition of claim 28 wherein the compound is enantiomerically pure.

31. A pharmaceutical composition comprising a compound of claim 2 and a second anti-HIV agent, wherein said composition is substantially free of the opposite enantiomer of said compound.

32. The pharmaceutical composition of claim 31 wherein the second anti-HIV agent is a protease inhibitor or an integrase inhibitor.

33. The pharmaceutical composition of claim 31 wherein the second anti-HIV agent is amprenavir, tipranavir, indinavir, saquinavir, lopinavir, ritronavir, fosamprenavir, darunavir, atazanavir, nelfinavir, brecanivir, GS-8374, Elvitegravir, GSK-364735, or raltegravir.

34. A method of treating an HIV infection comprising administering to a subject in need thereof an effective amount of a compound of claim 2.

35. The method of claim 34, wherein the compound is in a pharmaceutically acceptable oral dosage form.

36. The method of claim 35, wherein the oral dosage form is a capsule or tablet.

37. The method of claim 34, wherein the compound is enantiomerically pure.

38. The method of claim 34, wherein the compound is administered orally.

39. The method of claim 38, wherein the compound is administered orally once per day.

40. A method of inhibiting HIV replication comprising the step of contacting a cell infected with HIV with a compound of claim 2.

41. A pharmaceutical composition comprising the compound of claim 2 and a pharmaceutical carrier, excipient or diluent, wherein said composition comprises at least about 10%, 20%, 30%, 40%, 50%, 60%, 70%, 80%, 90%, or 99% by weight of the designated enantiomer, wherein the remaining weight percentage is made up by the pharmaceutical carrier, excipient or diluent, and wherein the weight is based upon the total weight of the composition.

42. A pharmaceutical composition comprising the compound of claim 2 and a pharmaceutical carrier, excipient or diluent, wherein said composition comprises at least about 80%, 90%, 95%, or 99% by weight of the designated enantiomer, and wherein the weight is based upon the total weight of the compound.

* * * * *

UNITED STATES PATENT AND TRADEMARK OFFICE
CERTIFICATE OF CORRECTION

Page 1 of 2

PATENT NO.        : 7,960,428 B2
APPLICATION NO.   : 11/906095
DATED             : June 14, 2011
INVENTOR(S)       : Storer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 355 days.

At columns 71-74 of the patent, replace Scheme 14 with the following scheme.

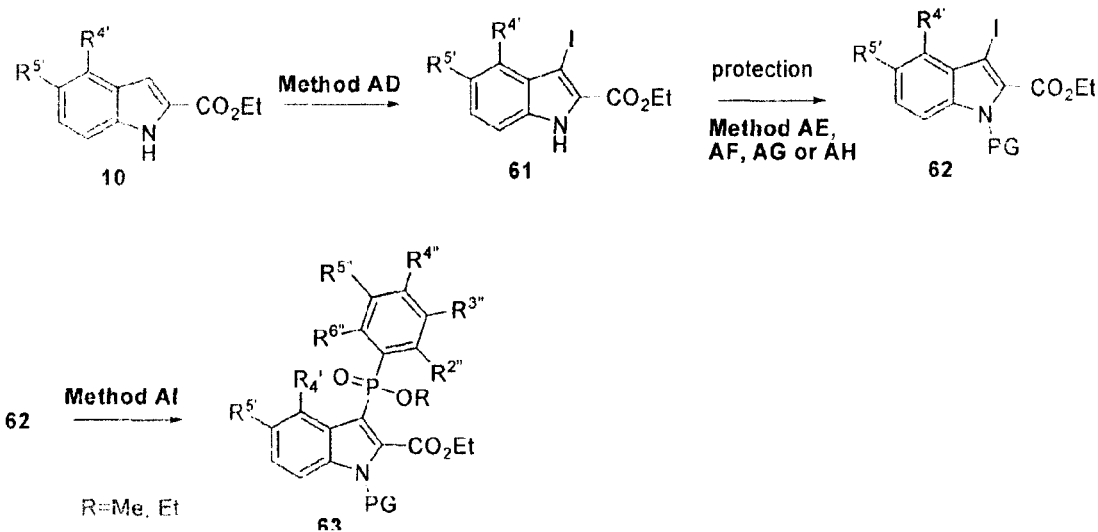

Signed and Sealed this
Thirteenth Day of September, 2011

David J. Kappos
*Director of the United States Patent and Trademark Office*

CERTIFICATE OF CORRECTION (continued)
U.S. Pat. No. 7,960,428 B2

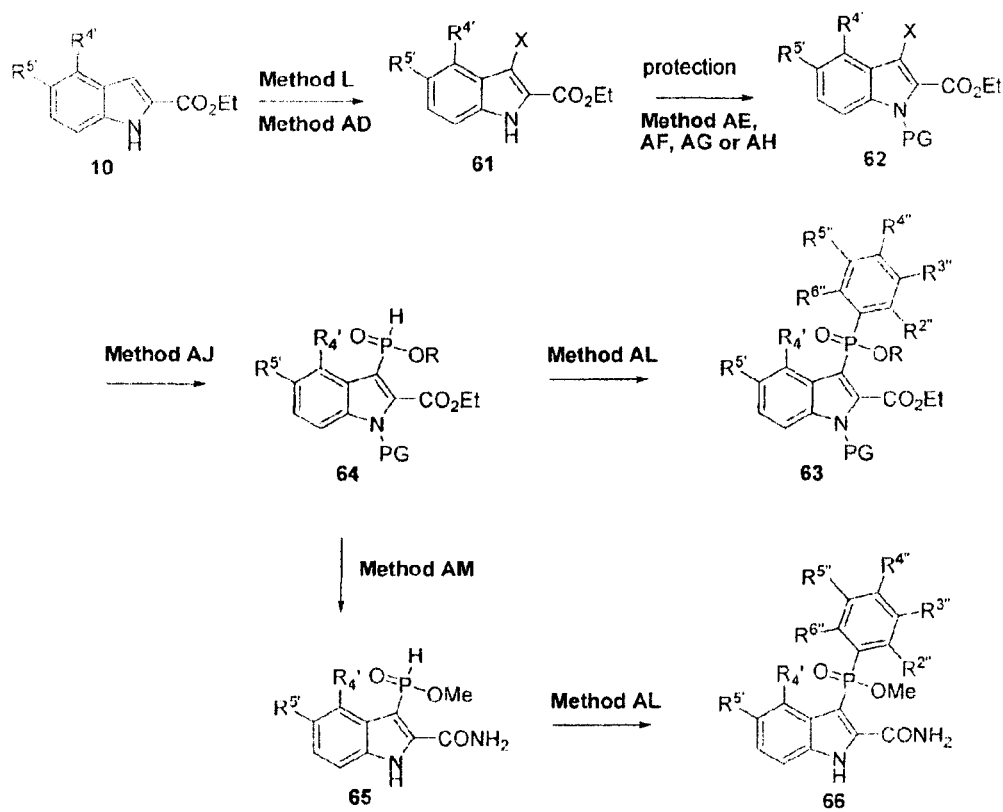

At columns 85 and 86 of the patent, replace Scheme 15 with the following scheme.